US012612418B2

(12) United States Patent
Kang et al.

(10) Patent No.: US 12,612,418 B2
(45) Date of Patent: Apr. 28, 2026

(54) ORGANIC ELECTROLUMINESCENT COMPOUND, A PLURALITY OF HOST MATERIALS, AND ORGANIC ELECTROLUMINESCENT DEVICE COMPRISING THE SAME

(71) Applicant: ROHM AND HAAS ELECTRONIC MATERIALS KOREA LTD., Chungcheongnam-do (KR)

(72) Inventors: Hyun-Ju Kang, Gyeonggi-do (KR); Eun-Joung Choi, Gyeonggi-do (KR); Hyo-Jung Lee, Gyeonggi-do (KR); Su-Hyun Lee, Gyeonggi-do (KR); Kyoung-Jin Park, Gyeonggi-do (KR); Sang-Hee Cho, Gyeonggi-do (KR); Hong-Yeop Na, Gyeonggi-do (KR)

(73) Assignee: DuPont Specialty Materials Korea Ltd. (KR)

( * ) Notice: Subject to any disclaimer, the term of this patent is extended or adjusted under 35 U.S.C. 154(b) by 719 days.

(21) Appl. No.: 17/516,947

(22) Filed: Nov. 2, 2021

(65) Prior Publication Data

US 2022/0144856 A1 May 12, 2022

(30) Foreign Application Priority Data

Nov. 10, 2020 (KR) ........................ 10-2020-0149124
Oct. 5, 2021 (KR) ........................ 10-2021-0131658

(51) Int. Cl.

| | |
|---|---|
| ***C07D 519/00*** | (2006.01) |
| ***C07D 498/04*** | (2006.01) |
| ***C07D 513/04*** | (2006.01) |
| ***H10K 50/11*** | (2023.01) |
| ***H10K 85/40*** | (2023.01) |
| ***H10K 85/60*** | (2023.01) |
| ***H10K 101/00*** | (2023.01) |
| ***H10K 101/10*** | (2023.01) |
| ***H10K 101/30*** | (2023.01) |
| ***H10K 101/40*** | (2023.01) |

(52) U.S. Cl.

CPC ......... *C07D 519/00* (2013.01); *C07D 498/04* (2013.01); *C07D 513/04* (2013.01); *H10K 85/40* (2023.02); *H10K 85/622* (2023.02); *H10K 85/623* (2023.02); *H10K 85/625* (2023.02); *H10K 85/626* (2023.02); *H10K 85/633* (2023.02); *H10K 85/636* (2023.02); *H10K 85/654* (2023.02); *H10K 85/6572* (2023.02); *H10K 85/6574* (2023.02); *H10K 85/6576* (2023.02); *H10K 50/11* (2023.02); *H10K 2101/10* (2023.02); *H10K 2101/30* (2023.02); *H10K 2101/40* (2023.02); *H10K 2101/90* (2023.02)

(58) Field of Classification Search

CPC .. C07D 519/00; C07D 498/04; C07D 513/04; C07D 498/10; C07D 513/10; H10K 85/40; H10K 85/622; H10K 85/623; H10K 85/625; H10K 85/626; H10K 85/633; H10K 85/636; H10K 85/654; H10K 85/6572; H10K 85/6574; H10K 85/6576; H10K 50/11; H10K 2101/10; H10K 2101/30; H10K 2101/40; H10K 2101/90; H10K 85/342; H10K 85/657; H10K 85/615; H10K 85/631; C09K 11/06; C09K 2211/1007; C09K 2211/1011; C09K 2211/1044; C09K 2211/1048; C09K 2211/1051; C09K 2211/1059; C09K 2211/1088

See application file for complete search history.

(56) References Cited

U.S. PATENT DOCUMENTS

| | | | | |
|---|---|---|---|---|
| 2013/0092922 A1* | 4/2013 | Stoessel | H10K 85/657 544/212 |
| 2017/0062730 A1 | 3/2017 | Ahn et al. | |
| 2018/0208837 A1 | 7/2018 | Ahn | |
| 2020/0028089 A1 | 1/2020 | Cho et al. | |
| 2021/0119147 A1* | 4/2021 | Yoon | C07D 513/04 |
| 2021/0135127 A1* | 5/2021 | Jung | H10K 85/631 |
| 2021/0359216 A1 | 11/2021 | Kim et al. | |
| 2022/0165960 A1* | 5/2022 | Lee | H10K 85/40 |

FOREIGN PATENT DOCUMENTS

| | | | |
|---|---|---|---|
| CN | 110746409 A | 2/2020 |
| JP | 3139321 B2 | 2/2001 |
| KR | 2015037712 A * | 4/2015 |
| KR | 20150037712 A | 4/2015 |

(Continued)

OTHER PUBLICATIONS

Mondal, Anirban, et al. "Molecular library of OLED host materials—Evaluating the multiscale simulation workflow." Chemical Physics Reviews 2.3 (2021). (Year: 2021).*

(Continued)

*Primary Examiner* — Dawn L Garrett

(74) *Attorney, Agent, or Firm* — G. Creston Campbell

(57) ABSTRACT

The present disclosure relates to an organic electroluminescent compound, a plurality of host materials, and an organic electroluminescent device comprising the same. By comprising the organic electroluminescent compound according to the present disclosure as a single host material, or the specific combination of compounds according to the present disclosure as a plurality of host materials, it is possible to provide an organic electroluminescent device having improved luminous efficiency.

6 Claims, No Drawings

(56) References Cited

FOREIGN PATENT DOCUMENTS

| | | | |
|---|---|---|---|
| KR | 20190033218 | A | 3/2019 |
| WO | 2018080067 | A | 5/2018 |

OTHER PUBLICATIONS

Machine-generated translation of KR 2015037712 A (publication date Apr. 8, 2015). (Year: 2015).*
Nazarenko, K. G., Shirokaya, T. I., & Shvidenko, K. V. (2007). Synthesis of derivatives of 4, 5-dihydro-imidazo [1, 2-a] phenanthroline. Chemistry of Heterocyclic Compounds, 43(5). (Year: 2007).*
Frontiers in Chemistry , Feb. 7, 2020, vol. 8, 5H-Benzo[d]Benzo[4,5]Imidazo[2,1-b][1,3]Thiazine as a Novel Electron-Acceptor Cored High Triplet Energy Bipolar Host Material for Efficient Solution-Processable Thermally Activated Delayed Fluorescence Organic Light-Emitting Diodes, 61 ( 1-9 ) abstract , Figure1-Figure 3 , Table1-Table2.
Search Report from China National Intellectual Property Administration for Chinese Patent Application No. 202111353812.0, Application Date: Nov. 9, 2021.
RSC Adv., 3, p. 13976-13982 (2013).
Chemistry of Heterocylic Compounds, 41 (2005).
Request for the Submission of an Opinion from Korea Intellectual Property Office, Application No. 10-2021-0131658, Filing Date: Oct. 5, 2021.

* cited by examiner

ORGANIC ELECTROLUMINESCENT COMPOUND, A PLURALITY OF HOST MATERIALS, AND ORGANIC ELECTROLUMINESCENT DEVICE COMPRISING THE SAME

TECHNICAL FIELD

The present disclosure relates to an organic electroluminescent compound, a plurality of host materials, and an organic electroluminescent device comprising the same.

BACKGROUND ART

A small molecular organic electroluminescent device (OLED) was first developed by Tang, et al., of Eastman Kodak in 1987 by using TPD/Alq3 bi-layer consisting of a light-emitting layer and a charge transport layer. Thereafter, the development of organic electroluminescent devices was rapidly effected and organic electroluminescent devices have been commercialized. At present, organic electroluminescent devices primarily use phosphorescent materials having excellent luminous efficiency in panel implementation. An organic electroluminescent device having high luminous efficiency is required for long time use and high resolution of a display.

Meanwhile, Korean Patent Application Laid-Open No. 2019-0033218 discloses an imidazole derivative or pyrrole derivative compound, but does not specifically disclose the specific compound claimed herein. In addition, there is a need to develop an organic electroluminescent material having improved performance, such as high luminous efficiency and/or improved lifetime properties, compared to the specific compound disclosed in said reference.

DISCLOSURE OF INVENTION

Technical Problem

The objective of the present disclosure is to provide an organic electroluminescent compound having a new structure suitable for applying to an organic electroluminescent device. Another objective of the present disclosure is to provide an improved organic electroluminescent material capable of providing an organic electroluminescent device having improved luminous efficiency properties. Another objective of the present disclosure is to provide an organic electroluminescent device having improved luminous efficiency and/or lifetime properties by comprising a specific combination of compounds as host materials.

Solution to Problem

The present inventors found that the above objective can be achieved by a compound represented by the following formula 1. The compound represented by formula 1 of the present disclosure may be applied to an organic electroluminescent device as a single host material, or as a plurality of host materials in combination with at least one compound represented by formula 2 and/or 3 of the present disclosure.

(1)

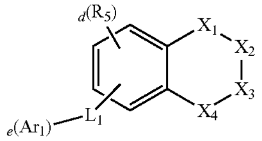

Formula 1 is fused with the following formula 11 to form a ring, wherein any two adjacent ones of $X_1$ to $X_4$, each independently, represent the carbon atom at position a and the nitrogen atom at position b of formula 11; and $X_1$ to $X_4$ not fused with formula 11, each independently, represent $NR_1$, $CR_2R_3$, O, S, P, or P═O.

(11)

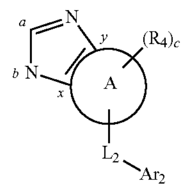

In formulas 1 and 11, $L_1$ and $L_2$, each independently, represent a single bond, a substituted or unsubstituted fused ring group of a (C3-C30) aliphatic ring(s) and a (C6-C30) aromatic ring(s), or a substituted or unsubstituted (C6-C30)arylene;

$Ar_1$ and $Ar_2$, each independently, represent hydrogen, a substituted or unsubstituted (C6-C30)aryl, a substituted or unsubstituted fused ring group of a (C3-C30) aliphatic ring(s) and a (C6-C30) aromatic ring(s), a substituted or unsubstituted (3- to 30-membered)heteroaryl, or —N—$(Ar_3)(Ar_4)$; with the proviso that the case where both $Ar_1$ and $Ar_2$ are hydrogen is excluded;

Ring A is not present, or represents a substituted or unsubstituted (C6-C30)arene, in which when ring A is not present, $-L_2-Ar_2$ is linked to either position x or position y, and $—(R_4)_c$ is linked to the other of position x and position y;

$R_1$ to $R_3$, each independently, represent hydrogen, deuterium, a halogen, a cyano, a substituted or unsubstituted (C1-C30)alkyl, a substituted or unsubstituted (C6-C30)aryl, or a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, or a substituted or unsubstituted fused ring group of a (C3-C30) aliphatic ring(s) and a (C6-C30) aromatic ring(s), and $R_2$ and $R_3$ may be linked to each other to form a spiro ring;

$R_4$ and $R_5$, each independently, represent hydrogen, deuterium, a halogen, a cyano, a substituted or unsubstituted (C1-C30)alkyl, a substituted or unsubstituted (C6-C30)aryl, or a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted fused ring group of a (C3-C30) aliphatic ring(s) and a (C6-C30) aromatic ring(s), or —N—$(Ar_3)(Ar_4)$; or may be linked to adjacent $R_4$ or adjacent $R_5$ to form a ring(s);

$Ar_3$ and $Ar_4$, each independently, represent hydrogen, a substituted or unsubstituted (C1-C30)alkyl, a substituted or unsubstituted (C2-C30)alkenyl, a substituted or unsubstituted (C6-C30)aryl, or a substituted or unsubstituted (3- to 30-membered)heteroaryl;

c and d, each independently, represent an integer of 1 to 3; in which when $R_4$ and $R_5$ are each present in plural, each of $R_4$ and each of $R_5$ may be the same as or different from each other; and e represents an integer of 1 or 2; in which when two $Ar_1$ are present, each of $Ar_1$ may be the same as or different from each other.

Advantageous Effects of Invention

The organic electroluminescent compound according to the present disclosure exhibits performances suitable for use in an organic electroluminescent device. In addition, it is possible to provide an organic electroluminescent device having improved luminous efficiency and/or lifetime properties compared to conventional organic electroluminescent devices by comprising the compound according to the present disclosure as a single host material, or the specific combination of compounds according to the present disclosure as a plurality of host materials.

MODE FOR THE INVENTION

Hereinafter, the present disclosure will be described in detail. However, the following description is intended to explain the present disclosure and is not meant in any way to restrict the scope of the present disclosure.

The term "organic electroluminescent compound" in the present disclosure refers to a compound that may be used in an organic electroluminescent device, and may be comprised in any layer constituting an organic electroluminescent device, as necessary.

The term "an organic electroluminescent material" in the present disclosure refers to a material that may be used in an organic electroluminescent device, and may comprise at least one compound. The organic electroluminescent material may be comprised in any layer constituting an organic electroluminescent device, as necessary. For example, the organic electroluminescent material may be a hole injection material, a hole transport material, a hole auxiliary material, a light-emitting auxiliary material, an electron blocking material, a light-emitting material (including a host material and a dopant material), an electron buffer material, a hole blocking material, an electron transport material, an electron injection material, etc.

The term "a plurality of organic electroluminescent materials" in the present disclosure refers to an organic electroluminescent material comprising a combination of at least two compounds, which may be comprised in any layer constituting an organic electroluminescent device. It may mean both a material before being comprised in an organic electroluminescent device (for example, before vapor deposition) and a material after being comprised in an organic electroluminescent device (for example, after vapor deposition). For example, a plurality of organic electroluminescent materials of the present disclosure may be a combination of at least two compounds, which may be comprised in at least one layer of a hole injection layer, a hole transport layer, a hole auxiliary layer, a light-emitting auxiliary layer, an electron blocking layer, a light-emitting layer, an electron buffer layer, a hole blocking layer, an electron transport layer, and an electron injection layer. At least two compounds may be comprised in the same layer or different layers, and may be mixture-evaporated or co-evaporated, or may be individually evaporated.

The term "a plurality of host materials" in the present disclosure refers to a host material comprising a combination of at least two compounds, which may be comprised in any light-emitting layer constituting an organic electroluminescent device. It may mean both materials before being comprised in an organic electroluminescent device (for example, before vapor deposition) and a material after being comprised in an organic electroluminescent device (for example, after vapor deposition). As one embodiment, the plurality of host materials of the present disclosure may be a combination of at least two host materials, and may optionally further include a conventional material(s) included in an organic electroluminescent device. At least two compounds comprised in the plurality of host materials of the present disclosure may be comprised together in one light-emitting layer or may respectively be comprised in different light-emitting layers. For example, at least two host materials may be mixture-evaporated or co-evaporated, or may be individually evaporated.

Herein, the term "(C1-C30)alkyl" is meant to be a linear or branched alkyl having 1 to 30 carbon atoms constituting the chain, in which the number of carbon atoms is preferably 1 to 10, and more preferably 1 to 6. The above alkyl may include methyl, ethyl, n-propyl, isopropyl, n-butyl, isobutyl, tert-butyl, sec-butyl, etc. The term "(C3-C30)cycloalkyl" is meant to be a mono- or polycyclic hydrocarbon having 3 to 30 ring backbone carbon atoms, in which the number of carbon atoms is preferably 3 to 20, and more preferably 3 to 7. The above cycloalkyl may include cyclopropyl, cyclobutyl, cyclopentyl, cyclohexyl, cyclopentylmethyl, cyclohexylmethyl, etc. The term "(3- to 7-membered)heterocycloalkyl" is meant to be a cycloalkyl having 3 to 7 ring backbone atoms, and including at least one heteroatom selected from the group consisting of B, N, O, S, Si, and P, and preferably the group consisting of O, S, and N. The above heterocycloalkyl may include tetrahydrofuran, pyrrolidine, thiolan, tetrahydropyran, etc. The term "(C6-C30)arene" is meant to be an aromatic hydrocarbon having 6 to 30 ring backbone carbon atoms. The term "(C6-C30)aryl(ene)" is meant to be a monocyclic or fused ring radical derived from an aromatic hydrocarbon having 6 to 30 ring backbone carbon atoms. The above aryl(ene) may be partially saturated, and may comprise a spiro structure. The above aryl may include phenyl, biphenyl, terphenyl, naphthyl, binaphthyl, phenylnaphthyl, naphthylphenyl, fluorenyl, phenyifluorenyl, diphenylfluorenyl, benzofluorenyl, dibenzofluorenyl, phenanthrenyl, phenylphenanthrenyl, anthracenyl, indenyl, triphenylenyl, pyrenyl, tetracenyl, perylenyl, chrysenyl, naphthacenyl, fluoranthenyl, spirobifluorenyl, spiro[fluorene-benzofluoren]yl, azulenyl, tetramethyldihydrophenanthrenyl, etc. Specifically, the above aryl may include phenyl, 1-naphthyl, 2-naphthyl, 1-anthryl, 2-anthryl, 9-anthryl, benzanthryl, 1-phenanthryl, 2-phenanthryl, 3-phenanthryl, 4-phenanthryl, 9-phenanthryl, naphthacenyl, pyrenyl, 1-chrysenyl, 2-chrysenyl, 3-chrysenyl, 4-chrysenyl, 5-chrysenyl, 6-chrysenyl, benzo[c]phenanthryl, benzo[g]chrysenyl, 1-triphenylenyl, 2-triphenylenyl, 3-triphenylenyl, 4-triphenylenyl, 1-fluorenyl, 2-fluorenyl, 3-fluorenyl, 4-fluorenyl, 9-fluorenyl, benzo[a]fluorenyl, benzo[b]fluorenyl, benzo[c]fluorenyl, dibenzofluorenyl, 2-biphenylyl, 3-biphenylyl, 4-biphenylyl, o-terphenyl, m-terphenyl-4-yl, m-terphenyl-3-yl, m-terphenyl-2-yl, p-terphenyl-4-yl, p-terphenyl-3-yl, p-terphenyl-2-yl, m-quaterphenyl, 3-fluoranthenyl, 4-fluoranthenyl, 8-fluoranthenyl, 9-fluoranthenyl, benzofluoranthenyl, o-tolyl, m-tolyl, p-tolyl, 2,3-xylyl, 3,4-xylyl, 2,5-xylyl, mesityl, o-cumenyl, m-cumenyl, p-cumenyl, p-tert-butylphenyl, p-(2-phenylpropyl)phenyl, 4'-methylbiphenylyl, 4"-tert-butyl-p-terphenyl-4-yl, 9,9-dimethyl-1-fluorenyl, 9,9-dimethyl-2-fluorenyl, 9,9-dimethyl-3- fluorenyl, 9,9-dimethyl-4-fluorenyl, 9,9-diphenyl-1-fluorenyl, 9,9-diphenyl-2-fluorenyl, 9,9-diphenyl-3-fluorenyl, 9,9-diphenyl-4-fluorenyl, 11,11-dimethyl-1-benzo[a]fluorenyl, 11,11-dimethyl-2-benzo[a]fluorenyl, 11,11-dimethyl-3-benzo[a]fluorenyl, 11,11-dimethyl-4-benzo[a]fluorenyl, 11,11-dimethyl-5-benzo[a]fluorenyl, 11,11-dimethyl-6-benzo[a]fluorenyl, 11,11-dimethyl-7-benzo[a]fluorenyl, 11,11-dimethyl-8-benzo[a]fluorenyl, 11,11-dimethyl-9-benzo[a]fluorenyl, 11,11-dimethyl-10-benzo[a]fluorenyl, 11,11-dimethyl-1-benzo[b]fluorenyl, 11,11-dimethyl-2-benzo[b]fluorenyl, 11,11-dimethyl-3-benzo[b]fluorenyl, 11,11-dimethyl-4-benzo[b]fluorenyl, 11,11-dimethyl-5-benzo[b]fluorenyl, 11,11-dimethyl-6-benzo[b]fluorenyl, 11,11-dimethyl-7-benzo[b]fluorenyl, 11,11-dimethyl-8-benzo[b]fluorenyl, 11,11-dimethyl-9-benzo[b]fluorenyl, 11,11-dimethyl-10-benzo[b]fluorenyl, 11,11-dimethyl-1-benzo[c]fluorenyl, 11,11-dimethyl-2-benzo[c]fluorenyl, 11,11-dimethyl-3-benzo[c]fluorenyl, 11,11-dimethyl-4-benzo[c]fluorenyl, 11,11-dimethyl-5-benzo[c]fluorenyl, 11,11-dimethyl-6-benzo[c]fluorenyl, 11,11-dimethyl-7-benzo[c]fluorenyl, 11,11-dimethyl-8-benzo[c]fluorenyl, 11,11-dimethyl-9-benzo[c]fluorenyl, 11,11-dimethyl-10-benzo[c]fluorenyl, 11,11-diphenyl-1-benzo[a]fluorenyl, 11,11-diphenyl-2-benzo[a]fluorenyl, 11,11-diphenyl-3-benzo[a]fluorenyl, 11,11-diphenyl-4-benzo[a]fluorenyl, 11,11-diphenyl-5-benzo[a]fluorenyl, 11,11-diphenyl-6-benzo[a]fluorenyl, 11,11-diphenyl-7-benzo[a]fluorenyl, 11,11-diphenyl-8-benzo[a]fluorenyl, 11,11-diphenyl-9-benzo[a]fluorenyl, 11,11-diphenyl-10-benzo[a]fluorenyl, 11,11-diphenyl-1-benzo[b]fluorenyl, 11,11-diphenyl-2-benzo[b]fluorenyl, 11,11-diphenyl-3-benzo[b]fluorenyl, 11,11-diphenyl-4-benzo[b]fluorenyl, 11,11-diphenyl-5-benzo[b]fluorenyl, 11,11-diphenyl-6-benzo[b]fluorenyl, 11,11-diphenyl-7-benzo[b]fluorenyl, 11,11-diphenyl-8-benzo[b]fluorenyl, 11,11-diphenyl-9-benzo[b]fluorenyl, 11,11-diphenyl-10-benzo[b]fluorenyl, 11,11-diphenyl-1-benzo[c]fluorenyl, 11,11-diphenyl-2-benzo[c]fluorenyl, 11,11-diphenyl-3-benzo[c]fluorenyl, 11,11-diphenyl-4-benzo[c]fluorenyl, 11,11-diphenyl-5-benzo[c]fluorenyl, 11,11-diphenyl-6-benzo[c]fluorenyl, 11,11-diphenyl-7-benzo[c]fluorenyl, 11,11-diphenyl-8-benzo[c]fluorenyl, 11,11-diphenyl-9-benzo[c]fluorenyl, 11,11-diphenyl-10-benzo[c]fluorenyl, 9,9,10,10-tetramethyl-9,10-dihydro-1-phenanthrenyl, 9,9,10,10-tetramethyl-9,10-dihydro-2-phenanthrenyl, 9,9,10,10-tetramethyl-9,10-dihydro-3-phenanthrenyl, 9,9,10,10-tetramethyl-9,10-dihydro-4-phenanthrenyl, etc.

The term "(3- to 50-membered)heteroaryl(ene)" is meant to be an aryl or an arylene having 3 to 50 ring backbone atoms, and including at least one, preferably 1 to 4 heteroatoms selected from the group consisting of B, N, O, S, Si, and P. The above heteroaryl or heteroarylene may be a monocyclic ring, or a fused ring condensed with at least one benzene ring; may be partially saturated: may be one formed by linking at least one heteroaryl or aryl group to a heteroaryl group via a single bond(s); and may comprise a spiro structure. The above heteroaryl may include a monocyclic ring-type heteroaryl such as furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, and pyridazinyl, and a fused ring-type heteroaryl such as benzofuranyl, benzothiophenyl, isobenzofuranyl, dibenzofuranyl, dibenzothiophenyl, dibenzoselenophenyl, naphthobenzofuranyl, naphthobenzothiophenyl, benzofuroquinolinyl, benzofuroquinazolinyl, benzofuronaphthyridinyl, benzofuropyrimidinyl, naphthofuropyrimidinyl, benzothienoquinolinyl, benzothienoquinazolinyl, benzothienonaphthyrdinyl, benzothienopyrimidinyl, naphthothienopyrmidinyl, pyrimidoindolyl, benzopyrmidoindolyl, benzofuropyrazinyl, naphthofuropyrazinyl, benzothienopyrazinyl, naphthothienopyrazinyl, pyrazinoindolyl, benzopyrazinoindolyl, benzimidazolyl, benzothiazolyl, benzoisothiazolyl, benzoisoxazolyl, benzoxazolyl, isoindolyl, indolyl, indazolyl, benzothiadiazolyl, quinolyl, isoquinolyl, cinnolinyl, quinazolinyl, quinoxalinyl, carbazolyl, benzocarbazolyl, dibenzocarbazolyl, phenoxazinyl, phenanthridinyl, benzodioxolyl, dihydroacridinyl, benzotriazolphenazinyl, imidazopyridyl, chromenoquinazolinyl, thiochromenoquinazolinyl, dimethylbenzopermidinyl, indolocarbazolyl, indenocarbazolyl, etc. More specifically, the above heteroaryl may include 1-pyrrolyl, 2-pyrrolyl, 3-pyrrolyl, pyrazinyl, 2-pyridyl, 2-pyrimidinyl, 4-pyrimidinyl, 5-pyrimidinyl, 6-pyrimidinyl, 1,2,3-triazin-4-yl, 1,2,4-triazin-3-yl, 1,3,5-triazin-2-yl, 1-imidazolyl, 2-imidazolyl, 1-pyrazolyl, 1-indolidinyl, 2-indolidinyl, 3-indolidinyl, 5-indolidinyl, 6-indolidinyl, 7-indolidinyl, 8-indolidinyl, 2-imidazopyridyl, 3-imidazopyridyl, 5-imidazopyridyl, 6-imidazopyridyl, 7-imidazopyridyl, 8-imidazopyridyl, 3-pyridyl, 4-pyridyl, 1-indolyl, 2-indolyl, 3-indolyl, 4-indolyl, 5-indolyl, 6-indolyl, 7-indolyl, 1-isoindolyl, 2-isoindolyl, 3-isoindolyl, 4-isoindolyl, 5-isoindolyl, 6-isoindolyl, 7-isoindolyl, 2-furyl, 3-furyl, 2-benzofuranyl, 3-benzofuranyl, 4-benzofuranyl, 5-benzofuranyl, 6-benzofuranyl, 7-benzofuranyl, 1-isobenzofuranyl, 3-isobenzofuranyl, 4-isobenzofuranyl, 5-isobenzofuranyl, 6-isobenzofuranyl, 7-isobenzofuranyl, 2-quinolyl, 3-quinolyl, 4-quinolyl, 5-quinolyl, 6-quinolyl, 7-quinolyl, 8-quinolyl, 1-isoquinolyl, 3-isoquinolyl, 4-isoquinolyl, 5-isoquinolyl, 6-isoquinolyl, 7-isoquinolyl, 8-isoquinolyl, 2-quinoxalinyl, 5-quinoxalinyl, 6-quinoxalinyl, 1-carbazolyl, 2-carbazolyl, 3-carbazolyl, 4-carbazolyl, 9-carbazolyl, azacarbazolyl-1-yl, azacarbazolyl-2-yl, azacarbazolyl-3-yl, azacarbazolyl-4-yl, azacarbazolyl-5-yl, azacarbazolyl-6-yl, azacarbazolyl-7-yl, azacarbazolyl-8-yl, azacarbazolyl-9-yl, 1-phenanthridinyl, 2-phenanthridinyl, 3-phenanthridinyl, 4-phenanthridinyl, 6-phenanthridinyl, 7-phenanthridinyl, 8-phenanthridinyl, 9-phenanthridinyl, 10-phenanthridinyl, 1-acridinyl, 2-acridinyl, 3-acridinyl, 4-acridinyl, 9-acridinyl, 2-oxazolyl, 4-oxazolyl, 5-oxazolyl, 2-oxadiazolyl, 5-oxadiazolyl, 3-furazanyl, 2-thienyl, 3-thienyl, 2-methylpyrrol-1-yl, 2-methylpyrrol-3-yl, 2-methylpyrrol-4-yl, 2-methylpyrrol-5-yl, 3-methylpyrrol-1-yl, 3-methylpyrrol-2-yl, 3-methylpyrrol-4-yl, 3-methylpyrrol-5-yl, 2-tert-butylpyrrol-4-yl, 3-(2-phenylpropyl)pyrrol-1-yl, 2-methyl-1-indolyl, 4-methyl-1-indolyl, 2-methyl-3-indolyl, 4-methyl-3-indolyl, 2-tert-butyl-1-indolyl, 4-tert-butyl-1-indolyl, 2-tert-butyl-3-indolyl, 4-tert-butyl-3-indolyl, 1-dibenzofuranyl, 2-dibenzofuranyl, 3-dibenzofuranyl, 4-dibenzofuranyl, 1-dibenzothiophenyl, 2-dibenzothiophenyl, 3-dibenzothiophenyl, 4-dibenzothiophenyl, 1-naphtho-[1,2-b]-benzofuranyl, 2-naphtho-[1,2-b]-benzofuranyl, 3-naphtho-[1,2-b]-benzofuranyl, 4-naphtho-[1,2-b]-benzofuranyl, 5-naphtho-[1,2-b]-benzofuranyl, 6-naphtho-[1,2-b]-benzofuranyl, 7-naphtho-[1,2-b]-benzofuranyl, 8-naphtho-[1,2-b]-benzofuranyl, 9-naphtho-[1,2-b]-benzofuranyl, 10-naphtho-[1,2-b]-benzofuranyl, 1-naphtho-[2,3-b]-benzofuranyl, 2-naphtho-[2,3-b]-benzofuranyl, 3-naphtho-[2,3-b]-benzofuranyl, 4-naphtho-[2,3-b]-benzofuranyl, 5-naphtho-[2,3-b]-benzofuranyl, 6-naphtho-[2,3-b]-benzofuranyl, 7-naphtho-[2,3-b]-benzofuranyl, 8-naphtho-[2,3-b]-benzofuranyl, 9-naphtho-[2,3-b]-benzofuranyl, 10-naphtho-[2,3-b]-benzofuranyl, 1-naphtho-[2,1-b]-benzofuranyl, 2-naphtho-[2,1-b]-benzofuranyl, 3-naphtho-[2,1-b]-benzofuranyl, 4-naphtho-[2,1-b]-benzofuranyl, 5-naphtho-[2,1-b]-benzofuranyl, 6-naphtho-[2,1-b]-benzofuranyl, 7-naphtho-[2,1-b]-benzofuranyl, 8-naphtho-[2,1-b]-benzofuranyl, 9-naphtho-[2,1-b]-benzofuranyl, 10-naphtho-[2,1-b]-benzofuranyl, 1-naphtho-[1,2-b]-benzothiophenyl, 2-naphtho-[1,2-b]-benzothiophenyl, 3-naphtho-[1,2-b]-benzothiophenyl, 4-naphtho-[1,2-b]-benzothiophenyl, 5-naphtho-[1,2-b]-benzothiophenyl, 6-naphtho-[1,2-b]-benzothiophenyl, 7-naphtho-[1,2-b]-benzothiophenyl, 8-naphtho-[1,2-b]-benzothiophenyl, 9-naphtho-[1,2-b]-benzothiophenyl, 10-naphtho-[1,2-b]-benzothiophenyl, 1-naphtho-[2,3-b]-benzothiophenyl, 2-naphtho-[2,3-b]-benzothiophenyl, 3-naphtho-[2,3-b]-benzothiophenyl, 4-naphtho-[2,3-b]-benzothiophenyl, 5-naphtho-[2,3-b]-benzothiophenyl, 1-naphtho-[2,1-b]-benzothiophenyl, 2-naphtho-[2,1-b]-benzothiophenyl, 3-naphtho-[2,1-b]-benzothiophenyl, 4-naphtho-[2,1-b]-benzothiophenyl, 5-naphtho-[2,1-b]-benzothiophenyl, 6-naphtho-[2,1-b]-benzothiophenyl, 7-naphtho-[2,1-b]-benzothiophenyl, 8-naphtho-[2,1-b]-benzothiophenyl, 9-naphtho-[2,1-b]-benzothiophenyl, 10-naphtho-[2,1-b]-benzothiophenyl, 2-benzofuro[3,2-d]pyrmidinyl, 6-benzofuro[3,2-d]pyrimidinyl, 7-benzofuro[3,2-d]pyrmidinyl, 8-benzofuro[3,2-d]pyrimidinyl, 9-benzofuro[3,2-d]pyrmidinyl, 2-benzothio[3,2-d]pyrmidinyl, 6-benzothio[3,2-d]pyrmidinyl, 7-benzothio[3,2-d]pyrmidinyl, 8-benzothio[3,2-d]pyrmidinyl, 9-benzothio[3,2-d]pyrmidinyl, 2-benzofuro[3,2-d]pyrazinyl, 6-benzofuro[3,2-d]pyrazinyl, 7-benzofuro[3,2-d]pyrazinyl, 8-benzofuro[3,2-d]pyrazinyl, 9-benzofuro[3,2-d]pyrazinyl, 2-benzothio[3,2-d]pyrazinyl, 6-benzothio[3,2-d]pyrazinyl, 7-benzothio[3,2-d]pyrazinyl, 8-benzothio[3,2-d]pyrazinyl, 9-benzothio[3,2-d]pyrazinyl, 1-silafluorenyl, 2-silafluorenyl, 3-silafluorenyl, 4-silafluorenyl, 1-germafluorenyl, 2-germafluorenyl, 3-germafluorenyl, 4-germafluorenyl, 1-dibenzoselenophenyl, 2-dibenzoselenophenyl, 3-dibenzoselenophenyl, 4-dibenzoselenophenyl, etc. Furthermore, "halogen" includes F, Cl, Br, and I.

In addition, "ortho (o-)," "meta (m-)," and "para (p-)" are prefixes, which represent the relative positions of substituents respectively. Ortho indicates that two substituents are adjacent to each other, and for example, when two substituents in a benzene derivative occupy positions 1 and 2, it is called an ortho position. Meta indicates that two substituents are at positions 1 and 3, and for example, when two substituents in a benzene derivative occupy positions 1 and 3, it is called a meta position. Para indicates that two substituents are at positions 1 and 4, and for example, when two substituents in a benzene derivative occupy positions 1 and 4, it is called a para position.

Herein, "substituted" in the expression "substituted or unsubstituted" means that a hydrogen atom in a certain functional group is replaced with another atom or another functional group, i.e., a substituent, and also includes that the hydrogen atom is replaced with a group formed by a linkage of two or more substituents of the above substituents. For example, the "group formed by a linkage of two or more substituents" may be pyridine-triazine. That is, pyridine-triazine may be interpreted as a heteroaryl substituent, or as substituents in which two heteroaryl substituents are linked. Herein, the substituent(s) of the substituted alkyl, the substituted alkenyl, the substituted aryl, the substituted arene, the substituted arylene, the substituted heteroaryl, the substituted heteroarylene, the substituted cycloalkyl, the substituted alkoxy, the substituted trialkylsilyl, the substituted dialkylarylsilyl, the substituted alkyldiarylsilyl, the substituted triarylsilyl, the substituted fused ring group of a aliphatic ring(s) and a aromatic ring(s), the substituted mono- or di-alkylamino, the substituted mono- or di-alkenylamino, the substituted alkylalkenylamino, the substituted mono- or di-arylamino, the substituted alkylarylamino, the substituted mono- or di-heteroarylamino, the substituted alkylheteroarylamino, the substituted alkenylarylamino, the substituted alkenylheteroarylamino, and the arylheteroarylamino, each independently, are at least one selected from the group consisting of deuterium; a halogen; a cyano; a carboxyl; a nitro; a hydroxyl; a (C1-C30)alkyl; a halo(C1-C30)alkyl; a (C2-C30)alkenyl; a (C2-C30)alkynyl; a (C1-C30)alkoxy; a (C1-C30)alkylthio; a (C3-C30)cycloalkyl; a (C3-C30)cycloalkenyl; a (3- to 7-membered)heterocycloalkyl; a (C6-C30)aryloxy; a (C6-C30)arylthio; a (3- to 30-membered)heteroaryl unsubstituted or substituted with at least one of deuterium and a (C6-C30)aryl(s); a (C6-C30)aryl unsubstituted or substituted with at least one of deuterium and a (3- to 30-membered)heteroaryl(s); a tri(C1-C30)alkylsilyl; a tri(C6-C30)arylsilyl; a di(C1-C30)alkyl(C6-C30)arylsilyl; a (C1-C30)alkyldi(C6-C30)arylsilyl; a fused ring group of a (C3-C30) aliphatic ring(s) and a (C6-C30) aromatic ring(s); an amino; a mono- or di-(C1-C30)alkylamino; a mono- or di-(C2-C30)alkenylamino; a (C1-C30)alkyl(C2-C30)alkenylamino; a mono- or di-(C6-C30)arylamino; a (C1-C30)alkyl(C6-C30)arylamino; a mono- or di-(3- to 30-membered)heteroarylamino; a (C1-C30)alkyl(3- to 30-membered)heteroarylamino; a (C2-C30)alkenyl(C6-C30)arylamino; a (C2-C30)alkenyl(3- to 30-membered)heteroarylamino; a (C6-C30)aryl(3- to 30-membered)heteroarylamino; a (C1-C30)alkylcarbonyl; a (C1-C30)alkoxycarbonyl; a (C6-C30)arylcarbonyl; a (C6-C30)arylphosphinyl; a di(C6-C30)arylboronyl; a di(C1-C30)alkylboronyl; a (C1-C30)alkyl(C6-C30)arylboronyl; a (C6-C30)aryl(C1-C30)alkyl; and a (C1-C30)alkyl(C6-C30)aryl. According to one embodiment of the present disclosure, the substituent(s), each independently, are at least one selected from the group consisting of deuterium; a cyano; a (C1-C20)alkyl; a (C5-C25)cycloalkyl; a (5- to 25-membered)heteroaryl unsubstituted or substituted with a (C6-C25)aryl(s); a (C6-C25)aryl unsubstituted or substituted with deuterium, a (C1-C10)alkyl(s), and/or a (C6-C18)aryl(s); and a mono- or di-(C6-C25)arylamino. According to another embodiment of the present disclosure, the substituent(s), each independently, are at least one selected from the group consisting of deuterium; a cyano; a (C1-C10)alkyl; a (C5-C20)cycloalkyl; a (5- to 20-membered)heteroaryl unsubstituted or substituted with a (C6-C18)aryl(s); a (C6-C20)aryl unsubstituted or substituted with deuterium, a (C1-C6)alkyl(s), and/or a (C6-C18)aryl(s); and a di(C6-C18)arylamino. For example, the substituent(s) may be at least one selected from the group consisting of deuterium; a cyano; a methyl; a cyclohexyl; a phenyl unsubstituted or substituted with at least one selected from the group consisting of deuterium, methyl and tert-butyl; a naphthyl, a biphenyl; an anthracenyl; a fluoranthenyl; a fluorenyl substituted with a phenyl(s); a pyridyl unsubstituted or substituted with a phenyl(s); a benzimidazolyl substituted with a phenyl(s); a phenoxazinyl; a dibenzofuranyl; and a diphenylamino.

Herein, a ring formed by a linkage of adjacent substituents means that at least two adjacent substituents are linked to or fused with each other to form a substituted or unsubstituted, mono- or polycyclic, (3- to 30-membered) alicyclic or aromatic ring, or the combination thereof. Preferably, the ring may be a substituted or unsubstituted, mono- or polycyclic, (3- to 26-membered) alicyclic or aromatic ring, or the combination thereof. More preferably, the ring may be a mono- or polycyclic, (5- to 25-membered) aromatic ring unsubstituted or substituted with at least one of a (C6-C18) aryl(s) and a (3- to 20-membered)heteroaryl(s). In addition, the formed ring may contain at least one heteroatom selected from B, N, O, S, Si, and P, preferably at least one heteroatom selected from N, O, and S. For example, the ring may be a benzene ring, a cyclopentane ring, an indane ring, a fluorene ring, a phenanthrene ring, an indole ring, a xanthene ring, etc.

In the present disclosure, heteroaryl, heteroarylene, and heterocycloalkyl may, each independently, contain at least one heteroatom selected from B, N, O, S. Si, and P. In addition, the heteroatom may be bonded to at least one selected from the group consisting of hydrogen, deuterium, a halogen, a cyano, a substituted or unsubstituted (C1-C30) alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C2-C30)alkenylamino, a substituted or unsubstituted mono- or di-(C6-C30)arylamino, a substituted or unsubstituted mono- or di-(3- to 30-membered)heteroarylamino, a substituted or unsubstituted (C1-C30)alkyl(C2-C30)alkenylamino, a substituted or a unsubstituted (C1-C30)alkyl(C6-C30)arylamino, a substituted or unsubstituted (C1-C30)alkyl(3- to 30-membered) heteroarylamino, a substituted or unsubstituted (C2-C30) alkenyl(C6-C30)arylamino, a substituted or unsubstituted (C2-C30)alkenyl(3- to 30-membered)heteroarylamino, and a substituted or unsubstituted (C6-C30)aryl(3- to 30-membered)heteroarylamino. The plurality of host materials of the present disclosure comprises a first host material(s) and a second host material(s), wherein the first host material comprises a compound(s) represented by formula 1, and the second host material comprises a compound(s) represented by formula 2 or 3. According to one embodiment of the present disclosure, the compound represented by formula 1 is different from the compound represented by formula 2 or 3.

Formula 1 is fused with formula 11 to form a ring(s), wherein any two adjacent ones of $X_1$ to $X_4$, each independently, represent the carbon atom at position a and the nitrogen atom at position b of formula 11. For example, $X_1$ and $X_2$, $X_2$ and $X_3$, and/or $X_a$ and $X_4$, each independently, represent the carbon atom at position a and the nitrogen atom at position b of formula 11. In formula 1, $X_1$ to $X_4$ not fused with formula 11, each independently, represent $NR_1$, $CR_2R_3$, O, S, P, or P═O. According to one embodiment of the present disclosure, $X_1$ to $X_4$ not fused with formula 11, each independently, represent $CR_2R_3$, S, or O.

$R_1$ to $R_3$, each independently, represent hydrogen, deuterium, a halogen, a cyano, a substituted or unsubstituted (C1-C30)alkyl, a substituted or unsubstituted (C6-C30)aryl, or a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, or a substituted or unsubstituted fused ring group of a (C3-C30) aliphatic ring(s) and a (C6-C30) aromatic ring(s), and $R_2$ and $R_3$ may be linked to each other to form a spiro ring. According to one embodiment of the present disclosure, $R_1$ to $R_3$, each independently, represent hydrogen, a substituted or unsubstituted (C1-C20)alkyl, a substituted or unsubstituted (C6-C25)aryl, or a substituted or unsubstituted (5- to 25-membered)heteroaryl, and $R_2$ and $R_3$ may be linked to each other to form a spiro ring. According to another embodiment of the present disclosure, $R_2$ to $R_3$, each independently, represent hydrogen, an unsubstituted (C1-C10) alkyl, or an unsubstituted (C6-C18)aryl, and $R_2$ and $R_3$ may be linked to each other to form a spiro ring. For example, $R_2$ to $R_3$, each independently, may be hydrogen, a methyl, a phenyl, etc., or $R_2$ and $R_3$ may be linked to each other to form a spiro fluorene ring.

In formulas 1 and 11, $L_1$ and $L_2$, each independently, represent a single bond, a substituted or unsubstituted fused ring group of a (C3-C30) aliphatic ring(s) and a (C6-C30) aromatic ring(s), or a substituted or unsubstituted (C6-C30) arylene. According to one embodiment of the present disclosure, $L_1$ and $L_2$, each independently, represent a single bond, or a substituted or unsubstituted (C6-C25)arylene. According to another embodiment of the present disclosure, $L_1$ and $L_2$, each independently, represent a single bond, or an unsubstituted (C6-C18)arylene. For example, $L_1$ and $L_2$, each independently, may be a single bond, a phenylene, a biphenylene, etc.

In formulas 1 and 11, $Ar_1$ and $Ar_2$, each independently, represent hydrogen, a substituted or unsubstituted (C6-C30) aryl, a substituted or unsubstituted fused ring group of a (C3-C30) aliphatic ring(s) and a (C6-C30) aromatic ring(s), a substituted or unsubstituted (3- to 30-membered)heteroaryl, or —N—($Ar_3$)($Ar_4$); with the proviso that the case where both $Ar_1$ and $Ar_2$ are hydrogen is excluded. According to one embodiment of the present disclosure, $Ar_1$ and $Ar_2$, each independently, represent hydrogen, a substituted or unsubstituted (C6-C25)aryl, or a substituted or unsubstituted (5- to 25-membered)heteroaryl. According to another embodiment of the present disclosure, $Ar_1$ and $Ar_2$, each independently, represent hydrogen; a (C6-C18)aryl unsubstituted or substituted with deuterium; or a (5- to 20-membered)heteroaryl unsubstituted or substituted with at least one of deuterium, a (C6-C18)aryl(s), and a (5- to 20-membered)heteroaryl(s). For example, $Ar_1$ and $Ar_2$, each independently, may be hydrogen; a phenyl unsubstituted or substituted with deuterium; a naphthyl; a biphenyl; a terphenyl; a substituted triazinyl; a quinazolinyl substituted with a phenyl(s); a quinoxalinyl substituted with a phenyl(s), etc., in which the substituents of the substituted triazinyl may be any two selected from the group consisting of phenyl, biphenyl, and dibenzofuranyl.

In formula 11, ring A is not present, or represents a substituted or unsubstituted (C6-C30)arene. When ring A is not present, -$L_2$-$Ar_2$ is linked to either position x or position y, and —$(R_4)_c$ is linked to the other of position x and position y. According to one embodiment of the present disclosure, ring A is not present, or represents a substituted or unsubstituted (C6-C25)arene. According to another embodiment of the present disclosure, ring A is not present, or represents an unsubstituted (C6-C18)arene. For example, ring A may be not present, or may be a benzene ring, etc.

In formulas 1 and 11, $R_4$ and $R_5$, each independently, represent hydrogen, deuterium, a halogen, a cyano, a substituted or unsubstituted (C1-C30)alkyl, a substituted or unsubstituted (C6-C30)aryl, or a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30) alkylsilyl, a substituted or unsubstituted di(C1-C30)alkyl (C6-C30)arylsilyl, a substituted or unsubstituted (C1-C30) alkyldi(C6-C30)arylsilyl, a substituted or unsubstituted tri (C6-C30)arylsilyl, a substituted or unsubstituted fused ring group of a (C3-C30) aliphatic ring(s) and a (C6-C30) aromatic ring(s), or —N—$(Ar_3)(Ar_4)$; or may be linked to adjacent $R_4$ or adjacent $R_5$ to form a ring(s). According to one embodiment of the present disclosure, $R_4$ and $R_5$, each independently, represent hydrogen, a substituted or unsubstituted (C6-C25)aryl, or a substituted or unsubstituted (5- to 25-membered)heteroaryl. According to another embodiment of the present disclosure, $R_4$ and $R_5$, each independently, represent hydrogen or an unsubstituted (C6-C20)aryl. For example, $R_4$ and $R_5$, each independently, may be hydrogen, a phenyl, etc.

$Ar_3$ and $Ar_4$, each independently, represent hydrogen, a substituted or unsubstituted (C1-C30)alkyl, a substituted or unsubstituted (C2-C30)alkenyl, a substituted or unsubstituted (C6-C30)aryl, or a substituted or unsubstituted (3- to 30-membered)heteroaryl.

In formulas 1 and 11, c and d, each independently, represent an integer of 1 to 3; in which when $R_4$ and $R_5$ are each present in plural, each of $R_4$ and each of $R_5$ may be the same as or different from each other.

In formula 1, e represents an integer of 1 or 2; in which when two $Ar_1$ are present, each of $Ar_1$ may be the same as or different from each other.

According to one embodiment of the present disclosure, formula 1 may be represented by any one of the following formulas 1-1 to 1-4.

(1-1)

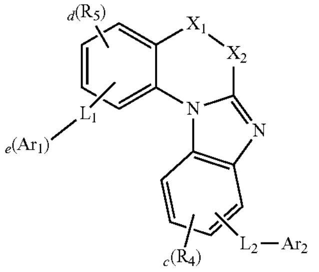

(1-2)

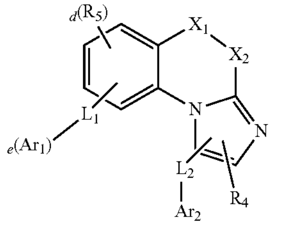

(1-3)

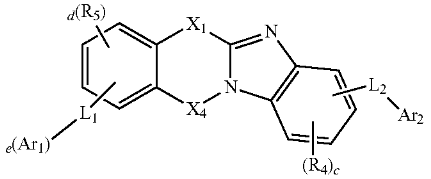

(1-4)

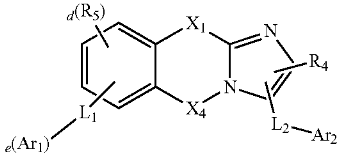

In formulas 1-1 to 1-4, $X_1$, $X_2$, $X_4$, $L_1$, $L_2$, $Ar_1$, $Ar_2$, $R_4$, $R_5$, c, d, and e are as defined in formula 1.

The compound represented by formula 1 may be at least one selected from the following compounds, but is not limited thereto.

C-1

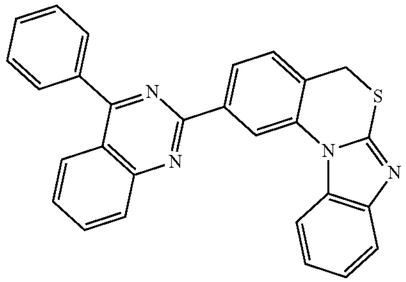

C-2

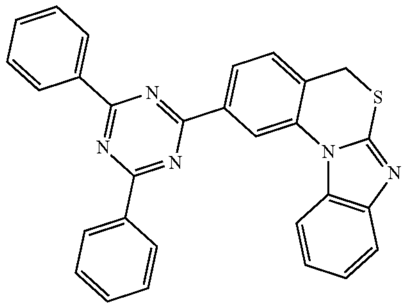

C-3

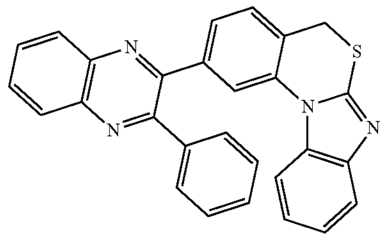

C-4

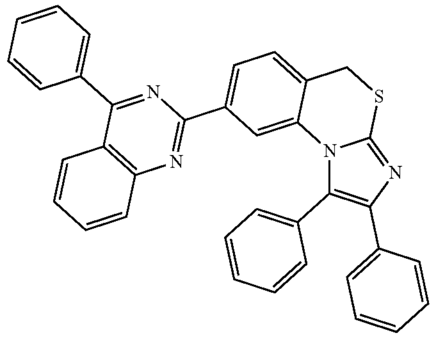

C-5

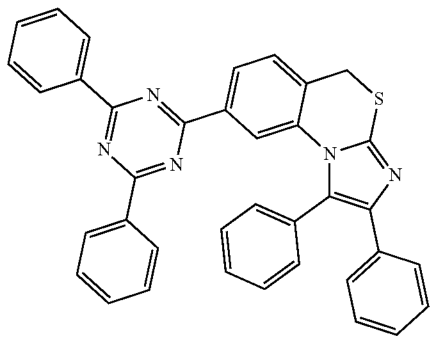

-continued
C-6
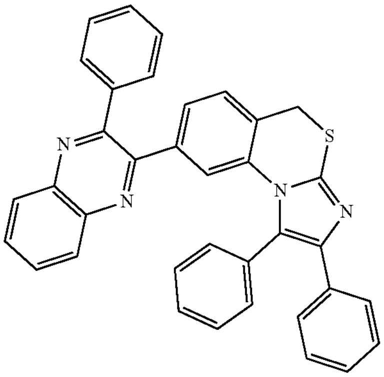
C-7
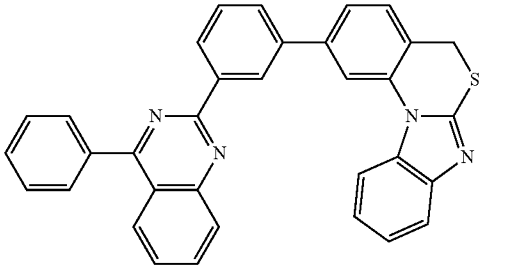
C-8
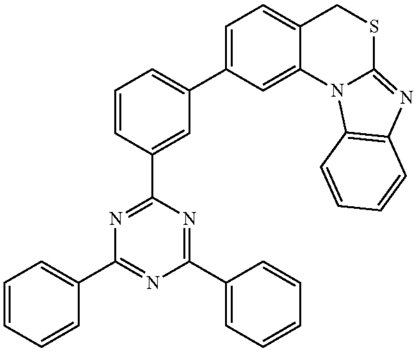
C-9
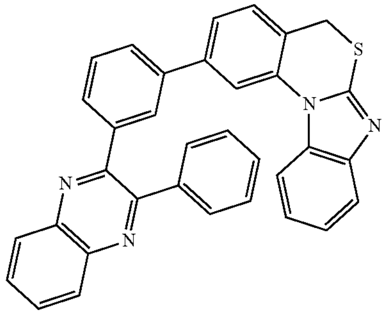
C-10
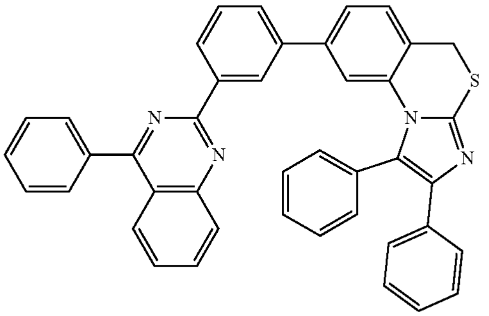
-continued
C-11
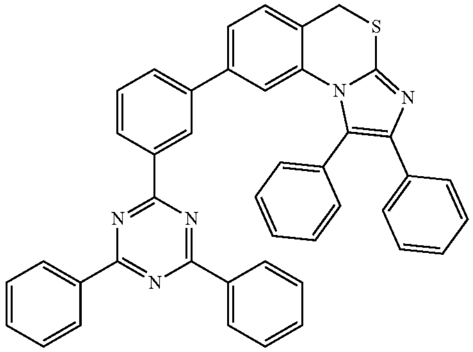
C-12
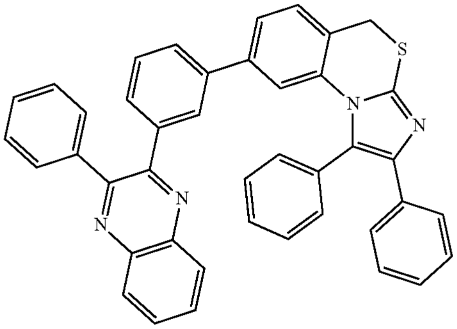
C-13
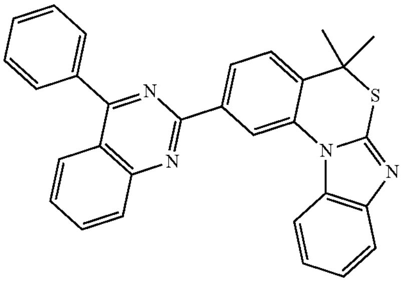
C-14
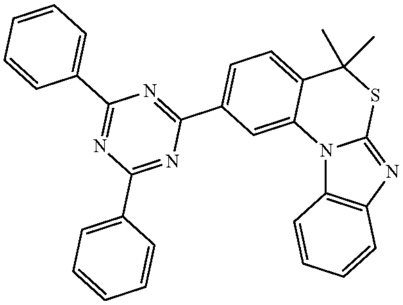
C-15
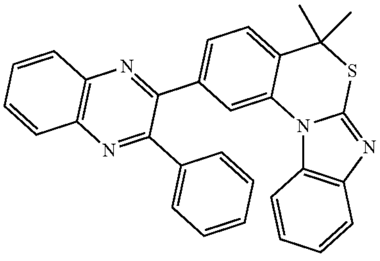

-continued
C-16
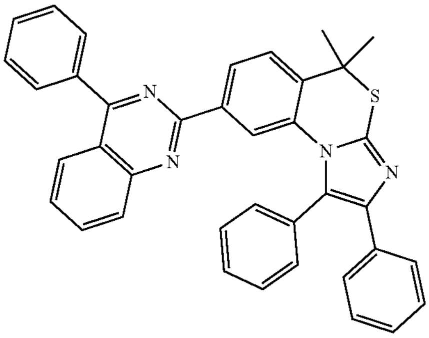
C-17
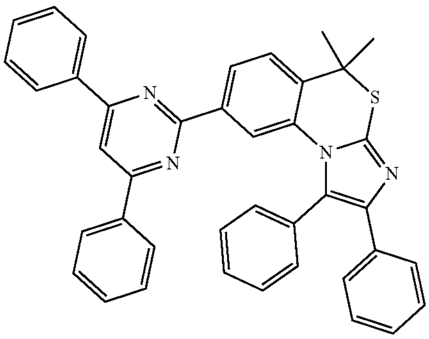
C-18
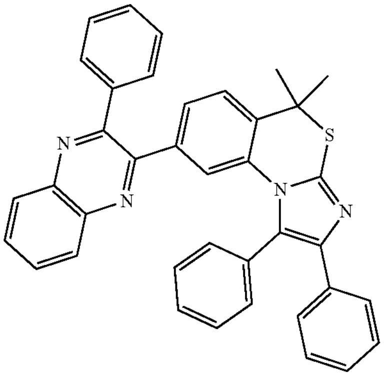
C-19
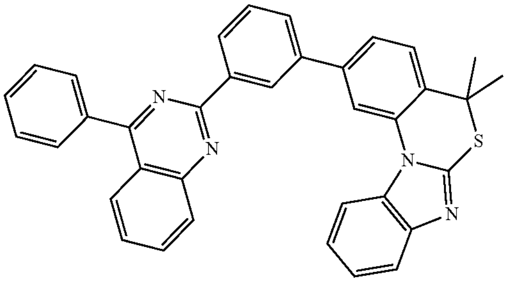
-continued
C-20
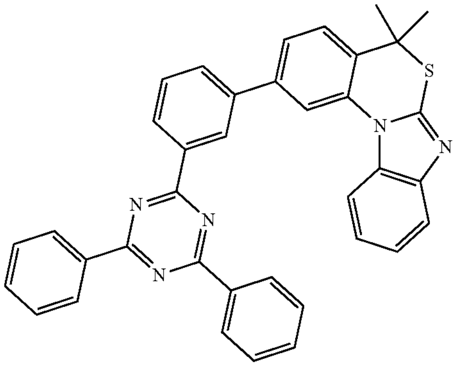
C-21
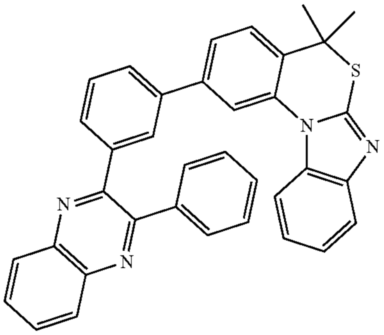
C-22
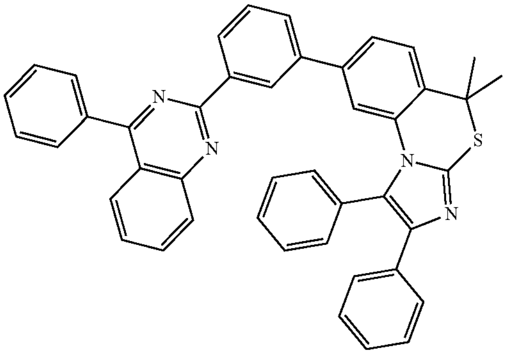
C-23
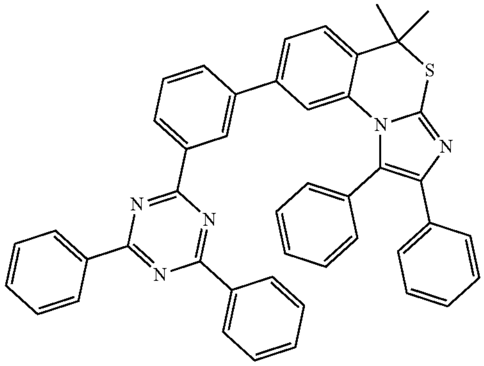

-continued
C-24
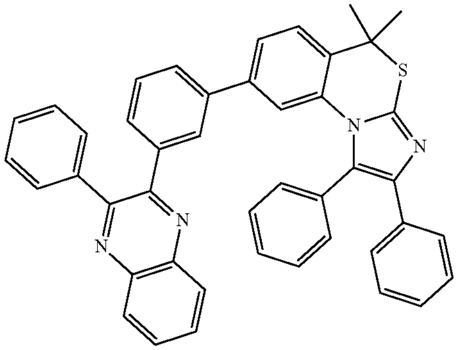
C-25
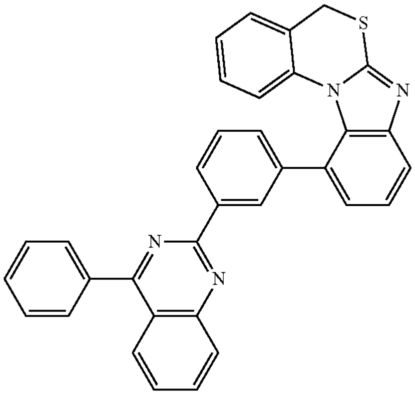
C-26
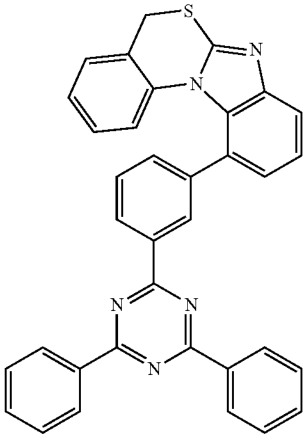
C-27
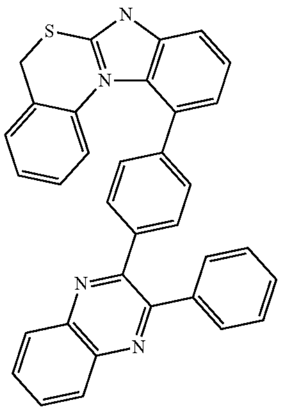
-continued
C-28
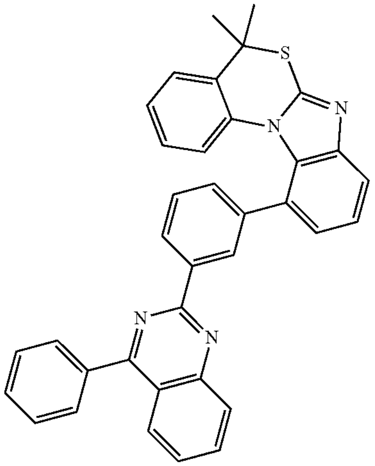
C-29
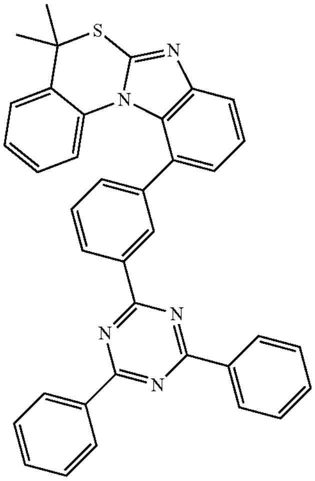
C-30
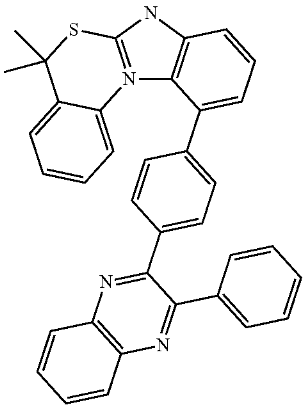

-continued
C-31
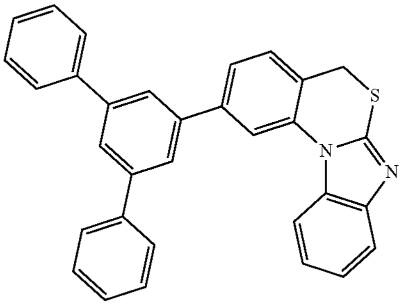
C-32
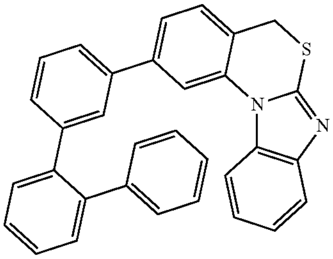
C-33
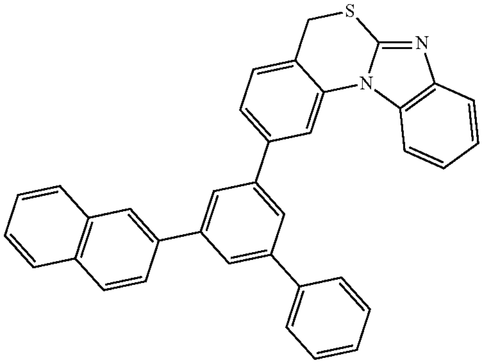
C-34
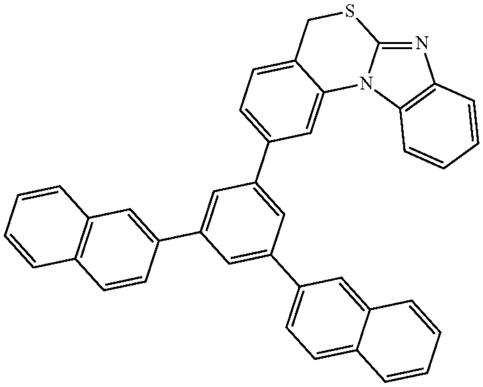
-continued
C-35
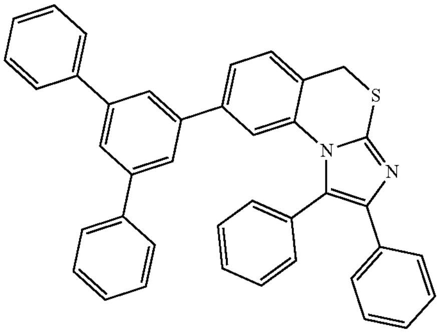
C-36
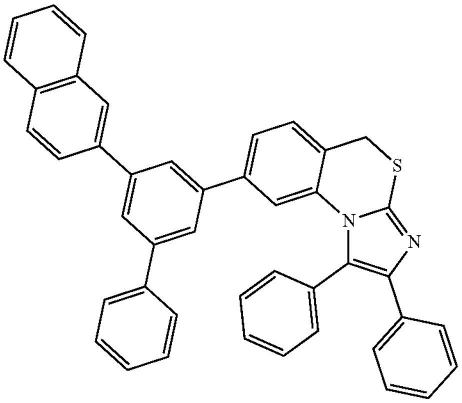
C-37
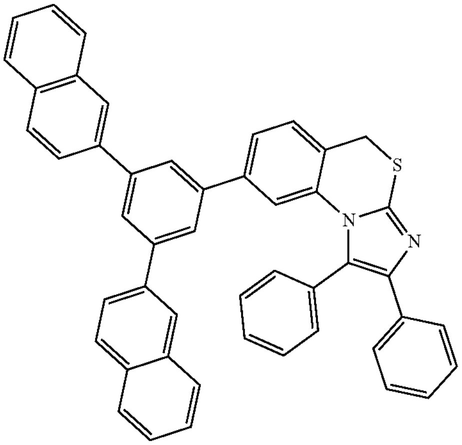
C-38
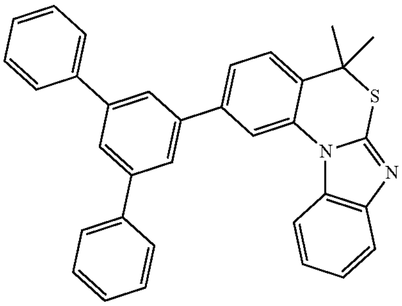

-continued
C-39
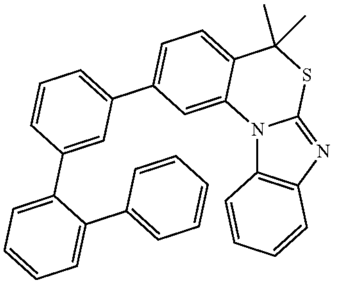
C-40
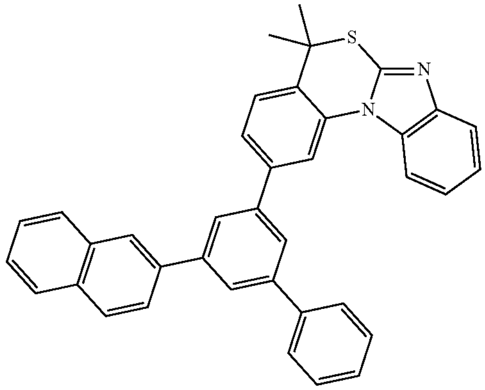
C-41
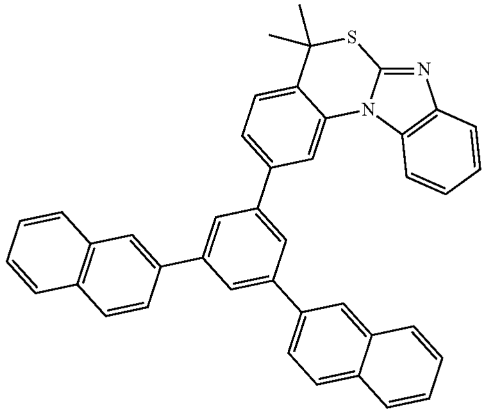
C-42
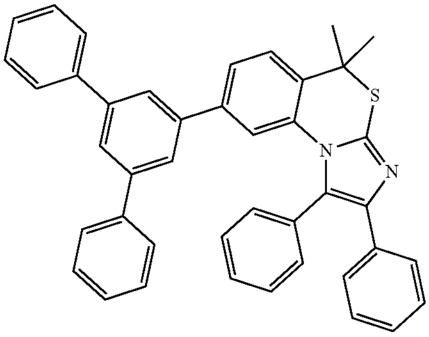
-continued
C-43
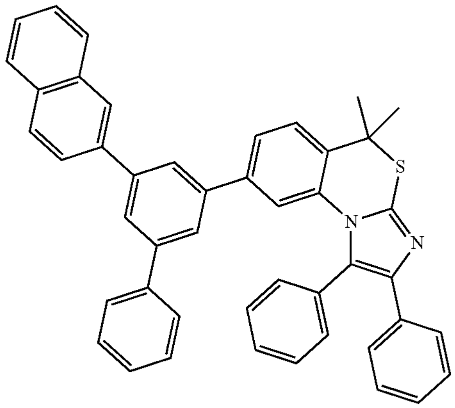
C-44
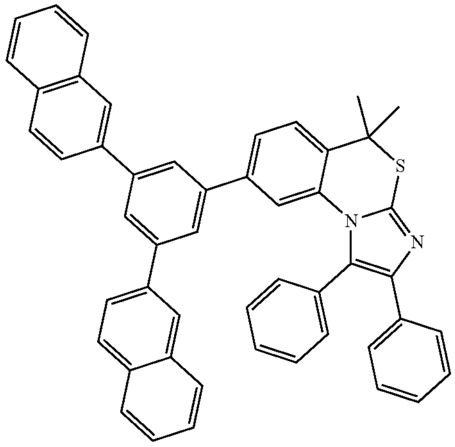
C-45
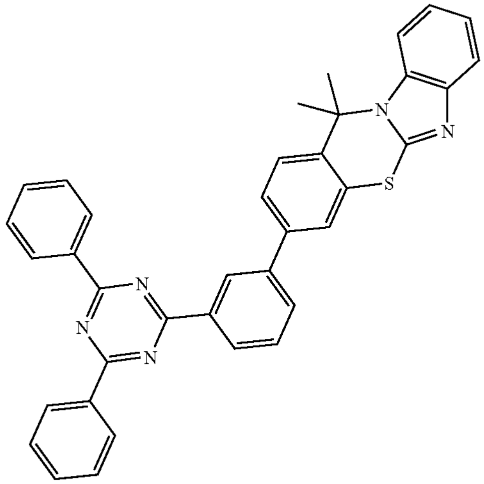

-continued
C-46
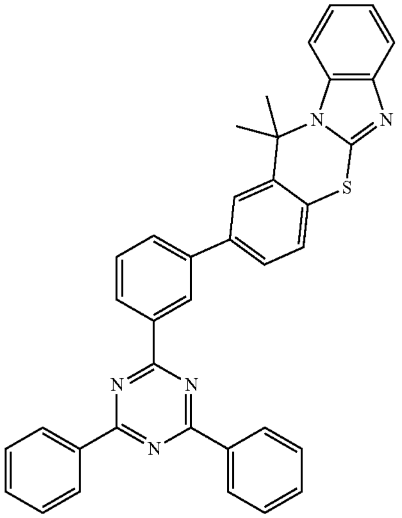
C-47
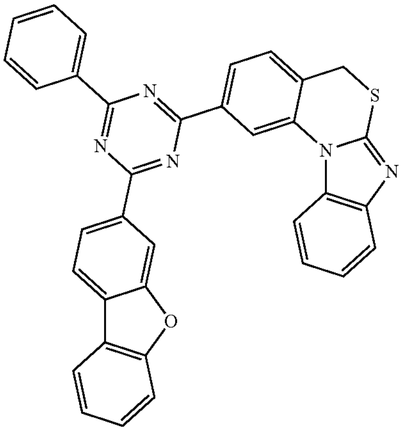
C-48
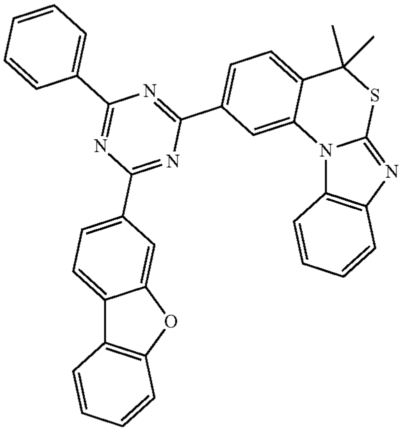
-continued
C-49
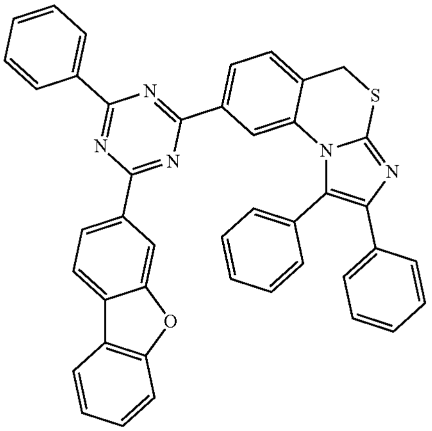
C-50
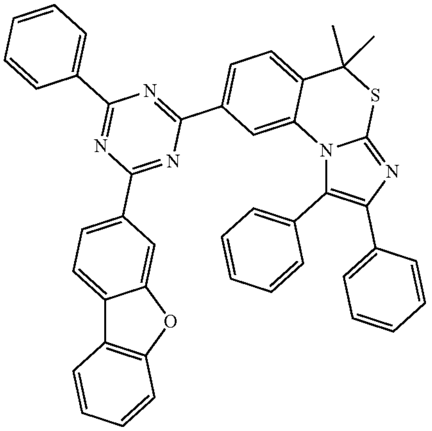
C-51
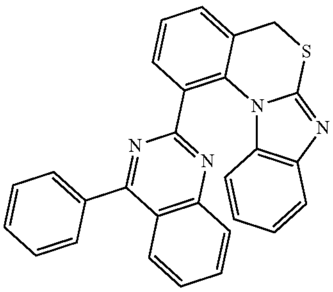
C-52
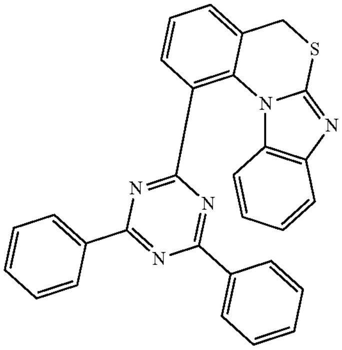

-continued
C-53
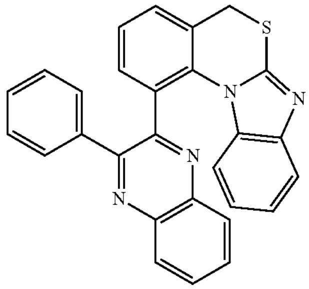
C-54
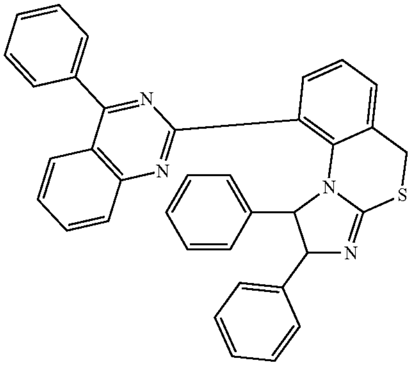
C-55
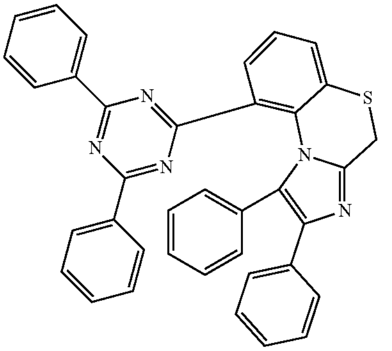
C-56
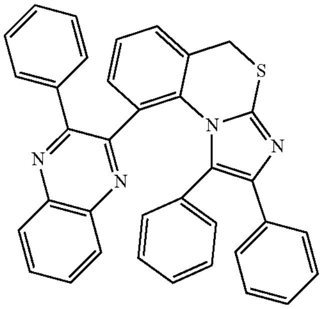
-continued
C-57
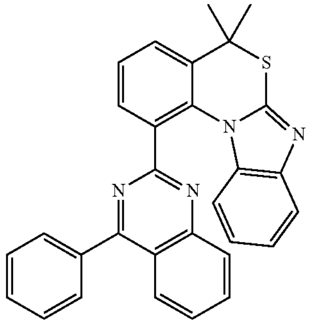
C-58
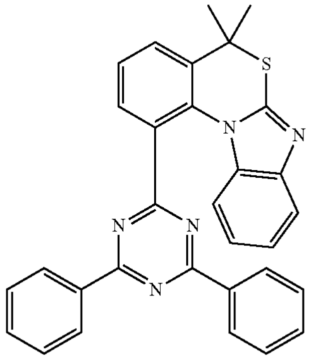
C-59
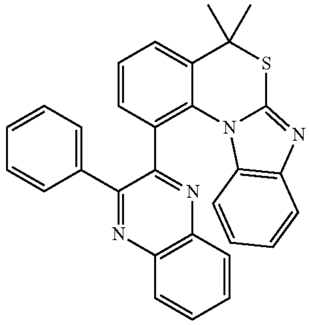
C-60
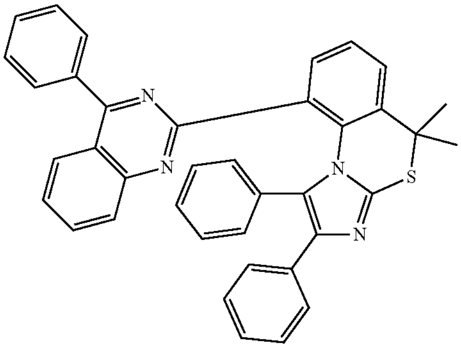

-continued
C-61
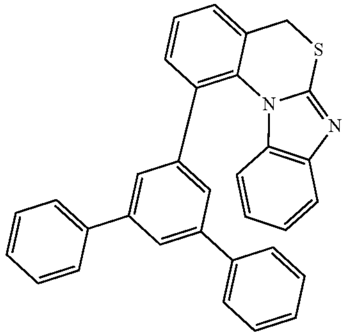
C-62
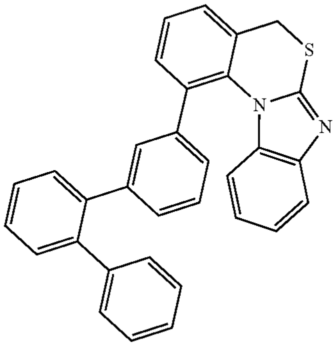
C-63
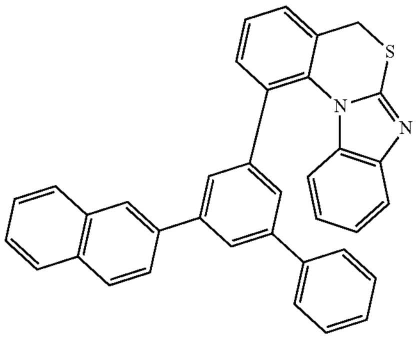
C-64
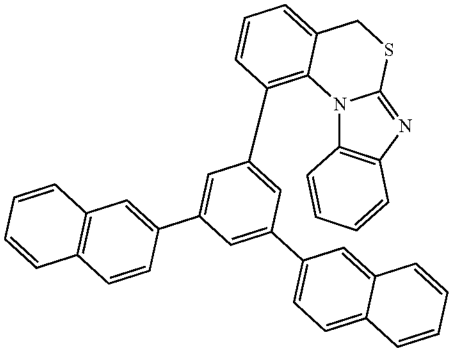
-continued
C-65
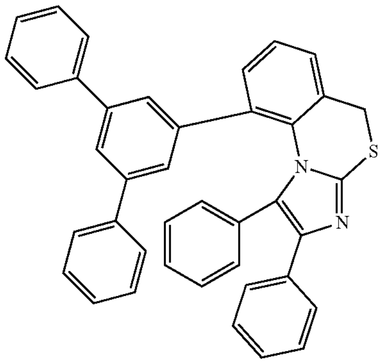
C-66
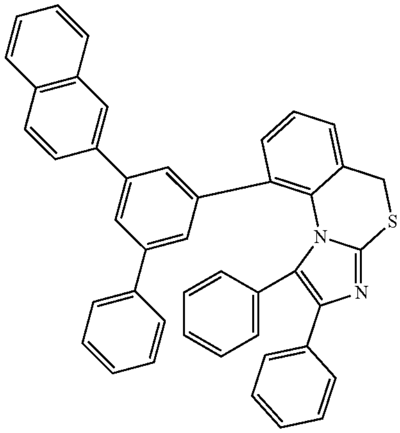
C-67
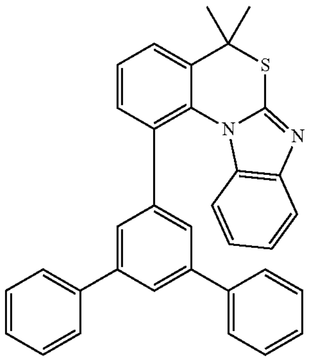
C-68
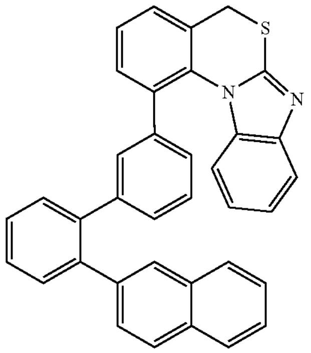

-continued
C-69
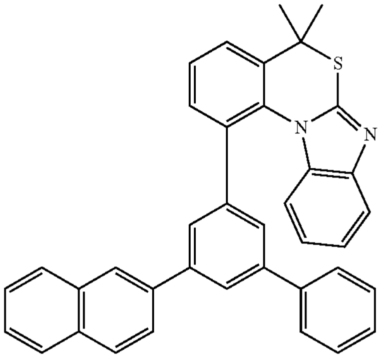
C-70
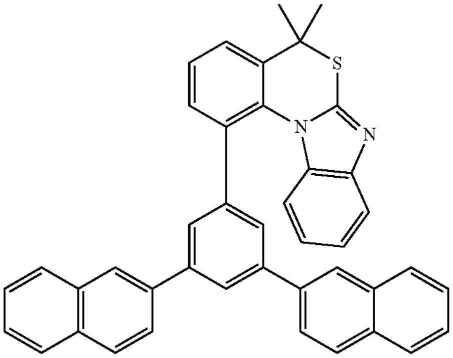
C-71
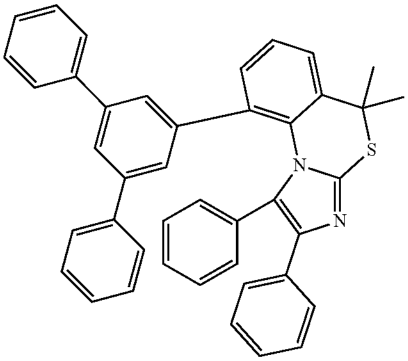
C-72
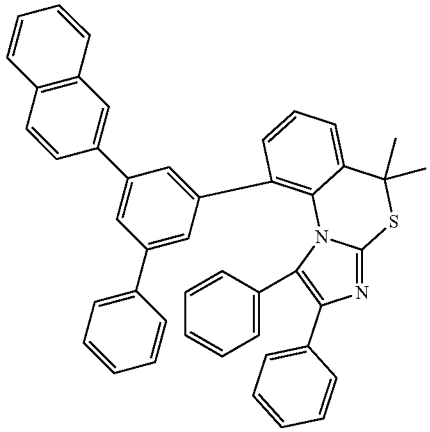
-continued
C-73
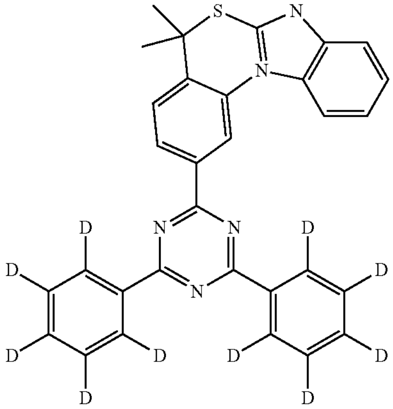
C-74
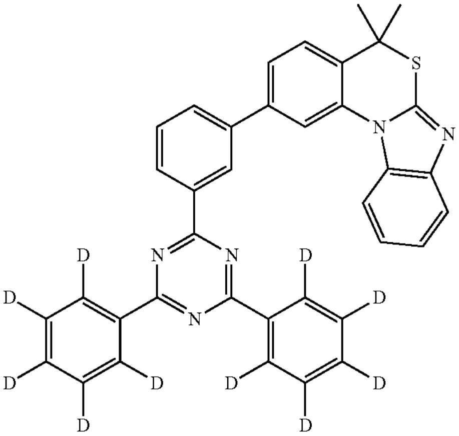
C-75
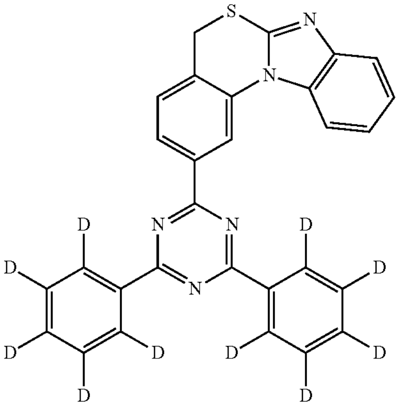

-continued
C-76
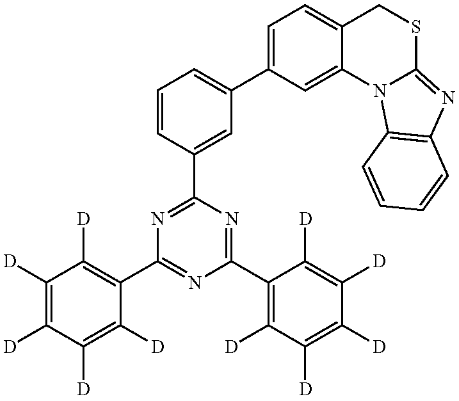
C-77
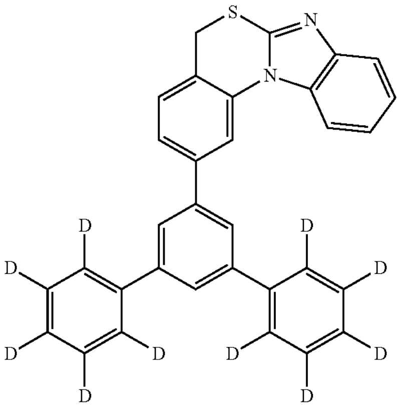
C-78
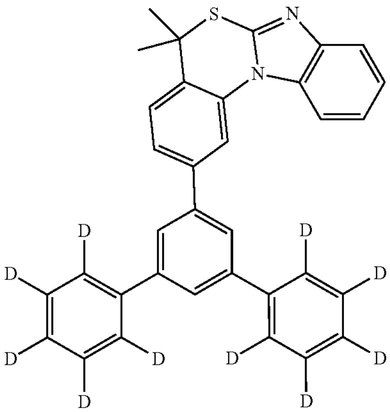
C-79
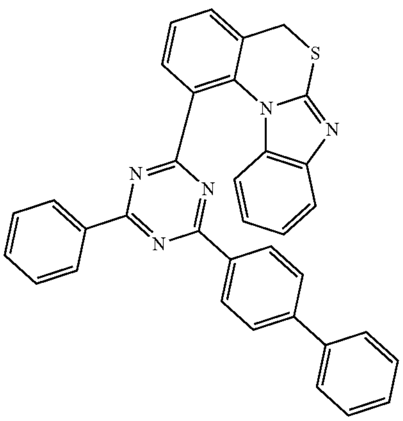
-continued
C-80
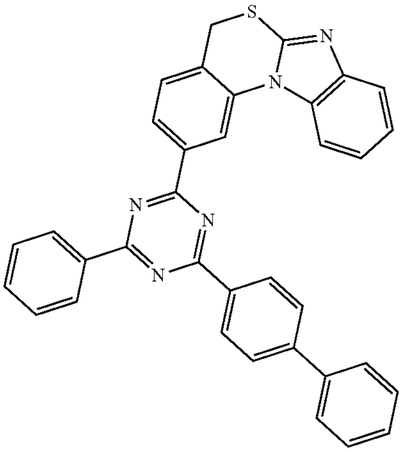
C-81
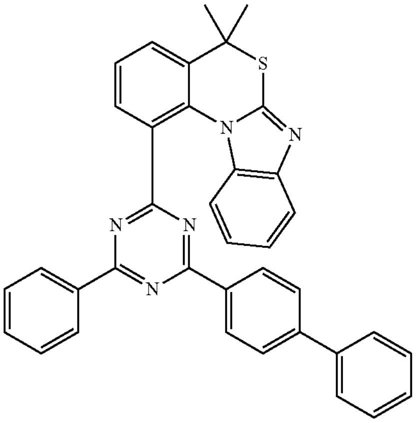
C-82
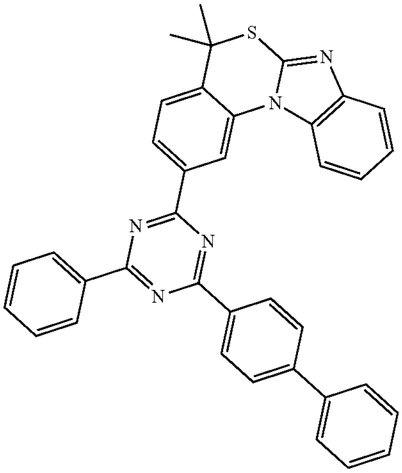

-continued
C-83
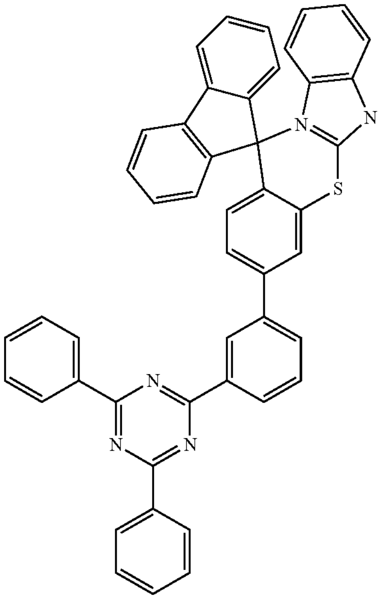
C-84
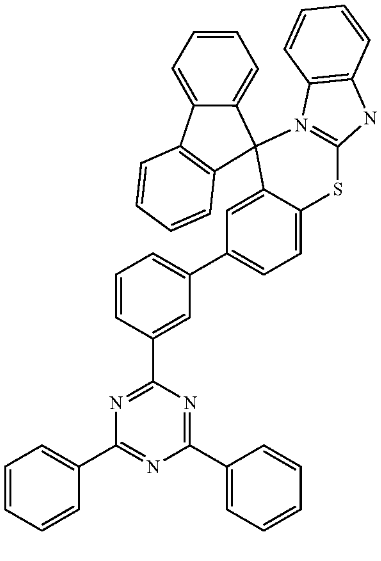
-continued
C-85
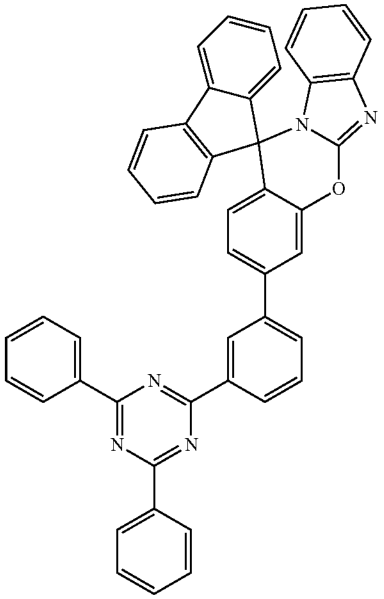
C-86
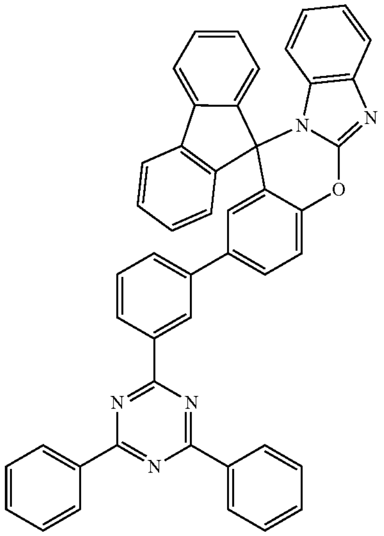
C-87
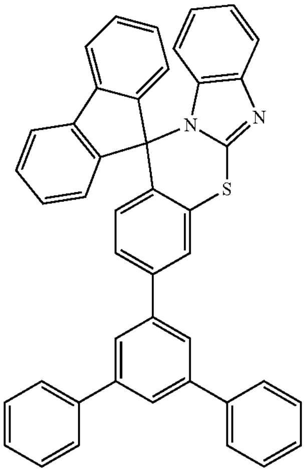

-continued
C-88
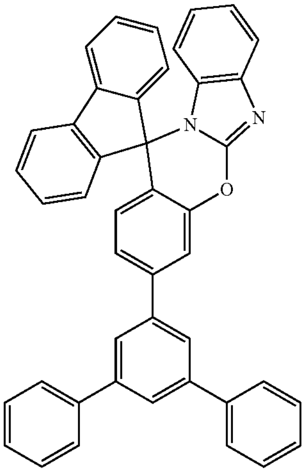
C-89
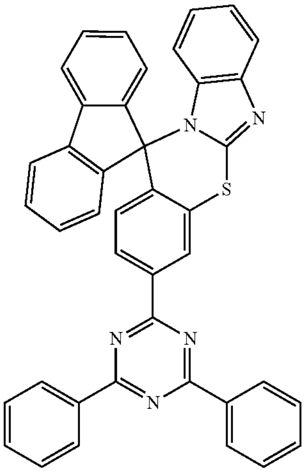
C-90
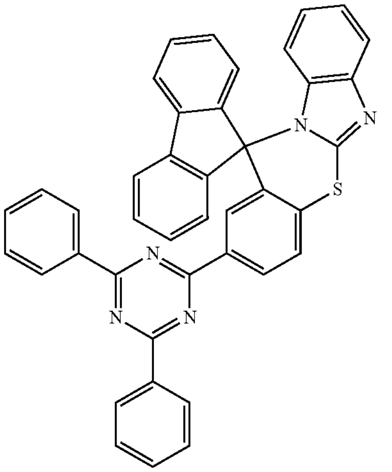
-continued
C-91
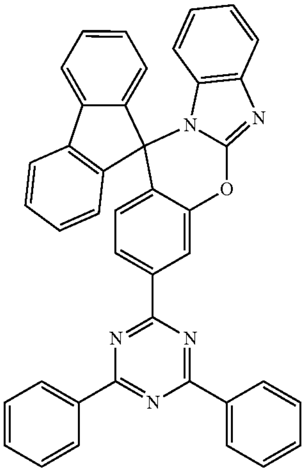
C-92
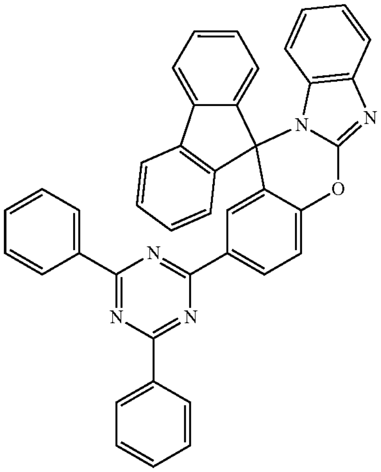
C-93
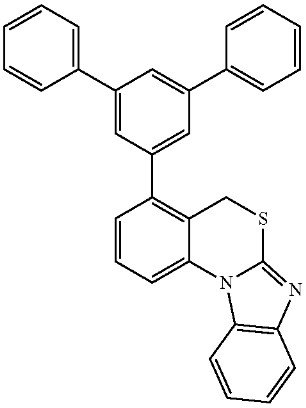

-continued

C-94

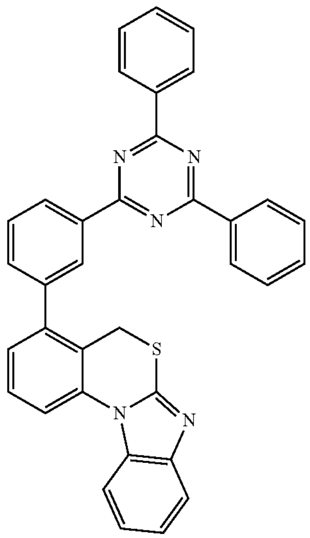

C-95

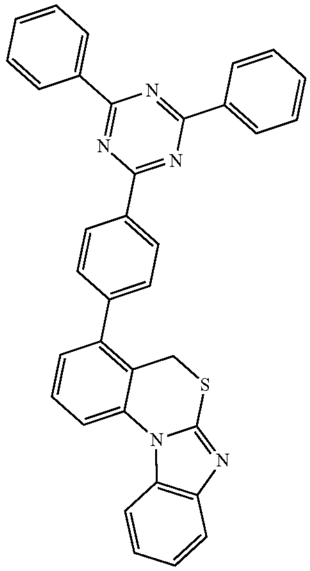

The compound represented by formula 1 according to the present disclosure may be prepared by a synthetic method known to one skilled in the art, and for example, referring to the following reaction schemes 1 and 2, but is not limited thereto.

[Reaction Scheme 1]

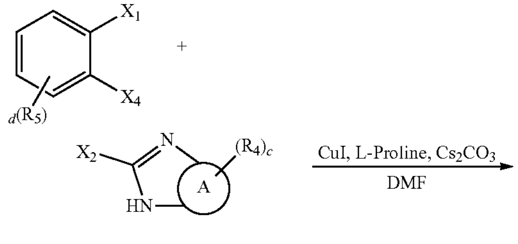

-continued

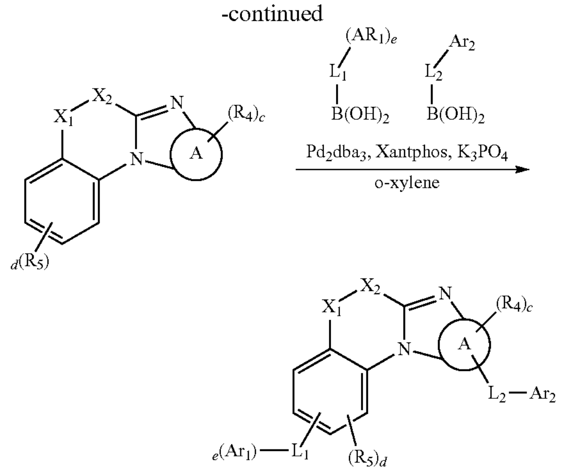

[Reaction Scheme 2]

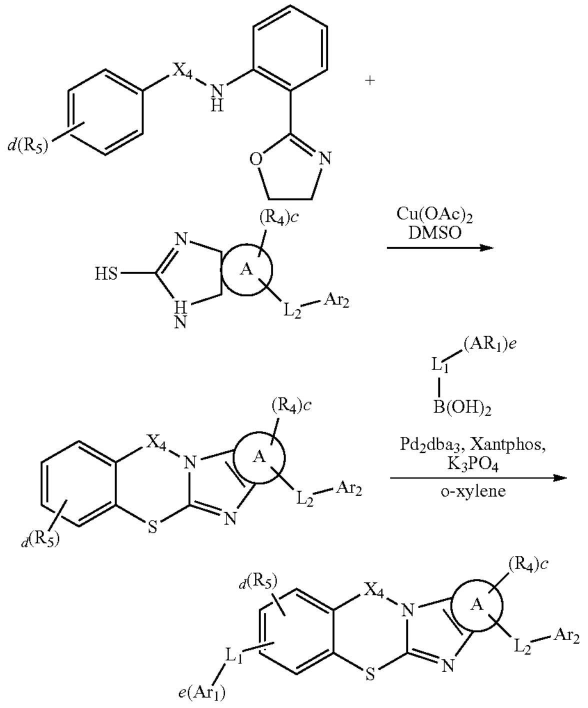

In reaction schemes 1 and 2, each of the substituents is as defined in formula 1.

Although illustrative synthesis examples of the compound represented by formula 1 are described above, one skilled in the art will be able to readily understand that all of them are based on a Buchwald-Hartwig cross-coupling reaction, an N-arylation reaction, a H-mont-mediated etherification reaction, a Miyaura borylation reaction, a Suzuki cross-coupling reaction, an Intramolecular acid-induced cyclization reaction, a Pd(II)-catalyzed oxidative cyclization reaction, a Grignard reaction, a Heck reaction, a Cyclic Dehydration reaction, an $SN_1$ substitution reaction, an $SN_2$ substitution reaction, and a Phosphine-mediated reductive cyclization reaction, etc., and the reactions above proceed even when substituents which are defined in formula 1 above, but are not specified in the specific synthesis examples, are bonded.

The organic electroluminescent material of the present disclosure may comprise at least one compound represented by formula 1 above. The compound of formula 1 may be comprised in the light-emitting layer, and when comprised in the light-emitting layer, the compound of formula 1 may be comprised as a host material, but is not limited thereto. If necessary, the organic electroluminescent compound of the present disclosure may be used as a co-host material. That is, the light-emitting layer may further comprise an organic electroluminescent compound other than the organic electroluminescent compound of formula 1 of the present disclosure (a first host material) as a second host material. In this case, the weight ratio of the first host material and the second host material is about 1:99 to about 99:1. When at least two materials are comprised in one layer, they may be mixture-evaporated to form a layer, or may be separately co-evaporated at the same time to form a layer.

The present disclosure provides a plurality of host materials comprising a first host material and a second host material, wherein the first host material comprises at least one of the compound represented by formula 1 above, and the second host material comprises at least one of the compound represented by the following formula 2 and the compound represented by following formula 3.

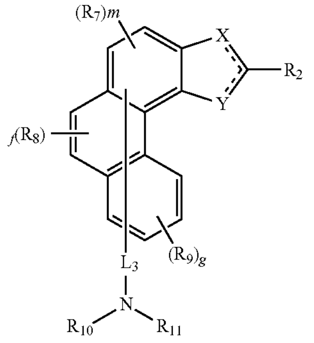

(2)

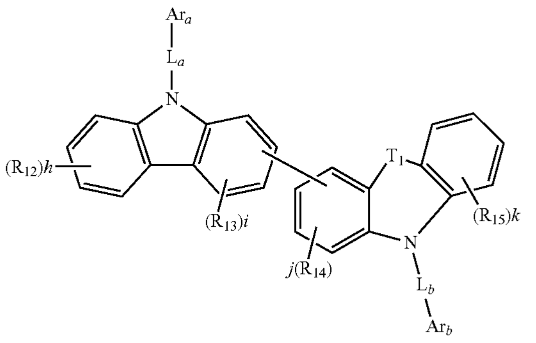

(3)

In formula 2,

X and Y, each independently, represent —N═, —$NR_{16}$—, —O—, or —S—; with the proviso that any one of X and Y represents —N═, and the other of X and Y represents —$NR_{16}$—, —O—, or —S—;

$R_6$ represents a substituted or unsubstituted (C6-C30)aryl, or a substituted or unsubstituted (3- to 30-membered)heteroaryl;

$R_7$ to $R_{11}$, and $R_{16}$, each independently, represent hydrogen, deuterium, a halogen, a cyano, a substituted or unsubstituted (C1-C30)alkyl, a substituted or unsubstituted (C6-C30)aryl, a substituted or unsubstituted (3- to 30-membered) heteroaryl, a substituted or unsubstituted (C3-C30) cycloalkyl, a substituted or unsubstituted (C1-C30)alkoxy, a substituted or unsubstituted ti(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C2-C30) alkenylamino, a substituted or unsubstituted (C1-C30)alkyl (C2-C30)alkenylamino, a substituted or unsubstituted (C1-C30)alkyl(3- to 30-membered)heteroarylamino, a substituted or unsubstituted (C2-C30)alkenyl(C6-C30)arylamino, a substituted or unsubstituted (C2-C30)alkenyl(3- to 30-membered)heteroarylamino, a substituted or unsubstituted mono- or di-(C6-C30)arylamino, a substituted or unsubstituted mono- or di-(3- to 30-membered)heteroarylamino, a substituted or unsubstituted (C6-C30)aryl(3- to 30-membered)heteroarylamino, or a substituted or unsubstituted (C1-C30)alkyl(C6-C30)arylamino, or may be linked to an adjacent substituent(s) to form a ring(s);

$L_3$ represents a single bond, a substituted or unsubstituted (C6-C30)arylene, or a substituted or unsubstituted (3- to 30-membered)heteroarylene; and m and f, each independently, represent an integer of 1 or 2, g represents an integer of 1 to 4; in which when $R_7$ to $R_9$ are each present in plural, each of $R_7$ to each of $R_9$ may be the same as or different from each other.

In formula 3, $T_1$ represents a single bond, O, or S;

$L_a$ and $L_b$, each independently, represent a single bond, a substituted or unsubstituted (C6-C30)arylene, or a substituted or unsubstituted (3- to 30-membered)heteroarylene;

$Ar_a$ and $Ar_b$, each independently, represent a substituted or unsubstituted (C6-C30)aryl, a substituted or unsubstituted (3- to 30-membered)heteroaryl, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, or a substituted or unsubstituted tri(C6-C30)arylsilyl;

$R_{12}$ to $R_{15}$, each independently, represent hydrogen, deuterium, a halogen, a cyano, a substituted or unsubstituted (C1-C30)alkyl, a substituted or unsubstituted (C6-C30)aryl, a substituted or unsubstituted (3- to 50-membered)heteroaryl, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30) arylsilyl, a substituted or unsubstituted fused ring group of an (C3-C30) aliphatic ring(s) and a (C6-C30) aromatic ring(s), a substituted or unsubstituted mono- or di-(C1-C30) alkylamino, a substituted or unsubstituted mono- or di-(C2-C30)alkenylamino, a substituted or unsubstituted (C1-C30) alkyl(C2-C30)alkenylamino, a substituted or unsubstituted (C1-C30)alkyl(C6-C30)arylamino, a substituted or unsubstituted (C1-C30)alkyl(3- to 30-membered)heteroarylamino, a substituted or unsubstituted (C2-C30)alkenyl(C6-C30)arylamino, a substituted or unsubstituted (C2-C30) alkenyl(3- to 30-membered)heteroarylamino, a substituted or unsubstituted mono- or di-(C6-C30)arylamino, a substituted or unsubstituted mono- or di-(3- to 30-membered) heteroarylamino, or a substituted or unsubstituted (C6-C30) aryl(3- to 30-membered)heteroarylamino, or may be linked to an adjacent substituent(s) to form a ring(s); and h and k, each independently, represent an integer of 1 to 4, and i and j, each independently, represent an integer of 1 to 3; in which when $R_{12}$ to $R_{15}$ are each present in plural, each of $R_{12}$ to each of $R_{15}$ may be the same as or different from each other.

In formula 2, according to one embodiment of the present disclosure, any one of X and Y represents —N═, and the other represents —O— or —S—. For example, X is —N═, and Y is —O— or —S—; or X is —O— or —S—, and Y is —N═.

In formula 2, according to one embodiment of the present disclosure, $R_6$ represents a substituted or unsubstituted (C6-C25)aryl, or a substituted or unsubstituted (5- to 25-membered)heteroaryl. According to another embodiment of the present disclosure, $R_6$ represents an unsubstituted (C6-C18) aryl, or an unsubstituted (5- to 20-membered)heteroaryl. For example, $R_6$ may be a phenyl, a biphenylyl, a pyridyl, etc.

In formula 2, according to one embodiment of the present disclosure, $R_7$ to $R_{11}$, and $R_{16}$, each independently, represent hydrogen, a substituted or unsubstituted (C6-C25)aryl, or a substituted or unsubstituted (3- to 25-membered)heteroaryl. According to another embodiment of the present disclosure, $R_7$ to $R_9$, each independently, represent hydrogen, or a substituted or unsubstituted (C6-C18)aryl; and $R_{10}$ and $R_{11}$ each independently, represent a substituted or unsubstituted (C6-C25)aryl, or a substituted or unsubstituted (5- to 25-membered)heteroaryl. For example, $R_7$ to $R_9$, each independently, may be hydrogen, a phenyl, etc.; and $R_{10}$ and $R_{11}$, each independently, may be a substituted or unsubstituted phenyl, a naphthyl, a biphenylyl, a phenanthrenyl, a dimethylfluorenyl, a diphenylfluorenyl, a naphthylphenyl, a phenylnaphthyl, a dimethylbenzofluorenyl, a terphenyl, a spirobifluorenyl, a (C22)aryl, a benzothiophenyl, a dibenzothiophenyl, a dibenzofuranyl unsubstituted or substituted with a phenyl(s) or a pyridyl(s), a carbazolyl substituted with a phenyl(s), a benzofuropyridyl, a benzonaphthofuranyl, a benzonaphthothiophenyl, etc., in which the substituent(s) of the substituted phenyl may be at least one selected from the group consisting of a phenyl substituted with at least one deuterium, a cyclohexyl, a pyridyl substituted with a phenyl (s), a phenoxazinyl, a diphenylamino, a phenyl substituted with a methyl(s), a phenyl substituted with a tert-butyl(s), an anthracenyl, a fluoranthenyl, a phenylfluorenyl, and a benzimidazole substituted with a phenyl(s).

In formula 2, according to one embodiment of the present disclosure, $L_3$ represents a single bond, or a substituted or unsubstituted (C6-C18)arylene. According to another embodiment of the present disclosure, $L_3$ represents a single bond, or an unsubstituted (C6-C12)arylene. For example, $L_3$ may be a single bond, a phenylene, a naphthylene, etc.

In formula 2, according to one embodiment of the present disclosure, m, f, and g, each independently, represent an integer of 1.

In formula 3, according to one embodiment of the present disclosure, $L_a$ and $L_b$, each independently, represent a single bond, or a substituted or unsubstituted (C6-C25)arylene. According to another embodiment of the present disclosure, $L_a$ and $L_b$, each independently, represent a single bond, or an unsubstituted (C6-C18)arylene. For example, $L_a$ and $L_b$, each independently, represent a single bond, a naphthylene, a biphenylene, etc.

In formula 3, according to one embodiment of the present disclosure, $Ar_a$ and $Ar_b$, each independently, represent a substituted or unsubstituted (C6-C25)aryl, a substituted or unsubstituted (5- to 25-membered)heteroaryl, or a substituted or unsubstituted tri(C6-C25)arylsilyl. According to another embodiment of the present disclosure, $Ar_a$ and $Ar_b$, each independently, represent a (C6-C25)aryl unsubstituted or substituted with cyano and/or a (C1-C6)alkyl(s); or an unsubstituted tri(C6-C18)arylsilyl. For example, $Ar_a$ and $Ar_b$, each independently, may be a phenyl unsubstituted or substituted with cyano or a methyl(s); a naphthyl; a biphenyl; a dimethylfluorenyl; a diphenylfluorenyl; a terphenyl; a triphenylenyl; a triphenylsilyl, etc.

In formula 3, according to one embodiment of the present disclosure, $R_{12}$ to $R_{15}$, each independently, represent hydrogen, a substituted or unsubstituted (C1-C20)alkyl, a substituted or unsubstituted (C6-C25)aryl, or a substituted or unsubstituted (5- to 30-membered)heteroaryl. According to one embodiment of the present disclosure, $R_{12}$ to $R_{15}$, each independently, represent hydrogen, an unsubstituted (C1-C10)alkyl, an unsubstituted (C6-C18)aryl, or a (5- to 25-membered)heteroaryl substituted with a (C6-C18)aryl(s). For example, $R_{12}$ and $R_{15}$, each independently, may be hydrogen, a methyl, a phenyl, or a carbazolyl substituted with a phenyl(s); and $R_{13}$ and $R_{14}$, each independently, may be hydrogen.

In formula 3, according to one embodiment of the present disclosure, h to k, each independently, represent an integer of 1.

The compound represented by formula 2 or 3 may be at least one selected from the following compounds, but is not limited thereto.

H-1

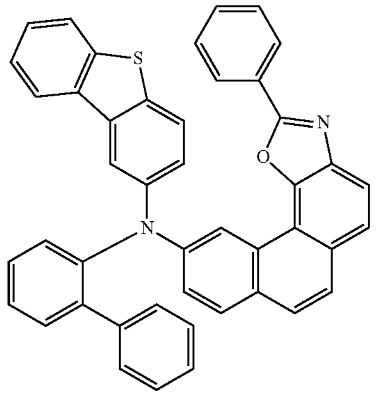

H-2

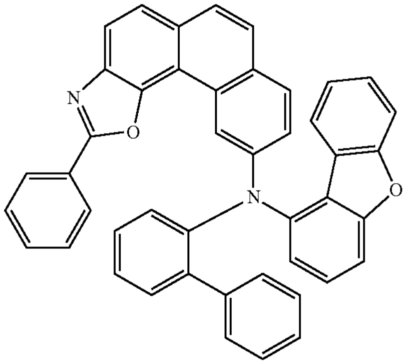

-continued
H-3
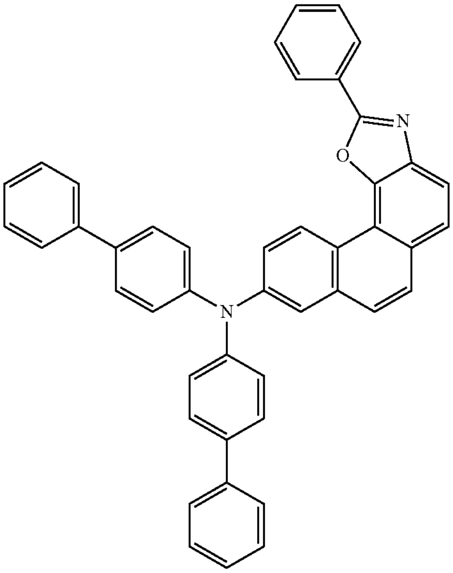
H-4
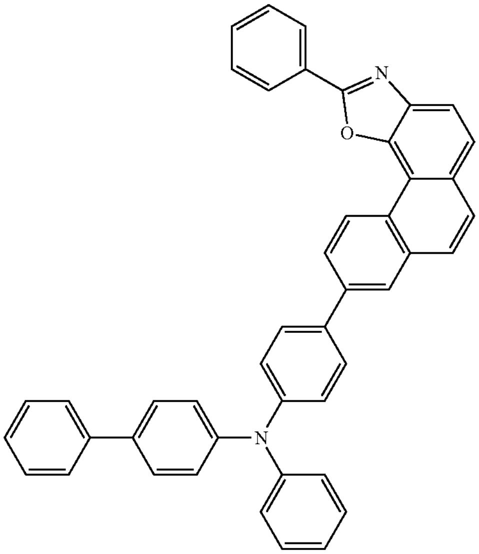
H-5
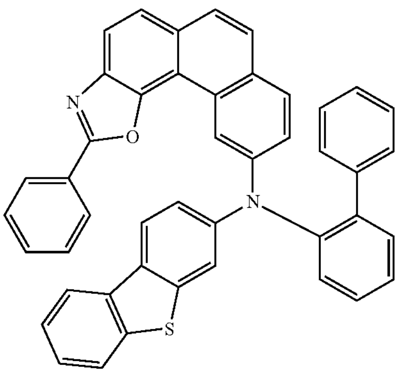
-continued
H-6
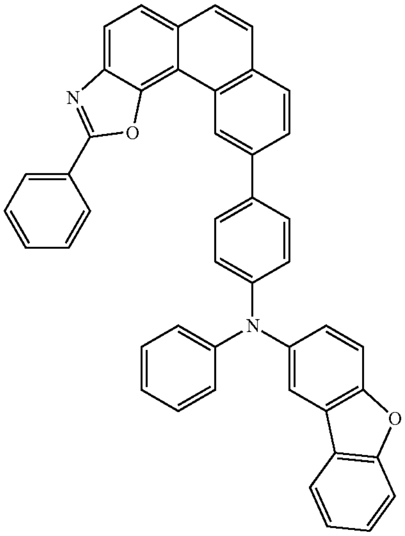
H-7
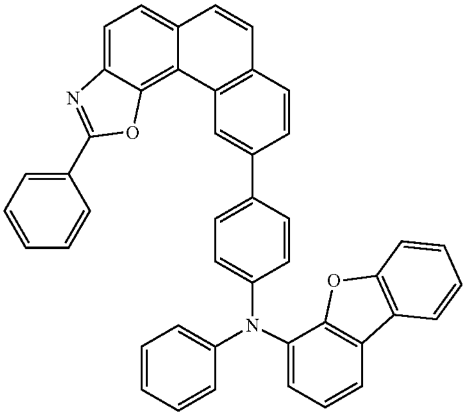
H-8
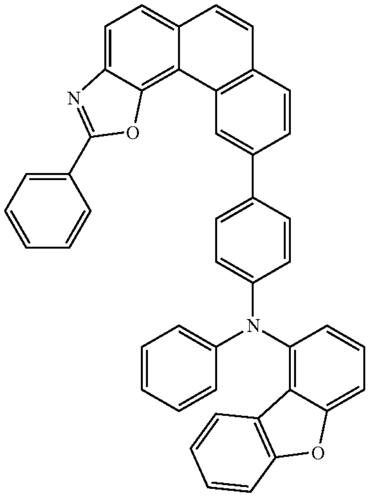

H-9
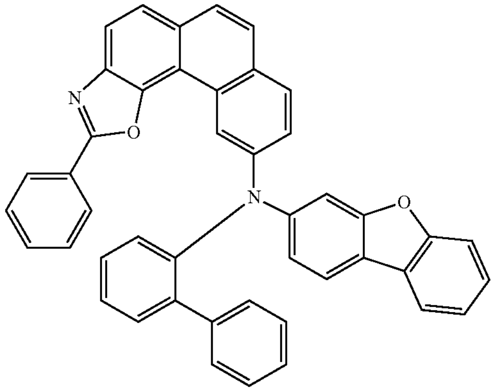
H-10
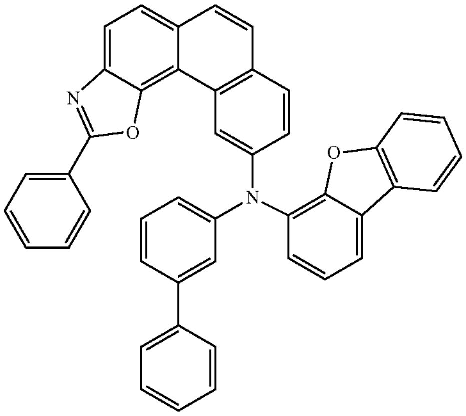
H-11
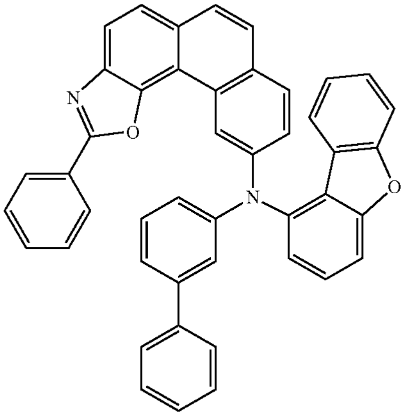
H-12
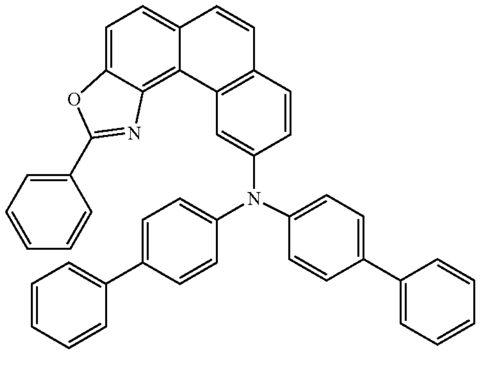
H-13
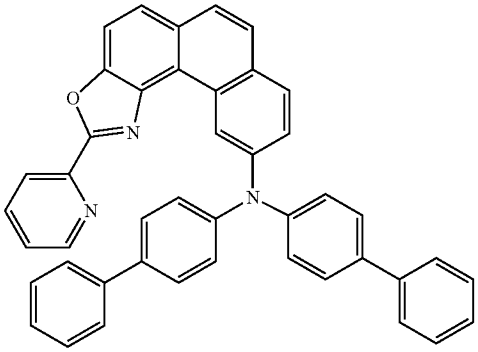
H-14
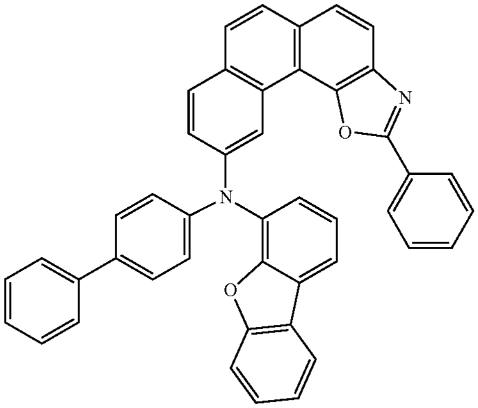
H-15
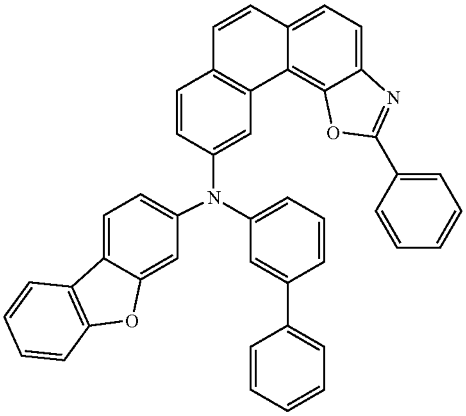
H-16
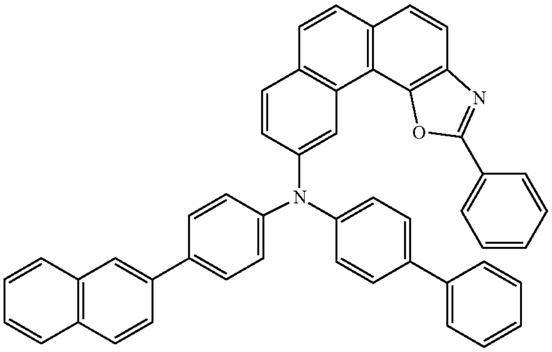

-continued
H-17
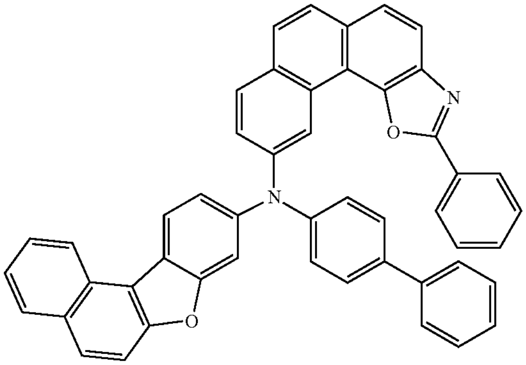
H-18
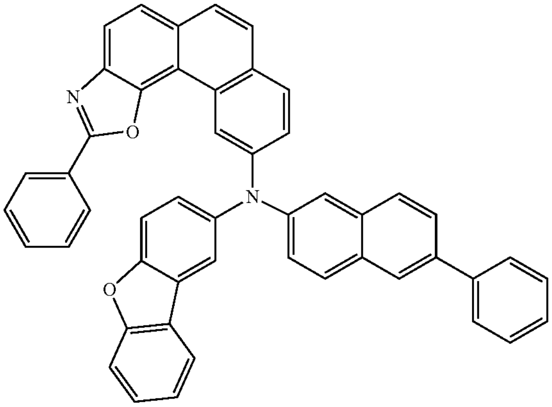
H-19
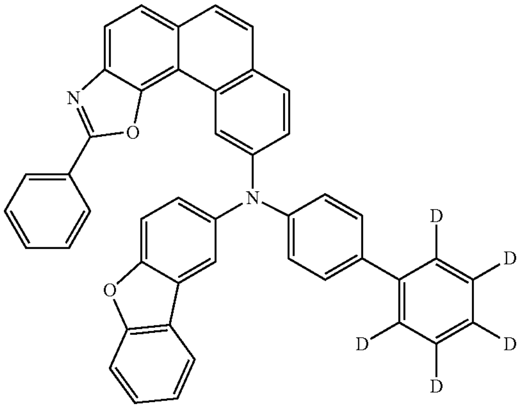
H-20
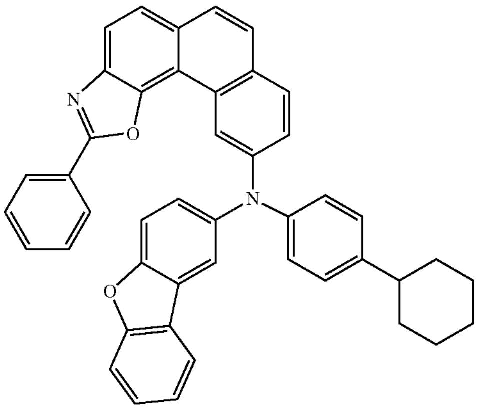
-continued
H-21
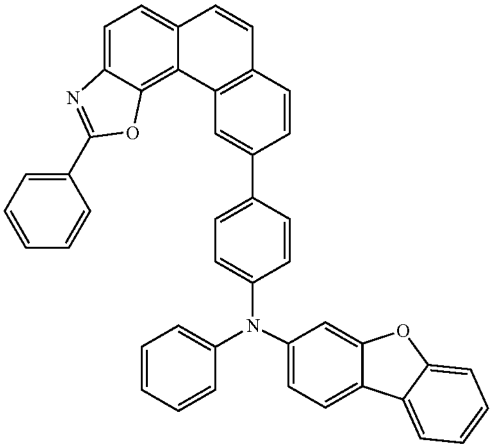
H-22
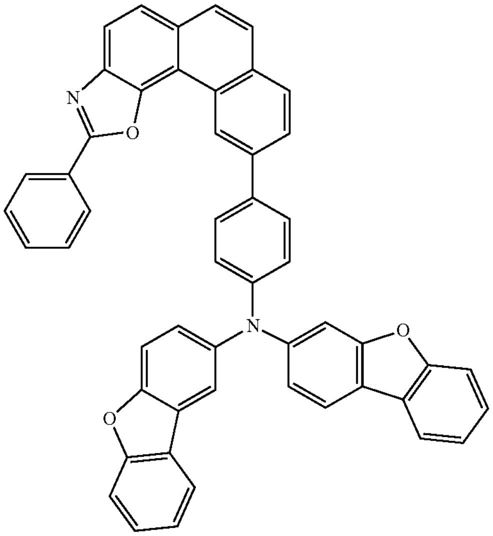
H-23
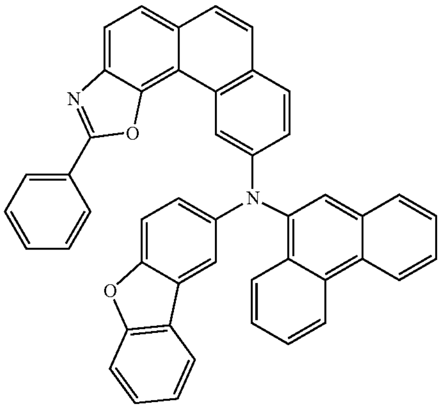

-continued
H-24
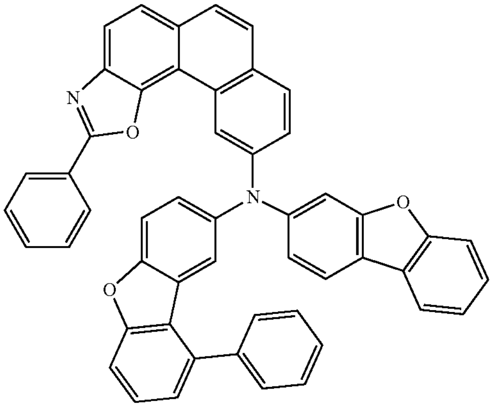
H-25
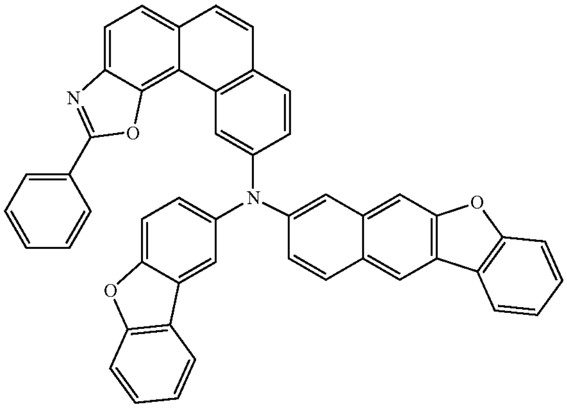
H-26
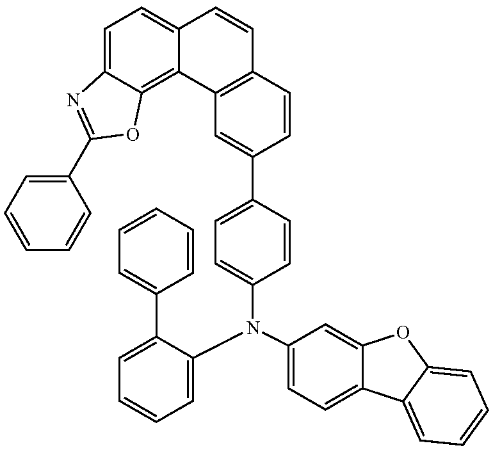
-continued
H-27
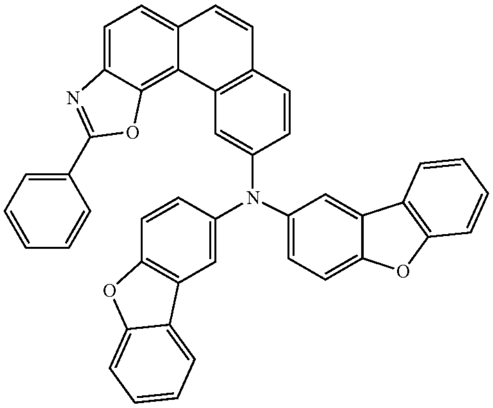
H-28
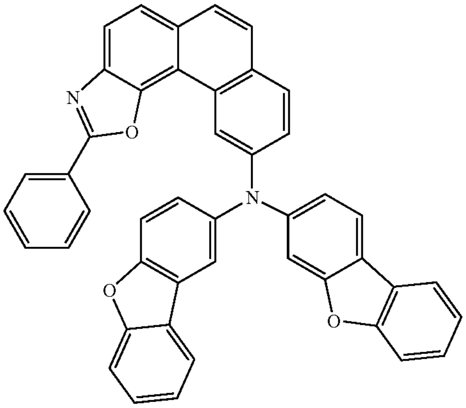
H-29
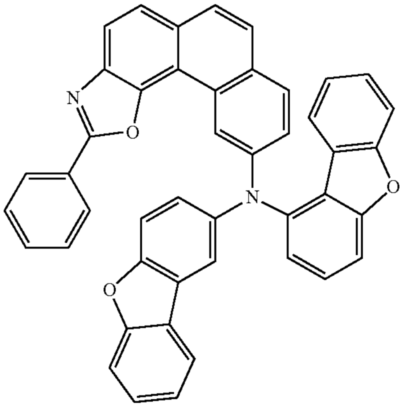
H-30
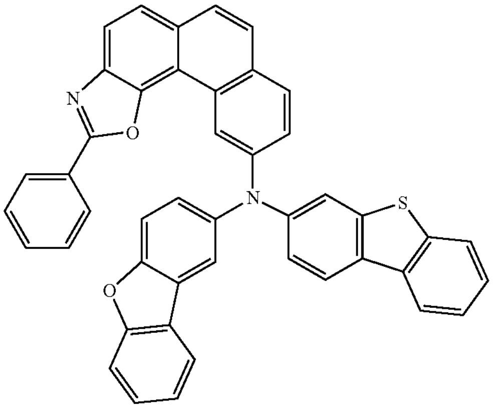

-continued
H-31
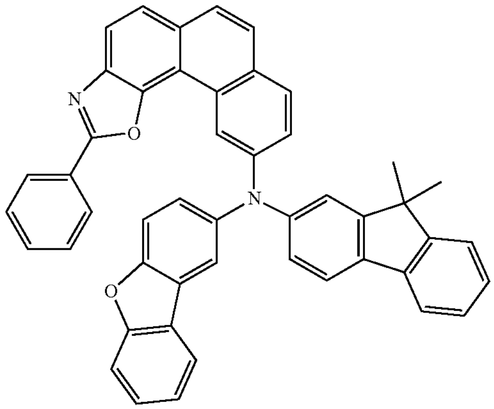
H-32
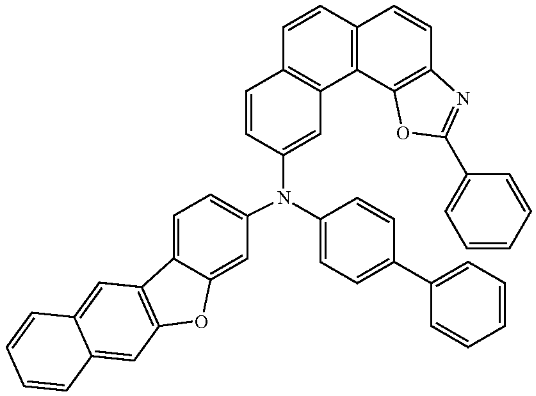
H-33
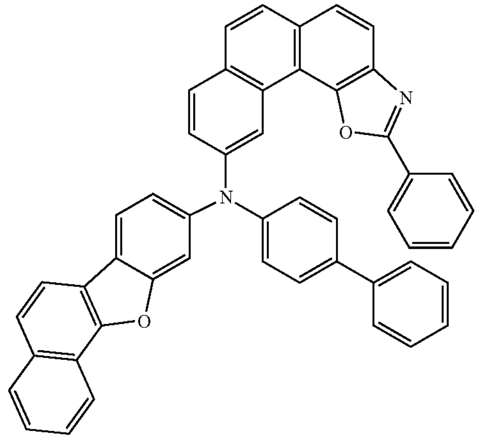
H-34
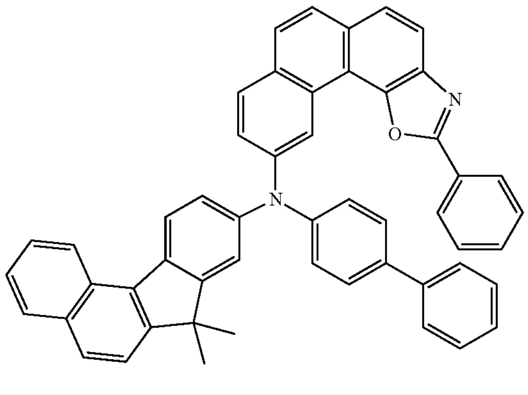
-continued
H-35
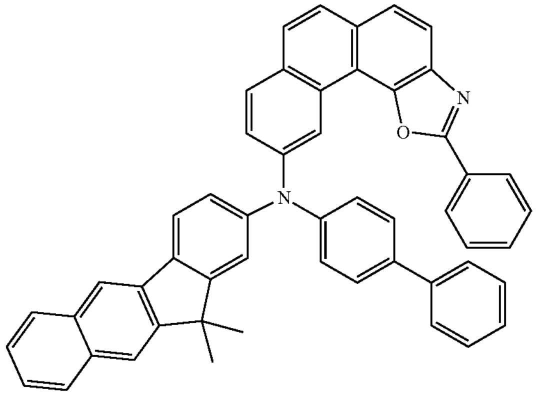
H-36
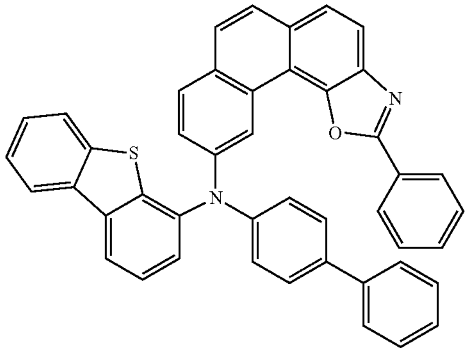
H-37
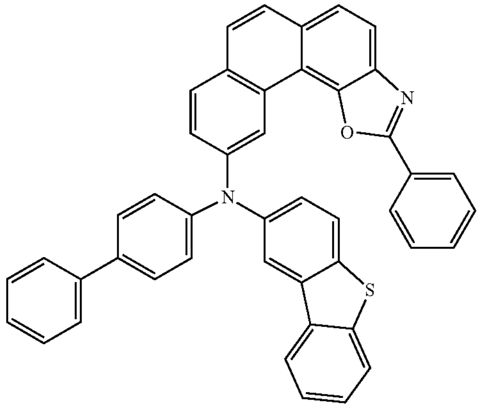
H-38
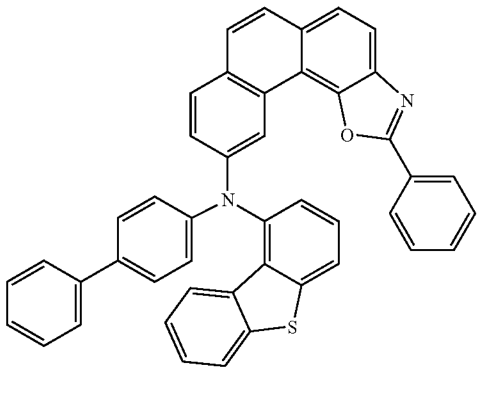

-continued
H-39
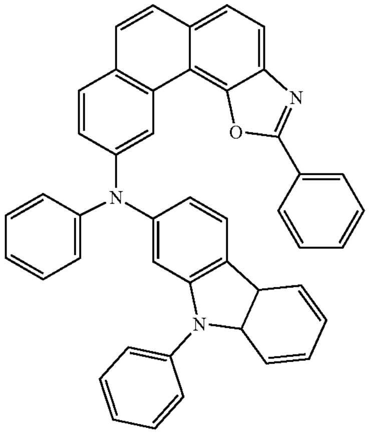
H-40
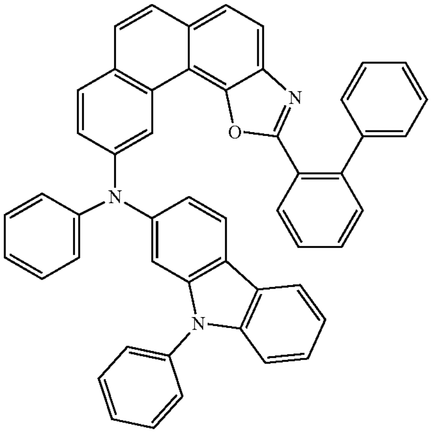
H-41
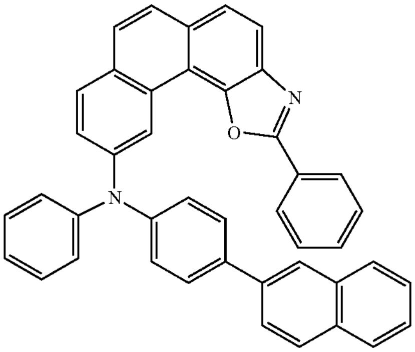
H-42
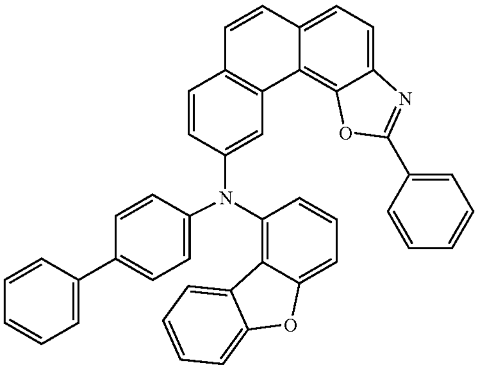
-continued
H-43
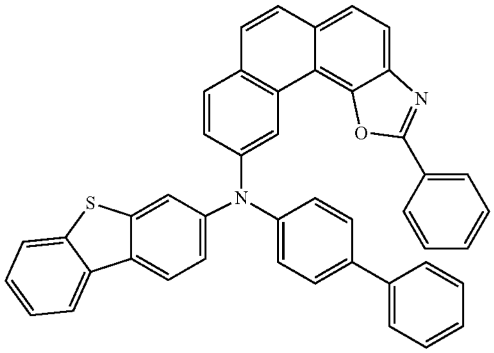
H-44
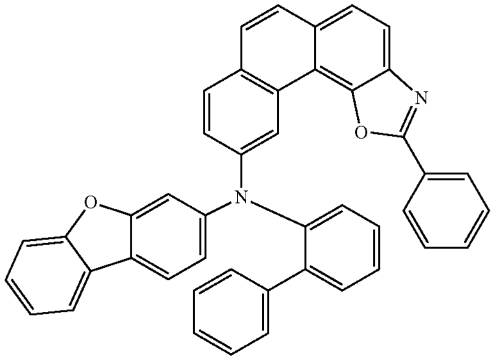
H-45
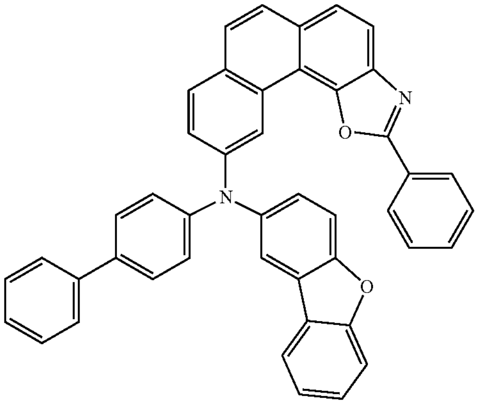
H-46
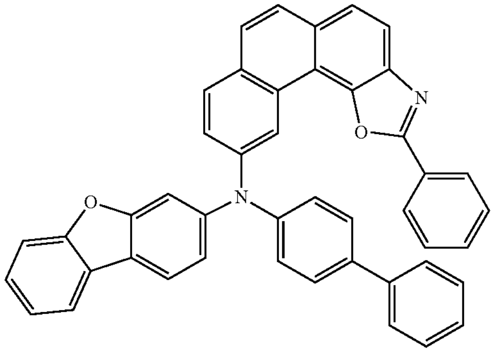

-continued
H-47
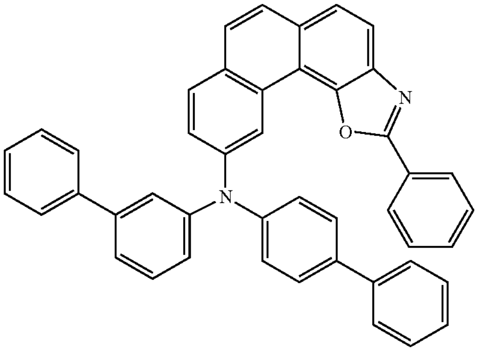
H-48
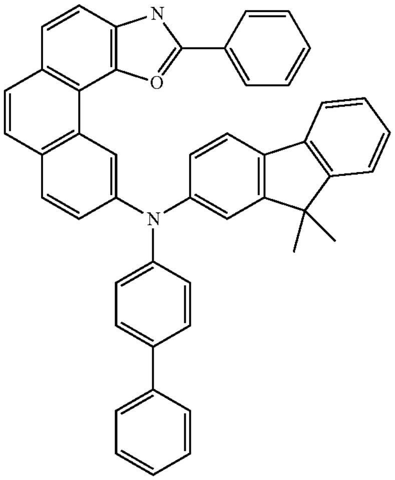
H-49
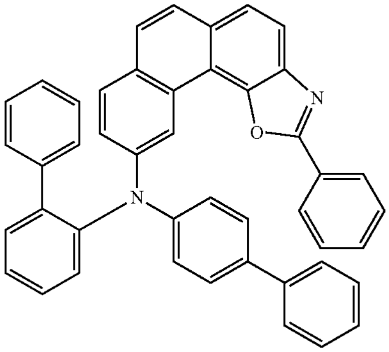
-continued
H-50
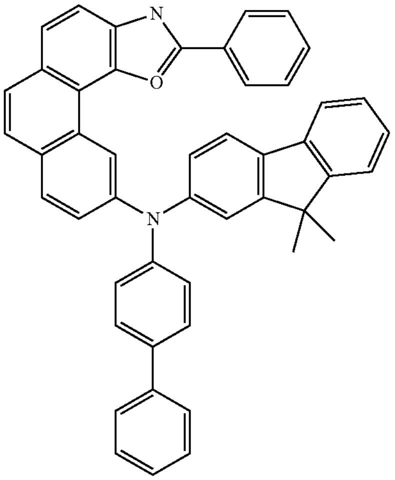
H-51
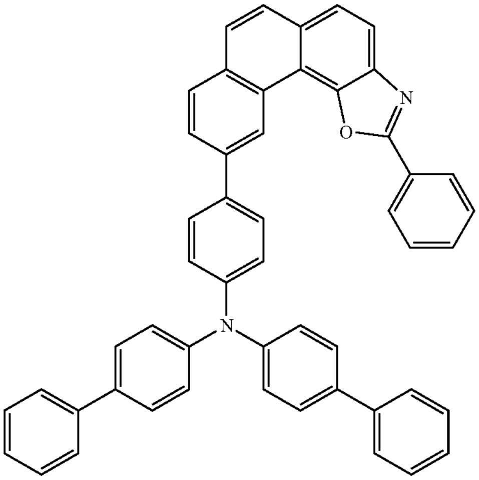
H-52
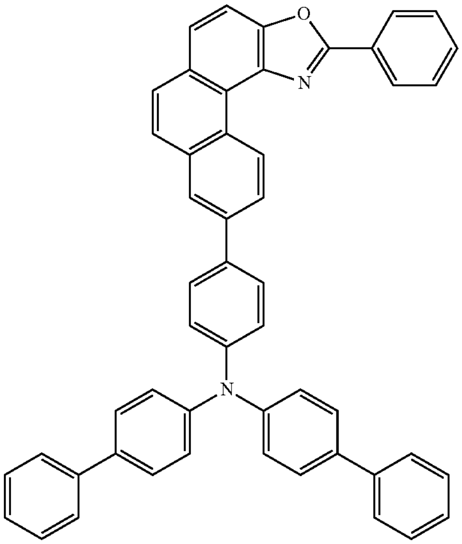

-continued
H-53
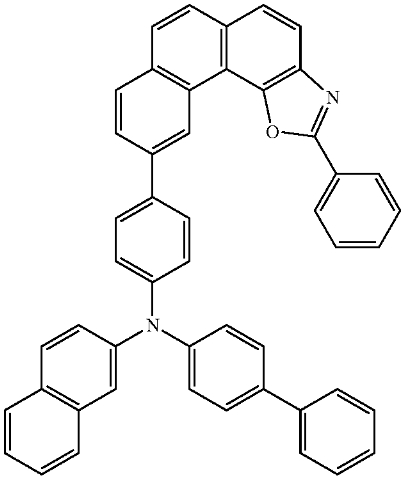
H-54
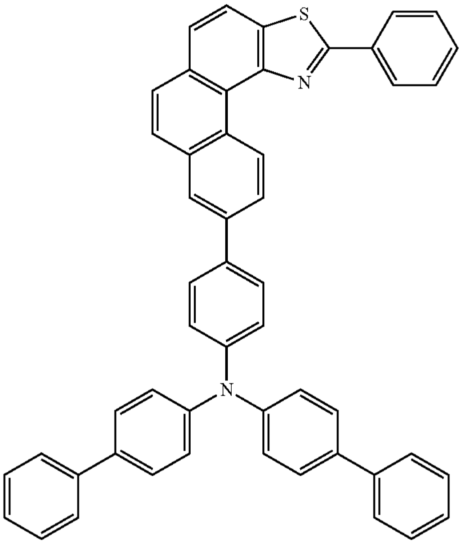
H-55
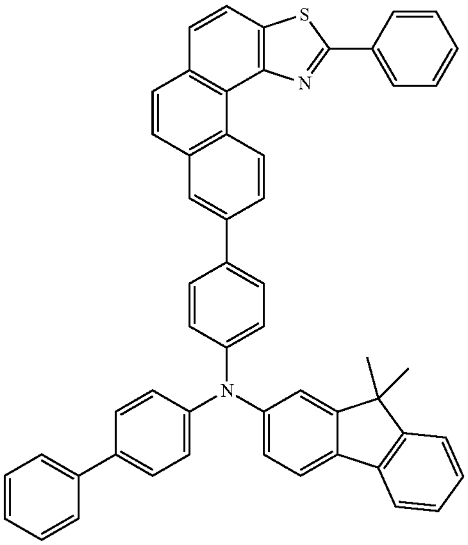
-continued
H-56
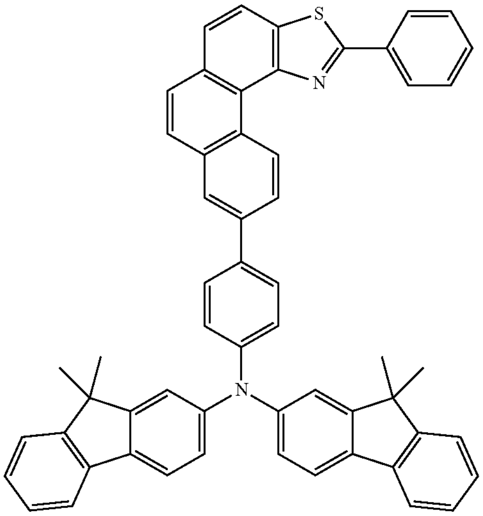
H-57
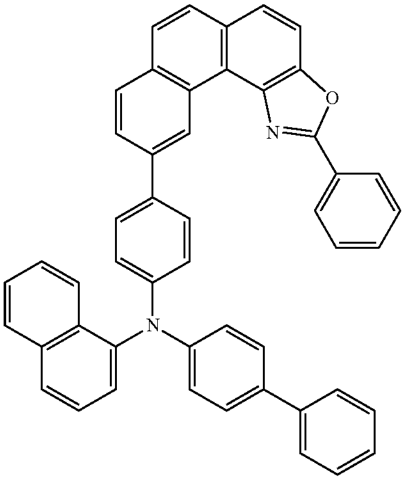
H-58
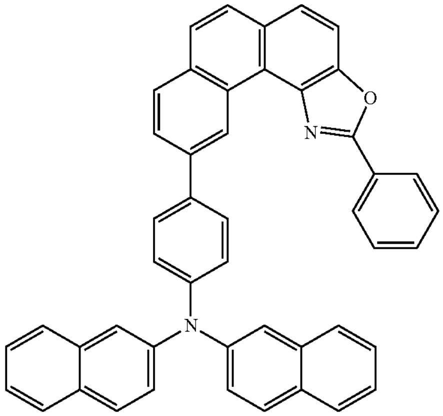

-continued
H-59
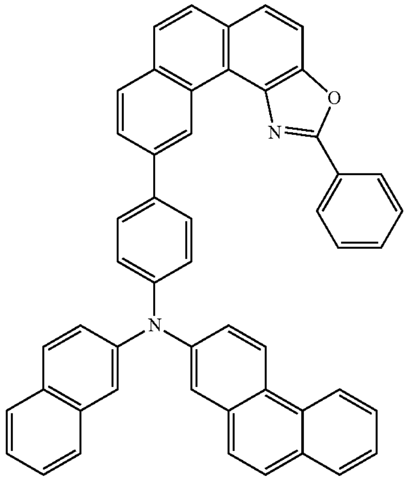
H-60
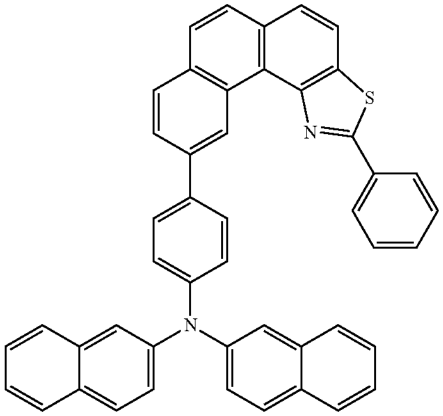
H-61
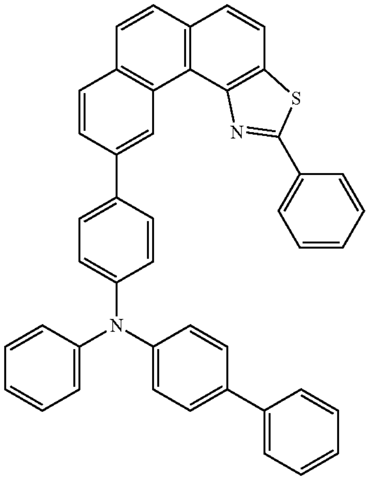
-continued
H-62
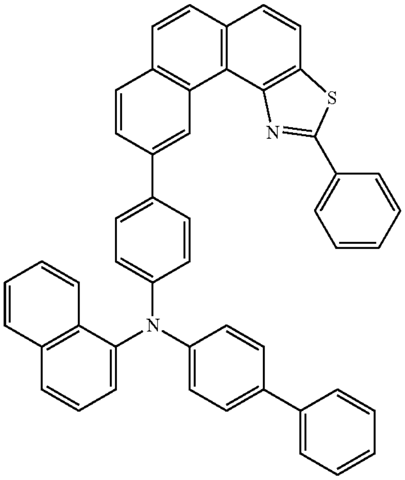
H-63
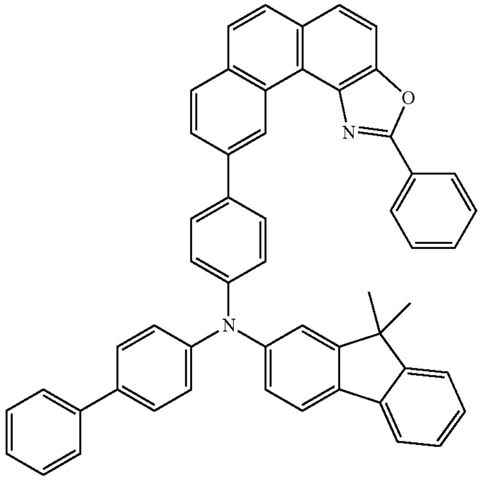
H-64
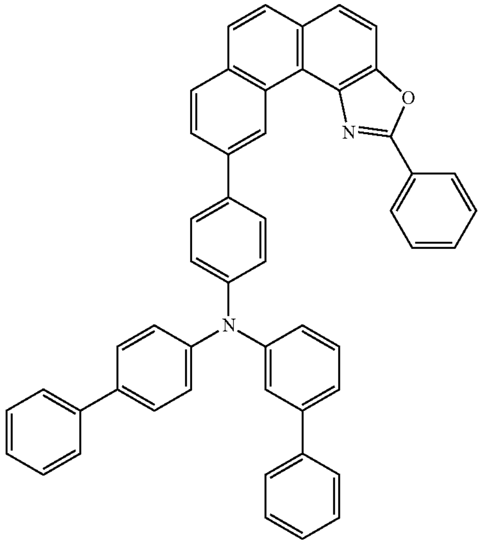

-continued
H-65
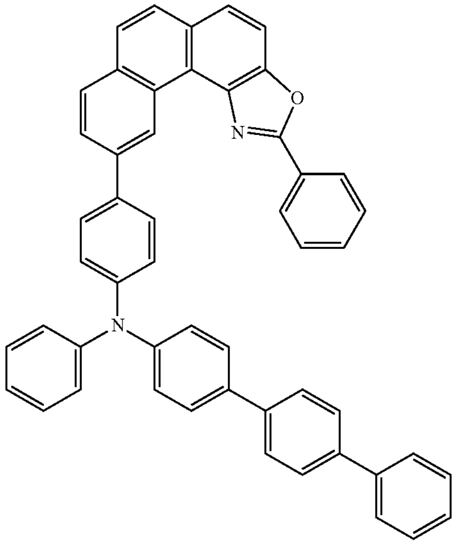
H-66
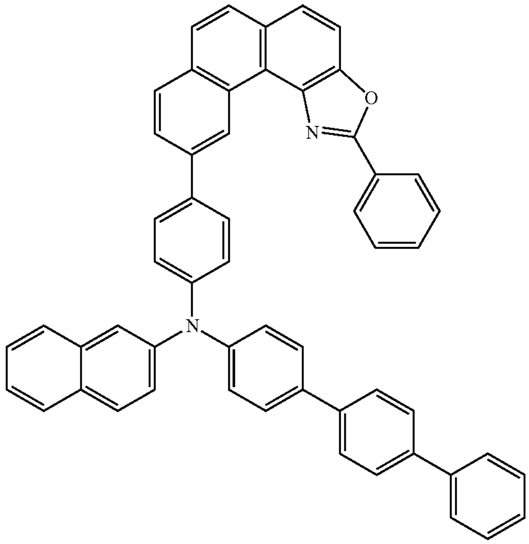
H-67
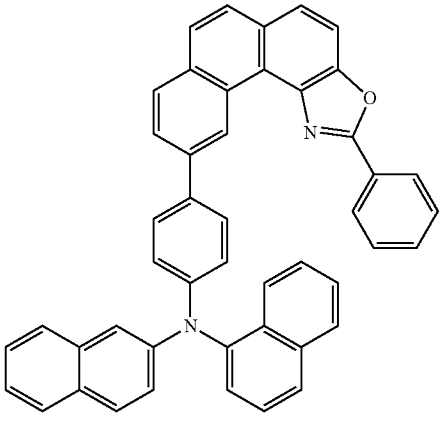
-continued
H-68
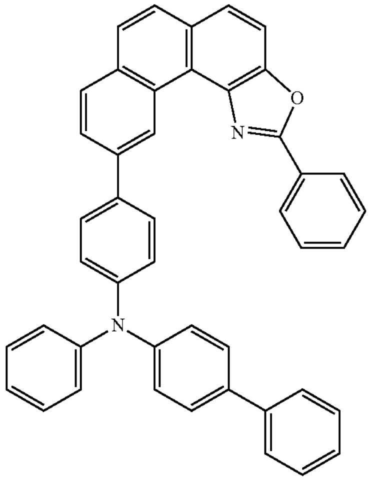
H-69
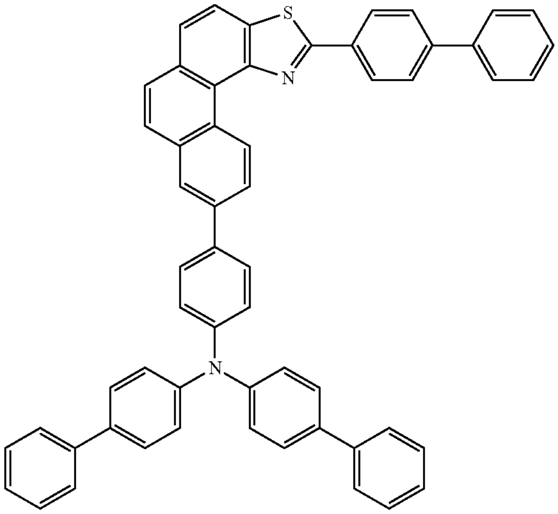
H-70
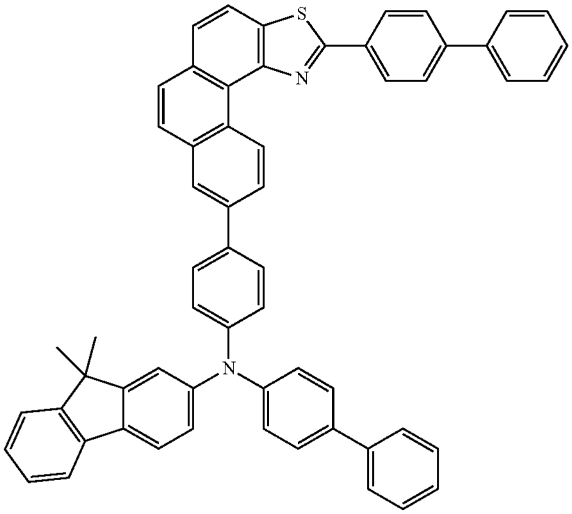

-continued
H-71
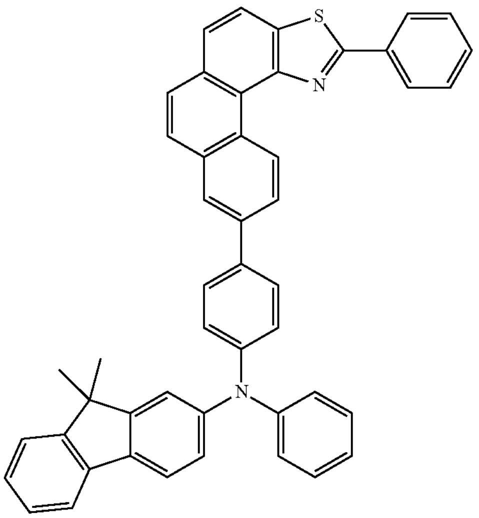
H-72
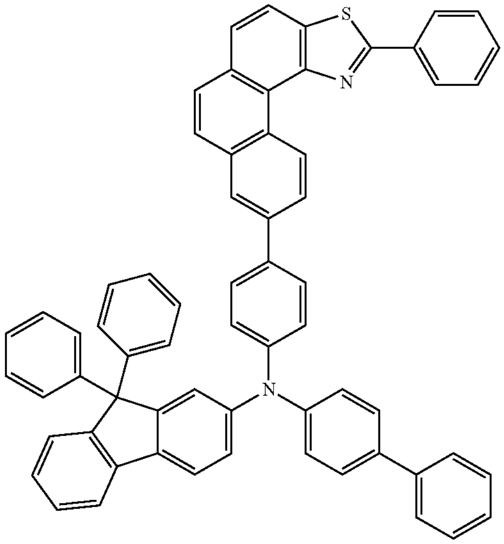
H-73
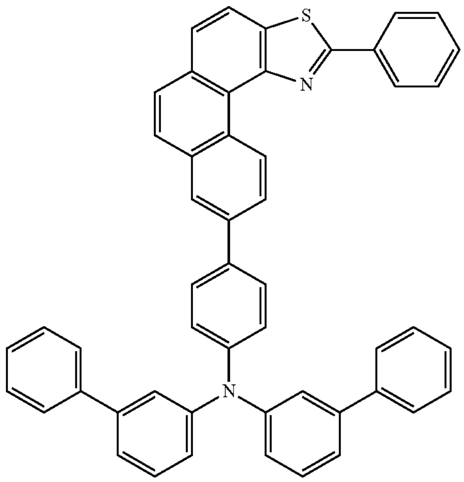
H-74
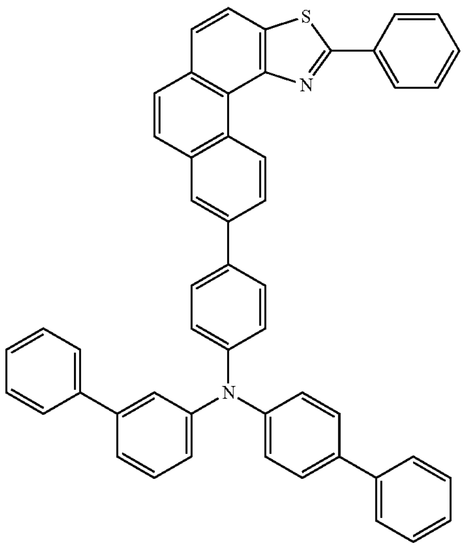
H-75
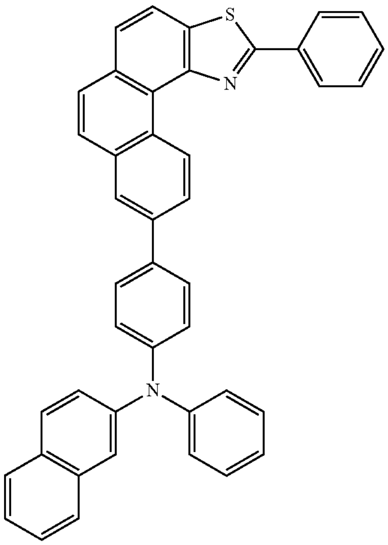
H-76
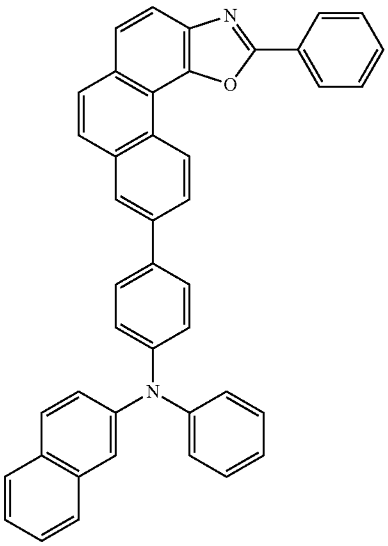

H-77
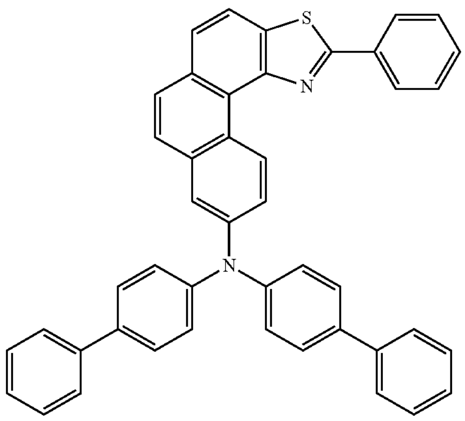
H-78
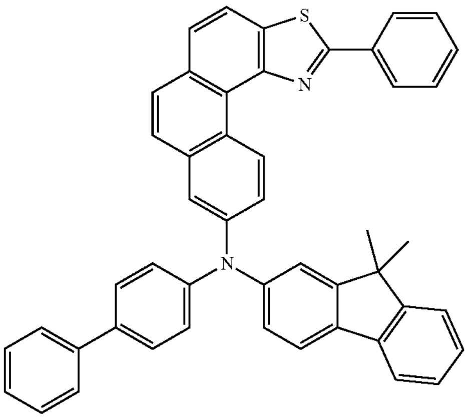
H-79
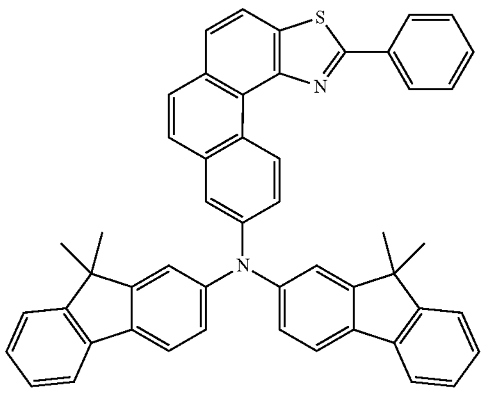
H-80
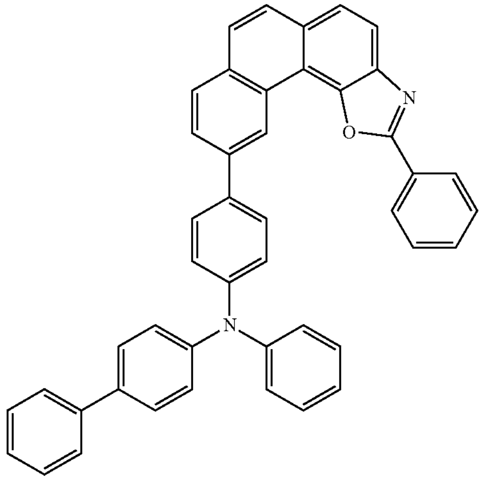
H-81
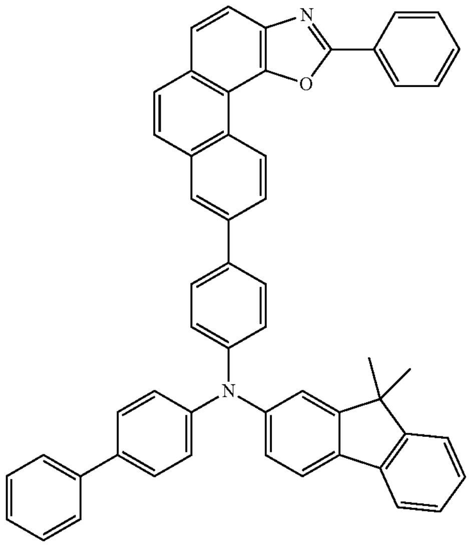
H-82
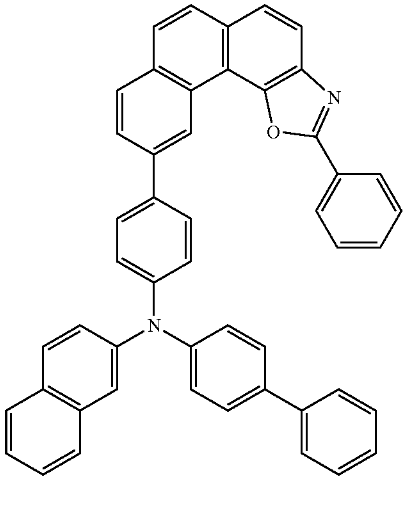

-continued
H-83
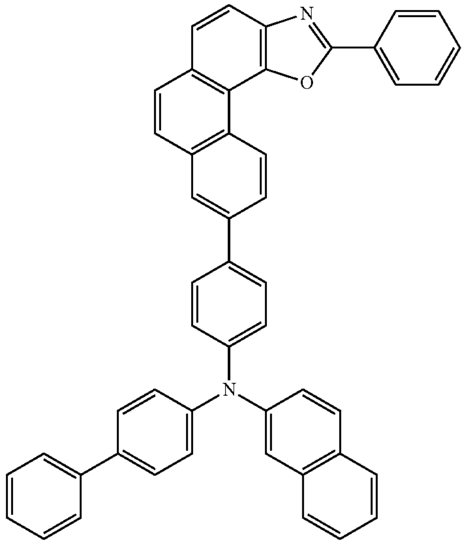
H-84
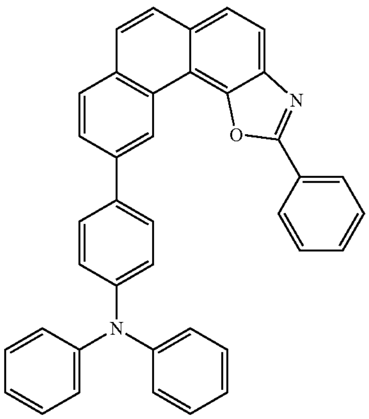
H-85
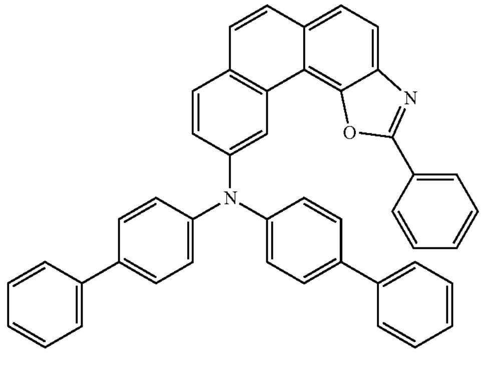
-continued
H-86
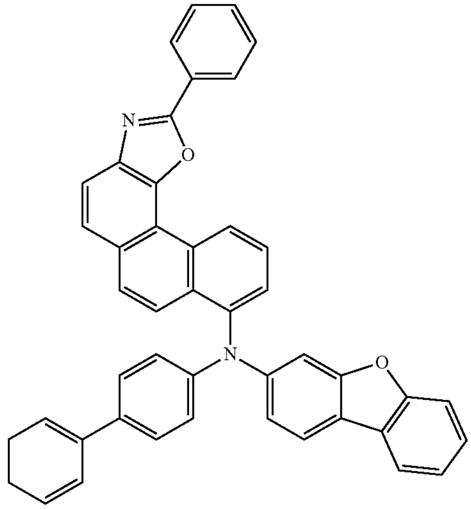
H-87
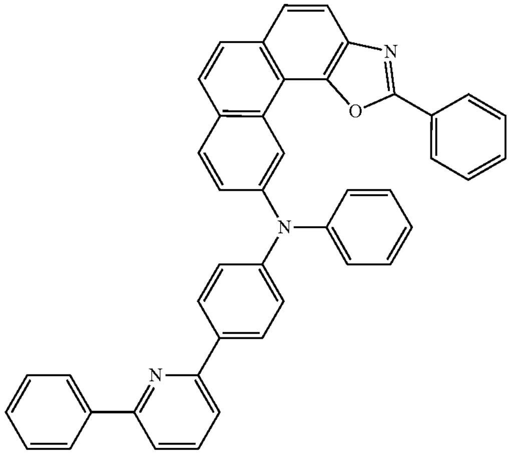
H-88
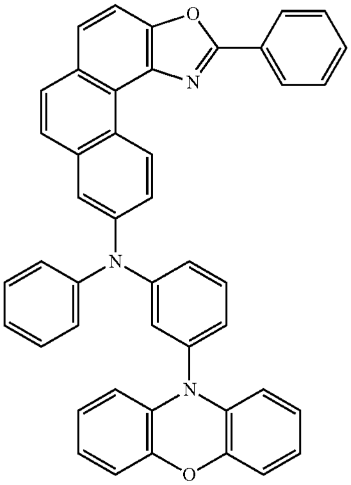

-continued
H-89
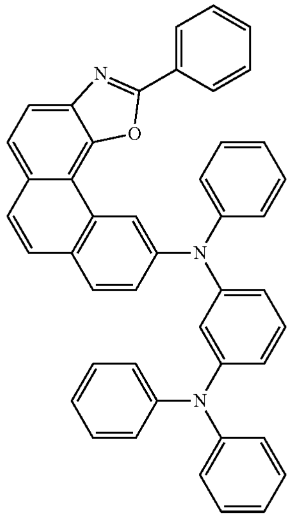
H-90
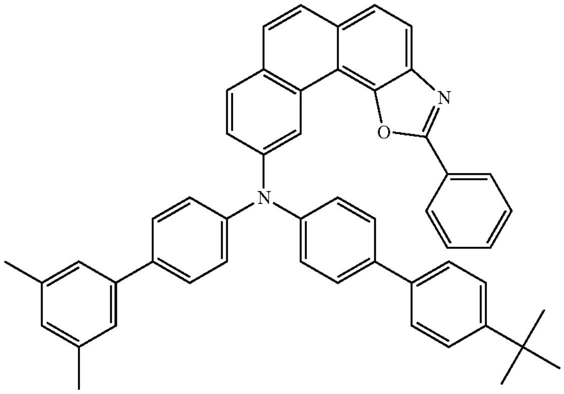
H-91
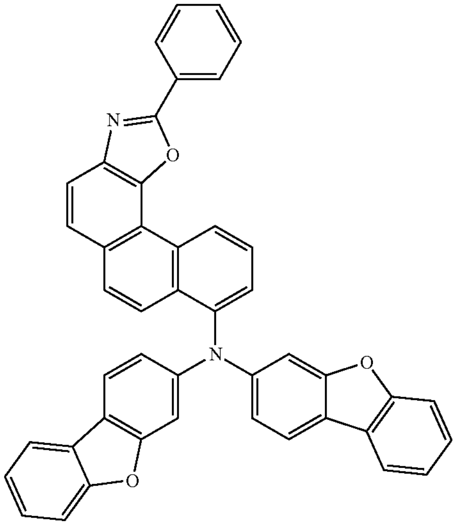
-continued
H-92
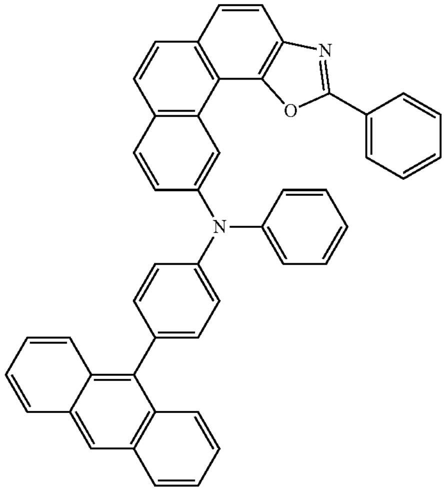
H-93
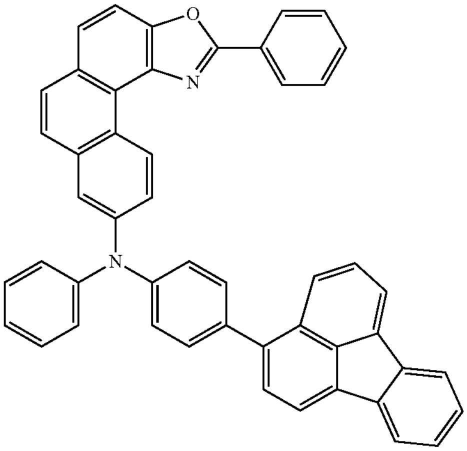
H-94
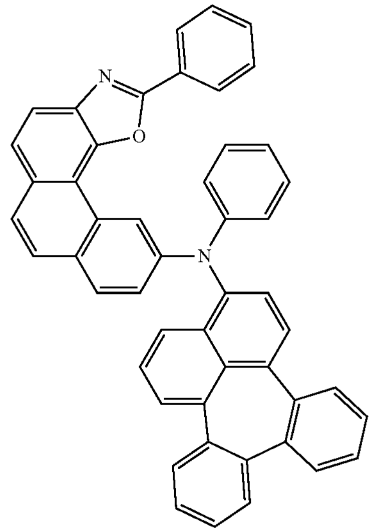

-continued
H-95
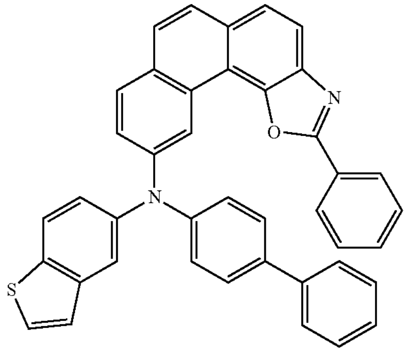
H-96
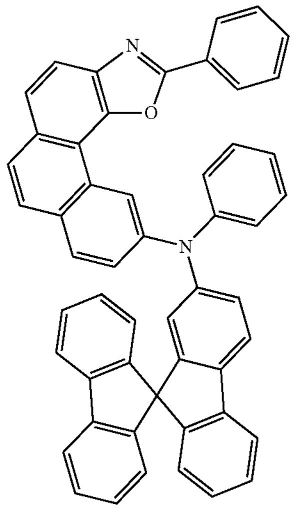
H-97
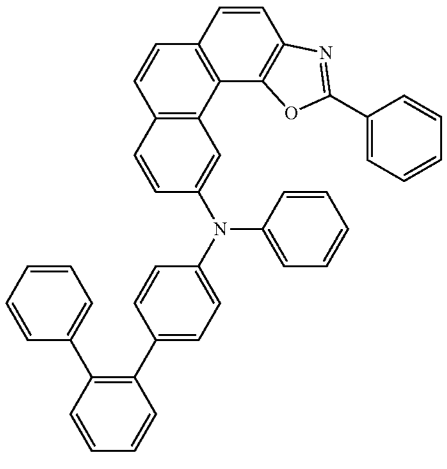
-continued
H-98
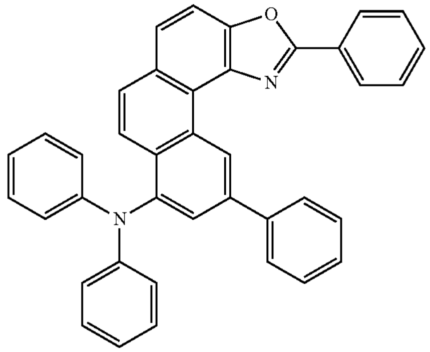
H-99
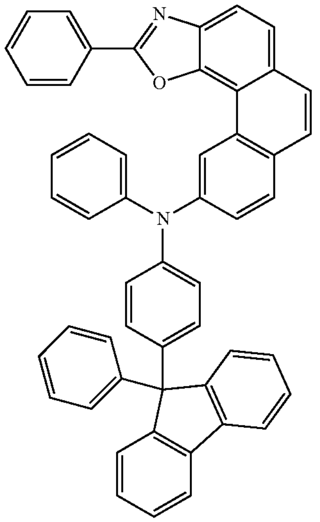
H-100
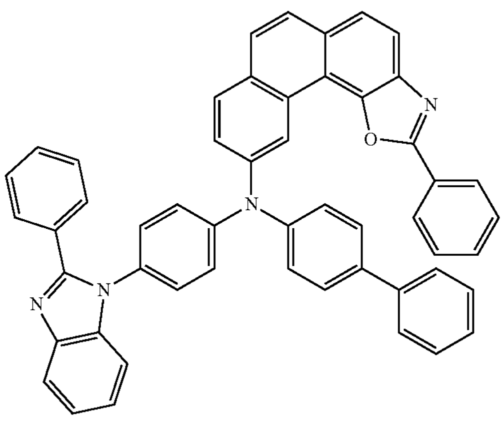

-continued
H-101
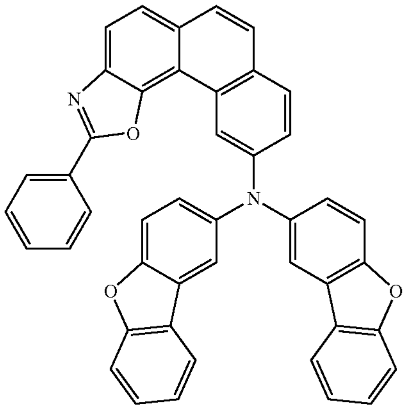
H-102
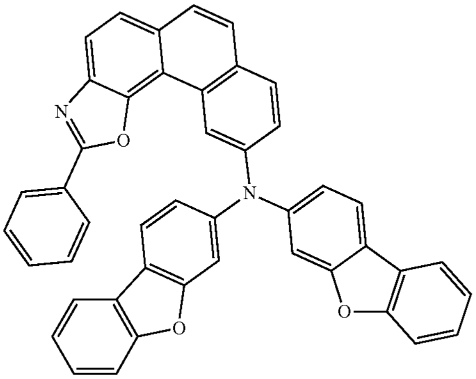
H-103
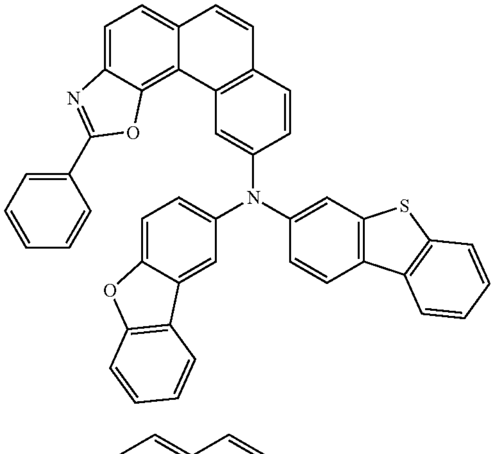
H-104
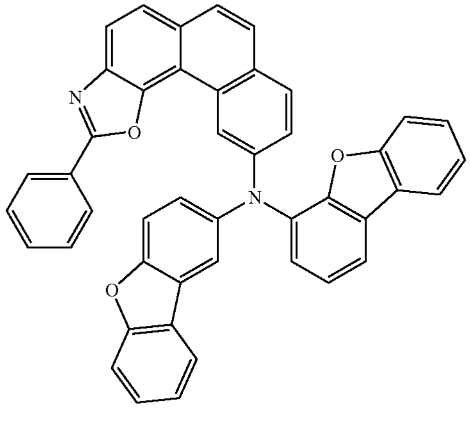
-continued
H-105
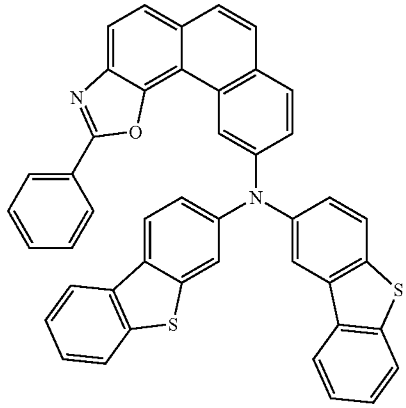
H-106
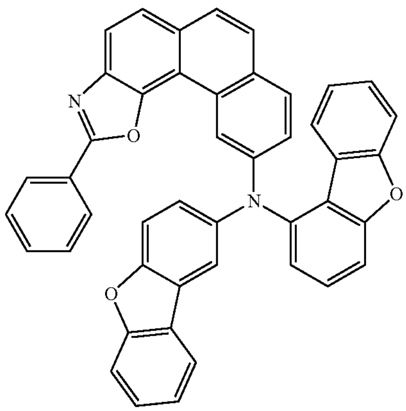
H-107
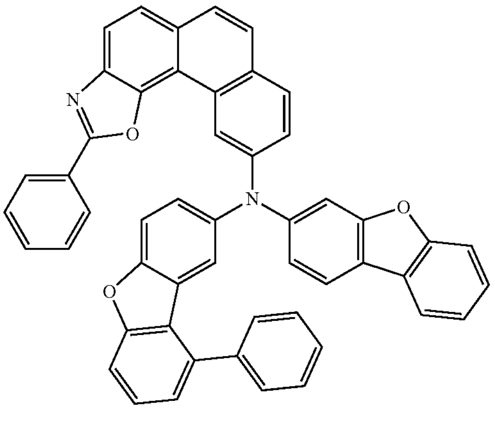

-continued
H-108
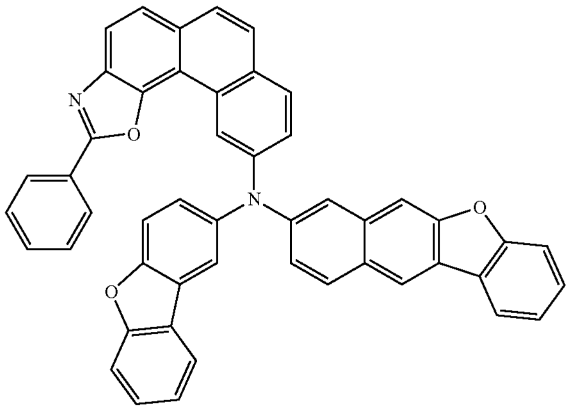
H-109
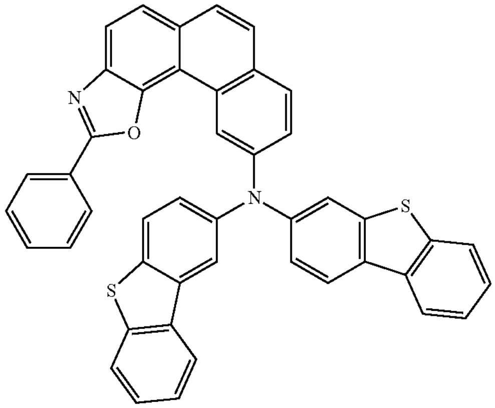
H-110
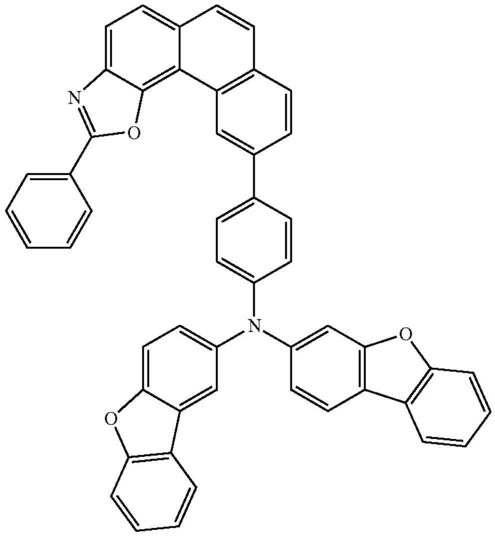
-continued
H-111
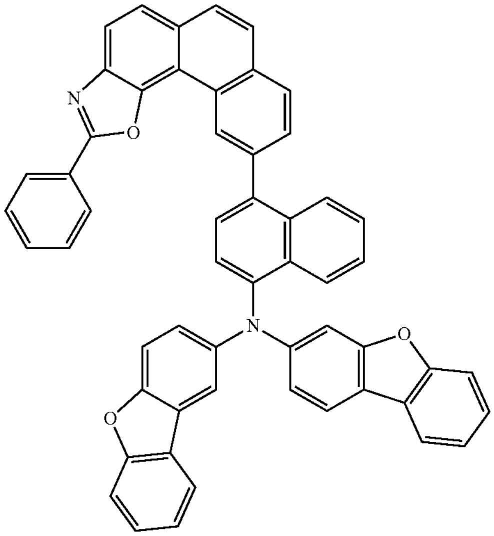
H-112
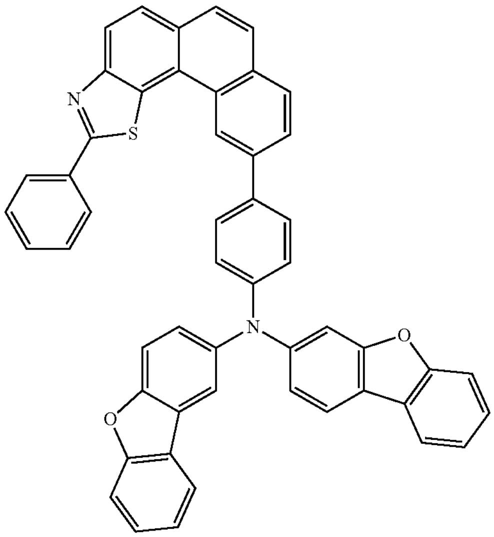
H-113
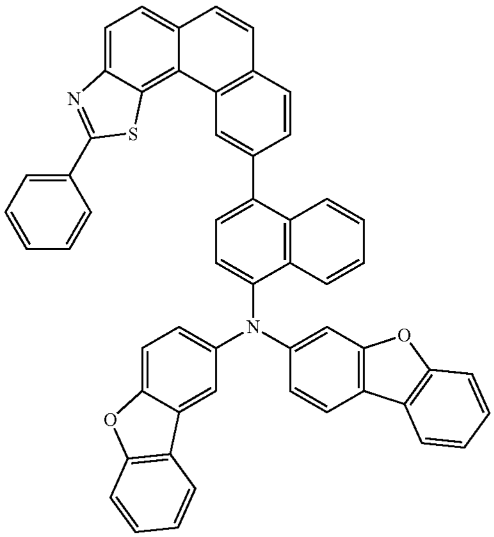

-continued
H-114
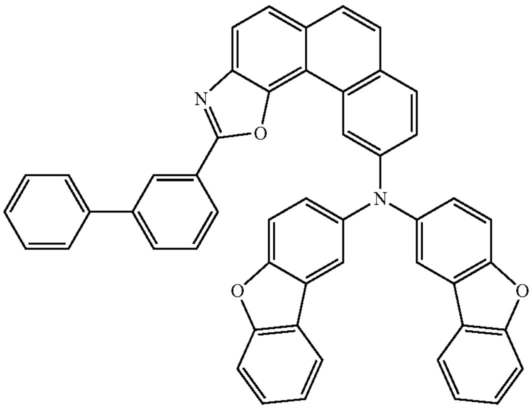
H-115
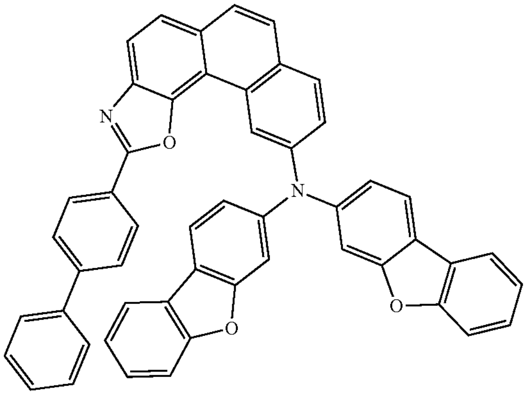
H-116
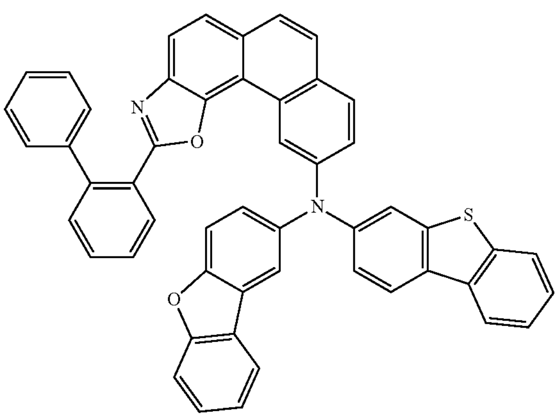
-continued
H-117
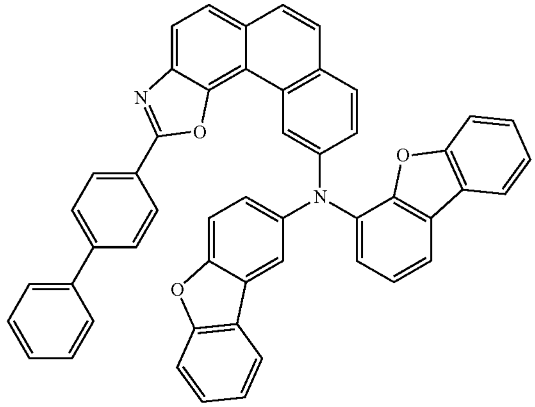
H-118
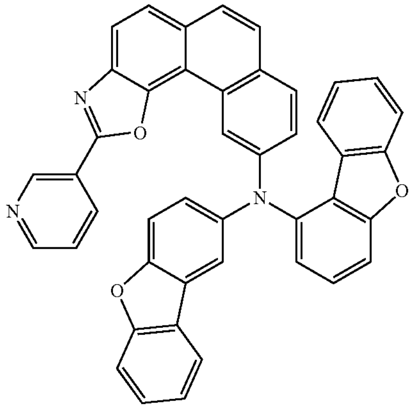
H-119
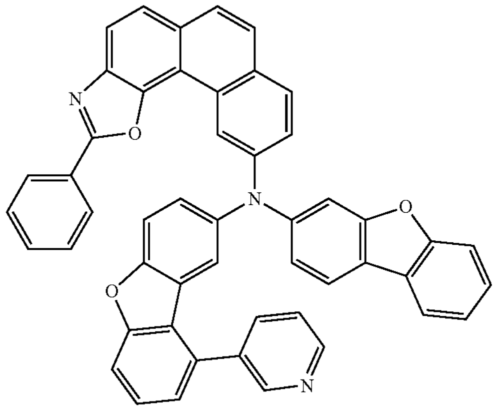

H-120
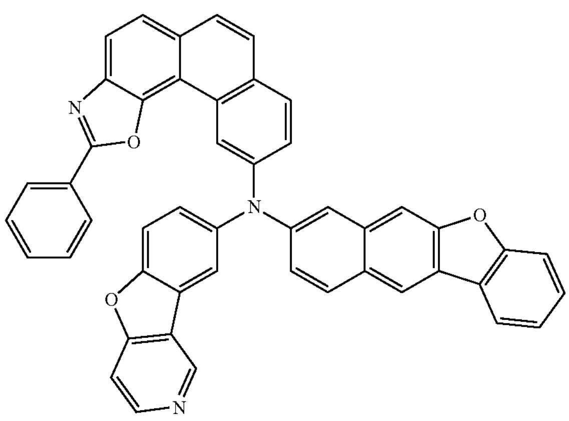
H-121
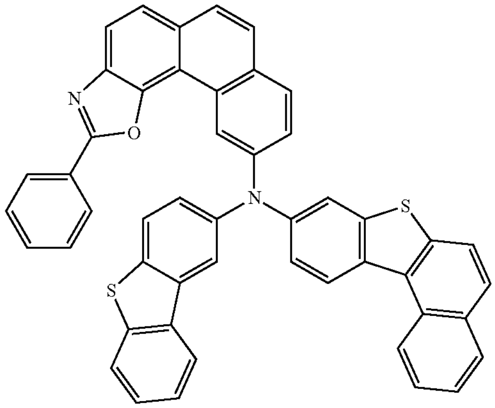
H-122
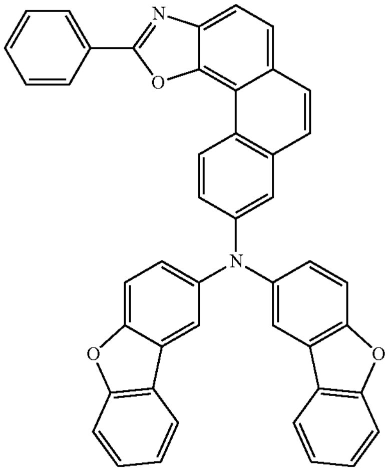
H-123
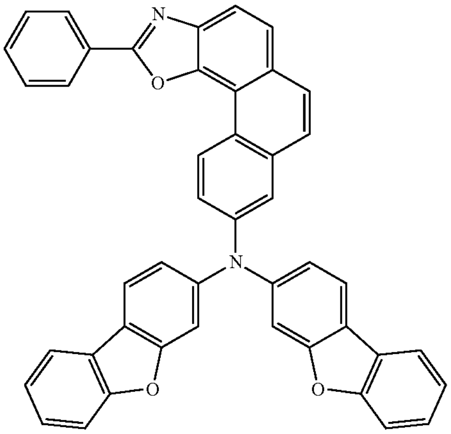
H-124
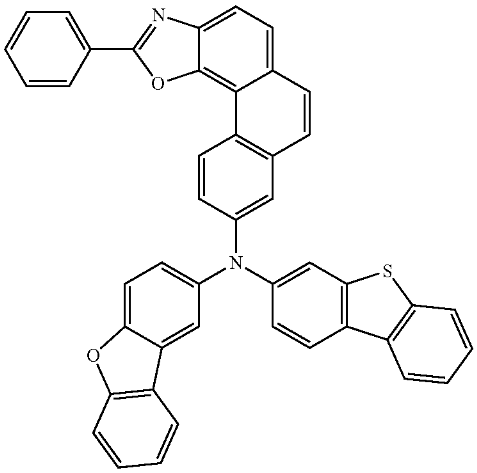
H-125
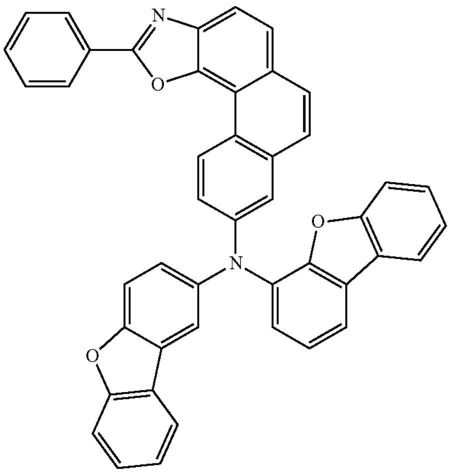

-continued
H-126
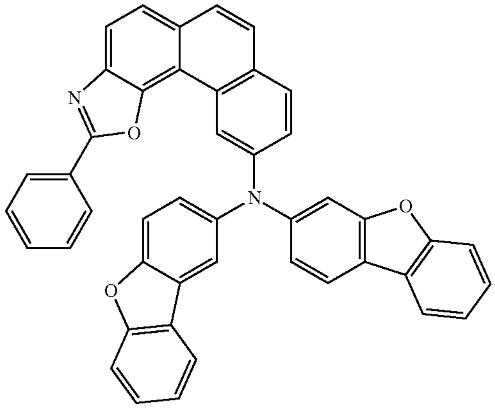
H-127
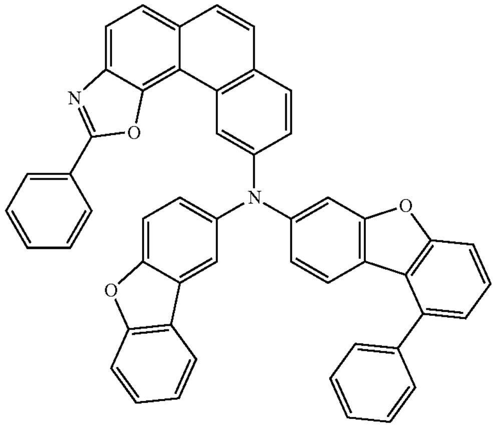
H-128
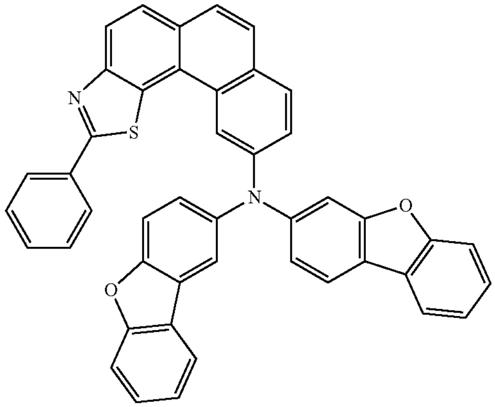
-continued
H-129
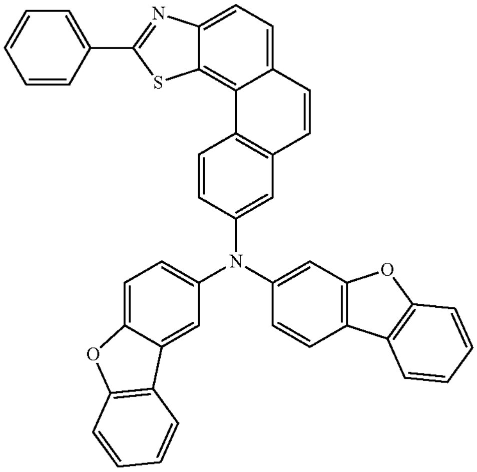
H-130
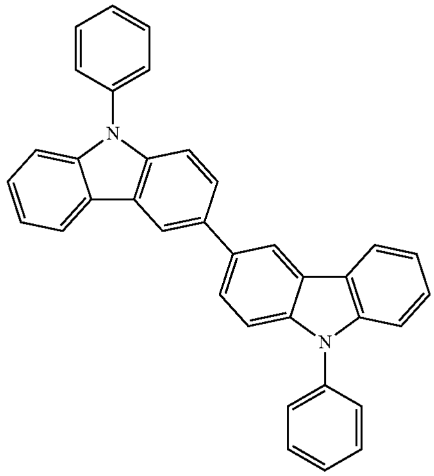
H-131
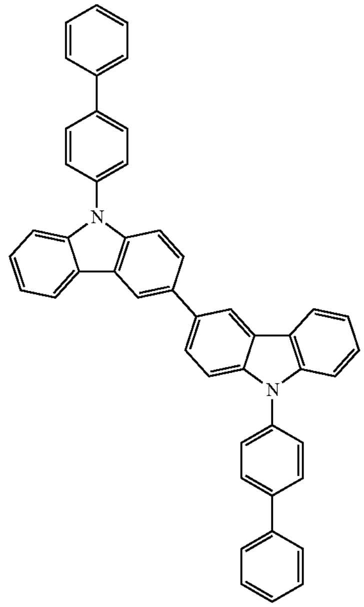

H-132
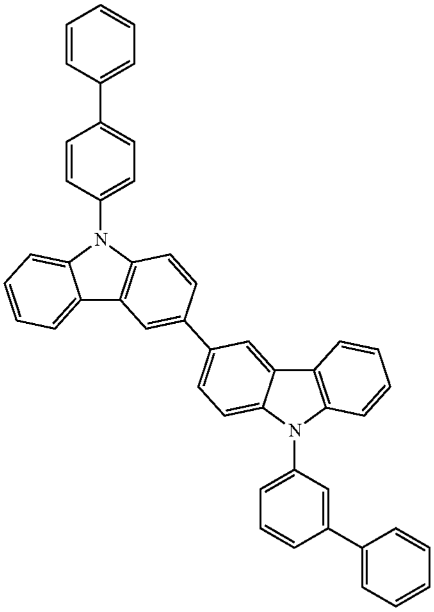
H-133
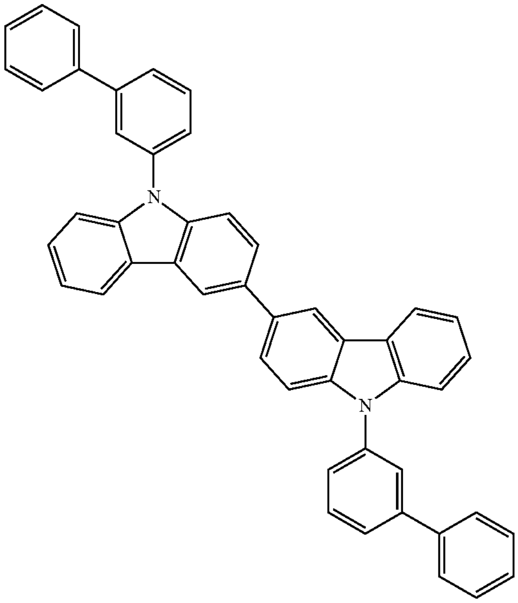
H-134
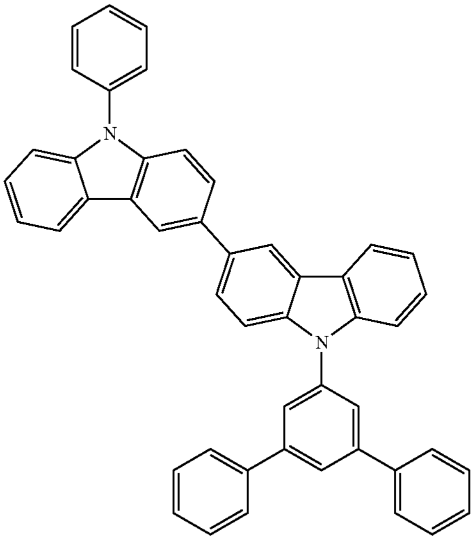
H-135
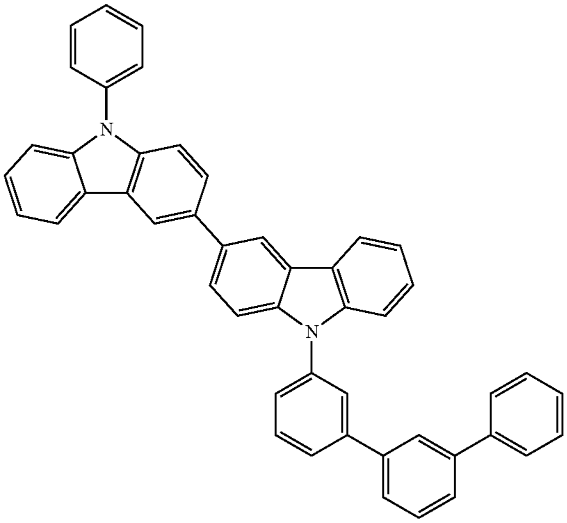
H-136
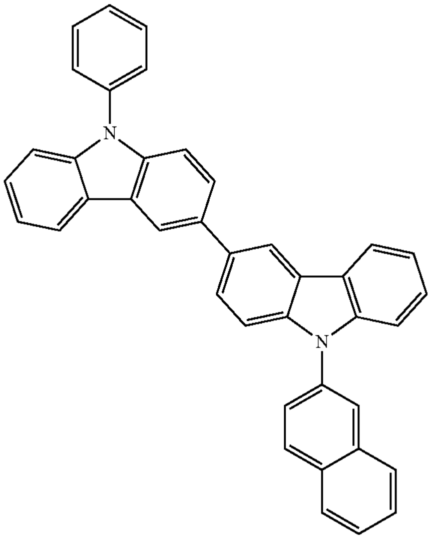

-continued
H-137
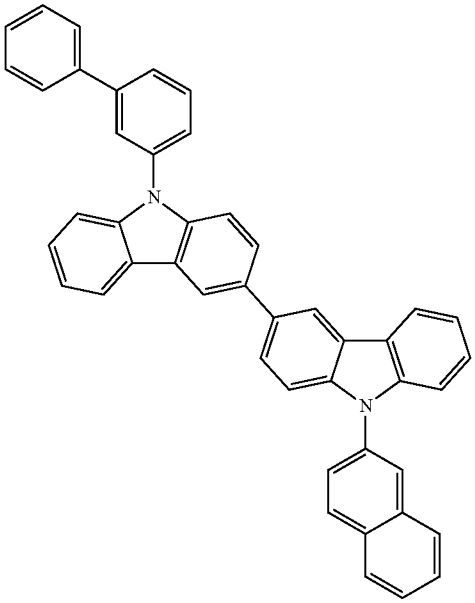
H-138
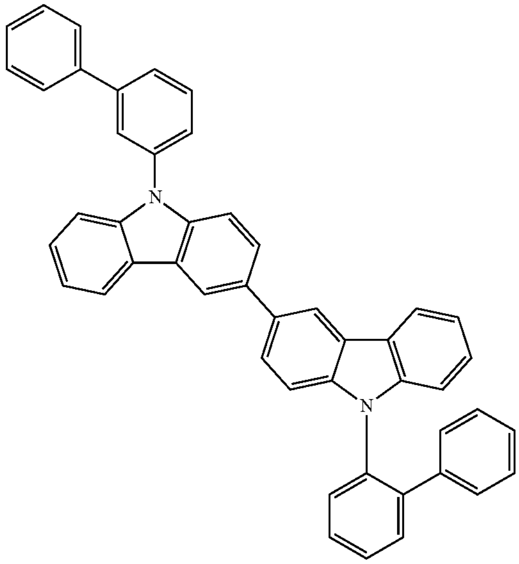
-continued
H-139
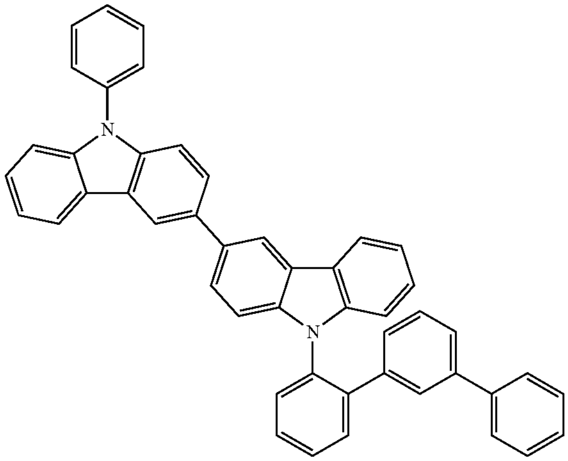
H-140
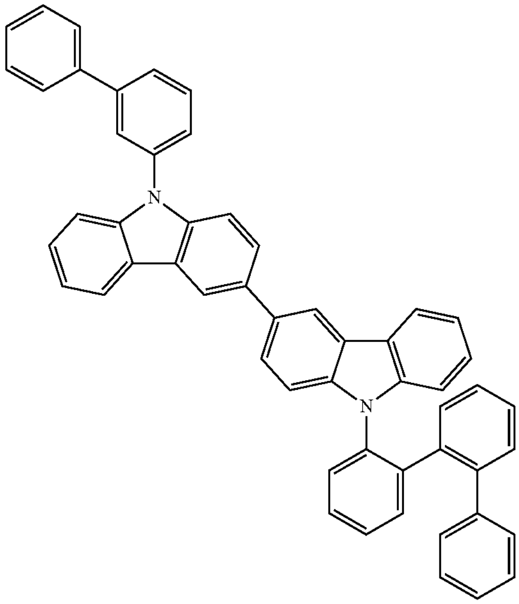

-continued
H-141
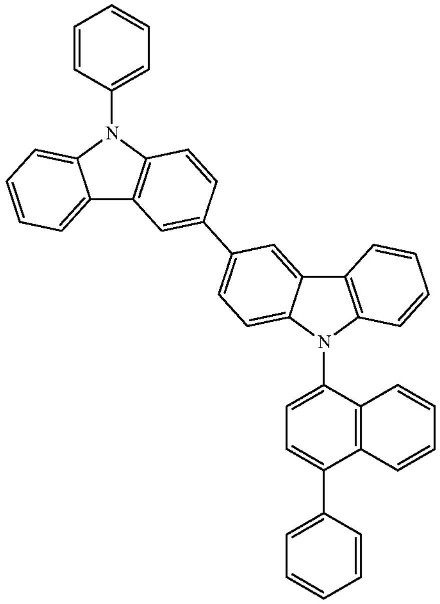
H-142
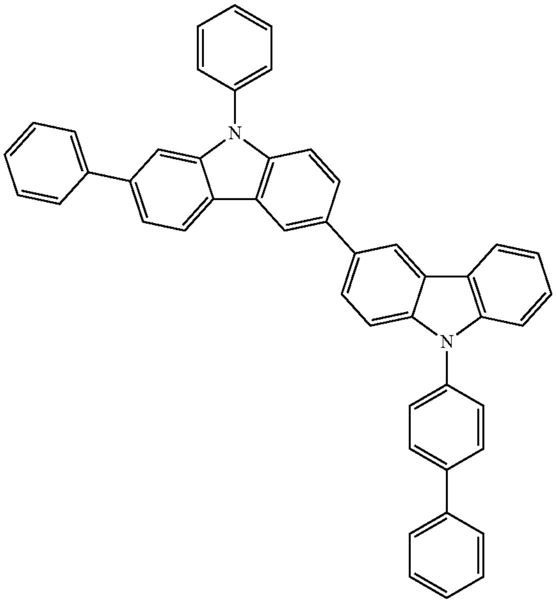
-continued
H-143
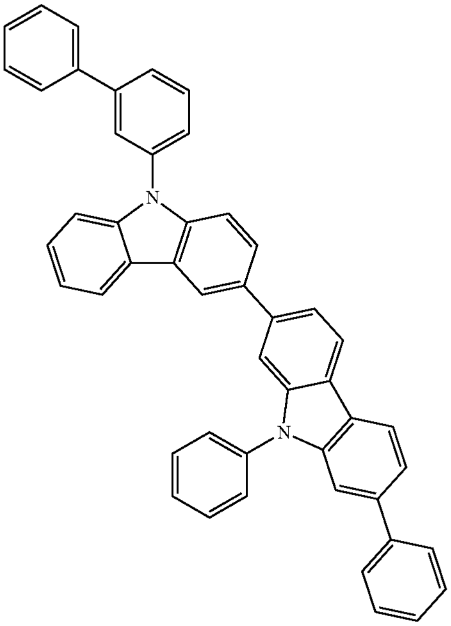
H-144
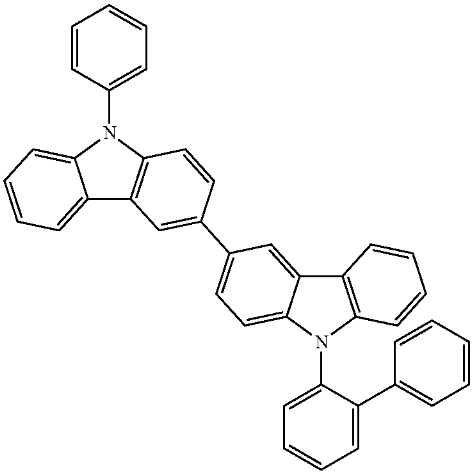
H-145
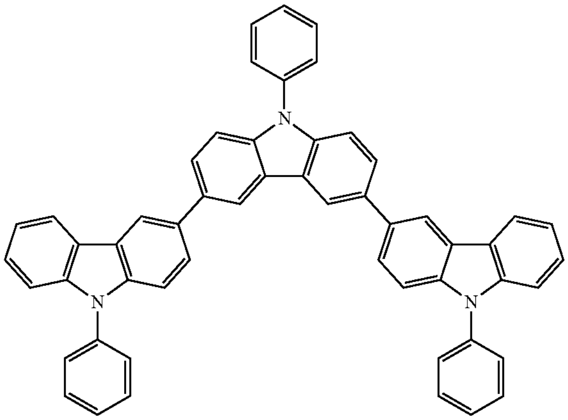

-continued
H-146
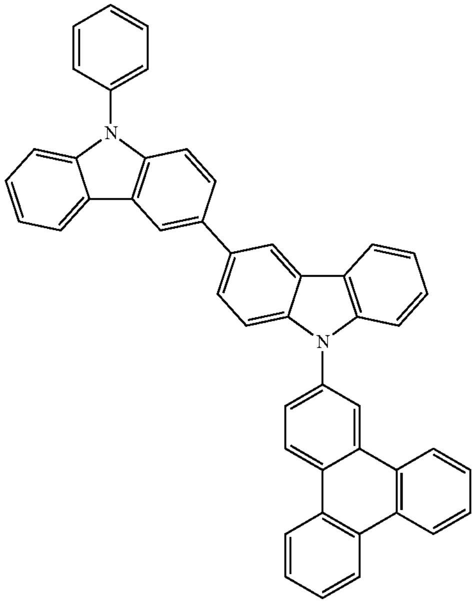
H-147
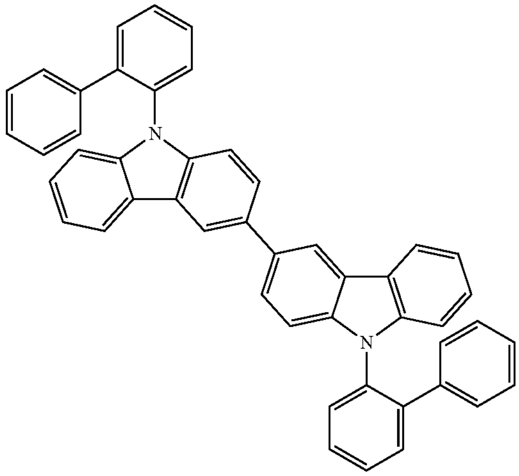
H-148
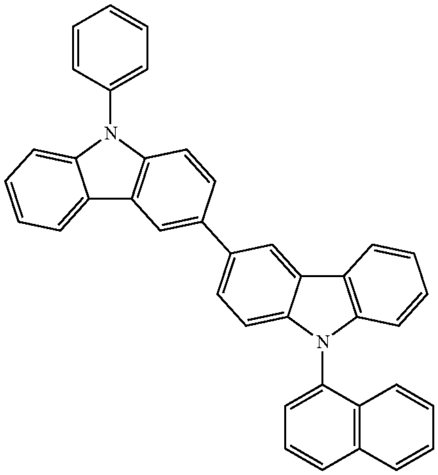
-continued
H-149
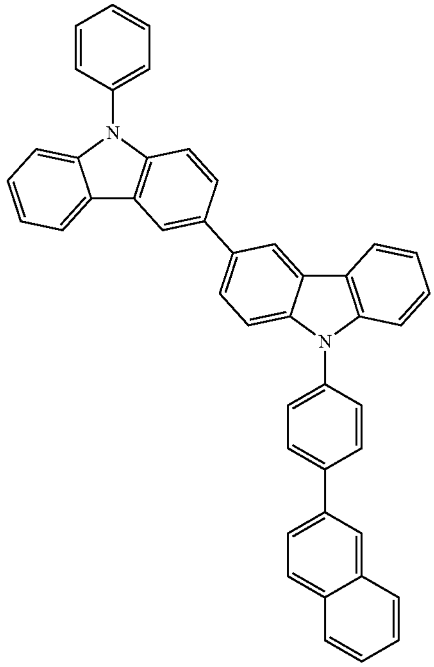
H-150
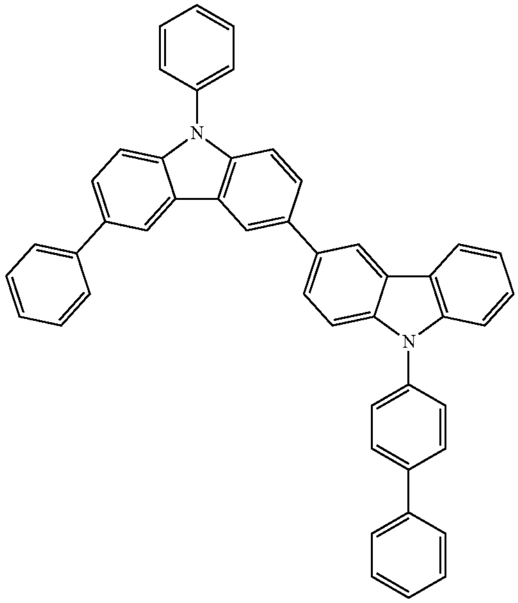

-continued
H-151
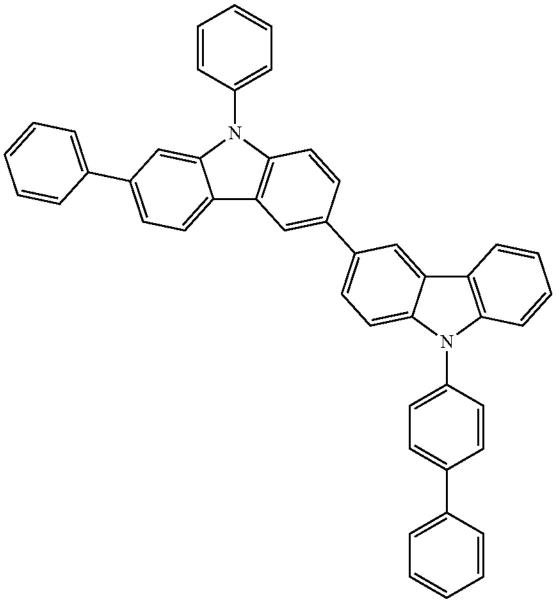
H-152
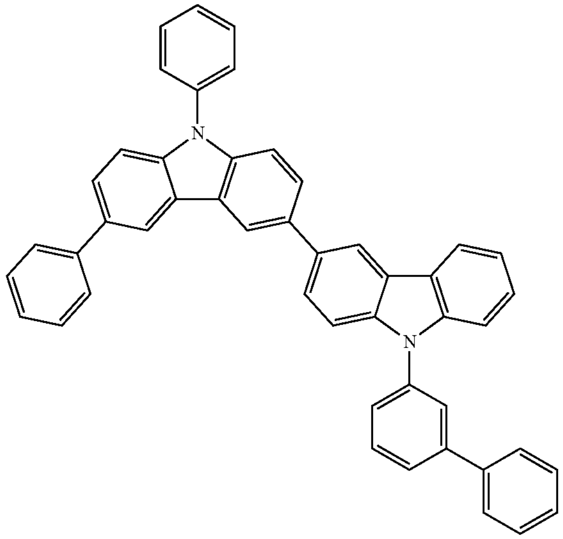
-continued
H-153
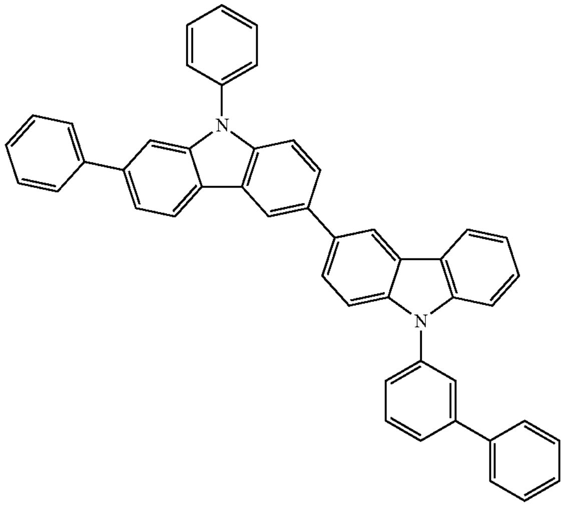
H-154
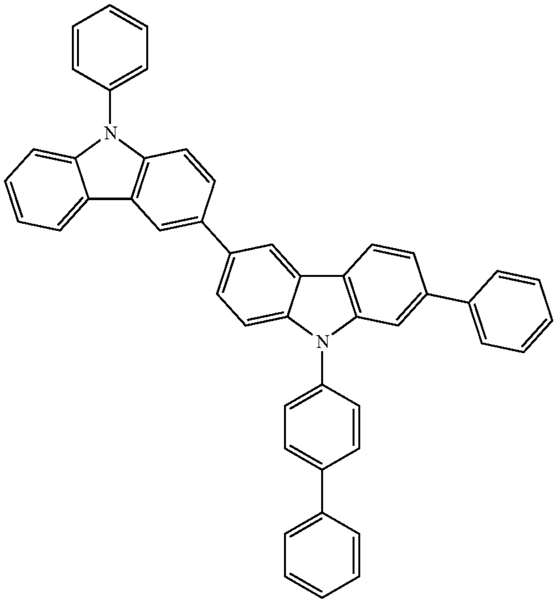

-continued
H-155
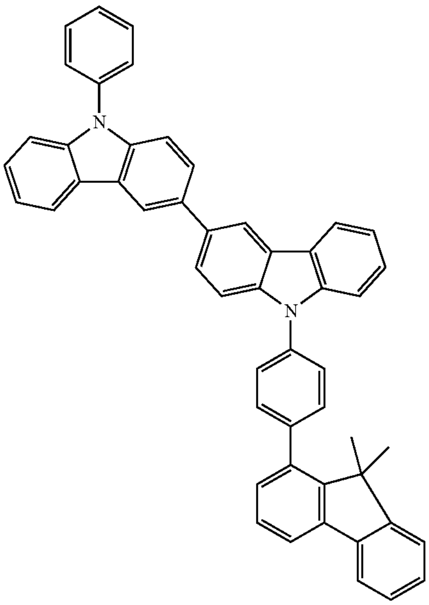
H-156
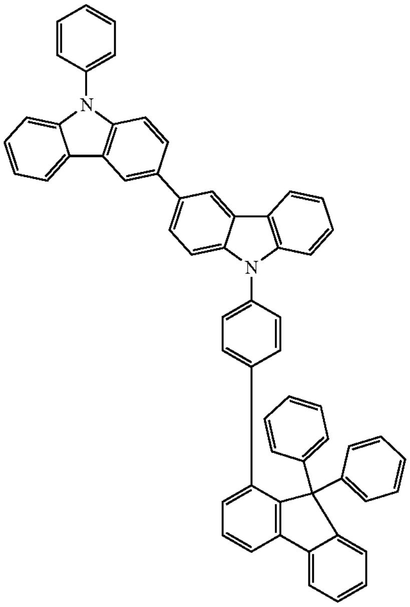
-continued
H-157
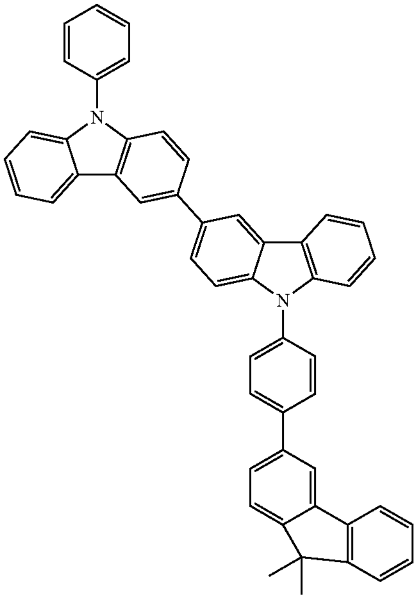
H-158
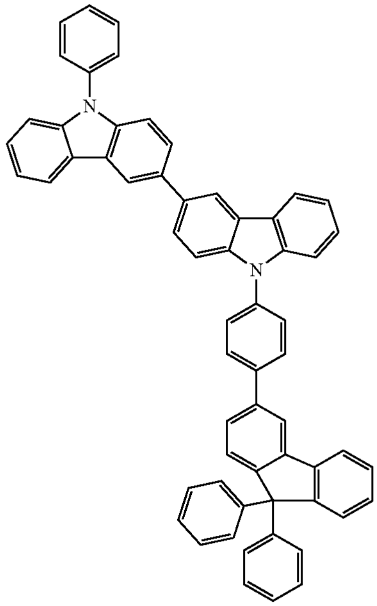

-continued
H-159
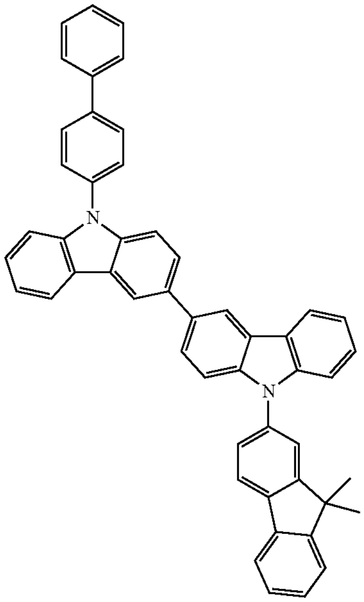
H-160
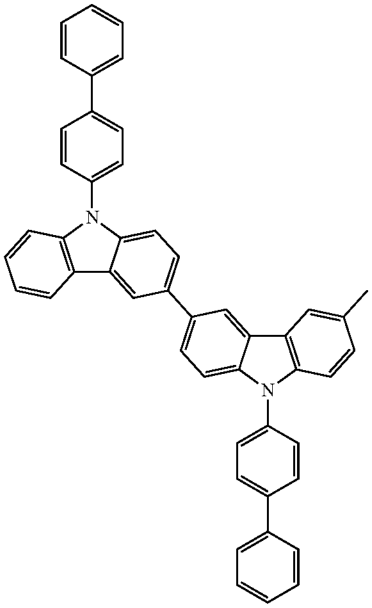
-continued
H-161
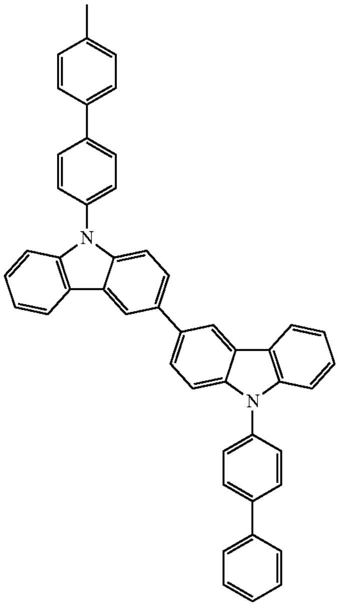
H-162
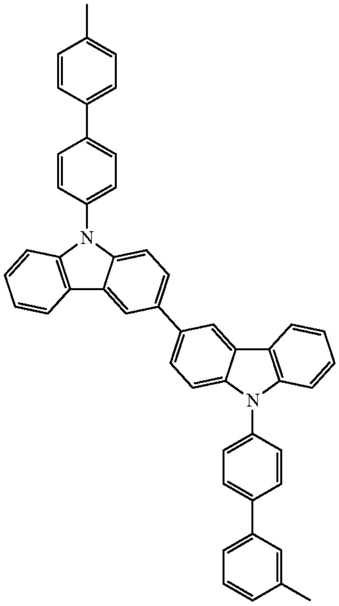

H-163
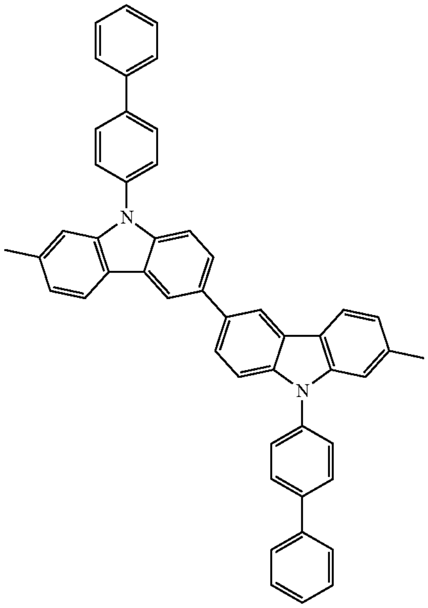
H-164
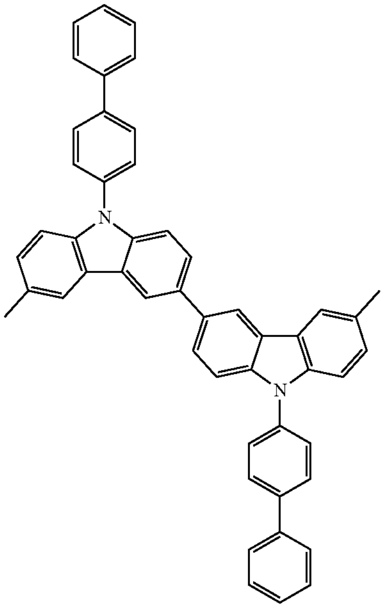
H-165
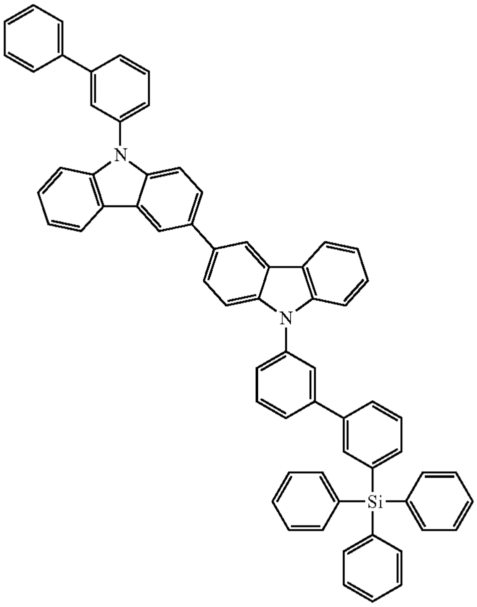
H-166
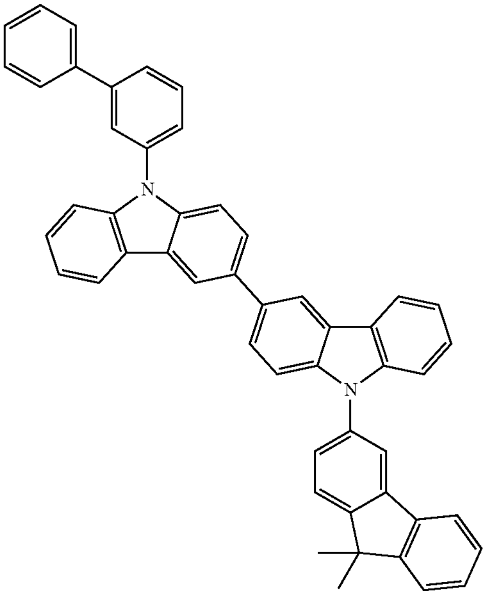

-continued

H-167

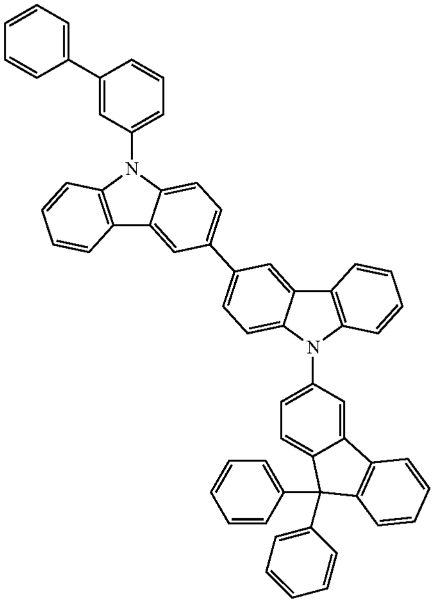

H-168

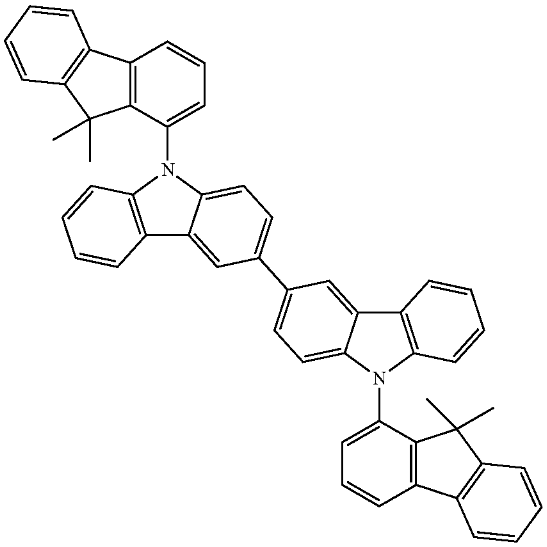

-continued

H-169

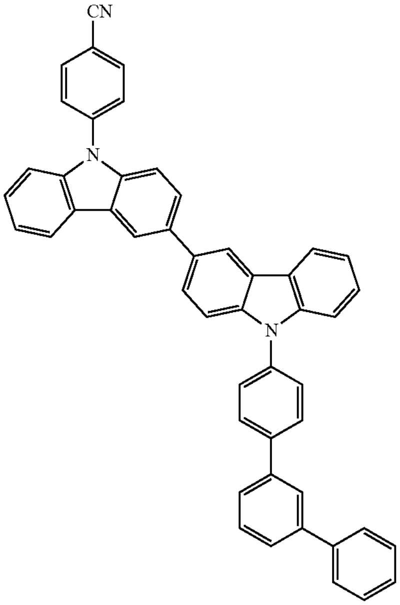

H-170

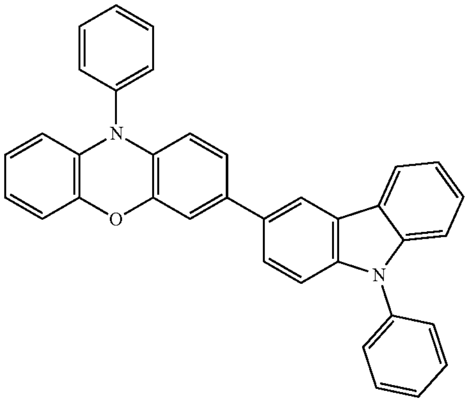

H-171

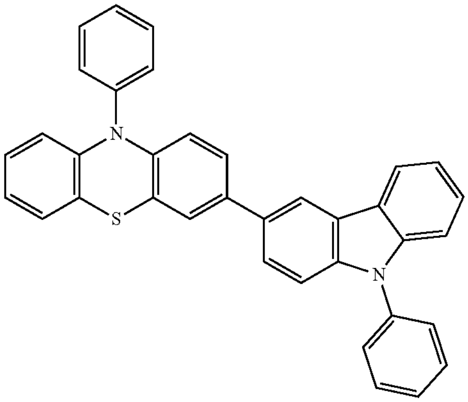

The combination of at least one of compounds C-1 to C-95 and at least one of compounds H-1 to H-171 may be used in an organic electroluminescent device.

The compound represented by formula 2 or 3 according to the present disclosure may be prepared by a synthetic method known to one skilled in the art. For example, the compound represented by formula 2 may be prepared by referring to Korean Patent Application Laid-Open Nos. 2017-0022865 (published on Mar. 2, 2017) and 2018-

0099487 (published on Sep. 5, 2018); and the compound represented by formula 3 may be prepared by referring to Japan Patent Publication No. 3139321 (Feb. 26, 2001), but are not limited thereto.

The dopant comprised in the organic electroluminescent device of the present disclosure may be at least one phosphorescent or fluorescent dopant, and preferably a phosphorescent dopant. The phosphorescent dopant material applied to the organic electroluminescent device of the present disclosure is not particularly limited, but may be preferably selected from the metallated complex compounds of iridium (Ir), osmium (Os), copper (Cu), and platinum (Pt), more preferably selected from ortho-metallated complex compounds of iridium (Ir), osmium (Os), copper (Cu), and platinum (Pt), and even more preferably ortho-metallated iridium complex compounds.

The dopant comprised in the organic electroluminescent device of the present disclosure may comprise a compound represented by the following formula 101, but is not limited thereto.

(101)

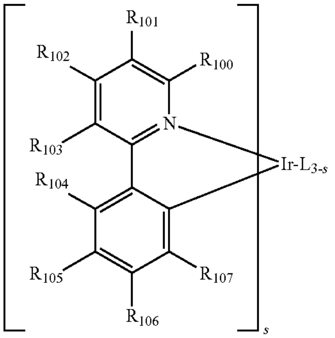

In formula 101,

L is selected from the following structures 1 to 3:

[Structure 1]

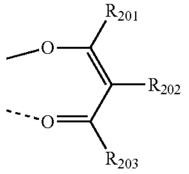

[Structure 2]

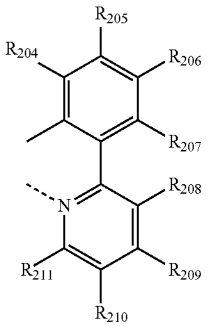

-continued

[Structure 3]

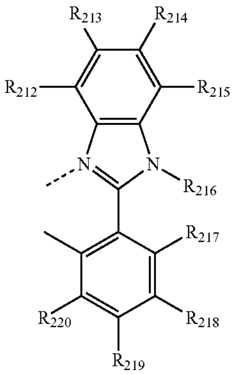

$R_{100}$ to $R_{103}$, each independently, represent hydrogen, deuterium, a halogen, a (C1-C30)alkyl unsubstituted or substituted with deuterium and/or a halogen(s), a substituted or unsubstituted (C3-C30)cycloalkyl, a substituted or unsubstituted (C6-C30)aryl, a cyano, a substituted or unsubstituted (3- to 30-membered)heteroaryl, or a substituted or unsubstituted (C1-C30)alkoxy; or at least two adjacent ones of $R_{100}$ to $R_{103}$ may be linked to each other to form a ring(s), e.g., a substituted or unsubstituted, quinoline, benzofuropyridine, benzothienopyridine, indenopyridine, benzofuroquinoline, benzothienoquinoline, or indenoquinoline, together with pyridine;

$R_{114}$ to $R_{107}$, each independently, represent hydrogen, deuterium, a halogen, a (C1-C30)alkyl unsubstituted or substituted with deuterium and/or a halogen(s), a substituted or unsubstituted (C3-C30)cycloalkyl, a substituted or unsubstituted (C6-C30)aryl, a substituted or unsubstituted (3- to 30-membered)heteroaryl, a cyano, or a substituted or unsubstituted (C1-C30)alkoxy; or at least two adjacent ones of $R_{104}$ to $R_{107}$ may be linked to each other to form a ring(s), e.g., a substituted or unsubstituted, naphthalene, fluorene, dibenzothiophene, dibenzofuran, indenopyridine, benzofuropyridine, or benzothienopyridine, together with benzene;

$R_{201}$ to $R_{220}$, each independently, represent hydrogen, deuterium, a halogen, a (C1-C30)alkyl unsubstituted or substituted with deuterium and/or a halogen(s), a substituted or unsubstituted (C3-C30)cycloalkyl, or a substituted or unsubstituted (C6-C30)aryl; or at least two adjacent ones of $R_{201}$ to $R_{220}$ may be linked to each other to form a substituted or unsubstituted ring(s); and s represents an integer of 1 to 3.

The specific examples of the dopant compound are as follows, but are not limited thereto.

D-1

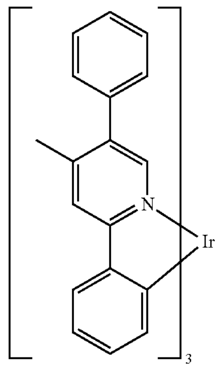

-continued
D-2
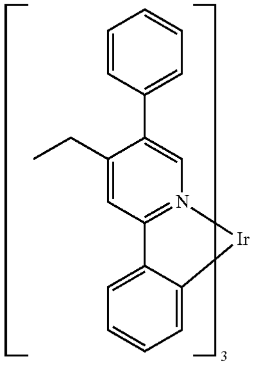
D-3
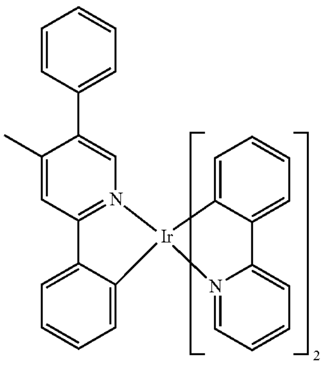
D-4
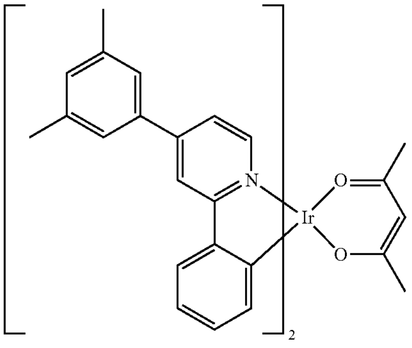
D-5
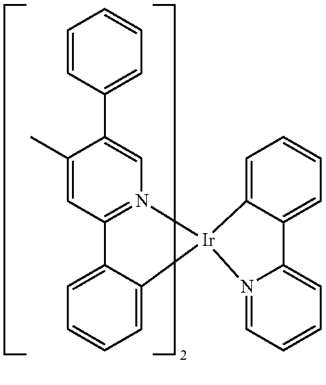
-continued
D-6
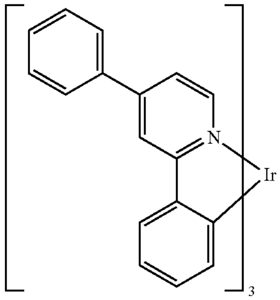
D-7
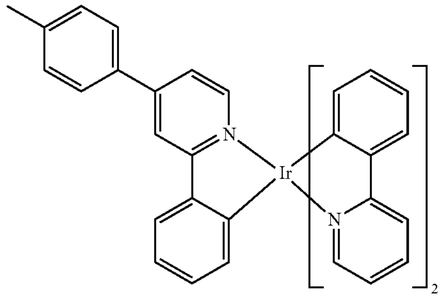
D-8
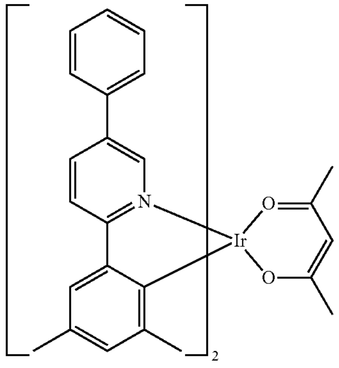
D-9
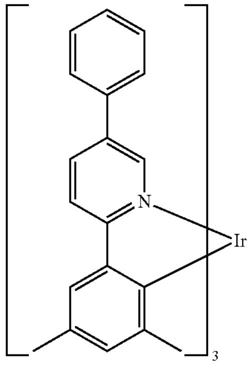

-continued
D-10
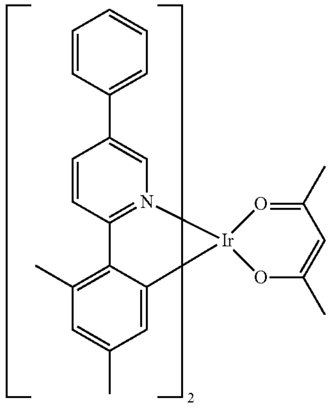
D-11
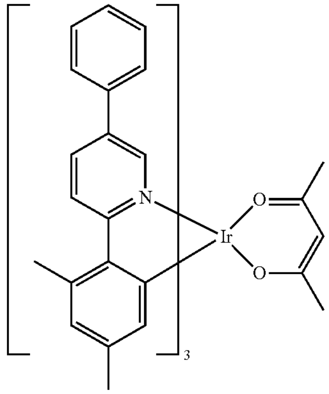
D-12
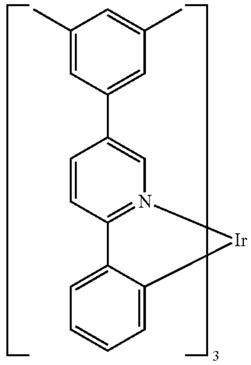
D-13
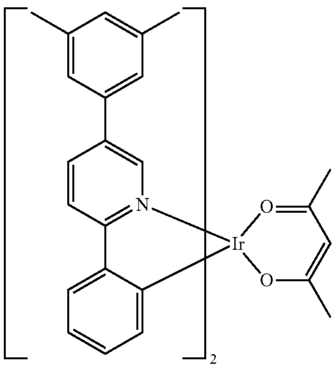
-continued
D-14
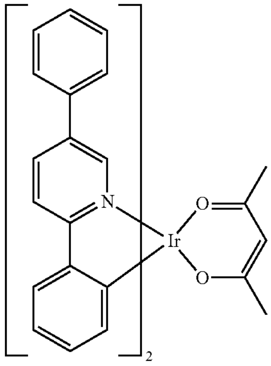
D-15
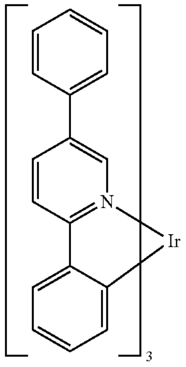
D-16
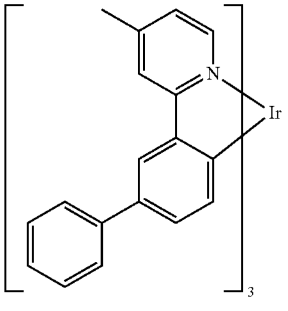
D-17
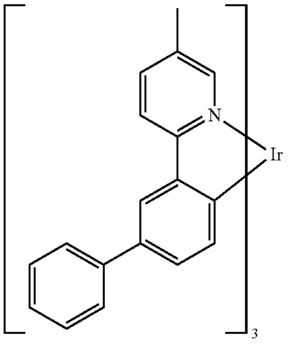

-continued
D-18
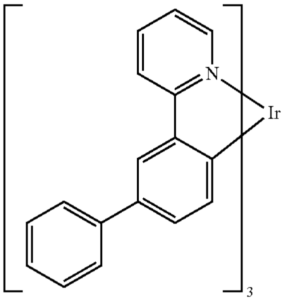
D-19
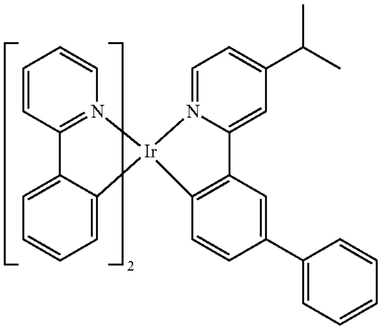
D-20
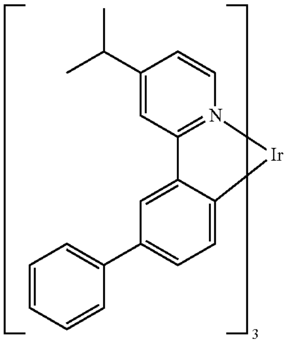
D-21
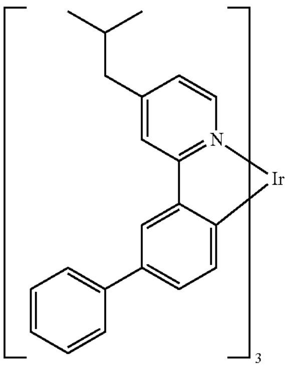
-continued
D-22
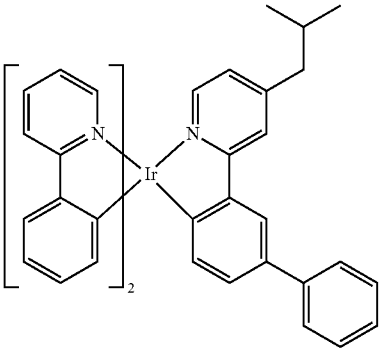
D-23
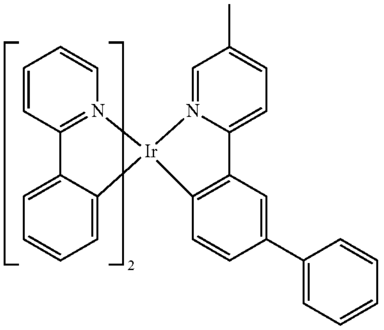
D-24
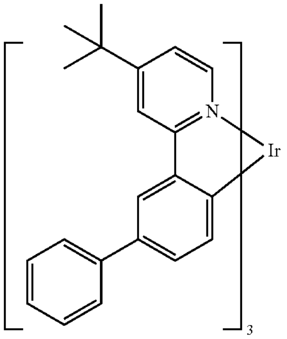
D-25
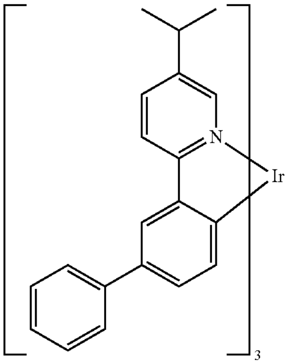

-continued
D-26
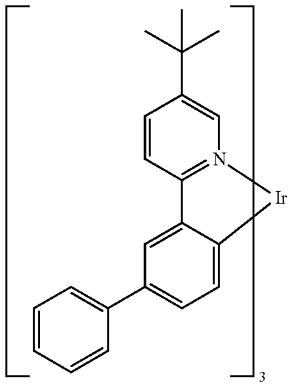
D-27
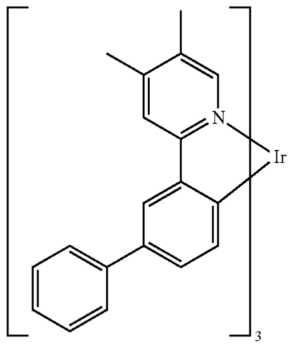
D-28
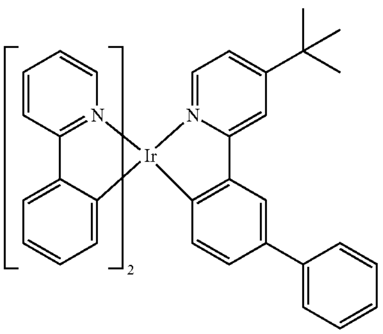
D-29
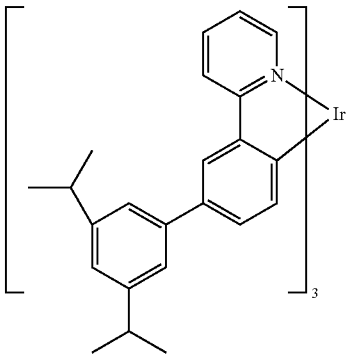
-continued
D-30
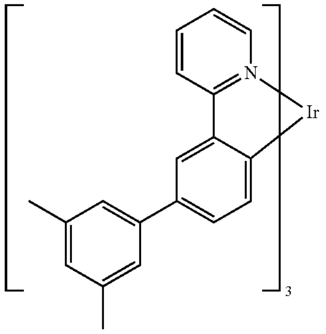
D-31
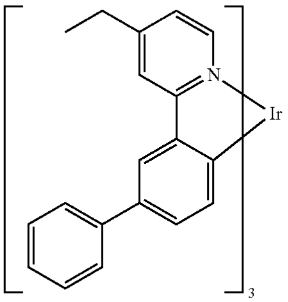
D-32
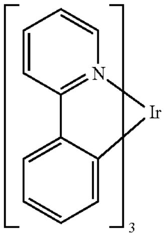
D-33
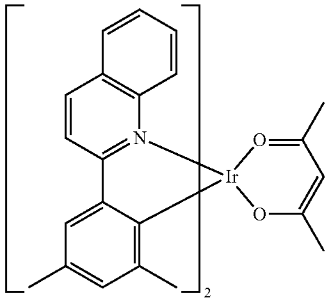
D-34
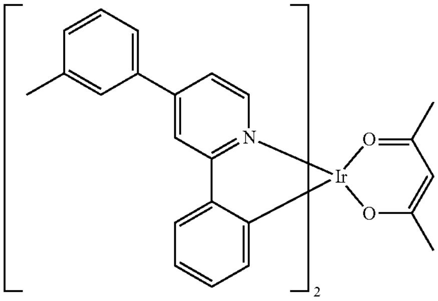

-continued
D-35
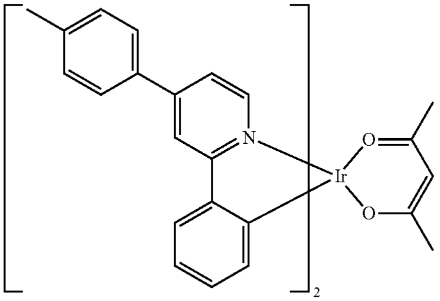
D-36
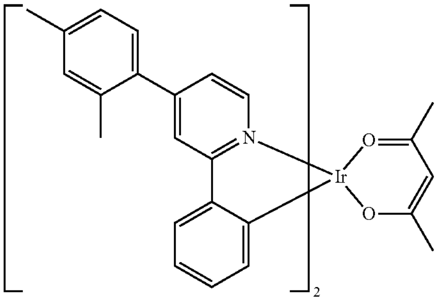
D-37
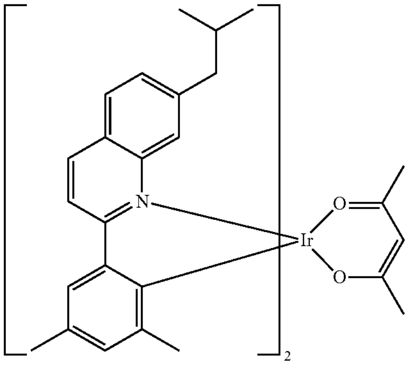
D-38
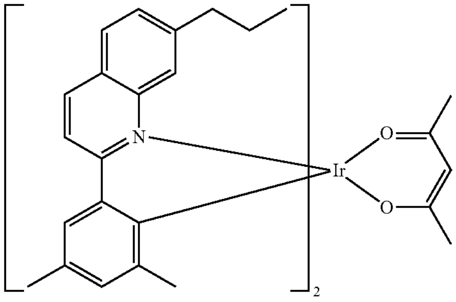
-continued
D-39
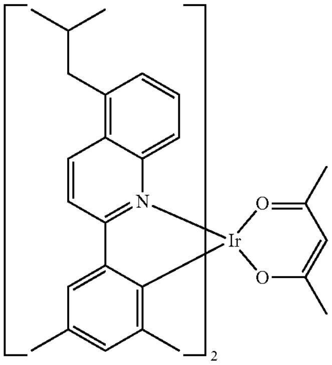
D-40
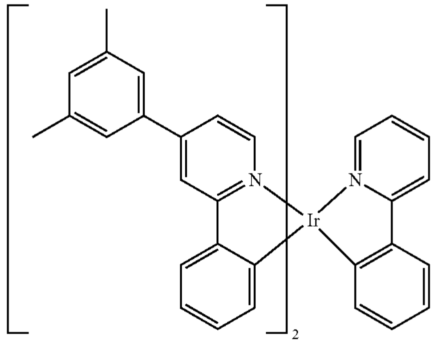
D-41
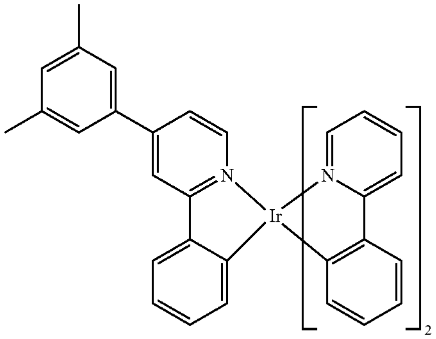
D-42
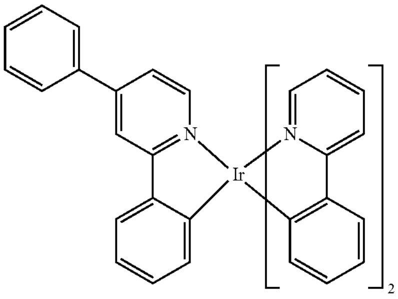

-continued
D-43
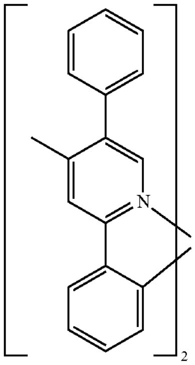
D-44
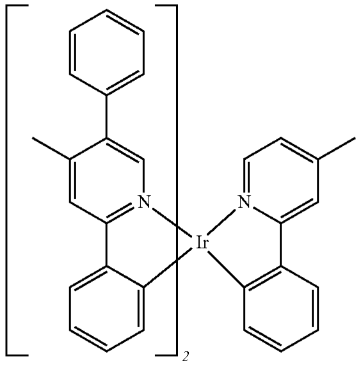
D-45
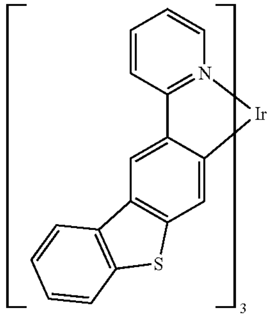
D-46
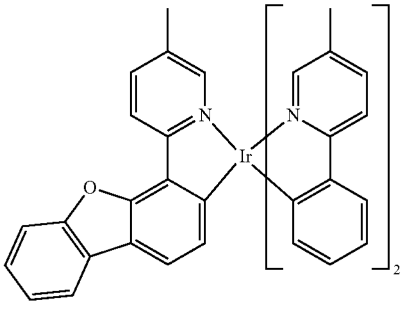
-continued
D-47
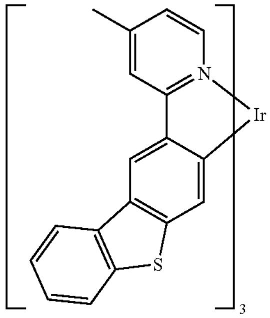
D-48
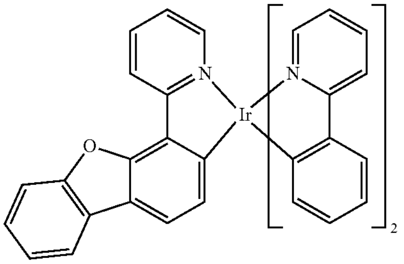
D-49
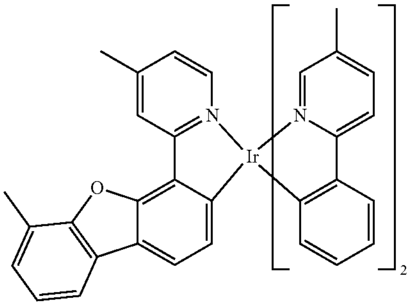
D-50
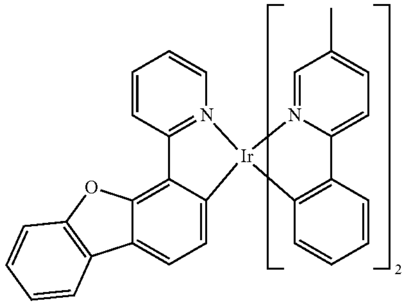
D-51
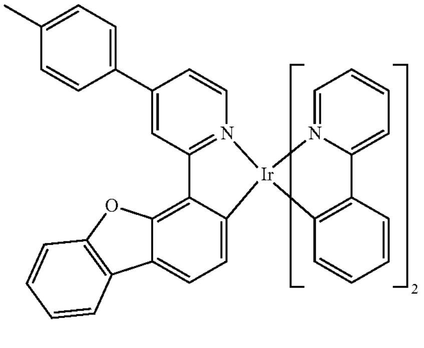

D-52
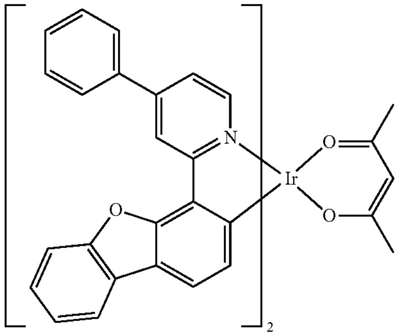
D-53
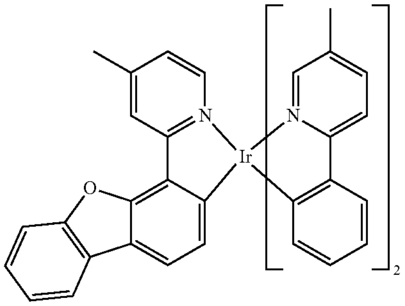
D-54
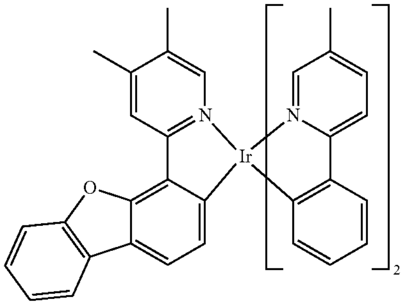
D-55
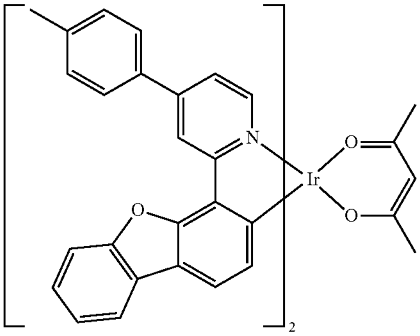
D-56
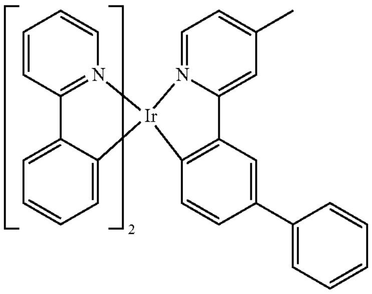
D-57
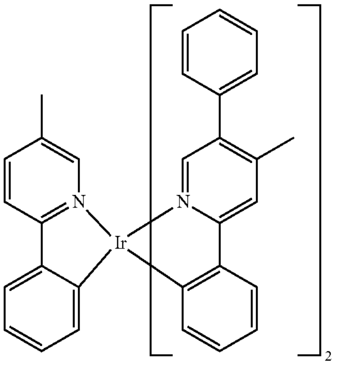
D-58
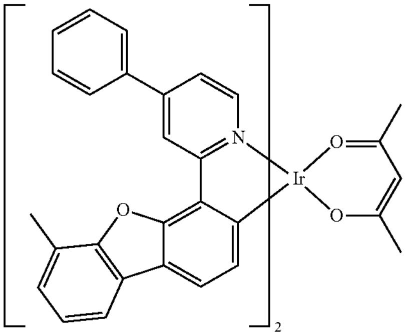
D-59
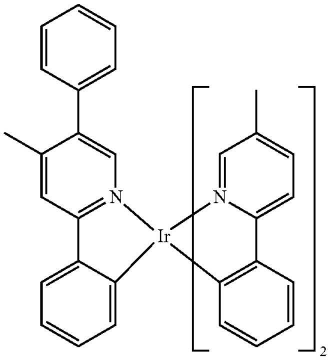
D-60
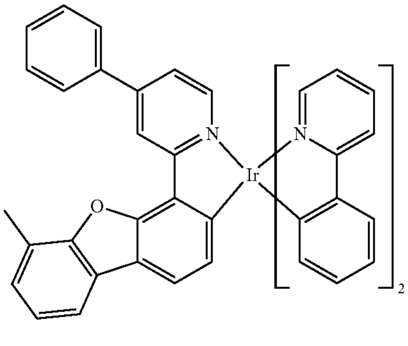

-continued
D-61
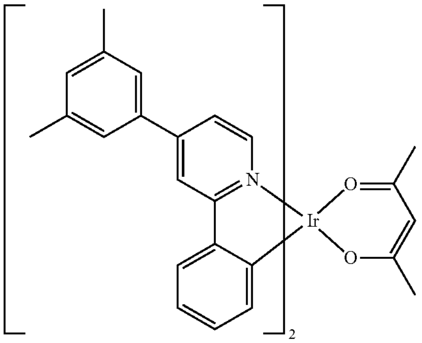
D-62
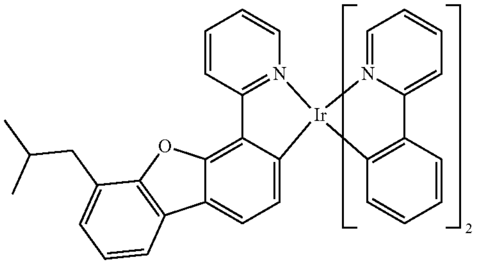
D-63
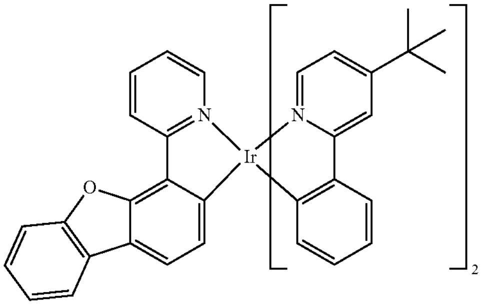
D-64
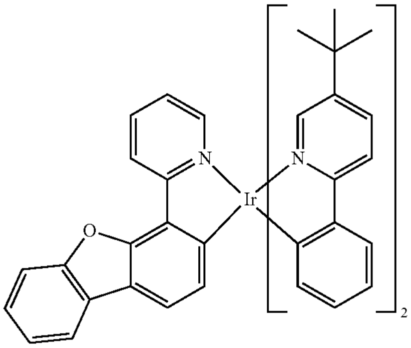
D-65
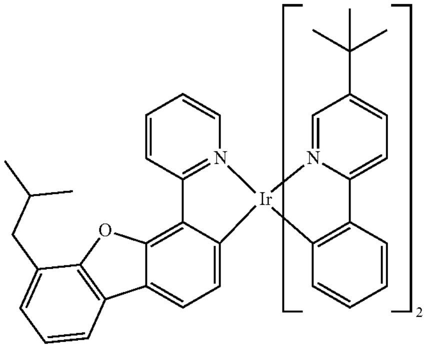
-continued
D-66
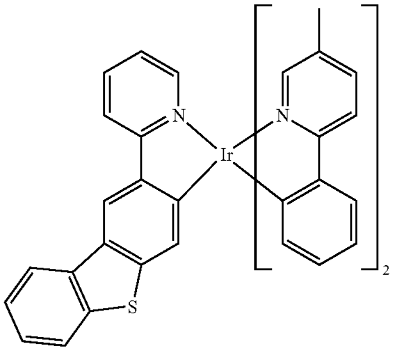
D-67
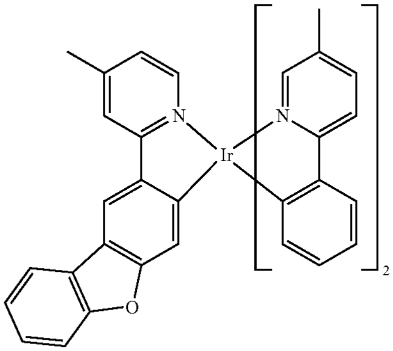
D-68
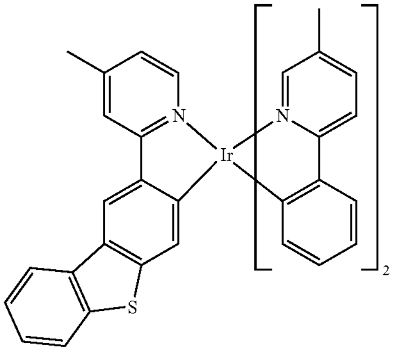
D-69
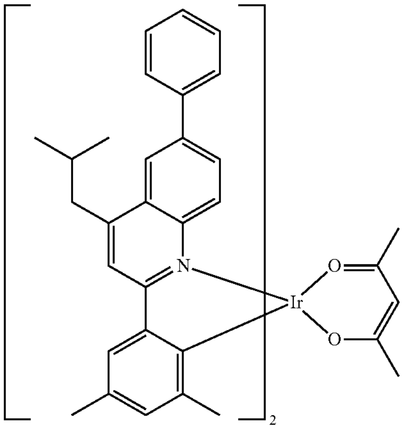

-continued
D-70
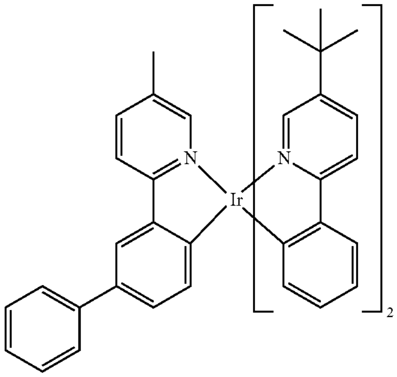
D-71
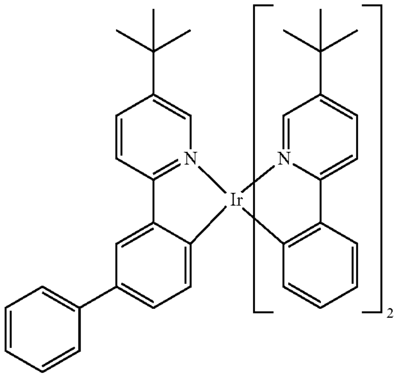
D-72
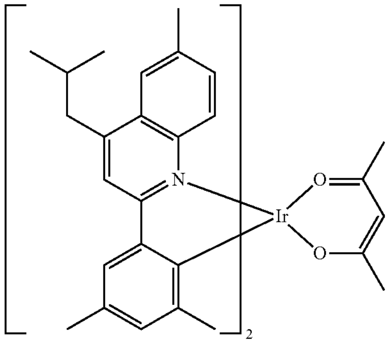
D-73
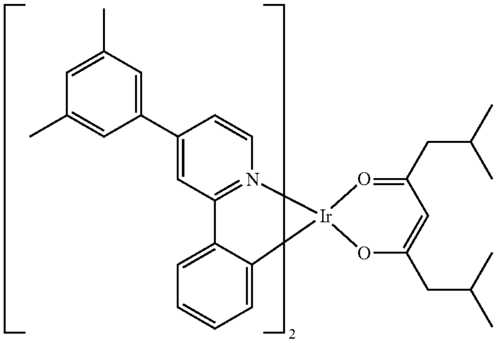
-continued
D-74
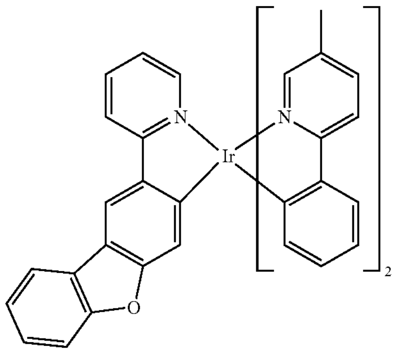
D-75
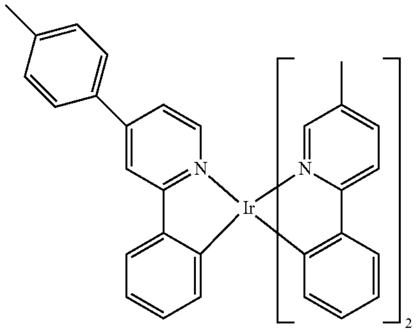
D-76
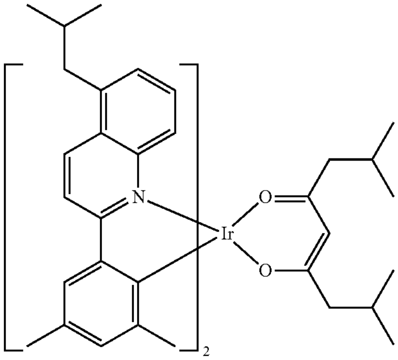
D-77
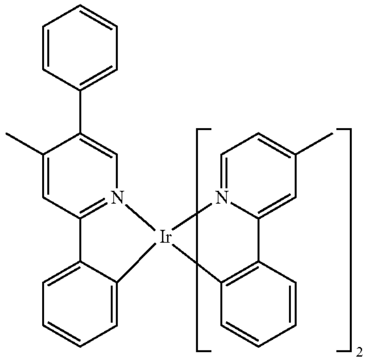

D-78
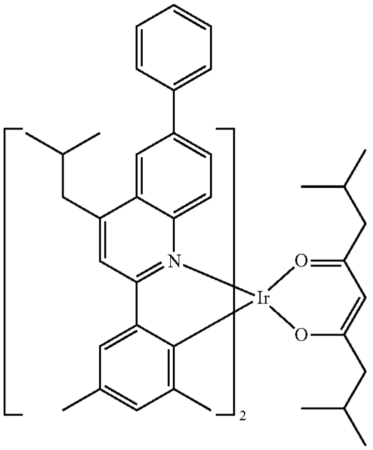
D-79
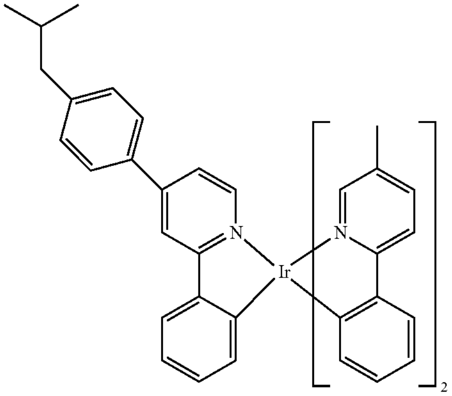
D-80
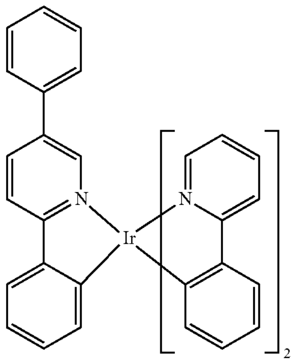
D-81
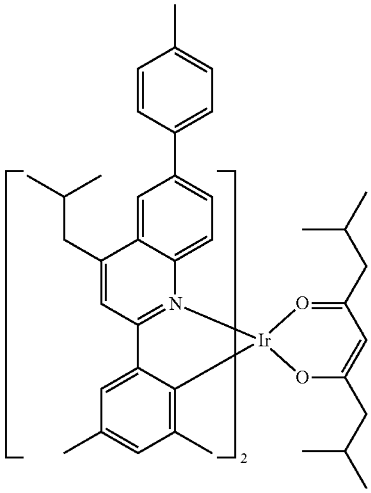
D-82
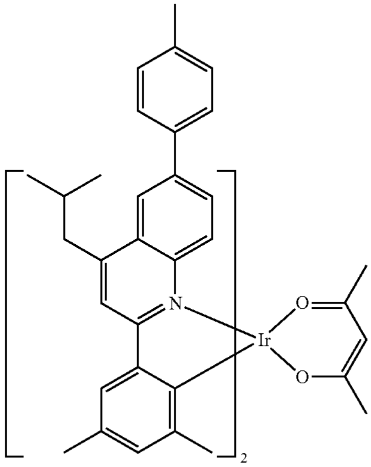
D-83
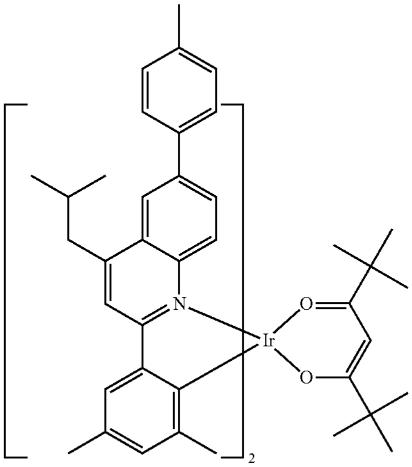

-continued
D-84
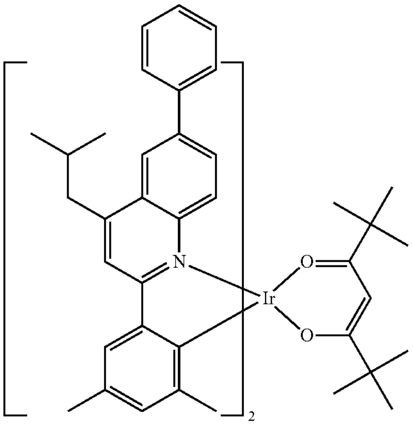
D-85
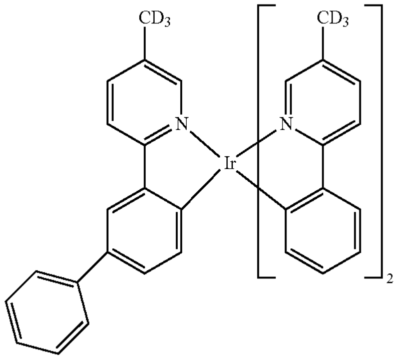
D-86
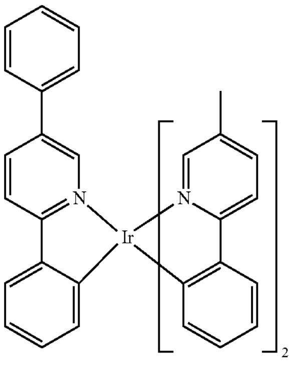
D-87
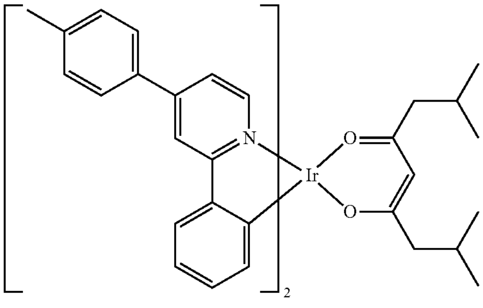
-continued
D-88
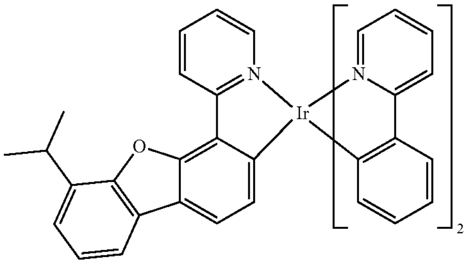
D-89
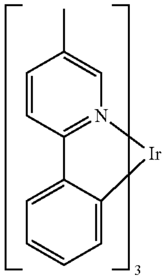
D-90
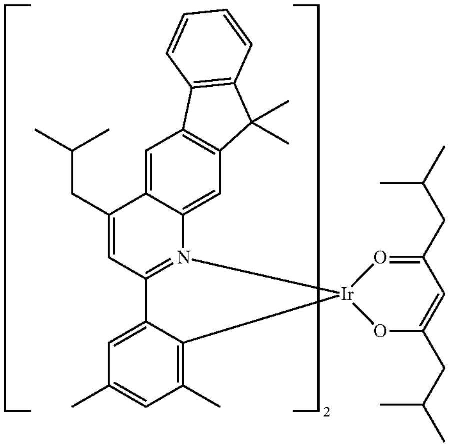
D-91
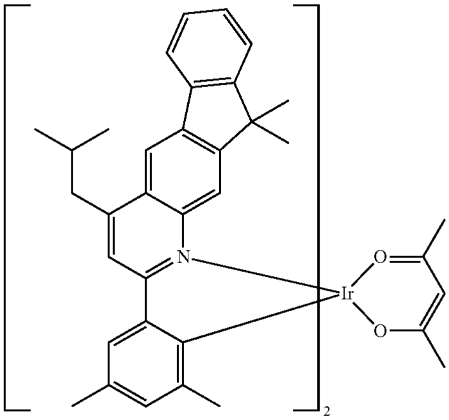

-continued
D-92
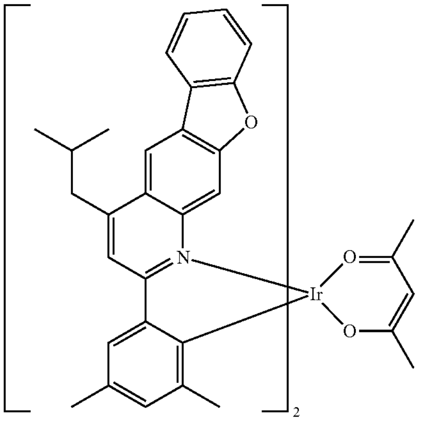
D-93
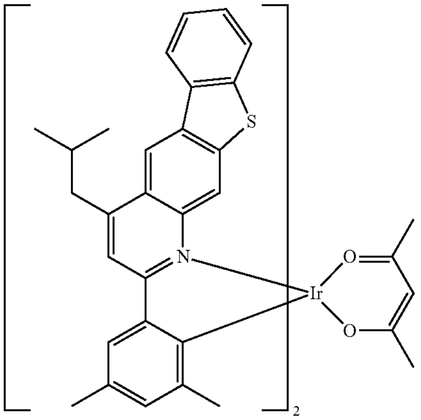
D-94
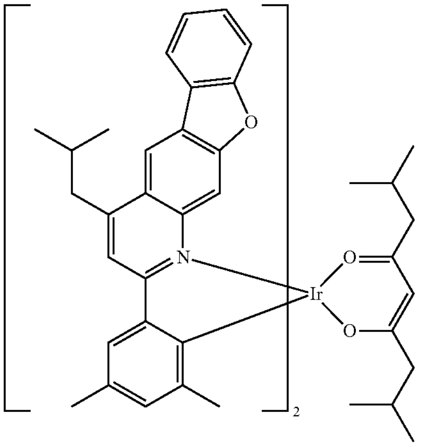
-continued
D-95
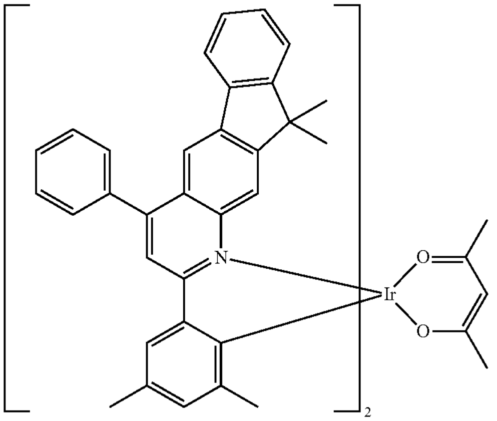
D-96
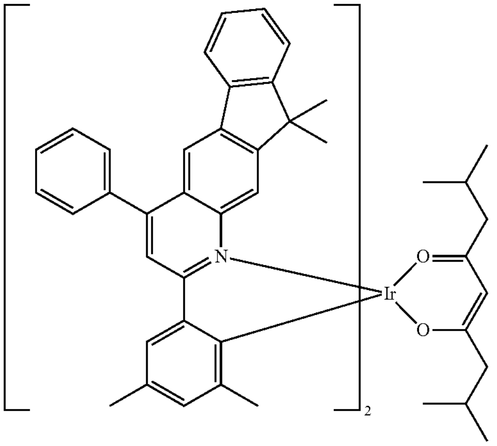
D-97
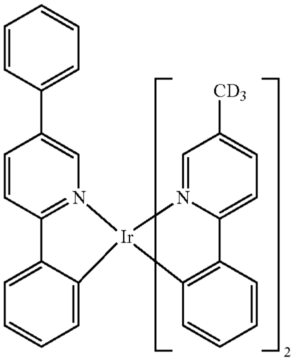
D-98
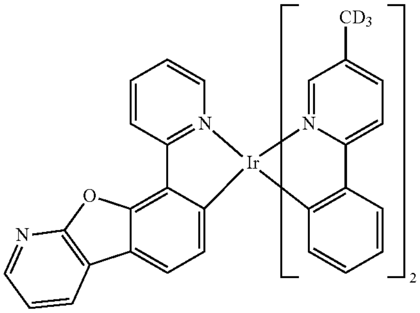

D-99
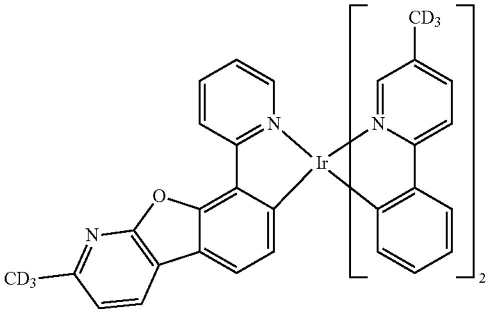
D-100
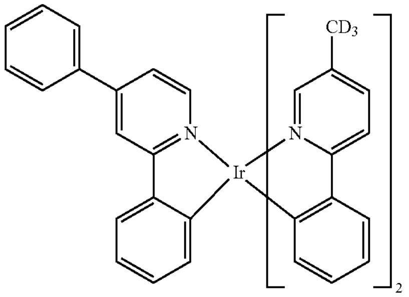
D-101
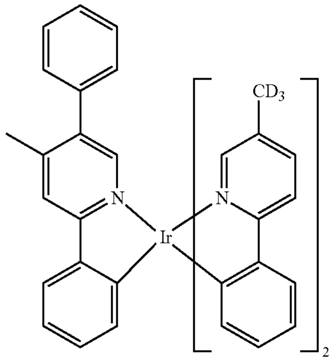
D-102
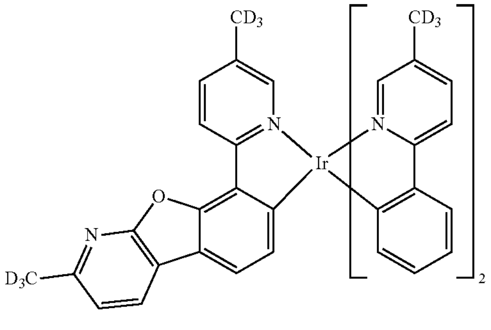
D-103
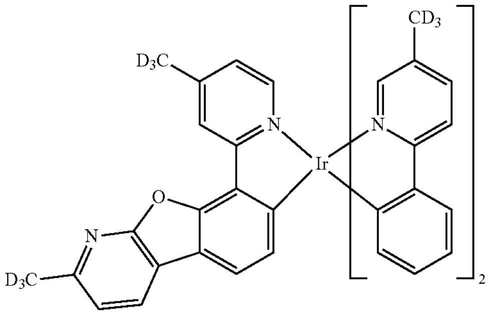
D-104
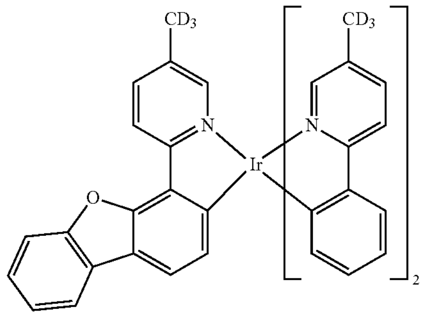
D-105
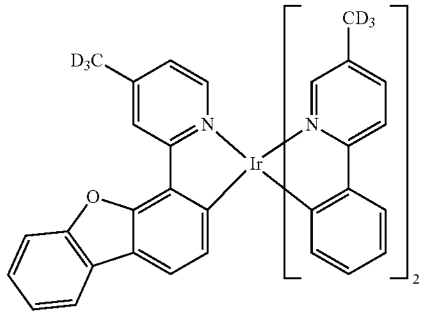
D-106
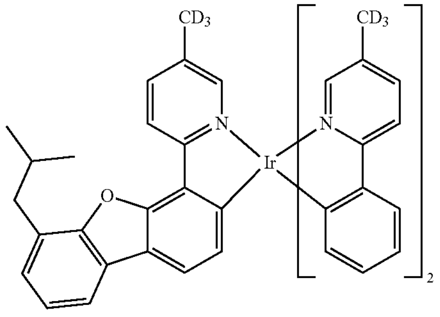
D-107
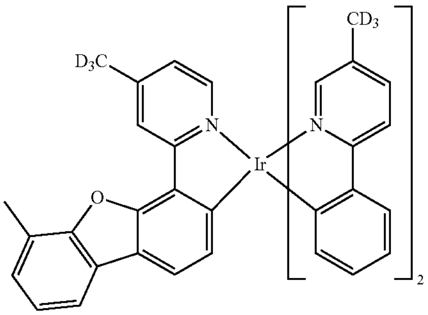

-continued
D-108
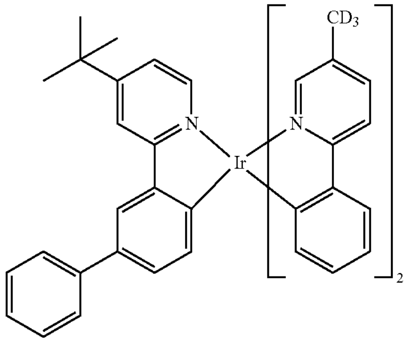
D-109
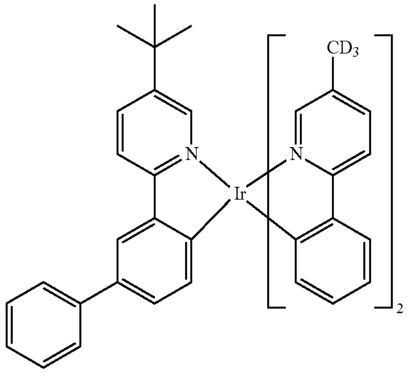
D-110
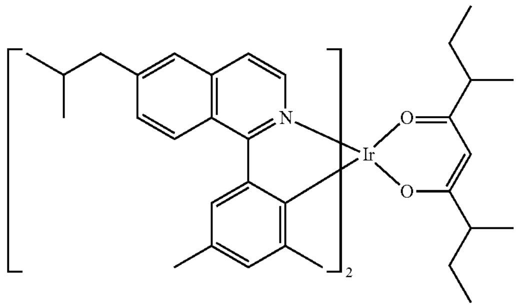
D-111
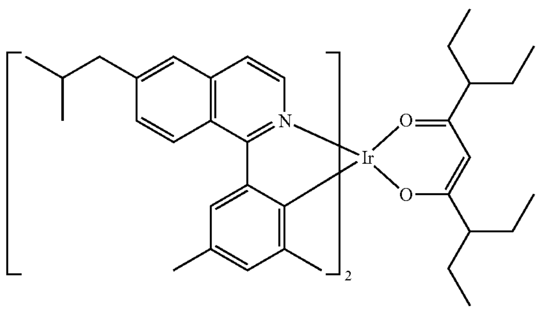
-continued
D-112
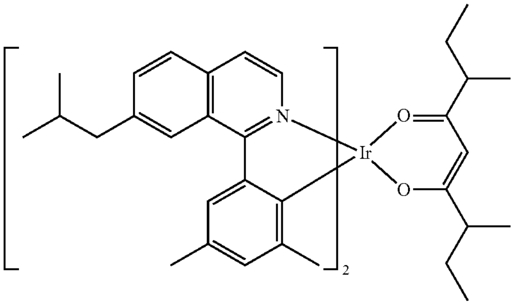
D-113
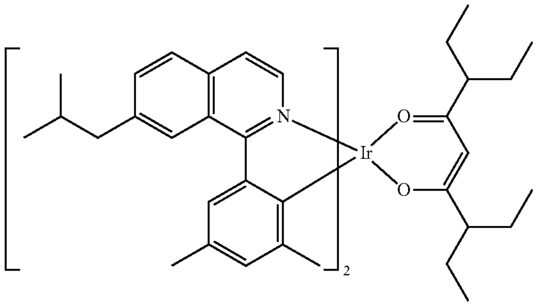
D-114
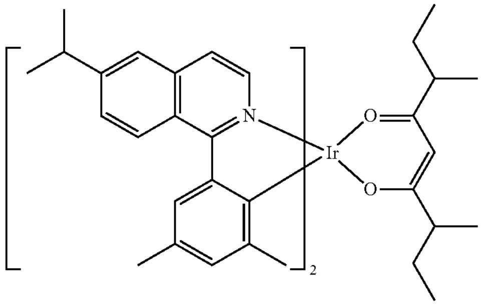
D-115
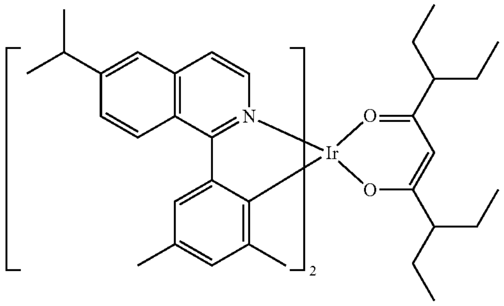
D-116
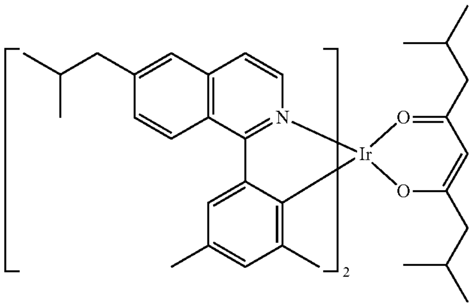

-continued
D-117
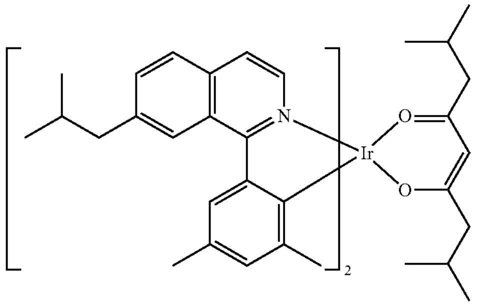
D-118
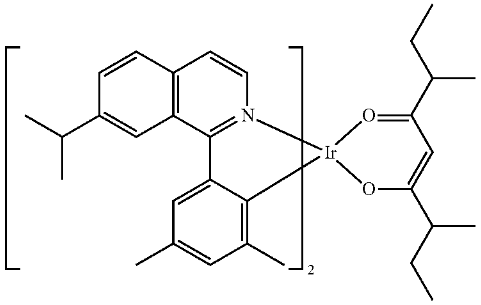
D-119
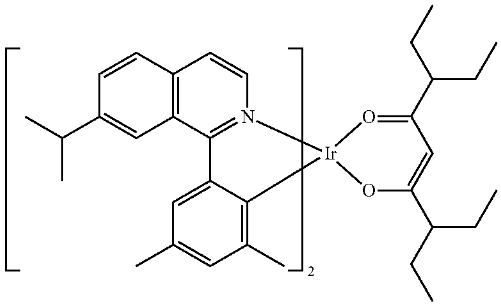
D-120
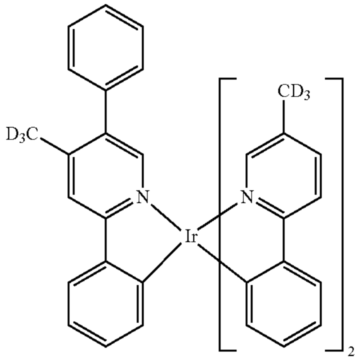
D-121
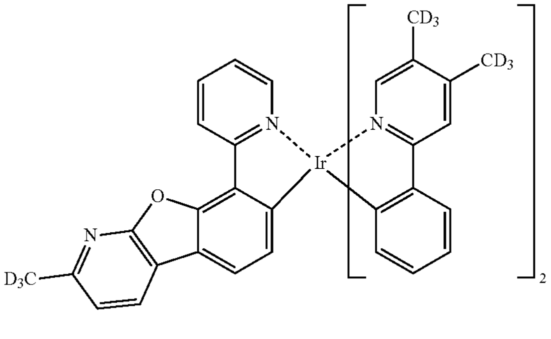
-continued
D-122
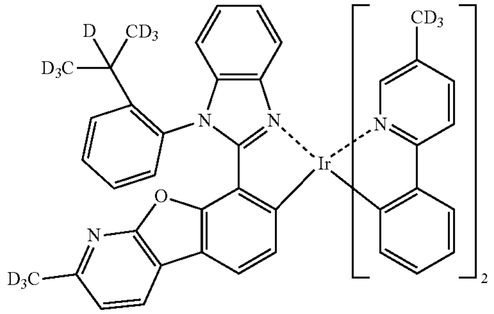
D-123
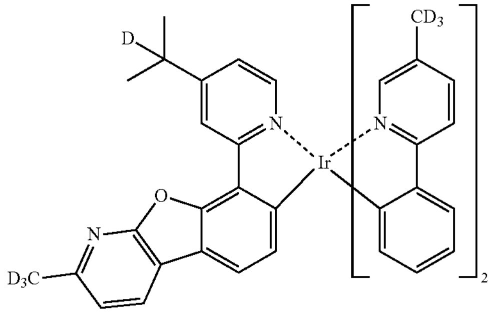
D-124
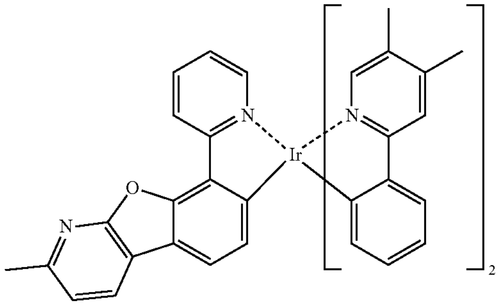
D-125
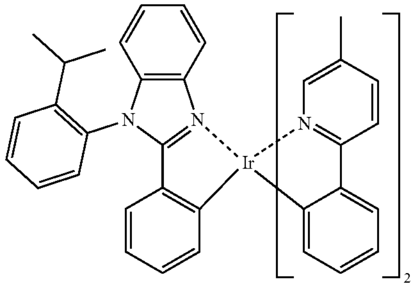
D-126
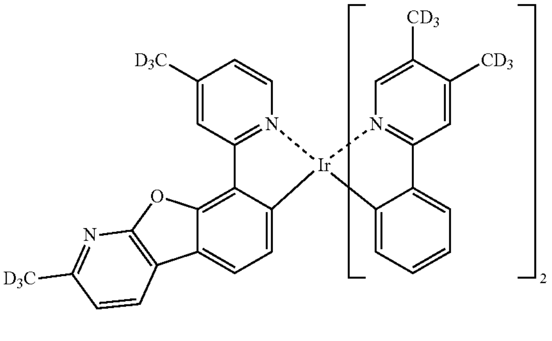

-continued
D-127
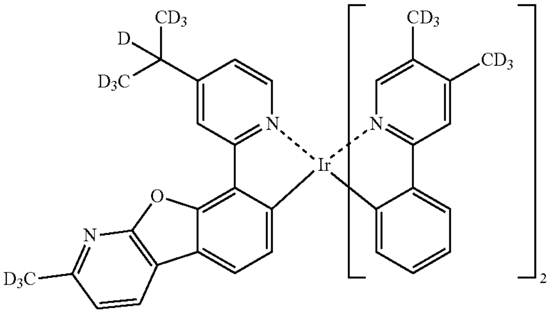
D-128
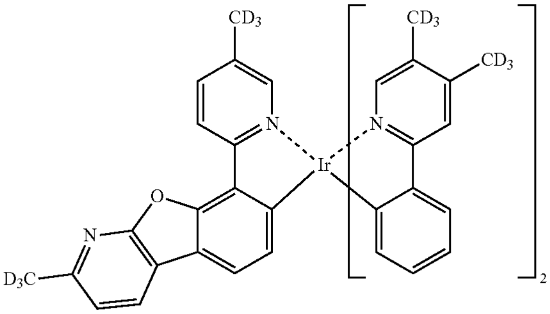
D129
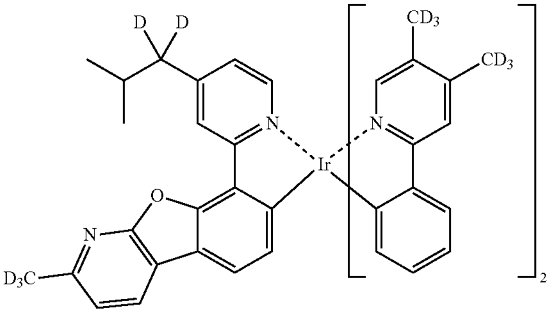
D-130
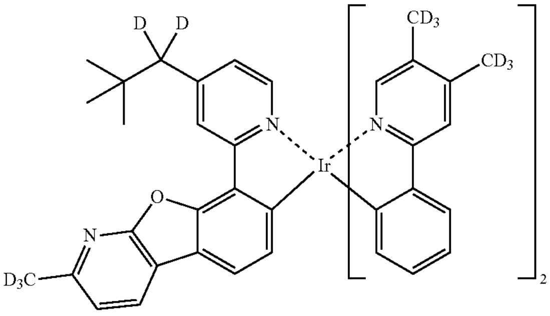
-continued
D-131
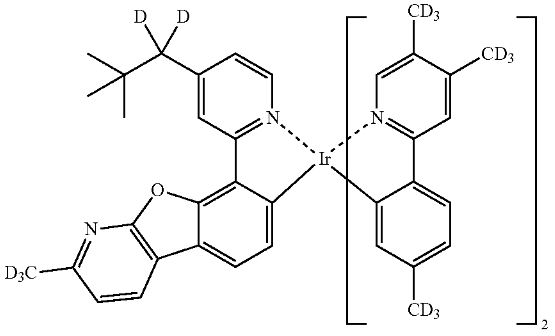
D-132
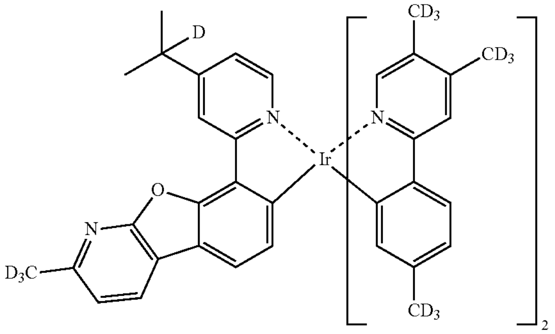
D-133
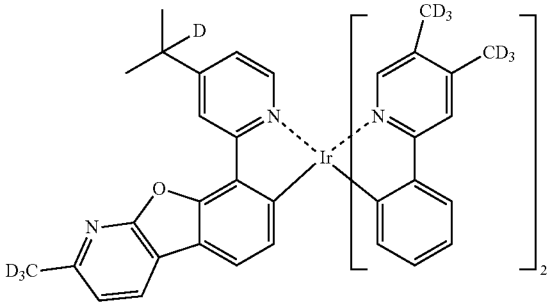
D-134
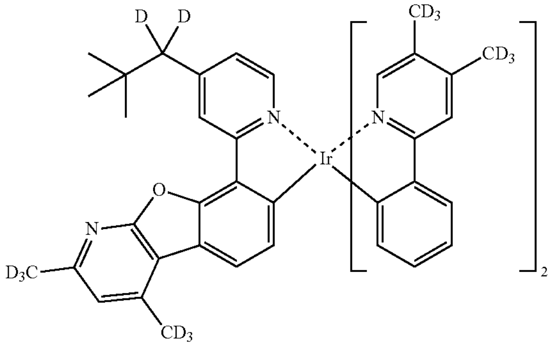

-continued
D-135
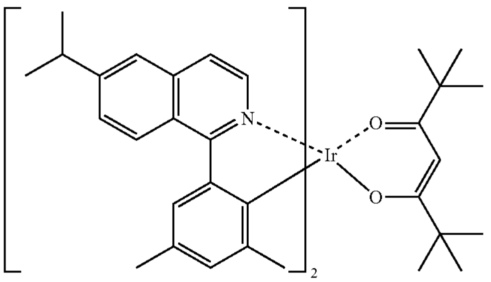
D-136
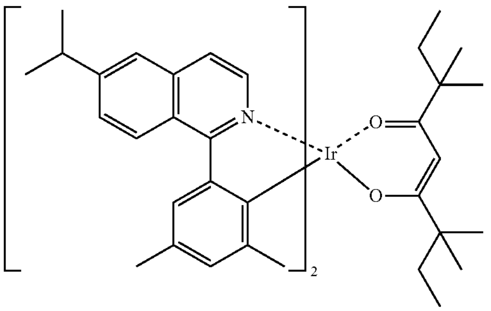
D-137
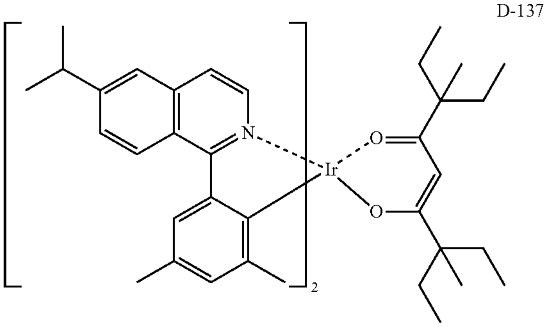
D-138
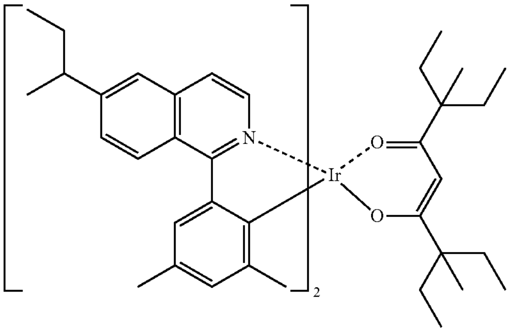
D-139
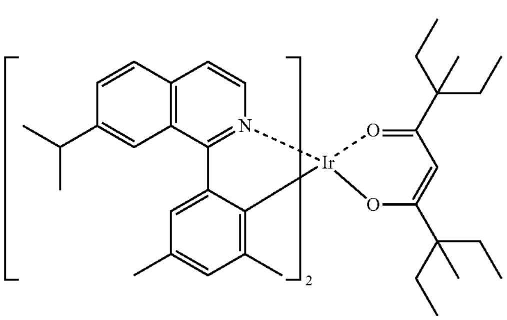
-continued
D-140
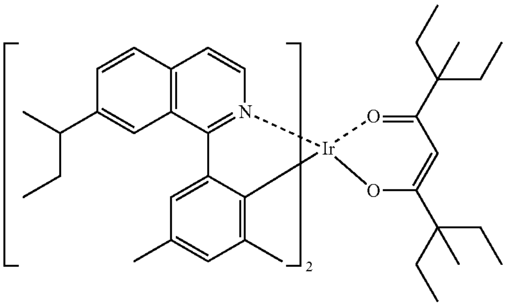
D-141
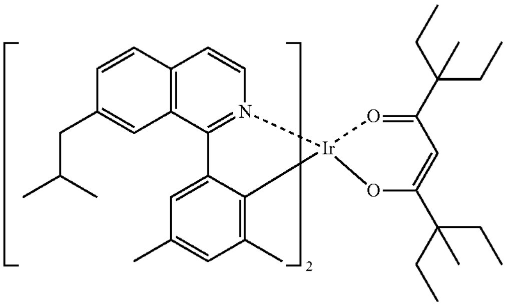
D-142
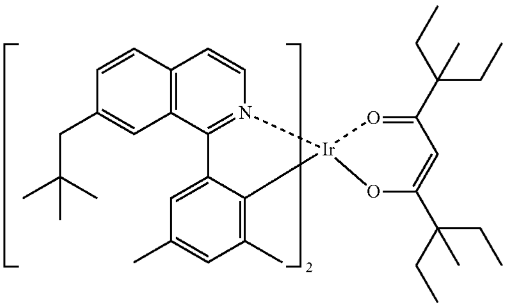
D-143
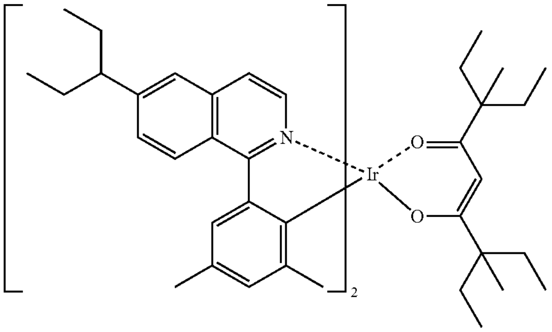

-continued

D-144

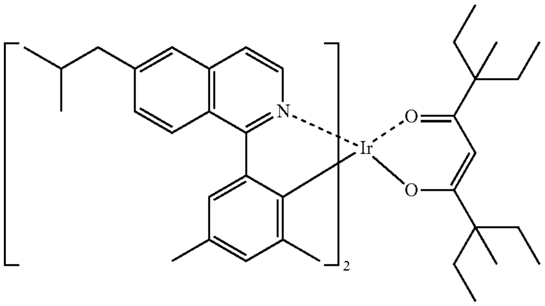

D-145

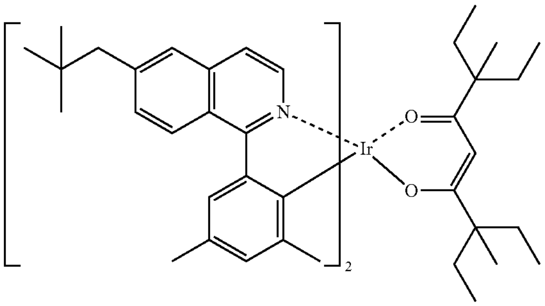

D-146

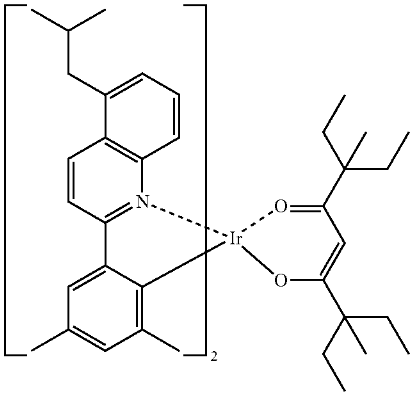

D-147

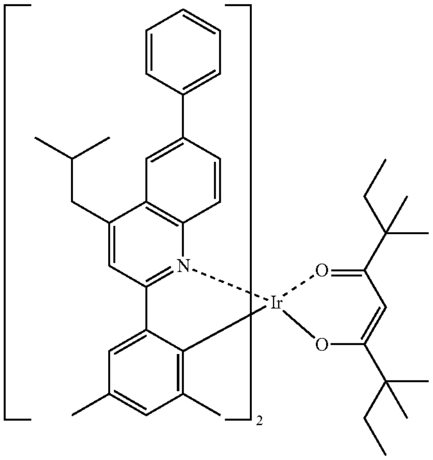

-continued

D-148

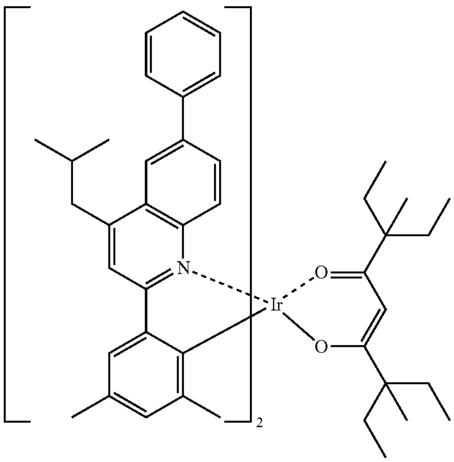

D-149

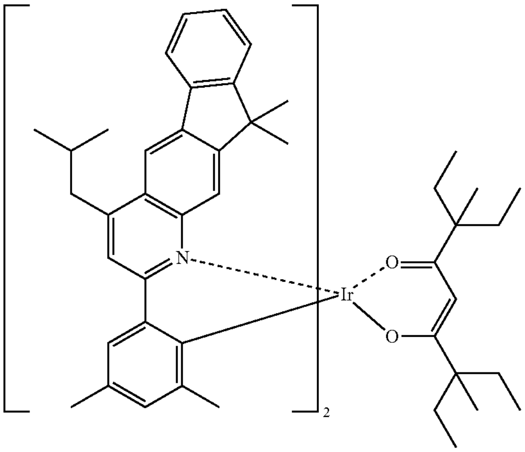

The present disclosure provides an organic electroluminescent device comprising an organic electroluminescent compound represented by formula 1 or a plurality of host materials according to the present disclosure. The organic electroluminescent device according to the present disclosure has a first electrode, a second electrode, and at least one organic layer between the first electrode and the second electrode.

One of the first and second electrodes may be an anode, and the other may be a cathode. The organic layer comprises a light-emitting layer and may further comprise at least one layer selected from a hole injection layer, a hole transport layer, a hole auxiliary layer, a light-emitting auxiliary layer, an electron transport layer, an electron buffer layer, an electron injection layer, an interlayer, a hole blocking layer, and an electron blocking layer. Each of the layers may be further configured as a plurality of layers.

The first and second electrodes may be respectively formed with a transparent conductive material, or a transflective or reflective conductive material. The organic electroluminescent device may be a top emission type, a bottom emission type, or a both-sides emission type, depending on the materials forming the first and second electrodes. In addition, the hole injection layer may be further doped with a p-dopant, and the electron injection layer may be further doped with an n-dopant.

The organic layer may further comprise at least one compound selected from the group consisting of an arylamine-based compound and a styrylarylamine-based compound.

In addition, in the organic electroluminescent device of the present disclosure, the organic layer may further comprise at least one metal selected from the group consisting of metals of Group 1, metals of Group 2, transition metals of the 4$^{th}$ period, transition metals of the 5$^{th}$ period, lanthanides, and organic metals of the d-transition elements of the Periodic Table, or at least one complex compound comprising the metal.

In addition, the organic electroluminescent device of the present disclosure may emit white light by further comprising at least one light-emitting layer, which comprises a blue, a red, or a green electroluminescent compound known in the field, besides the compound of the present disclosure. If necessary, it may further comprise a yellow or an orange light-emitting layer.

In the organic electroluminescent device of the present disclosure, preferably, at least one layer selected from a chalcogenide layer, a metal halide layer, and a metal oxide layer (hereinafter, "a surface layer") may be placed on an inner surface(s) of one or both electrode(s). Specifically, a chalcogenide (including oxides) layer of silicon or aluminum is preferably placed on an anode surface of an electroluminescent medium layer, and a metal halide layer or a metal oxide layer is preferably placed on a cathode surface of an electroluminescent medium layer. Such a surface layer provides operation stability for the organic electroluminescent device. Preferably, the chalcogenide includes $SiO_X$ ($1 \leq X \leq 2$), $AlO_X$($1 \leq X \leq 1.5$), SiON, SiAlON, etc.; the metal halide includes LiF, $MgF_2$, $CaF_2$, a rare earth metal fluoride, etc.; and the metal oxide includes $Cs_2O$, $Li_2O$, MgO, SrO, BaO, CaO, etc.

A hole injection layer, a hole transport layer, an electron blocking layer, or a combination thereof can be used between the anode and the light-emitting layer. The hole injection layer may be multi-layers in order to lower the hole injection barrier (or hole injection voltage) from the anode to the hole transport layer or the electron blocking layer, wherein each of the multi-layers may use two compounds simultaneously. The hole transport layer or the electron blocking layer may also be multi-layers.

An electron buffer layer, a hole blocking layer, an electron transport layer, an electron injection layer, or a combination thereof can be used between the light-emitting layer and the cathode. The electron buffer layer may be multi-layers in order to control the injection of the electron and improve the interfacial properties between the light-emitting layer and the electron injection layer, wherein each of the multi-layers may use two compounds simultaneously. The hole blocking layer or the electron transport layer may also be multi-layers, wherein each of the multi-layers may use a plurality of compounds.

The light-emitting auxiliary layer may be placed between the anode and the light-emitting layer, or between the cathode and the light-emitting layer. When the light-emitting auxiliary layer is placed between the anode and the light-emitting layer, it can be used for promoting the hole injection and/or hole transport, or for preventing the overflow of electrons. When the light-emitting auxiliary layer is placed between the cathode and the light-emitting layer, it can be used for promoting the electron injection and/or electron transport, or for preventing the overflow of holes. Also, the hole auxiliary layer may be placed between the hole transport layer (or hole injection layer) and the light-emitting layer, and may be effective to promote or block the hole transport rate (or hole injection rate), thereby enabling the charge balance to be controlled. Further, the electron blocking layer may be placed between the hole transport layer (or hole injection layer) and the light-emitting layer, and can confine the excitons within the light-emitting layer by blocking the overflow of electrons from the light-emitting layer to prevent a light-emitting leakage. When an organic electroluminescent device includes two or more hole transport layers, the hole transport layer which is further included, may be used as a hole auxiliary layer or an electron blocking layer. The light-emitting auxiliary layer, the hole auxiliary layer or the electron blocking layer may have an effect of improving the efficiency and/or the lifetime of the organic electroluminescent device.

Preferably, in the organic electroluminescent device of the present disclosure, a mixed region of an electron transport compound and a reductive dopant, or a mixed region of a hole transport compound and an oxidative dopant may be placed on at least one surface of a pair of electrodes. In this case, the electron transport compound is reduced to an anion, and thus it becomes easier to inject and transport electrons from the mixed region to the light-emitting medium. Furthermore, the hole transport compound is oxidized to a cation, and thus it becomes easier to inject and transport holes from the mixed region to the light-emitting medium. Preferably, the oxidative dopant includes various Lewis acids and acceptor compounds; and the reductive dopant includes alkali metals, alkali metal compounds, alkaline earth metals, rare-earth metals, and mixtures thereof. In addition, the reductive dopant layer may be employed as a charge-generating layer to prepare an organic electroluminescent device having two or more light-emitting layers and emitting white light.

The organic electroluminescent material according to the present disclosure may be used as a light-emitting material for a white organic light-emitting device. The white organic light-emitting device has been suggested to have various structures such as a side-by-side structure or a stacking structure depending on the arrangement of R (red), G (green) or YG (yellow green), and B (blue) light-emitting parts, or color conversion material (CCM) method, etc. The organic electroluminescent material according to the present disclosure may also be used in an organic electroluminescent device comprising a quantum dot (QD).

In order to form each layer of the organic electroluminescent device of the present disclosure, dry film-forming methods such as vacuum evaporation, sputtering, plasma, ion plating methods, etc., or wet film-forming methods such as ink jet printing, nozzle printing, slot coating, spin coating, dip coating, flow coating methods, etc., can be used. The first host compound and the second host compound of the present disclosure may be film-formed by a co-evaporation process or a mixture-evaporation process.

When using a wet film-forming method, a thin film can be formed by dissolving or diffusing materials forming each layer into any suitable solvent such as ethanol, chloroform, tetrahydrofuran, dioxane, etc. The solvent can be any one where the materials forming each layer can be dissolved or diffused, and where there are no problems in film-formation capability.

In addition, it is possible to produce a display system, e.g., a display system for smart phones, tablets, notebooks, PCs, TVs, or cars; or a lighting system, e.g., an outdoor or indoor lighting system, by using the organic electroluminescent device of the present disclosure.

Hereinafter, the preparation method of the compounds according to the present disclosure and the properties thereof will be explained in detail with reference to the representative compounds of the present disclosure. However, the present disclosure is not limited by the following examples.

Example 1: Preparation of Compound C-8

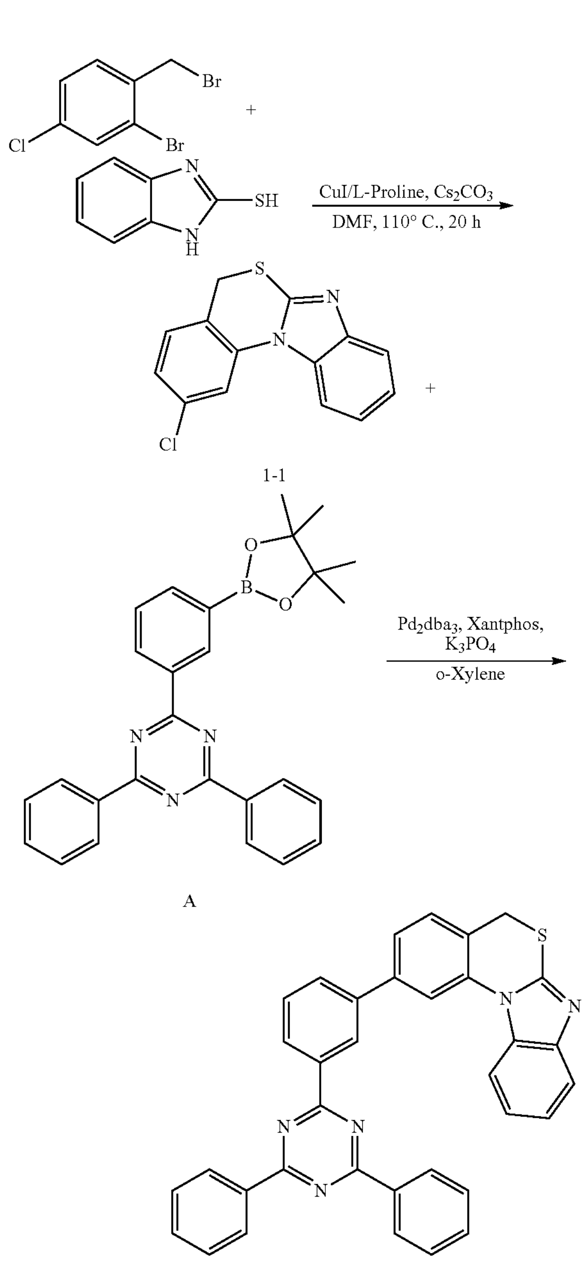

1-1

A

C-8

Synthesis of Compound 1-1

In a flask, 2-bromo-1-(bromomethyl)-4-chlorobenzene (30 g, 105.49 mmol), 1H-benzo[d]imidazole-2-thiol (15.8 g, 105.49 mmol), CuI (502 mg, 2.637 mmol), L-Proline (607 mg, 5.274 mmol), and $Cs_2CO_3$ (85 g, 263.72 mmol) were dissolved in 530 mL of N,N-dimethylformamide (DMF), and the mixture was refluxed at 130° C. for 6 hours. After completion of the reaction, the mixture was added dropwise to methanol, and the resulting solid was filtered to obtain compound 1-1 (24.9 g, yield: 89%).

Synthesis of Compound C-8

Compound 1-1 (5 g, 18.36 mmol), compound A (9.5 g, 22.03 mmol), $Pd_2dba_3$ (840 mg, 0.918 mmol), Xantphos (1 g, 1.836 mmol), and $K_3PO_4$ (9.7 g, 45.90 mmol) were dissolved in 150 mL of o-xylene, and the mixture was refluxed at 180° C. for 6 hours. The mixture was cooled to room temperature, and distilled water was added thereto. An organic layer was extracted with methylene chloride (MC), and dried with magnesium sulfate. The residue was distilled under reduced pressure, and separated by column chromatography to obtain compound C-8 (3.6 g, yield: 36%).

| | MW | M.P. |
|---|---|---|
| C-8 | 545.66 | 316.4° C. |

Example 2: Preparation of Compound C-31

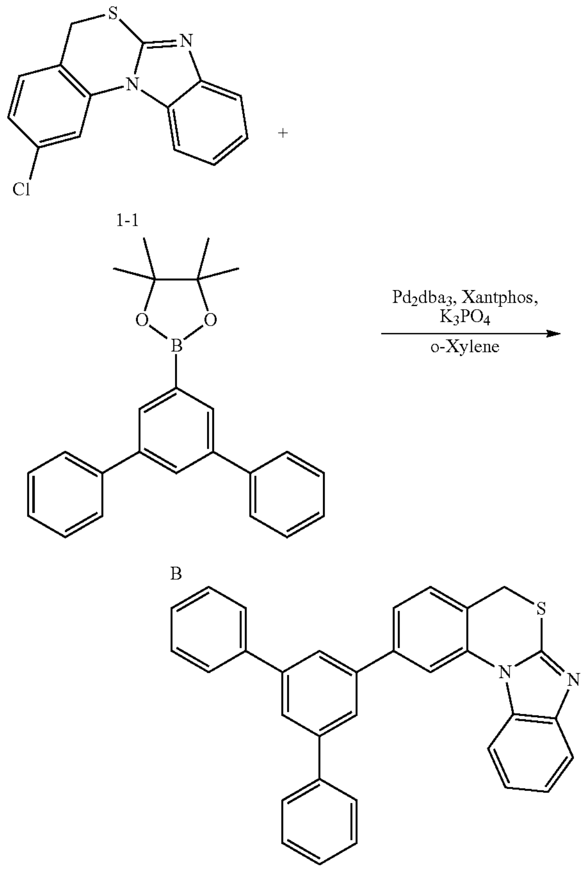

1-1

B

C-31

Compound 1-1 (5 g, 18.36 mmol), compound B (7.8 g, 22.03 mmol), $Pd_2dba_3$ (840 mg, 0.918 mmol), Xantphos (1 g, 1.836 mmol), and $K_3PO_4$ (9.7 g, 45.90 mmol) were dissolved in 150 mL of o-xylene, and the mixture was refluxed at 180° C. for 6 hours. The mixture was cooled to room temperature, and distilled water was added thereto. An organic layer was extracted with MC, and dried with magnesium sulfate. The residue was distilled under reduced pressure, and separated by column chromatography to obtain compound C-31 (1.1 g, yield: 13%).

| | MW | M.P. |
|---|---|---|
| C-31 | 466.60 | 174.3° C. |

Example 3 Preparation of Compound C-83

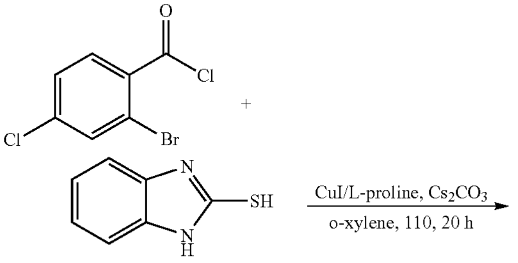

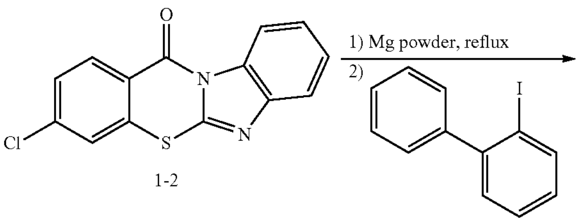

1-2

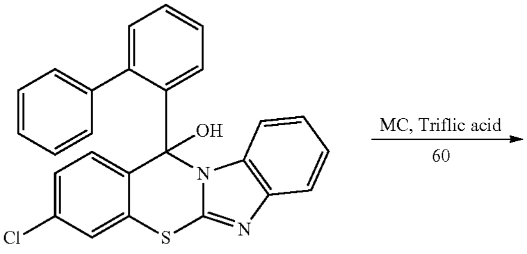

1-3

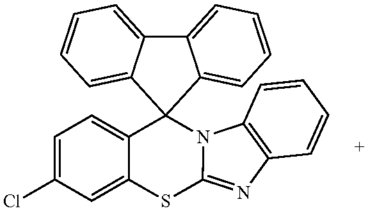

1-4

-continued

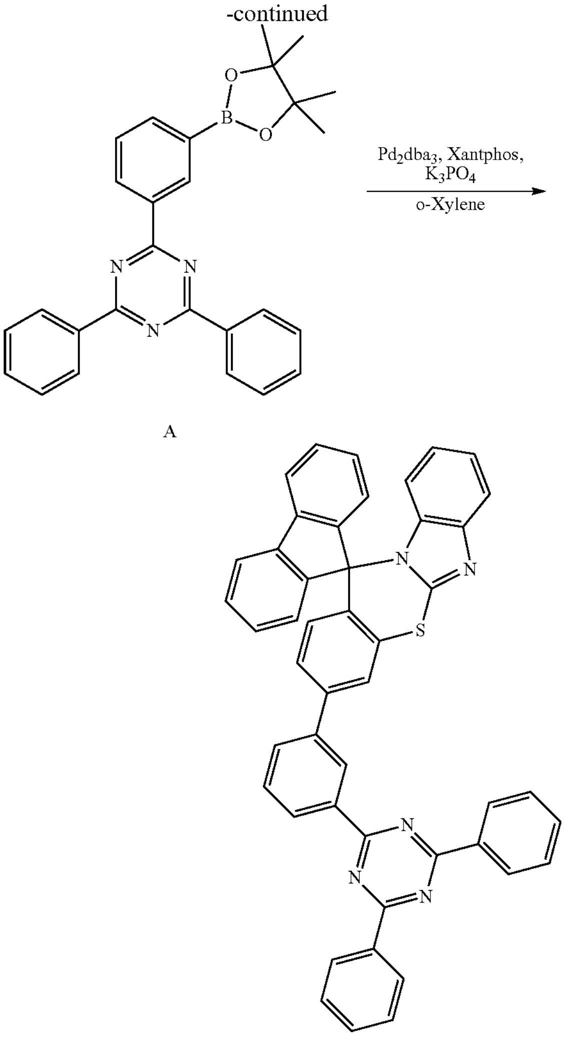

A

C-83

Synthesis of Compound 1-2

In a flask, 2-bromo-4-chlorobenzoyl chloride (45 g, 177.2 mmol), 2-mercaptobenzimidazole (20.5 g, 136.31 mmol), CuI (1.3 g, 6.81 mmol), L-Proline (1.57 g, 13.63 mmol), and $Cs_2CO_3$ (22.2 g, 22.2 mmol) were dissolved in 150 mL of o-xylene, and the mixture was refluxed at 110° C. for 20 hours. The mixture was cooled to room temperature, and distilled water was added thereto. An organic layer was extracted with MC, and dried with magnesium sulfate. The residue was distilled under reduced pressure, and separated by column chromatography to obtain compound 1-2 (18.9 g, yield: 46%).

Synthesis of Compound 1-3

In the first flask, 2-iodobiphenyl (18.6 mL, 105.64 mmol) and Mg powder (2.57 g, 105.64 mmol) were dissolved in 40 mL of tetrahydrofuran (THE), and the mixture was fluxed at 60° C. for 3 hours. In the second flask, compound 1-2 (23.3 g, 81.26 mmol) was dissolved in 40 mL of THF. The reaction product in the second flask was added to that in the first flask, and they were refluxed at 60° C. for 15 hours. The mixture was cooled to room temperature, and distilled water was added thereto. An organic layer was extracted with MC, and dried with magnesium sulfate. The residue was distilled under reduced pressure, and separated by column chromatography to obtain compound 1-3 (25 g, overyield).

Synthesis of Compound 1-4

In a flask, 25 g of compound 1-3 was dissolved in 20 mL of triflic acid and 50 mL MC, and the mixture was refluxed at 60° C. for 15 hours. The mixture was cooled to room temperature, and distilled water was added thereto. An organic layer was extracted with MC, and dried with magnesium sulfate. The residue was distilled under reduced pressure, and separated by column chromatography to obtain compound 1-4 (5 g, yield: 15%).

Synthesis of Compound C-83

Compound 1-4 (100 mg, 0.23 mmol), compound A (122 mg, 0.28 mmol), $Pd_2dba_3$ (11 mg, 0.012 mmol), Xantphos (13 mg, 0.023 mmol), and $K_3PO_4$ (124 mg, 0.58 mmol) were dissolved in 150 mL of o-xylene, and the mixture was refluxed at 180° C. for 6 hours. The mixture was cooled to room temperature, and distilled water was added thereto. An organic layer was extracted with MC, and dried with magnesium sulfate. The residue was distilled under reduced pressure, and separated by column chromatography to obtain compound C-83 (100 mg, yield: 61%).

| | MW | M.P. |
|---|---|---|
| C-83 | 695.83 | 194.5° C. |

Hereinafter, the luminous efficiency properties of an organic electroluminescent device (OLED) according to the present disclosure will be explained in detail. However, the following examples merely illustrate the properties of an OLED according to the present disclosure, but the present disclosure is not limited to the following examples.

Device Example 1: Producing a Green OLED Comprising the Compound According to the Present Disclosure An OLED according to the present disclosure was produced. A transparent electrode indium tin oxide (ITO) thin film (10 Ω/sq) on a glass substrate for an OLED (GEOMATEC CO., LTD., Japan) was subjected to an ultrasonic washing with acetone and isopropyl alcohol, sequentially, and then was stored in isopropanol. The ITO substrate was then mounted on a substrate holder of a vacuum vapor deposition apparatus. Compound HI-1 was introduced into a cell of the vacuum vapor deposition apparatus, and compound HT-1 was introduced into another cell of the vacuum vapor deposition apparatus. The two materials were evaporated at different rates, and compound HI-1 was deposited in a doping amount of 3 wt % based on the total amount of compound HI-1 and compound HT-1 to form a hole injection layer having a thickness of 10 nm on the ITO substrate. Next, compound HT-1 was deposited on the hole injection layer to form a first hole transport layer having a thickness of 80 nm. Compound HT-4 was then introduced into another cell of the vacuum vapor deposition apparatus and was evaporated by applying an electric current to the cell, thereby forming a second hole transport layer having a thickness of 30 nm on the first hole transport layer. After forming the hole injection layer and the hole transport layers, a light-emitting layer was formed thereon as follows: Compound C-8 was introduced into one cell of the vacuum vapor deposition apparatus as a host, and compound D-130 was introduced into another cell as a dopant. The two materials were evaporated at different rates and the dopant was deposited in a doping amount of 10 wt % based on the total amount of the host and dopant to form a light-emitting layer having a thickness of 40 nm on the second hole transport layer. Next, compound ETL-1 and compound EIL-1 were deposited at a weight ratio of 40:60 to form an electron transport layer having a thickness of 35 nm on the light-emitting layer. After depositing compound EIL-1 as an electron injection layer having a thickness of 2 nm on the electron transport layer, an Al cathode having a thickness of 80 nm was deposited on the electron injection layer by another vacuum vapor deposition apparatus. Thus, an OLED was produced. All the materials used for producing the OLED were purified by vacuum sublimation at $10^{-6}$ torr.

Comparative Example 1: Producing an OLED Comprising A Conventional Compound

An OLED was produced in the same manner as in Device Example 1, except for the following: Compound CBP as a host and compound D-130 as a dopant were used to form a light-emitting layer having a thickness of 40 nm on the second hole transport layer. Next, compound Balq was deposited as a hole blocking layer of a thickness of 5 nm on the light-emitting layer. Thereafter, compound ETL-1 and compound EIL-1 were deposited at a weight ratio of 40:60 to form an electron transport layer having a thickness of 30 nm on the hole blocking layer.

The driving voltage, power efficiency, and light-emitting color at a luminance of 1,000 nit of the OLEDs produced in Device Example 1 and Comparative Example 1 are provided in Table 1 below.

TABLE 1

| | Host | Driving Voltage [V] | Power Efficiency [lm/W] | Light-Emitting Color |
|---|---|---|---|---|
| Device Example 1 | C-8 | 3.3 | 73.3 | Green |
| Comparative Example 1 | CBP | 6.0 | 44.2 | Green |

Device Example 2: Producing a Green OLED According to the Present Disclosure An OLED was produced in the same manner as in Device Example 1, except that the second hole transport layer, the light-emitting layer, and the electron transport layer were deposited as follows: As the second hole transport layer, compound HT-3 was introduced into another cell of the vacuum vapor deposition apparatus and was evaporated by applying an electric current to the cell, thereby forming a second hole transport layer having a thickness of 60 nm on the first hole transport layer. As the light-emitting layer, compound C-8 and compound H-131 were introduced into two cells of the vacuum vapor deposition apparatus as hosts, and compound D-130 was introduced into another cell as a dopant. The two host materials were evaporated at a rate of 1:2 (the first host: the second host) and the dopant material was simultaneously evaporated at a different rate, and the dopant was deposited in a doping amount of 10 wt % based on the total amount of the hosts and the dopant to form a light-emitting layer having a thickness of 40 nm on the second hole transport layer. Next, compound ETL-1 and compound EIL-1 were deposited at a weight ratio of 40:60 to form an electron transport layer having a thickness of 35 nm on the light-emitting layer.

Comparative Example 2: Producing an OLED Comprising a Conventional Compound as a Host An OLED was produced in the same manner as in Device Example 2, except for the following: Compound CBP as a single host and compound D-130 as a dopant were used to form a light-emitting layer having a thickness of 40 nm on the second hole transport layer. Compound Balq was deposited as a hole blocking layer of a thickness of 5 nm on the light-emitting layer. Next, compound ETL-1 and compound EIL-1 were deposited at a weight ratio of 40:60 to form an electron transport layer having a thickness of 30 nm on the hole blocking layer.

The driving voltage, luminous efficiency, and light-emitting color at a luminance of 1,000 nit of the OLEDs produced in Device Example 2 and Comparative Example 2 are provided in Table 2 below.

TABLE 2

| | First Host | Second Host | Driving Voltage [V] | Luminous Efficiency [cd/A] | Light-Emitting Color |
|---|---|---|---|---|---|
| Device Example 2 | C-8 | H-131 | 3.3 | 101.0 | Green |
| Comparative Example 2 | CBP | — | 5.8 | 79.5 | Green |

Device Example 3: Producing a Red OLED According to the Present Disclosure

An OLED was produced in the same manner as in Device Example 1, except that the second hole transport layer, the light-emitting layer, and the electron transport layer were deposited as follows: As the second hole transport layer, compound HT-2 was introduced into another cell of the vacuum vapor deposition apparatus and was evaporated by applying an electric current to the cell, thereby forming a second hole transport layer having a thickness of 60 nm on the first hole transport layer. As the light-emitting layer, the first host compound and the second host compound shown in Table 3 below were introduced into two cells of the vacuum vapor deposition apparatus as hosts, and compound D-39 was introduced into another cell as a dopant. The two host materials were evaporated at a rate of 1:1 (the first host: the second host) and the dopant material was simultaneously evaporated at a different rate, and the dopant was deposited in a doping amount of 3 wt % based on the total amount of the hosts and the dopant to form a light-emitting layer having a thickness of 40 nm on the second hole transport layer. Next, compound ETL-1 and compound EIL-1 were deposited at a weight ratio of 50:50 to form an electron transport layer having a thickness of 35 nm on the light-emitting layer.

Comparative Example 3: Producing an OLED Comprising a Comparative Compound as a Host An OLED was produced in the same manner as in Device Example 3, except that the first host compound shown in Table 3 below was used as a single host of the light-emitting layer.

The driving voltage, luminous efficiency, and light-emitting color at a luminance of 1,000 nit of the OLEDs produced in Device Example 3 and Comparative Example 3 are provided in Table 3 below.

TABLE 3

| | First Host | Second Host | Driving Voltage [V] | Luminous Efficiency [cd/A] | Light-Emitting Color |
|---|---|---|---|---|---|
| Comparative Example 3 | CBP | — | 9.0 | 14.3 | Red |
| Device Example 3 | C-8 | H-45 | 3.1 | 31.2 | Red |

From Tables 1 to 3 above, it can be confirmed that the OLEDs using the compound represented by formula 1 of the present disclosure as a host material exhibit improved driving voltage and/or luminous efficiency properties compared to the OLEDs using the conventional compound. It can also be confirmed that the OLEDs using a plurality of host materials comprising a compound represented by formula 1 and a compound represented by formula 2 or 3 exhibit higher luminous efficiency while having a lower driving voltage compared to the OLEDs using a conventional compound as a single host material.

The compounds used in the Device Examples and the Comparative Examples are shown in Table 4 below.

TABLE 4

Hole Injection Layer/ Hole Transport Layer

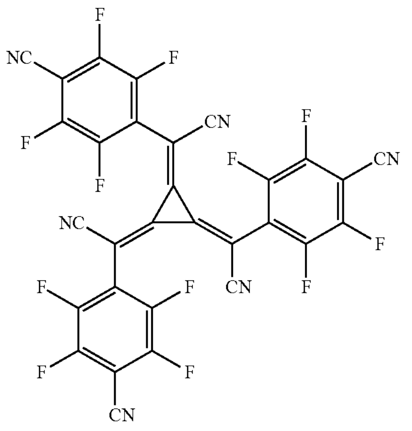

HI-1

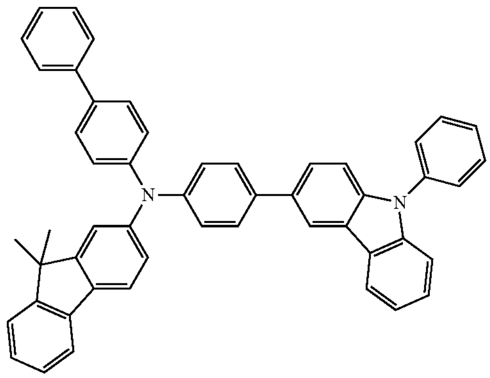

HT-1

TABLE 4-continued
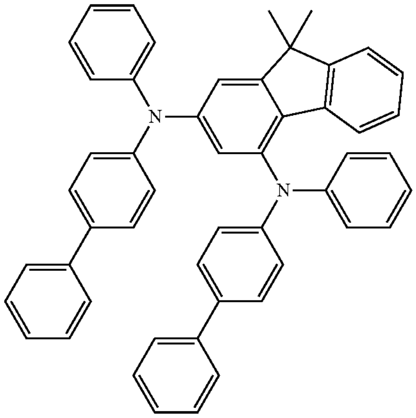
HT-2
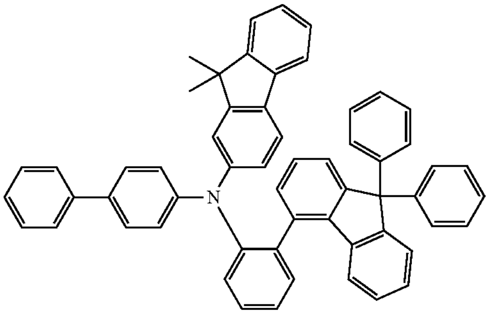
HT-3
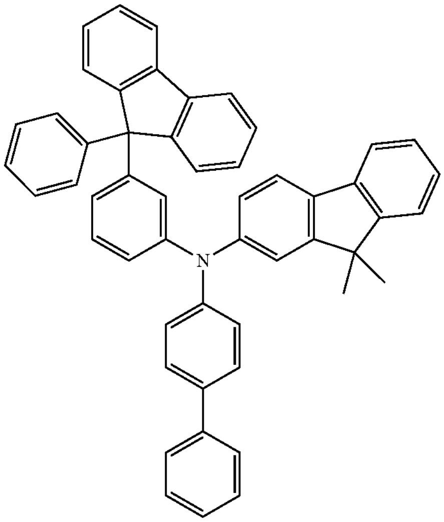
HT-4
TABLE 4-continued
Light-Emitting Layer
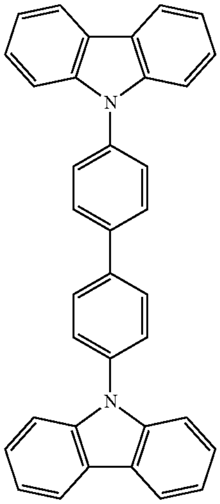
CBP
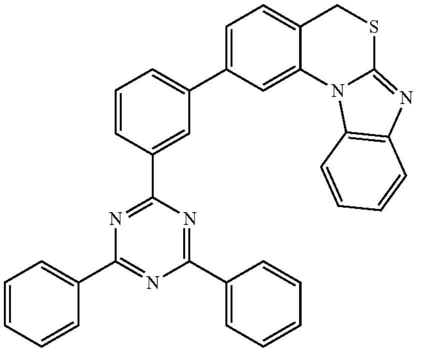
C-8
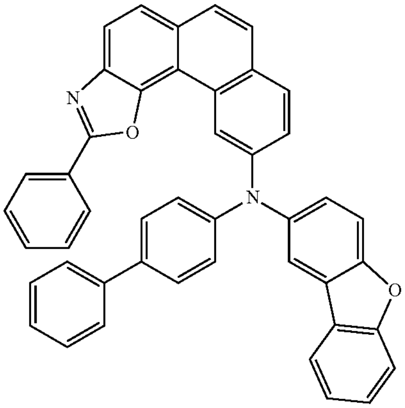
H-45

TABLE 4-continued

| | |
|---|---|
| | 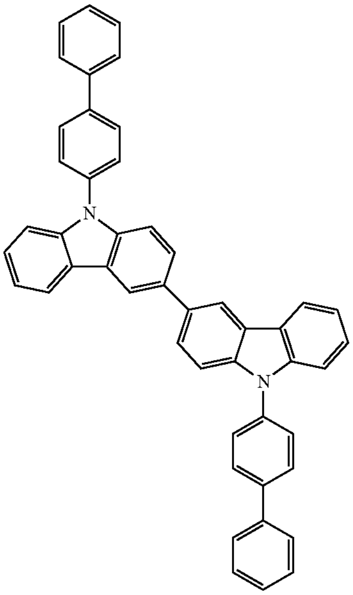<br>H-131 |
| | 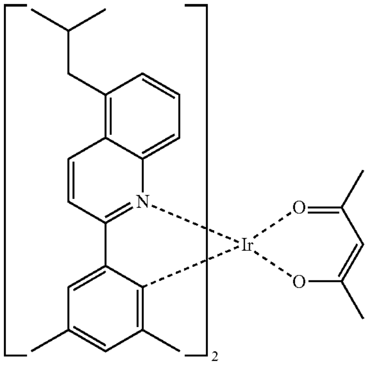<br>D-39 |
| | 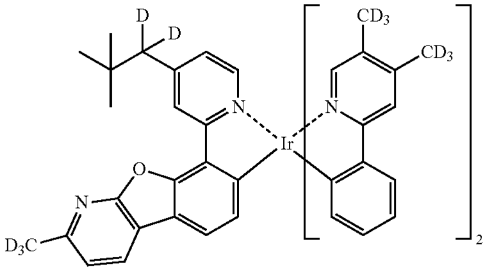<br>D-130 |

TABLE 4-continued

| | |
|---|---|
| Hole Blocking Layer | 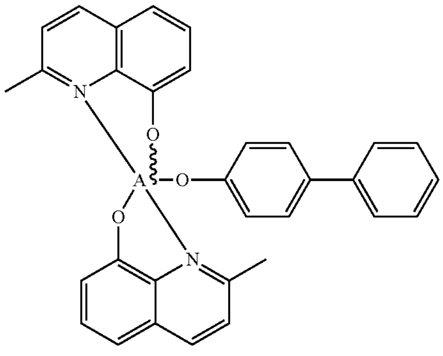<br>Balq |
| Electron transport Layer/Electron Injection Layer | 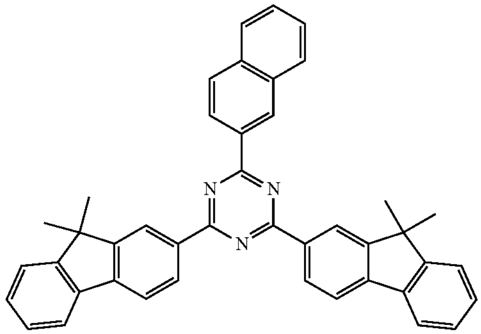<br>ETL-1 |
| | 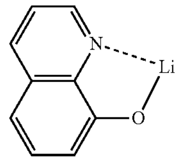<br>EIL-1 |

The LUMO (lowest unoccupied molecular orbital) energy level, the HOMO (highest occupied molecular orbital) level, and the triplet energy of the scaffolds of the compound represented by formula 1 according to one embodiment of the present disclosure were respectively measured and shown in Table 5 below.

TABLE 5

| | LUMO (eV) | HOMO (eV) | Triplet (eV) |
|---|---|---|---|
| 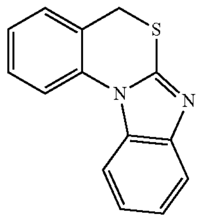 [SMILES: c1ccc2c(c1)CSc1nc3ccccc3n1-2] | −0.840 | −5.619 | 3.252 |

TABLE 5-continued

| | LUMO (eV) | HOMO (eV) | Triplet (eV) |
|---|---|---|---|
| 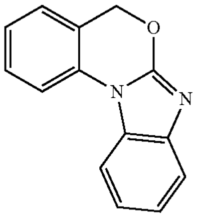 [SMILES: c1ccc2c(c1)COc1nc3ccccc3n1-2] | −0.696 | −5.672 | 3.377 |
| 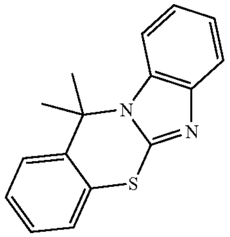 [SMILES: CC1(C)c2ccccc2Sc2nc3ccccc3n21] | −0.704 | −5.487 | 3.296 |
| 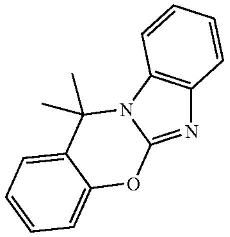 [SMILES: CC1(C)c2ccccc2Oc2nc3ccccc3n21] | −0.602 | −5.620 | 3.472 |
| 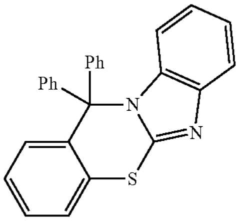 [SMILES: c1ccc(C2(c3ccccc3)c3ccccc3Sc3nc4ccccc4n32)cc1] | −0.715 | −5.532 | 3.395 |
| 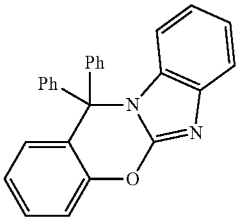 [SMILES: c1ccc(C2(c3ccccc3)c3ccccc3Oc3nc4ccccc4n32)cc1] | −0.683 | −5.617 | 3.534 |
| 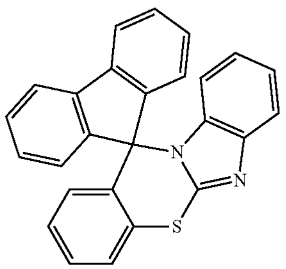 [SMILES: c1ccc2c(c1)Sc1nc3ccccc3n1C21c2ccccc2-c2ccccc21] | −1.237 | −5.416 | 2.985 |

TABLE 5-continued

| | LUMO (eV) | HOMO (eV) | Triplet (eV) |
|---|---|---|---|
| 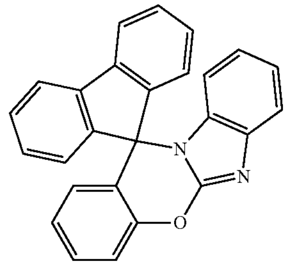 [SMILES: c1ccc2c(c1)Oc1nc3ccccc3n1C21c2ccccc2-c2ccccc21] | −1.235 | −5.549 | 2.996 |

With Gaussian16, Gaussian's quantum chemistry calculation program, the structure was optimized by applying the background sets of B3LYP, which is hybrid Density Functional Theory (hybrid DFT), and 6-31 G(d), and TD-DFT (time dependent DFT) was used to calculate the triplet state.

From Table 5, it can be confirmed that all scaffolds of the compound represented by formula 1 of the present disclosure have similar HOMO and/or triplet energy levels. Thus, even if another compound represented by formula 1 is used instead of compound C-8, the OLED properties are expected to be similar to those of the Device Examples above.

The invention claimed is:

1. An organic electroluminescent compound represented by the following formulas 1-1 or 1-2:

(1-1)

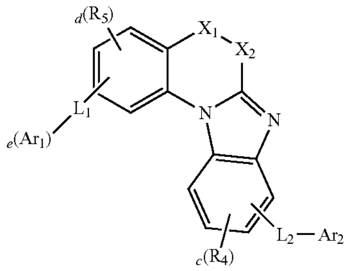

(1-2)

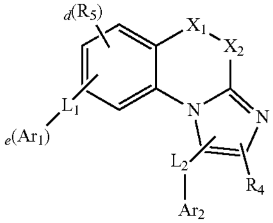

wherein $X_1$ and $X_2$, each independently, represents $NR_1$, $CR_2R_3$, O, S, P, or P═O;

$L_1$ and $L_2$, each independently, represent a single bond, a substituted or unsubstituted fused ring group of a (C3-C30) aliphatic ring(s) and a (C6-C30) aromatic ring(s), or a substituted or unsubstituted (C6-C30) arylene;

$Ar_1$ represents hydrogen, or a substituted or unsubstituted triazinyl, pyridyl, pyrazinyl, pyrimidinyl, pyridazinyl, quinolyl, isoquinolyl, cinnolinyl, quinazolinyl, quinoxalinyl, benzofuroquinolinyl, benzofuroquinazolinyl, benzofuronaphthyridinyl, benzofuropyrimidinyl, naphthofuropyrimidinyl, benzothienoquinolinyl, benzothienoquinazolinyl, benzothienonaphthyridinyl, benzothienopyrimidinyl, naphthothienopyrimidinyl, pyrimidoindolyl, benzopyrimidoindolyl, benzofuropyrazinyl, naphthofuropyrazinyl, benzothienopyrazinyl, naphthothienopyrazinyl or pyrazinoindolyl;

$Ar_2$ represents hydrogen, a substituted or unsubstituted (C6-C30)aryl, a substituted or unsubstituted fused ring group of a (C3-C30) aliphatic ring(s) and a (C6-C30) aromatic ring(s), a substituted or unsubstituted (3-to 30-membered)heteroaryl, or —N—($Ar_3$)($Ar_4$); with the proviso that the case where both $Ar_1$ and $Ar_2$ are hydrogen is excluded;

$R_1$ to $R_3$, each independently, represent hydrogen, deuterium, a halogen, a cyano, a substituted or unsubstituted (C1-C30) alkyl, a substituted or unsubstituted (C6-C30)aryl, or a substituted or unsubstituted (3-to 30-membered) heteroaryl, a substituted or unsubstituted (C3-C30) cycloalkyl, a substituted or unsubstituted (C1-C30) alkoxy, a substituted or unsubstituted tri (C1-C30)alkylsilyl, a substituted or unsubstituted di(C1-C30)alkyl (C6-C30) arylsilyl, a substituted or unsubstituted (C1-C30) alkyldi (C6-C30)arylsilyl, a substituted or unsubstituted tri(C6-C30)arylsilyl, or a substituted or unsubstituted fused ring group of a (C3-C30) aliphatic ring(s) and a (C6-C30) aromatic ring(s), and $R_2$ and $R_3$ may be linked to each other to form a spiro ring;

$R_4$ represents hydrogen, deuterium, a halogen, a cyano, a substituted or unsubstituted (C1-C30)alkyl, a substituted or unsubstituted (C6-C30)aryl, or a substituted or unsubstituted (3-to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30) alkyldi(C6-C30) arylsilyl, a substituted or unsubstituted tri(C6-C30) arylsilyl, a substituted or unsubstituted fused ring group of a (C3-C30) aliphatic ring(s) and a (C6-C30) aromatic ring(s), or —N—($Ar_3$)($Ar_4$); or may be linked to adjacent $R_4$ to form a ring(s);

$R_5$ represents hydrogen or deuterium;

$Ar_3$ and $Ar_4$, each independently, represent hydrogen, a substituted or unsubstituted (C1-C30)alkyl, a substituted or unsubstituted (C2-C30)alkenyl, a substituted or unsubstituted (C6-C30)aryl, or a substituted or unsubstituted (3-to 30-membered) heteroaryl;

c and d, each independently, represent an integer of 1 to 3; in which when $R_4$ and $R_5$ are each present in plural, each of $R_4$ and each of $R_5$ may be the same as or different from each other; and e represents an integer of 1 or 2; in which when two $Ar_1$ are present, each of $Ar_1$ may be the same as or different from each other.

2. The organic electroluminescent compound according to claim 1, wherein the substituents of the substituted alkyl, the substituted alkenyl, the substituted aryl, the substituted arene, the substituted arylene, the substituted heteroaryl, the substituted cycloalkyl, the substituted alkoxy, the substituted trialkylsilyl, the substituted dialkylarylsilyl, the substituted alkyldiarylsilyl, the substituted triarylsilyl, and the substituted fused ring group of a aliphatic ring(s) and a aromatic ring(s), each independently, are at least one selected from the group consisting of deuterium; a halogen; a cyano; a carboxyl; a nitro; a hydroxyl; a (C1-C30)alkyl; a halo(C1-C30) alkyl; a (C2-C30)alkenyl; a (C2-C30)alkynyl; a (C1-C30) alkoxy; a (C1-C30)alkylthio; a (C3-C30)cycloalkyl; a (C3-C30)cycloalkenyl; a (3- to 7-membered)heterocycloalkyl; a (C6-C30)aryloxy; a (C6-C30)arylthio; a (3- to 30-membered)heteroaryl unsubstituted or substituted with at least one of deuterium and a (C6-C30)aryl(s); a (C6-C30)aryl unsubstituted or substituted with at least one of deuterium and a (3- to 30-membered)heteroaryl(s); a tri(C1-C30)alkylsilyl; a tri(C6-C30)arylsilyl; a di(C1-C30)alkyl(C6-C30)arylsilyl; a (C1-C30)alkyldi(C6-C30)arylsilyl; a fused ring group of a (C3-C30) aliphatic ring(s) and a (C6-C30) aromatic ring(s); an amino; a mono- or di-(C1-C30)alkylamino; a mono- or di-(C2-C30)alkenylamino; a (C1-C30) alkyl(C2-C30)alkenylamino; a mono- or di-(C6-C30)arylamino; a (C1-C30)alkyl(C6-C30)arylamino; a mono- or di-(3- to 30-membered)heteroarylamino; a (C1-C30)alkyl (3- to 30-membered)heteroarylamino; a (C2-C30)alkenyl (C6-C30)arylamino; a (C2-C30)alkenyl(3- to 30-membered)heteroarylamino; a (C6-C30)aryl(3- to 30-membered) heteroarylamino; a (C1-C30)alkylcarbonyl; a (C1-C30) alkoxycarbonyl; a (C6-C30)arylcarbonyl; a (C6-C30) arylphosphinyl; a di(C6-C30)arylboronyl; a di(C1-C30) alkylboronyl; a (C1-C30)alkyl(C6-C30)arylboronyl; a (C6-C30)aryl(C1-C30)alkyl; and a (C1-C30)alkyl(C6-C30)aryl.

3. An organic electroluminescent compound selected from the following compounds:

C-1

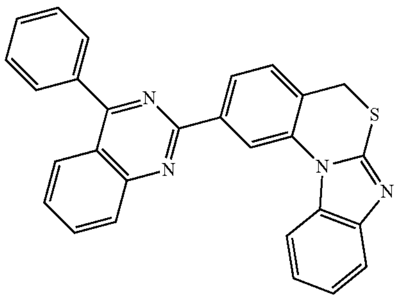

C-2

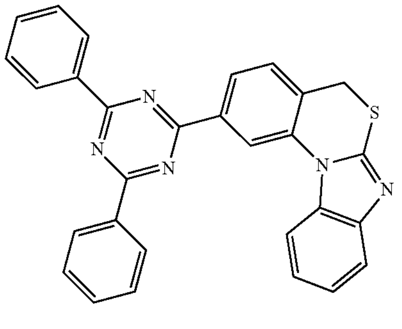

C-3

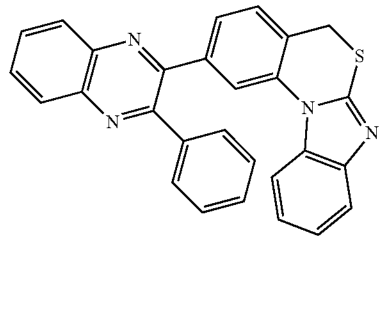

-continued
C-4
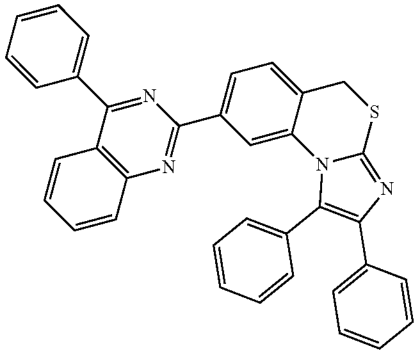
C-5
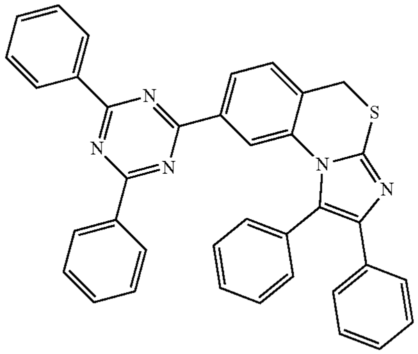
C-6
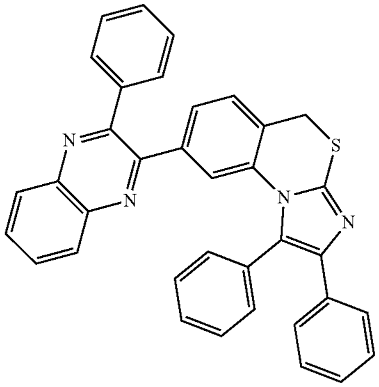
C-7
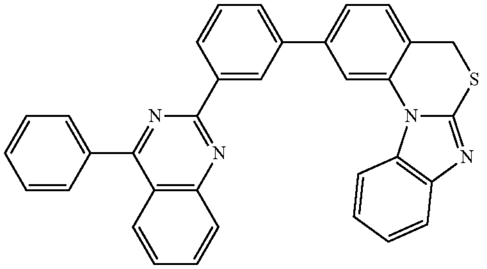
-continued
C-8
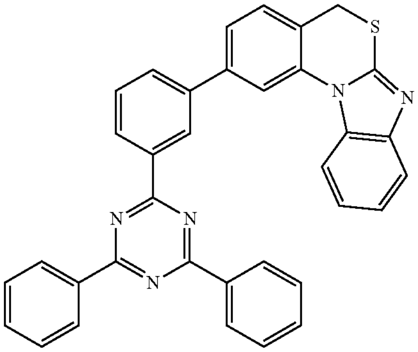
C-9
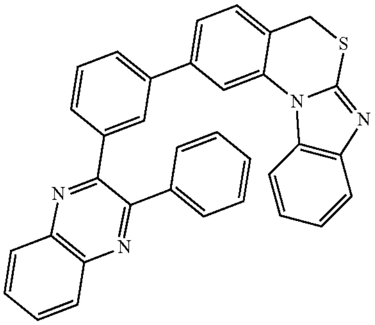
C-10
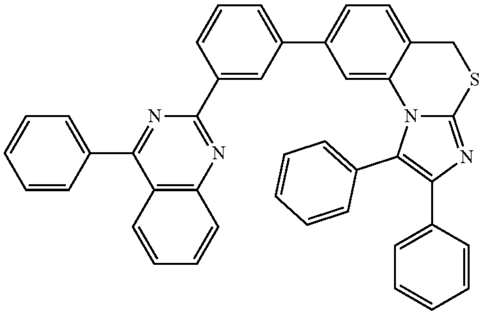
C-11
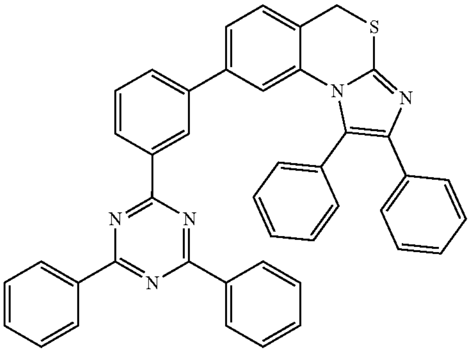

C-12
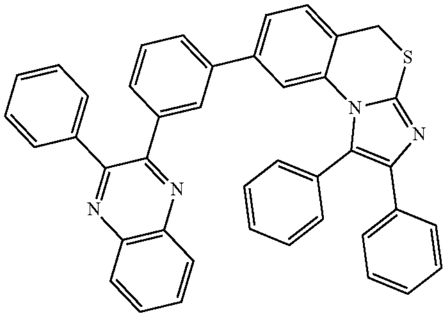
C-13
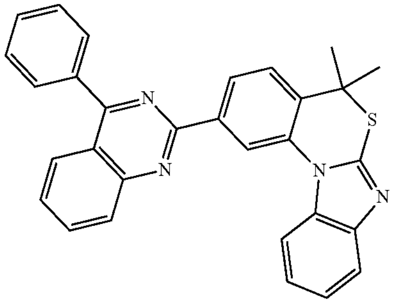
C-14
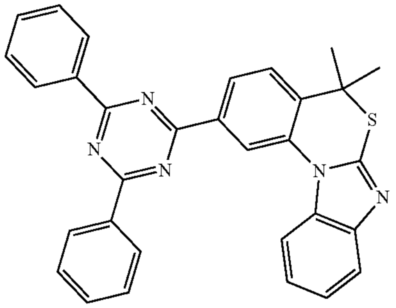
C-15
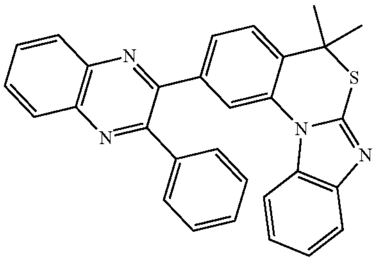
C-16
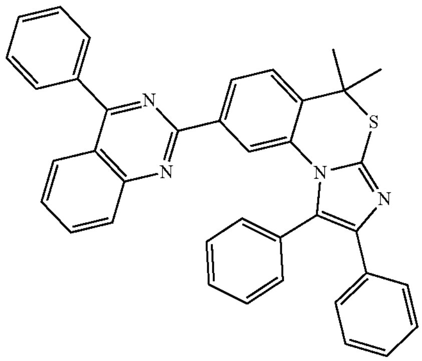
C-17
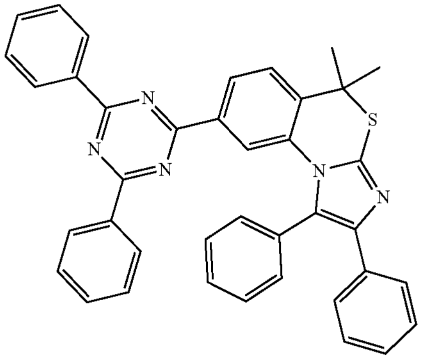
C-18
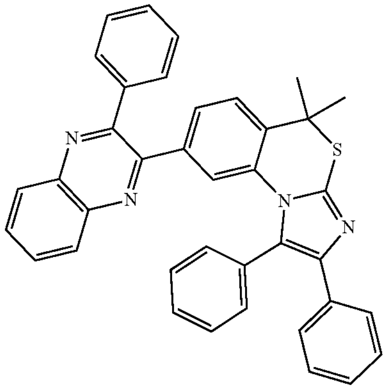
C-19
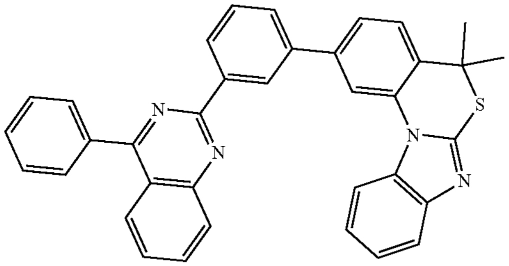
C-20
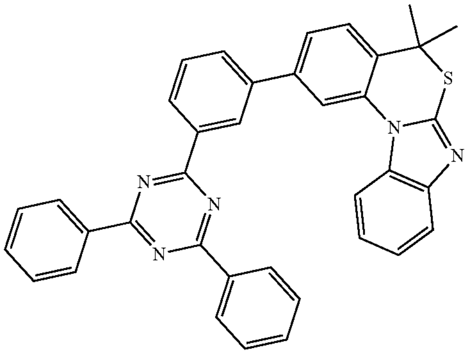

-continued
C-21
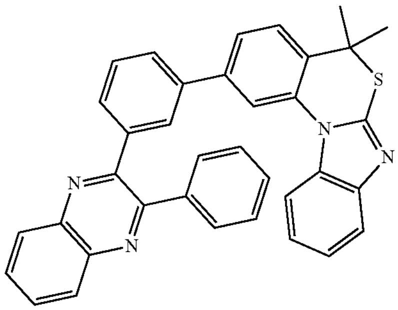
C-22
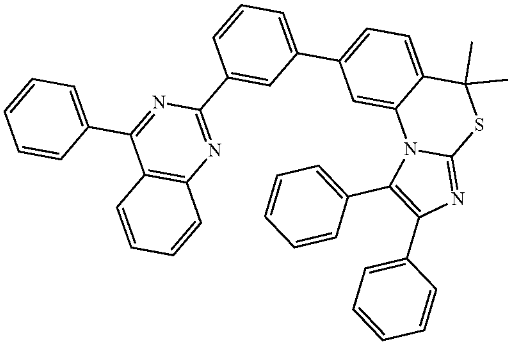
C-23
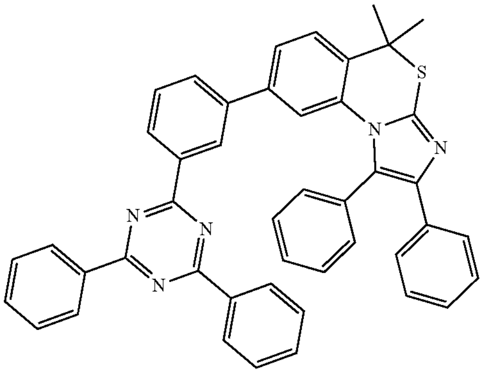
C-24
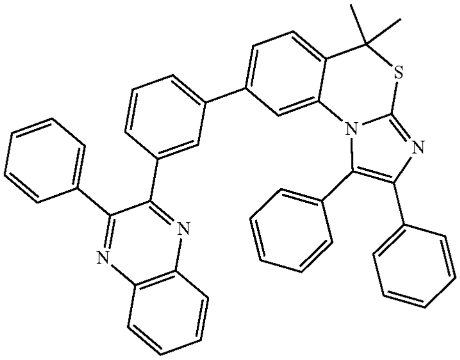
-continued
C-25
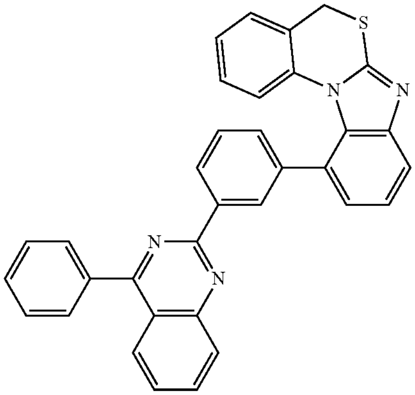
C-26
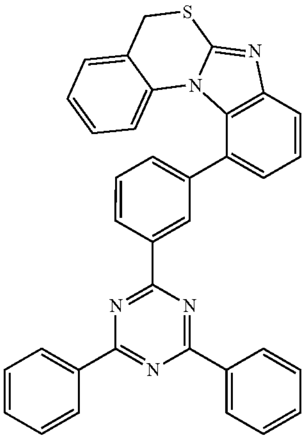
C-27
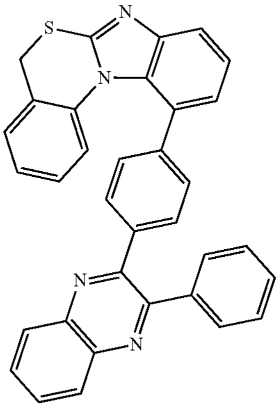

-continued
C-28
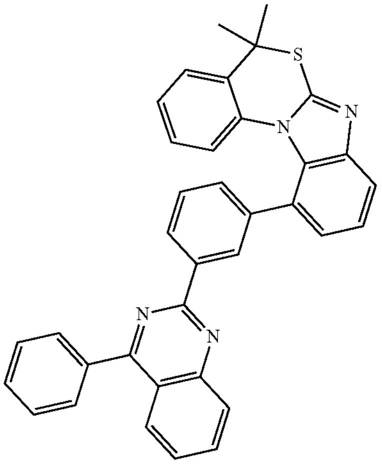
C-29
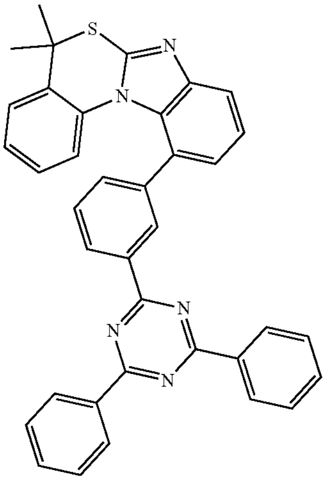
C-30
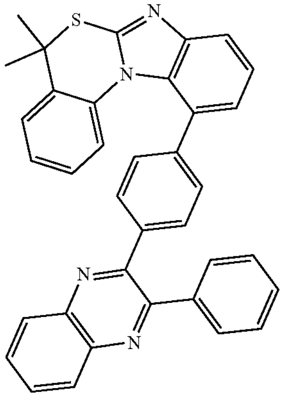
-continued
C-45
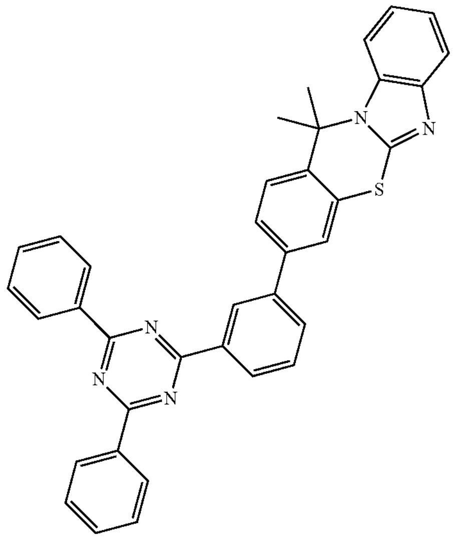
C-46
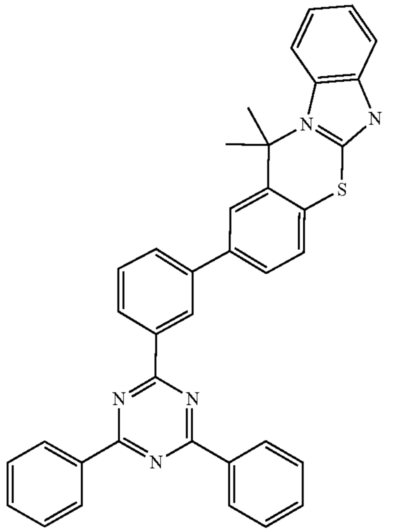
C-47
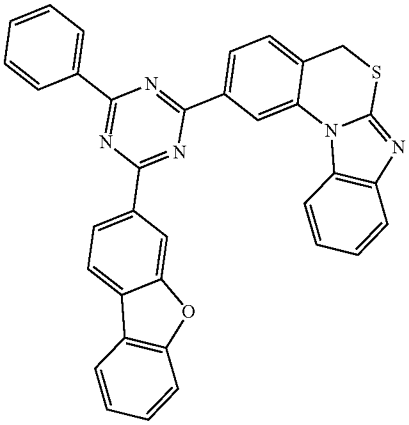

-continued
C-48
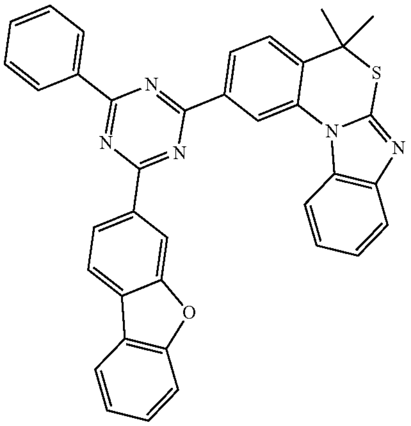
C-49
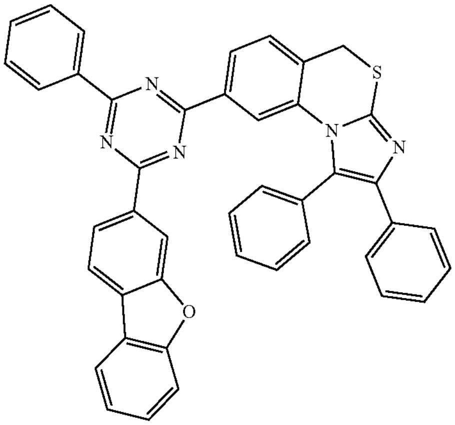
C-50
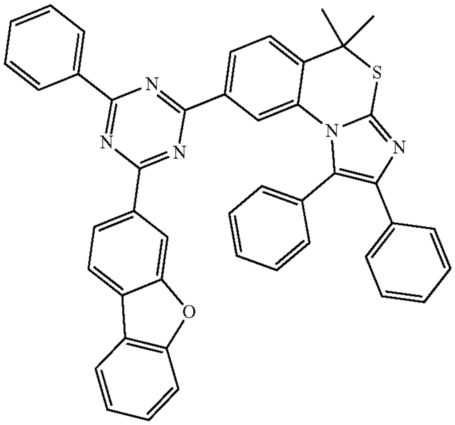
C-51
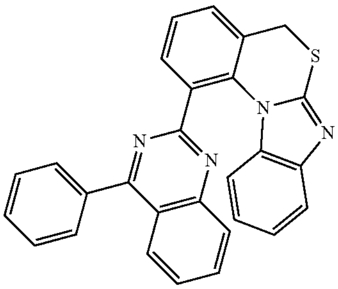
-continued
C-52
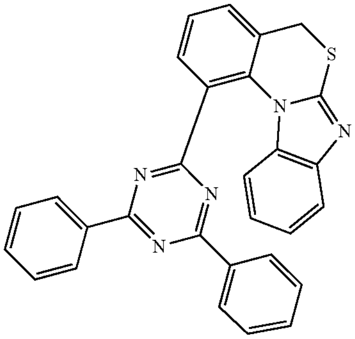
C-53
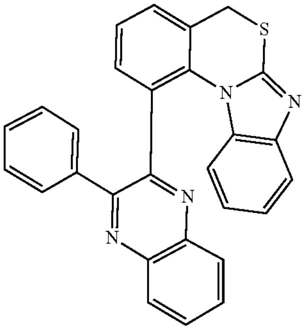
C-54
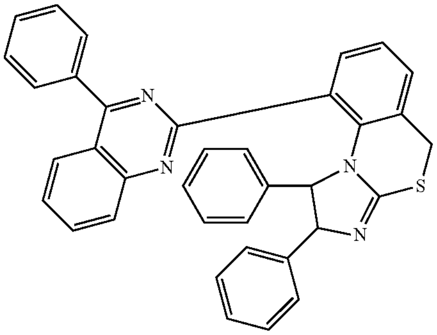
C-55
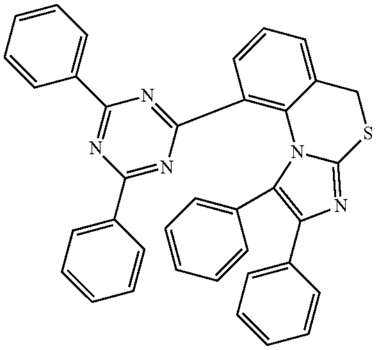

-continued
C-56
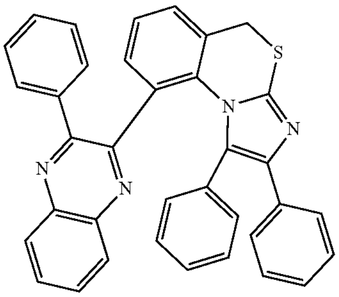
C-57
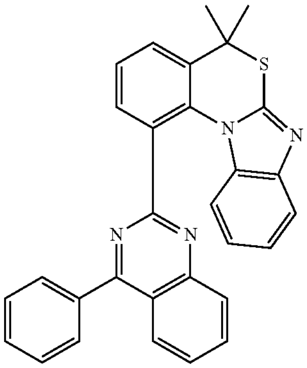
C-58
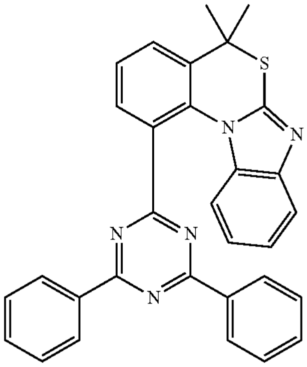
C-59
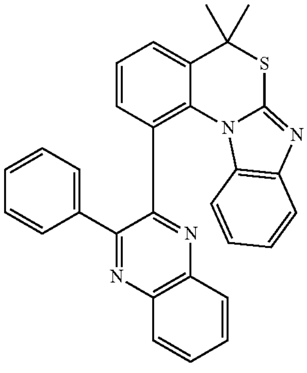
-continued
C-60
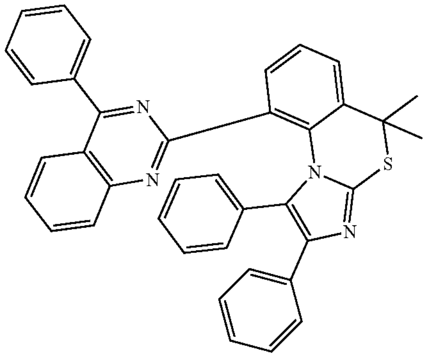
C-73
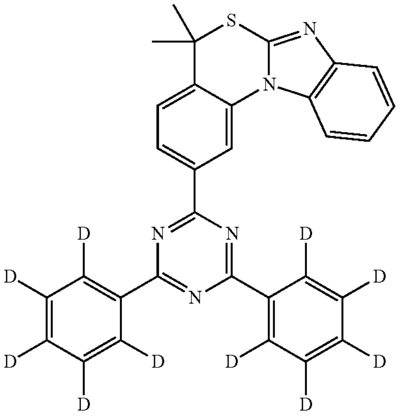
C-74
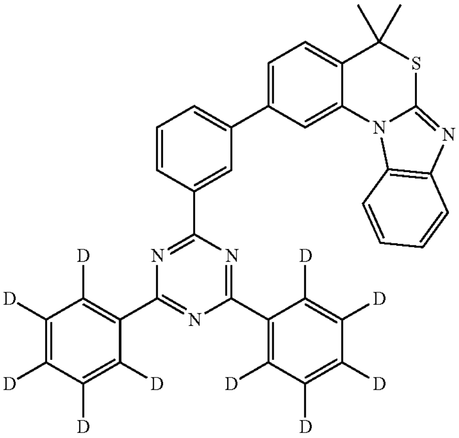
C-75
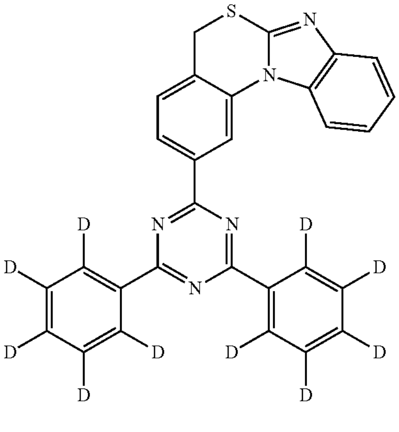

-continued
C-76
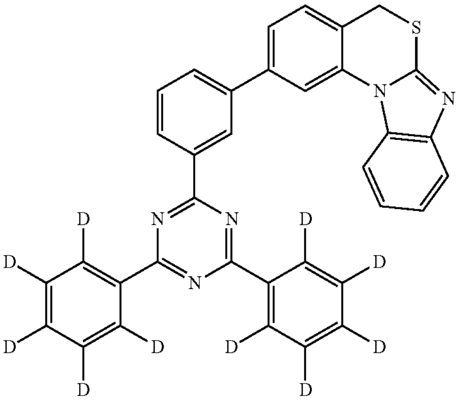
C-79
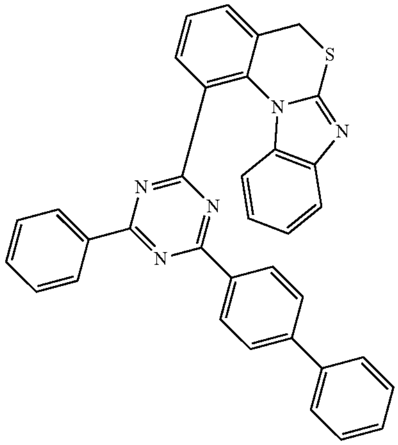
C-80
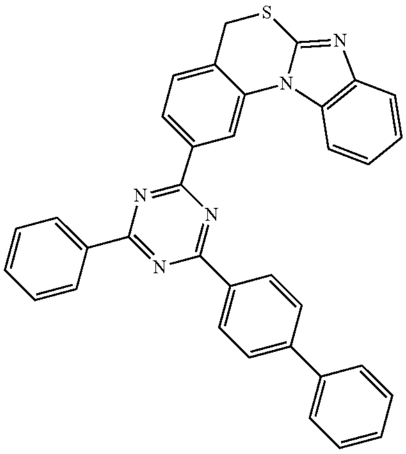
-continued
C-81
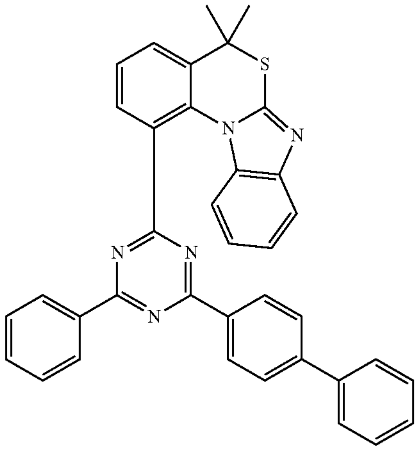
C-82
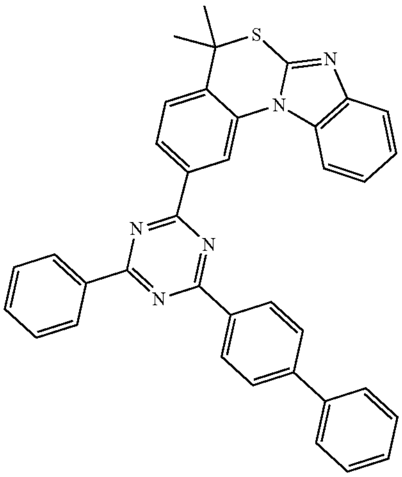
C-83
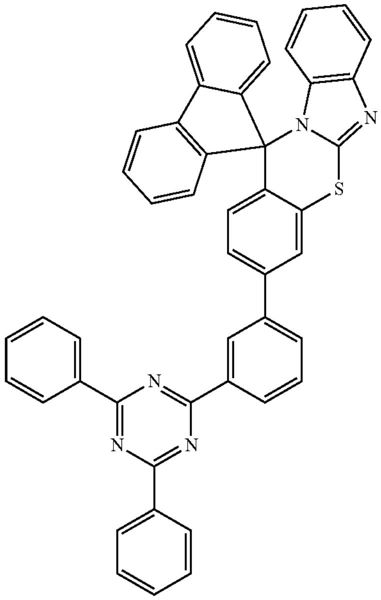

-continued
C-84
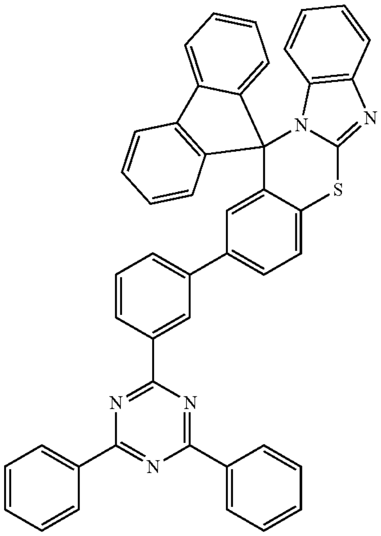
C-85
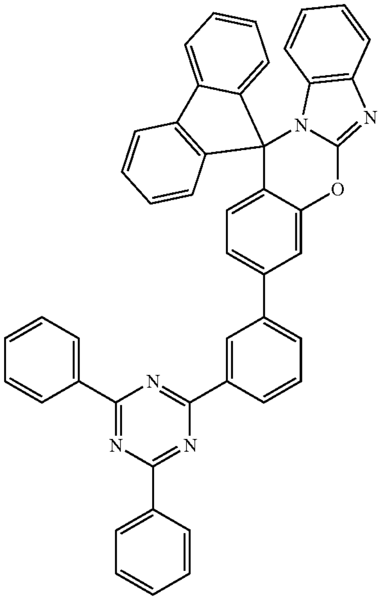
C-86
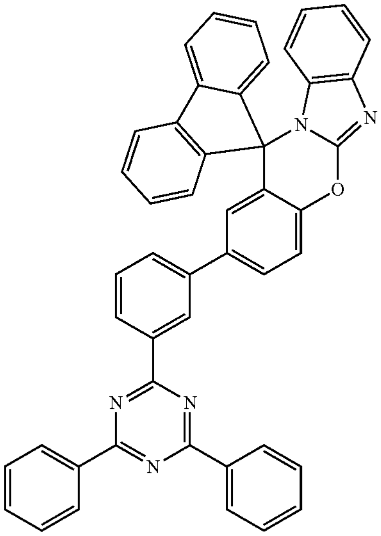
-continued
C-89
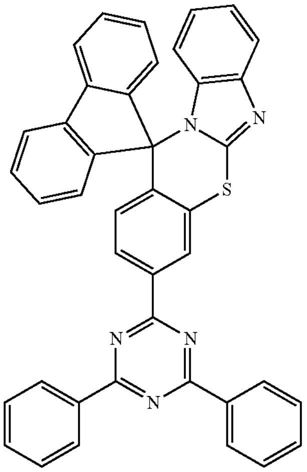
C-90
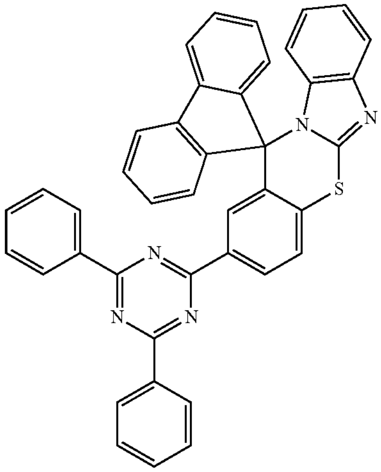
C-91
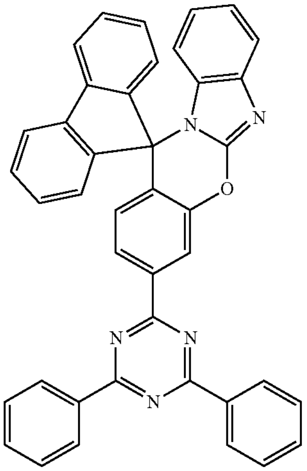

-continued

C-92

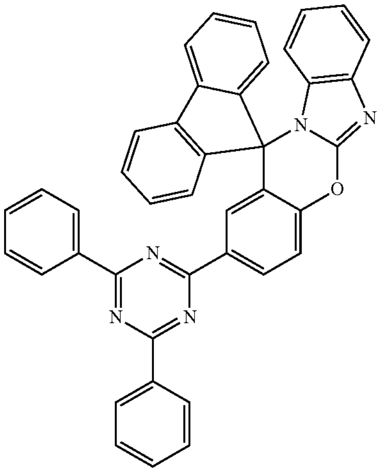

C-94

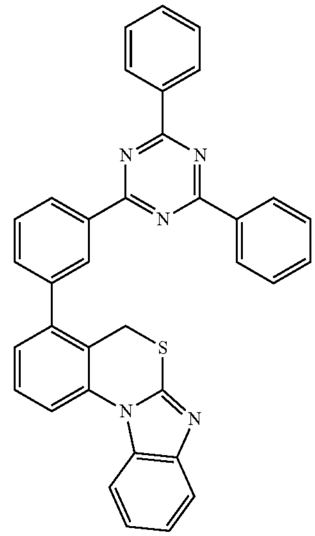

and

C-95

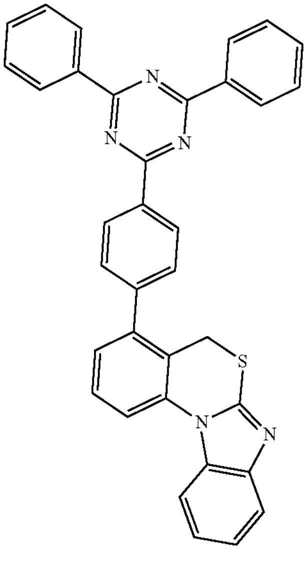

.

4. A plurality of host materials comprising a first host material(s) and a second host material(s), wherein the first host material comprises at least one of the compound represented by formulas 1-1 or 1-2 according to claim 1, and the second host material comprises at least one of the compounds represented by the following formula 2 or at least one of the compounds represented by the following formula 3:

(2)

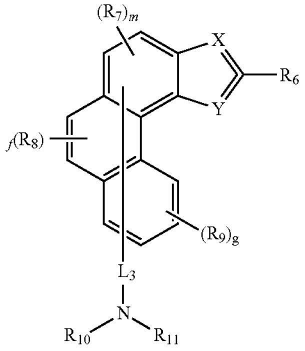

(3)

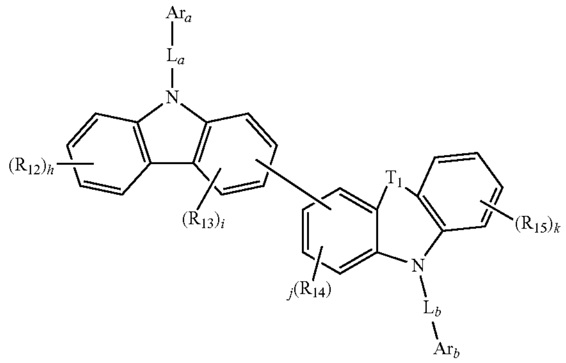

in formula 2,

X and Y, each independently, represent —N═, —$NR_{16}$—, —O—, or —S—; with the proviso that any one of X and Y represents —N═, and the other represents —$NR_{16}$—, —O—, or —S—;

$R_6$ represents a substituted or unsubstituted (C6-C30)aryl, or a substituted or unsubstituted (3- to 30-membered) heteroaryl;

$R_7$ to $R_{11}$, and $R_{16}$, each independently, represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C2-C30)alkenylamino, a substituted or unsubstituted (C1-C30) alkyl(C2-C30)alkenylamino, a substituted or unsubstituted (C1-C30)alkyl(3- to 30-membered)heteroarylamino, a substituted or unsubstituted (C2-C30) alkenyl(C6-C30)arylamino, a substituted or unsubstituted (C2-C30)alkenyl(3- to 30-membered) heteroarylamino, a substituted or unsubstituted mono- or di-(C6-C30)arylamino, a substituted or unsubstituted mono- or di-(3- to 30-membered)heteroarylamino, a substituted or unsubstituted (C6-C30)aryl(3- to 30-membered)heteroarylamino, or a substituted or unsubstituted (C1-C30)alkyl(C6-C30)arylamino, or may be linked to an adjacent substituent(s) to form a ring(s);

$L_3$ represents a single bond, a substituted or unsubstituted (C6-C30)arylene, or a substituted or unsubstituted (3- to 30-membered)heteroarylene; and m and f, each independently, represent an integer of 1 or 2, g represents an integer of 1 to 4; in which when $R_7$ to $R_9$ are each present in plural, each of $R_7$ to each of $R_9$ may be the same as or different from each other; and in formula 3, $T_1$ represents a single bond, O, or S;

$L_a$ and $L_b$, each independently, represent a single bond, a substituted or unsubstituted (C6-C30)arylene, or a substituted or unsubstituted (3- to 30-membered)heteroarylene;

$Ar_a$ and $Ar_b$, each independently, represent a substituted or unsubstituted (C6-C30)aryl, a substituted or unsubstituted (3- to 30-membered)heteroaryl, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, or a substituted or unsubstituted tri(C6-C30)arylsilyl;

$R_{12}$ to $R_{15}$, each independently, represent hydrogen, deuterium, a halogen, a cyano, a substituted or unsubstituted (C1-C30)alkyl, a substituted or unsubstituted (C6-C30)aryl, a substituted or unsubstituted (3- to 50-membered)heteroaryl, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted fused ring group of an (C3-C30) aliphatic ring(s) and a (C6-C30) aromatic ring(s), a substituted or unsubstituted mono- or di-(C1-C30) alkylamino, a substituted or unsubstituted mono- or di-(C2-C30)alkenylamino, a substituted or unsubstituted (C1-C30)alkyl(C2-C30)alkenylamino, a substituted or unsubstituted (C1-C30)alkyl(C6-C30)arylamino, a substituted or unsubstituted (C1-C30)alkyl(3- to 30-membered)heteroarylamino, a substituted or unsubstituted (C2-C30)alkenyl(C6-C30)arylamino, a substituted or unsubstituted (C2-C30)alkenyl(3- to 30-membered)heteroarylamino, a substituted or unsubstituted mono- or di-(C6-C30)arylamino, a substituted or unsubstituted mono- or di-(3- to 30-membered) heteroarylamino, or a substituted or unsubstituted (C6-C30)aryl(3- to 30-membered)heteroarylamino, or may be linked to an adjacent substituent(s) to form a ring(s); and h and k, each independently, represent an integer of 1 to 4, and i and j, each independently, represent an integer of 1 to 3; in which when $R_{12}$ to $R_{15}$ are each present in plural, each of $R_{12}$ to each of $R_{15}$ may be the same as or different from each other.

5. The plurality of host materials according to claim 4, wherein the compound represented by formula 2 or 3 is selected from the following compounds:

H-1

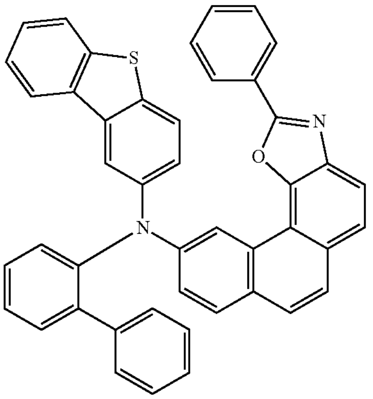

H-2

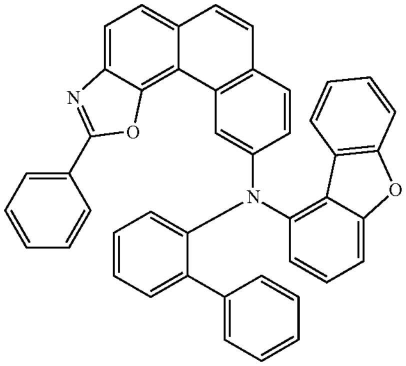

H-3

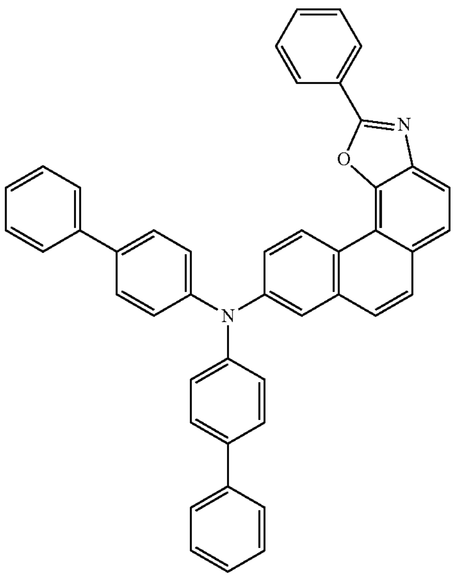

-continued
H-4
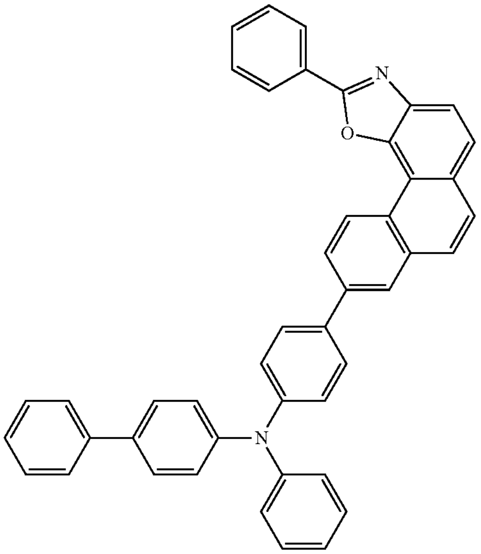
H-5
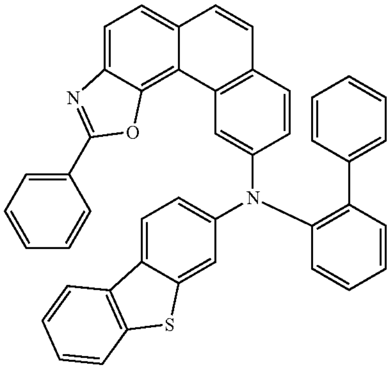
H-6
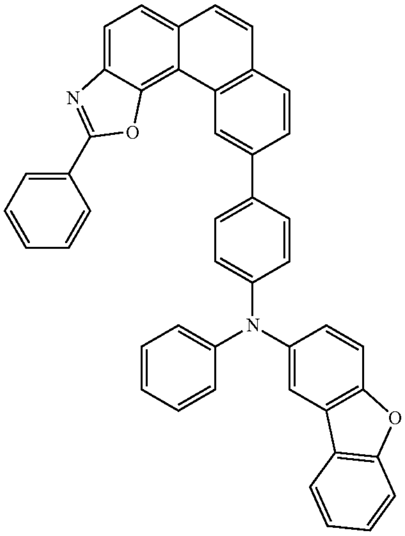
-continued
H-7
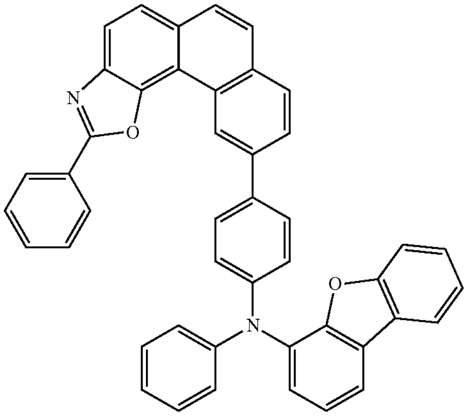
H-8
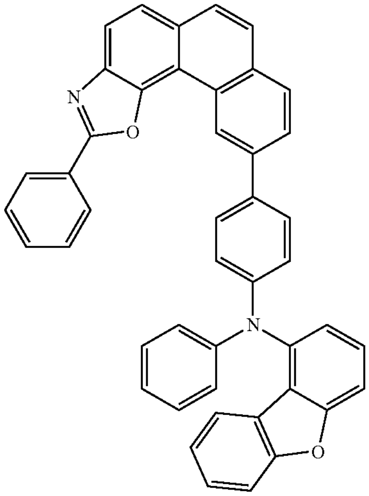
H-9
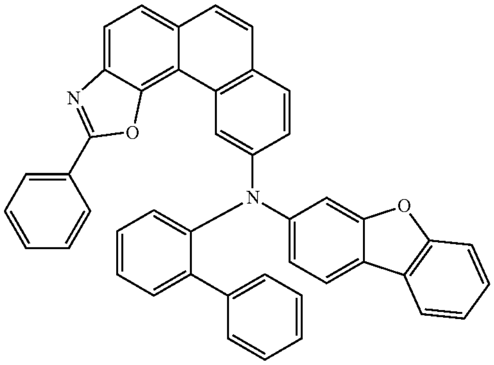

-continued
H-10
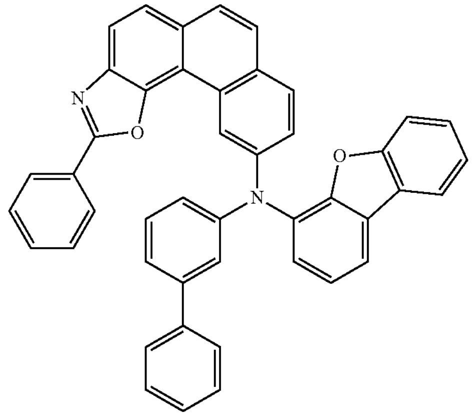
H-11
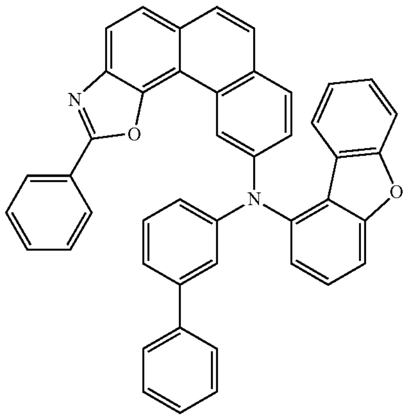
H-12
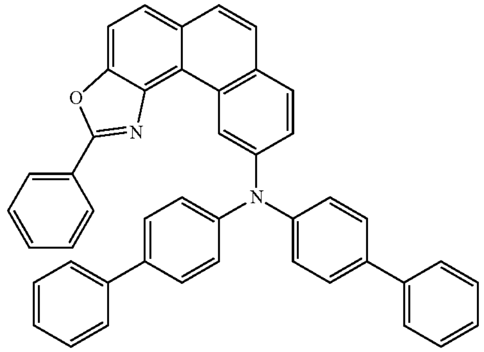
H-13
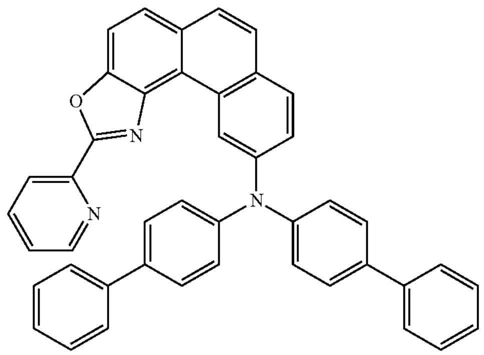
-continued
H-14
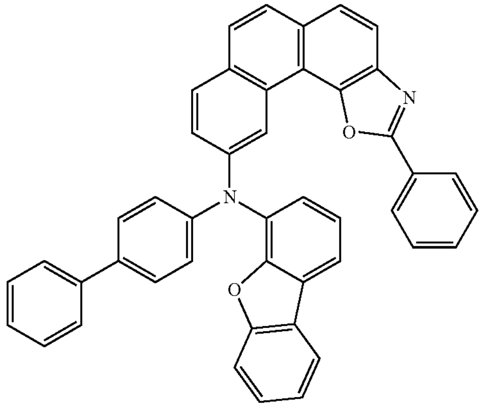
H-15
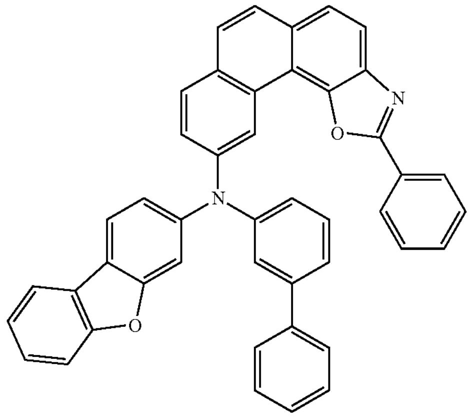
H-16
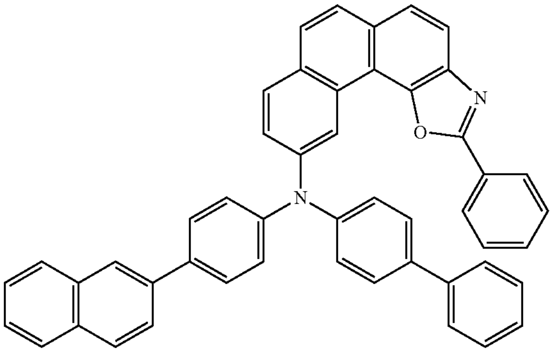
H-17
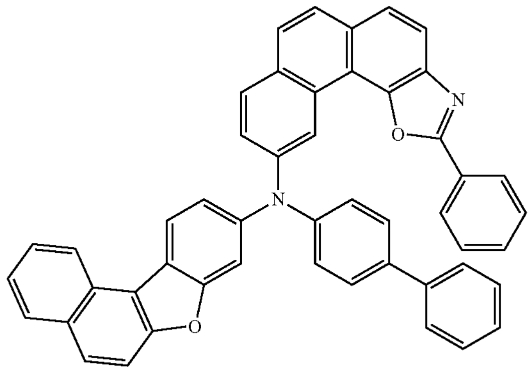

-continued
H-18
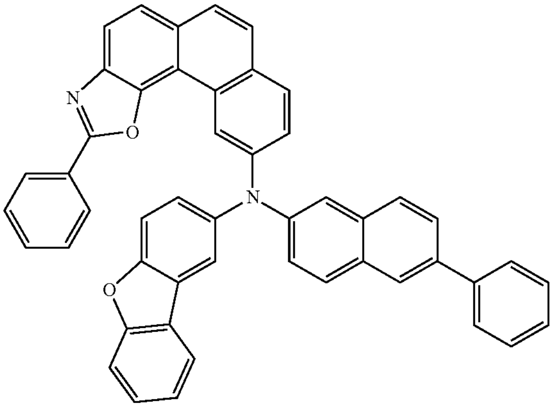
H-19
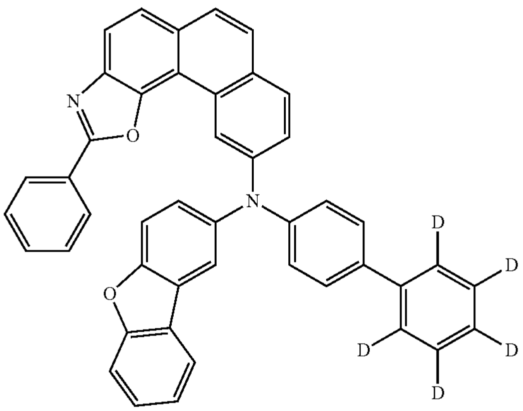
H-20
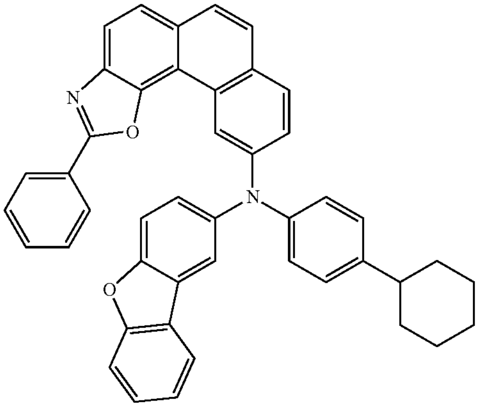
-continued
H-21
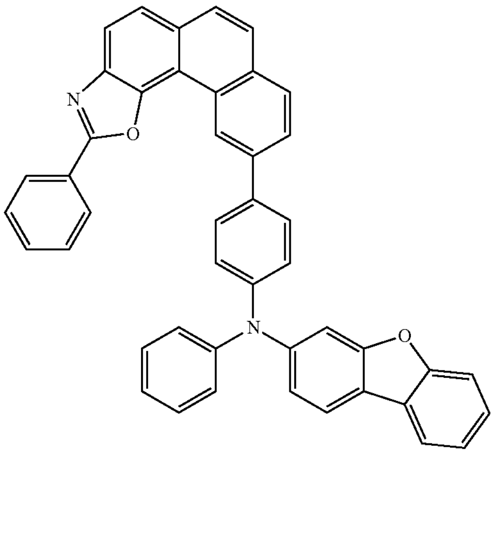
H-22
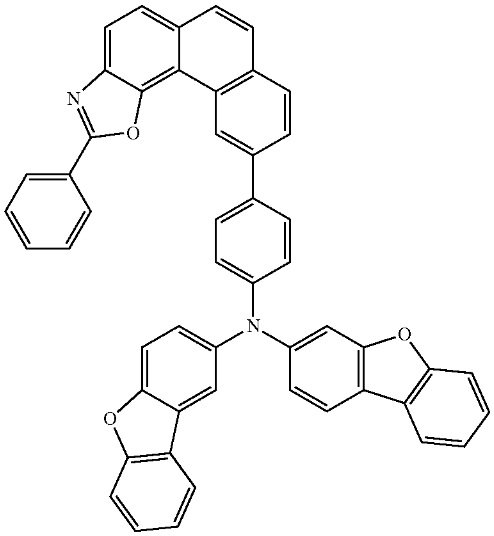
H-23
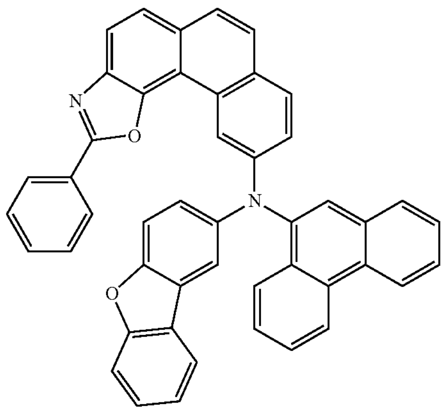

-continued
H-24
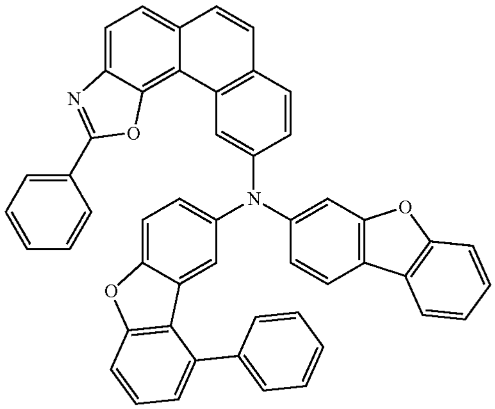
H-25
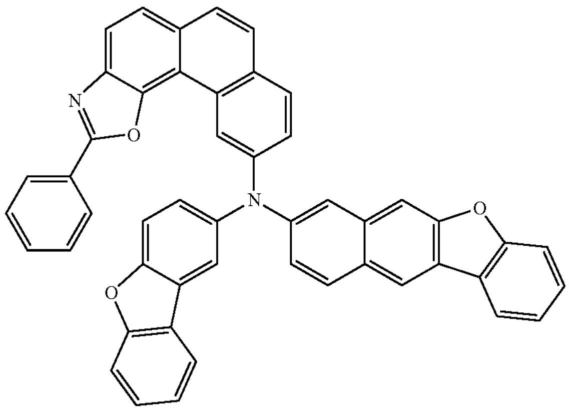
H-26
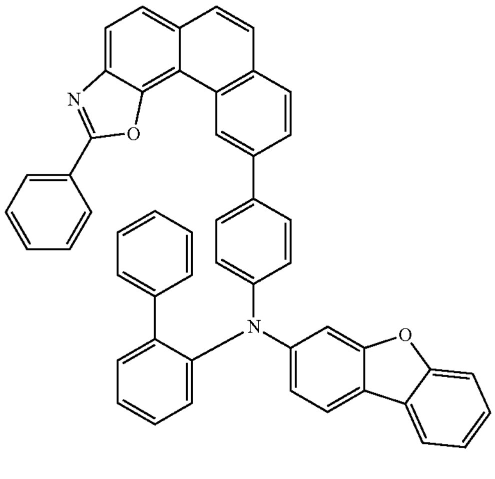
-continued
H-27
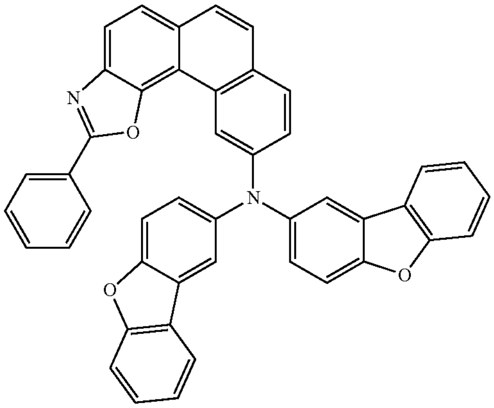
H-28
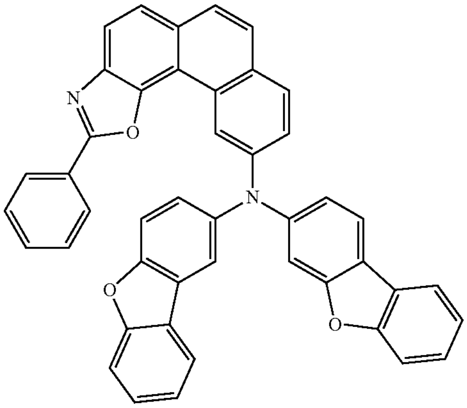
H-29
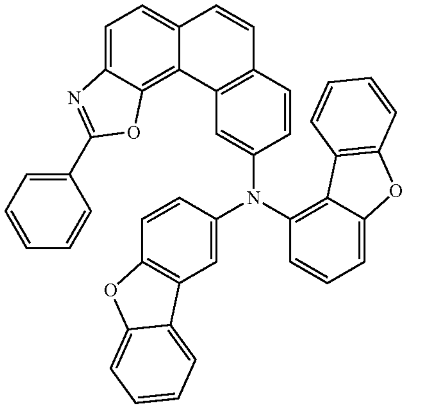
H-30
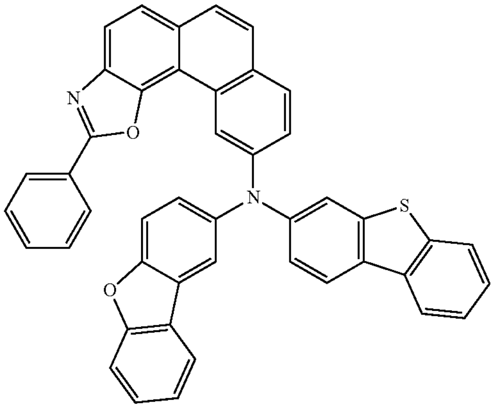

-continued
H-31
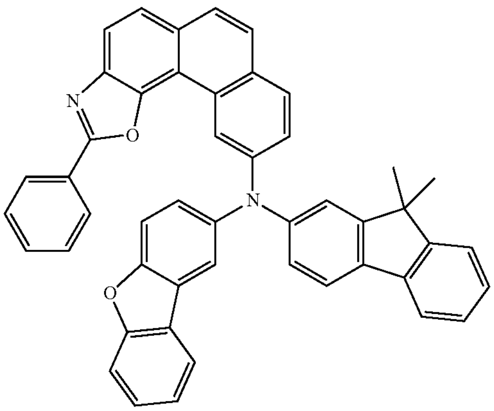
H-32
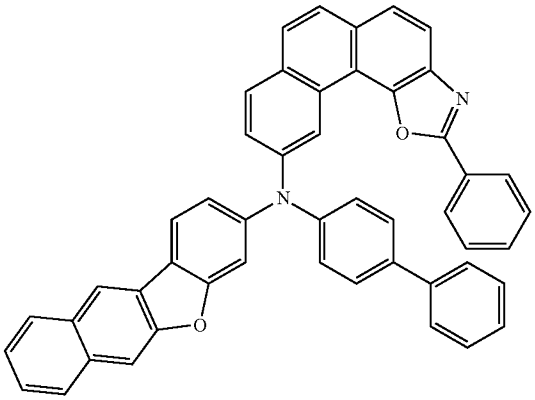
H-33
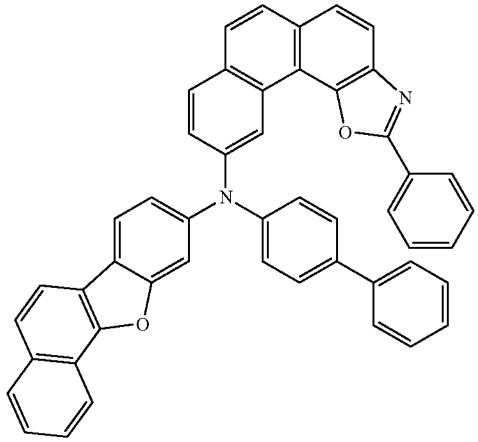
-continued
H-34
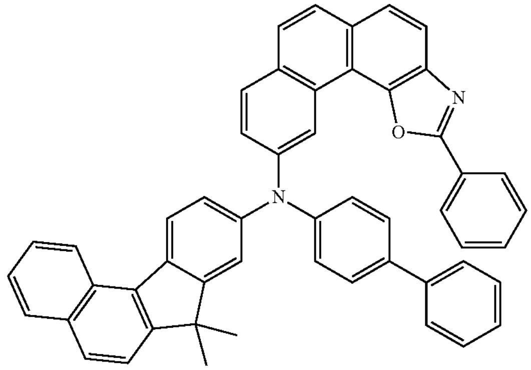
H-35
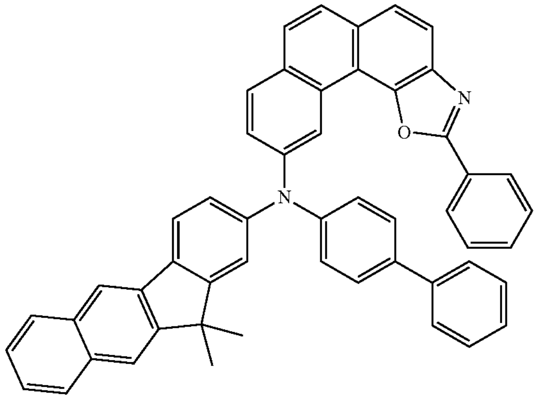
H-36
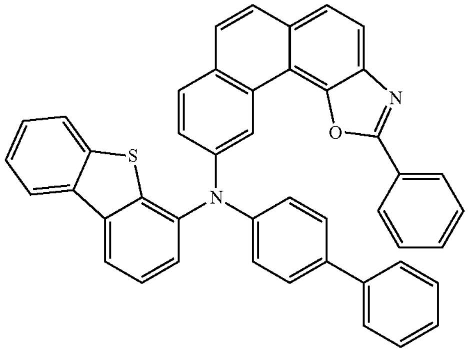
H-37
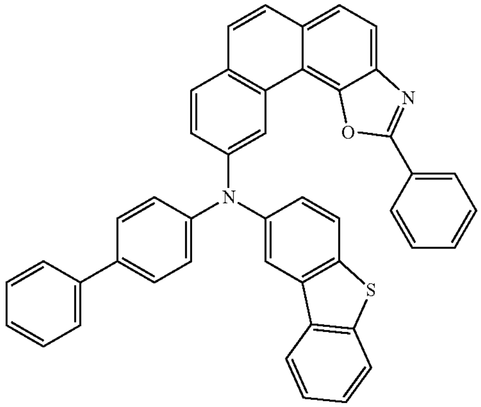

-continued
H-38
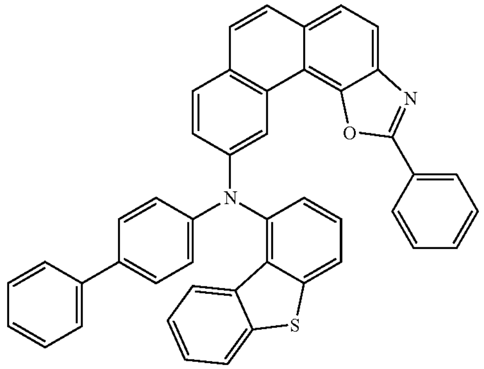
H-39
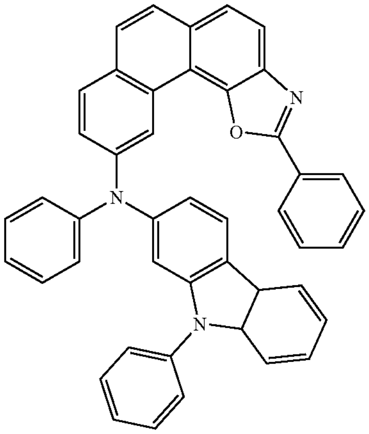
H-40
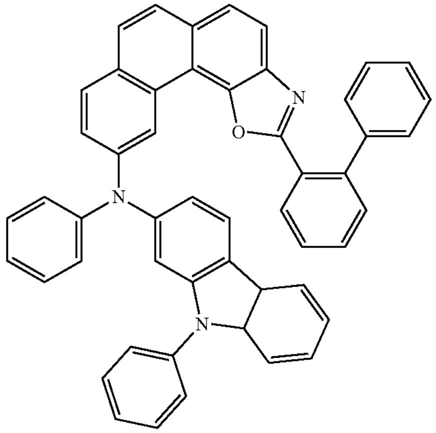
H-41
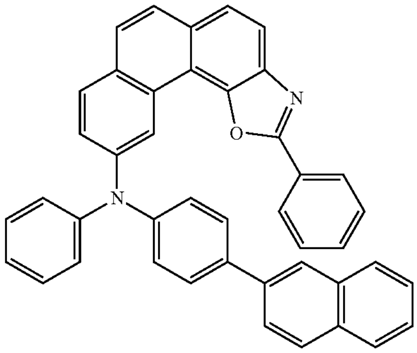
-continued
H-42
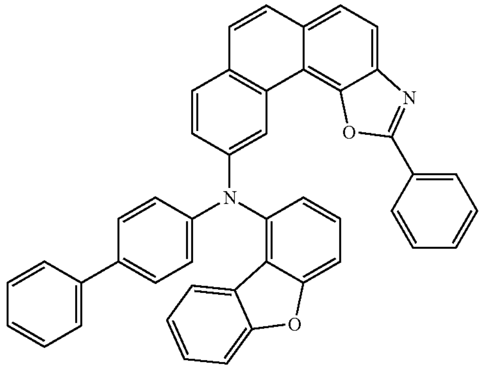
H-43
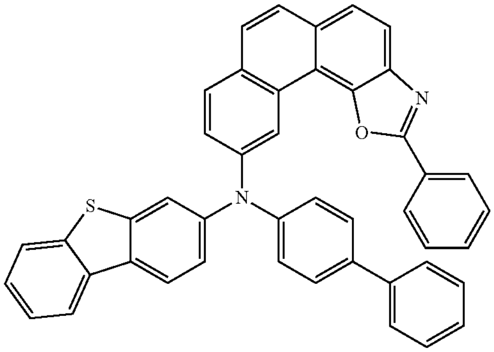
H-44
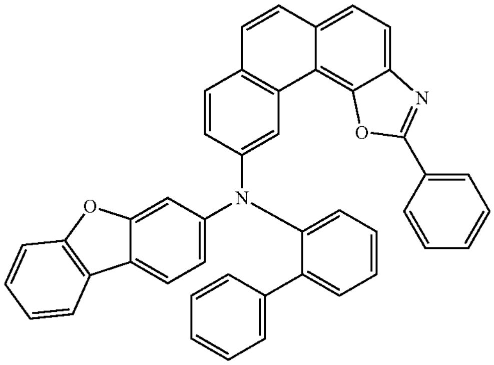
H-45
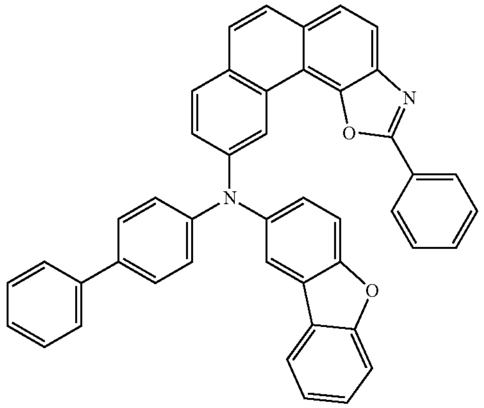

-continued
H-46
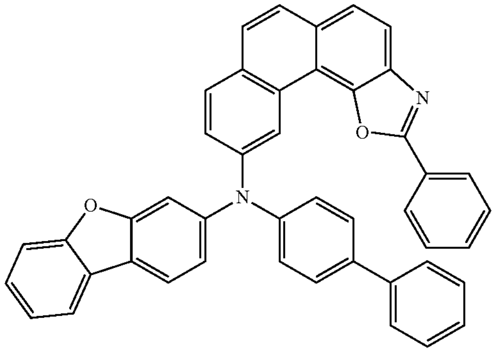
H-47
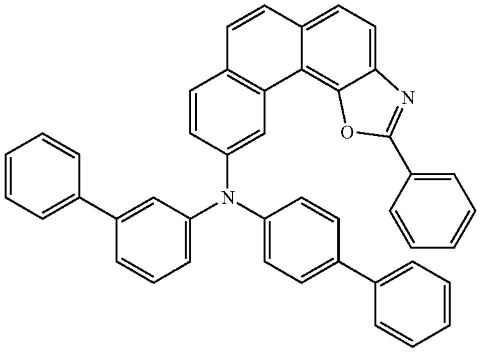
H-48
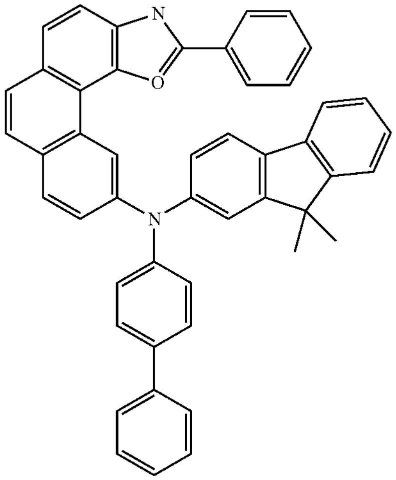
H-49
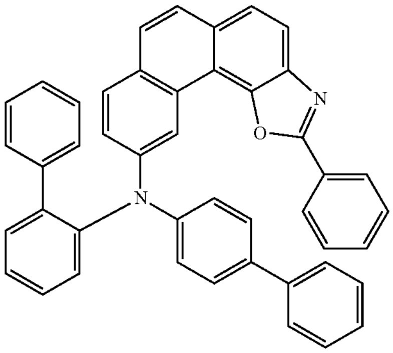
-continued
H-50
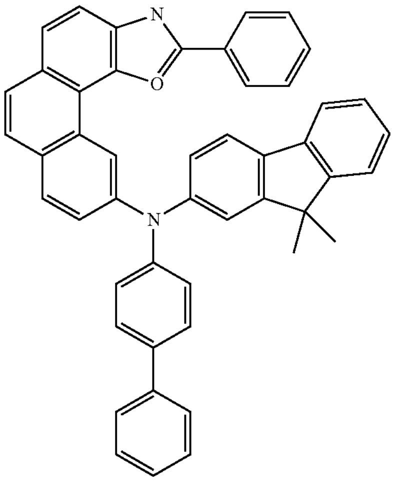
H-51
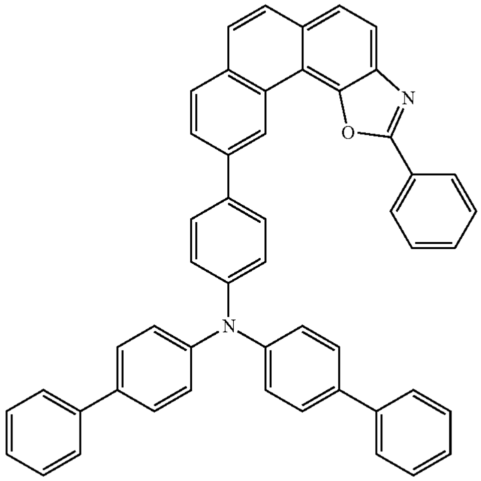
H-52
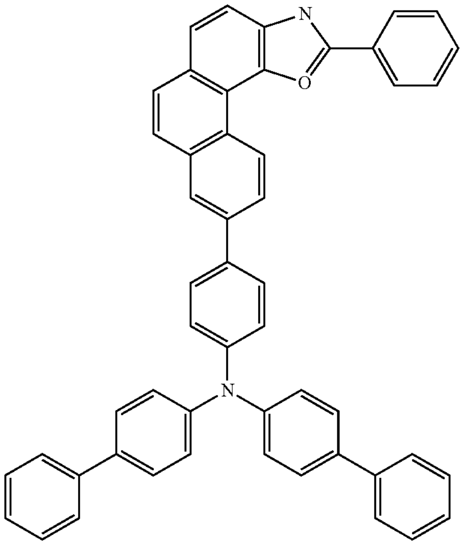

-continued
H-53
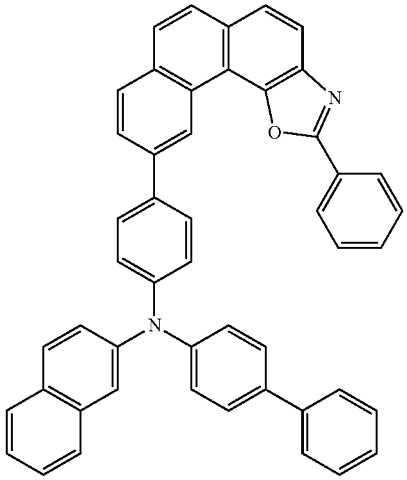
H-54
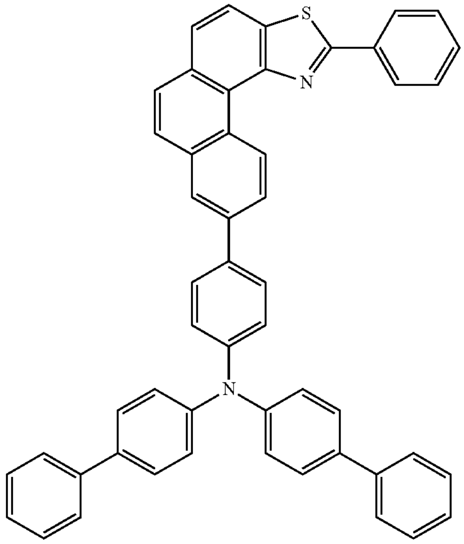
H-55
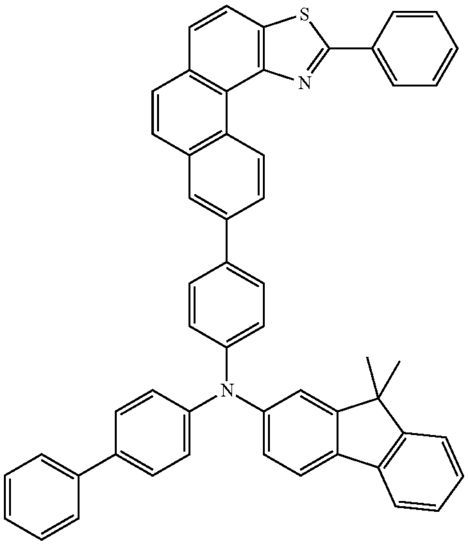
-continued
H-56
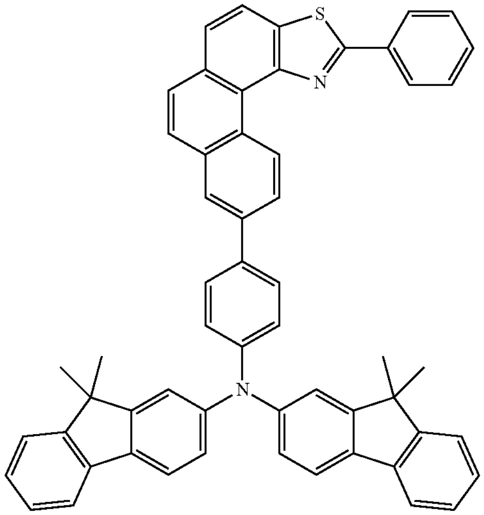
H-57
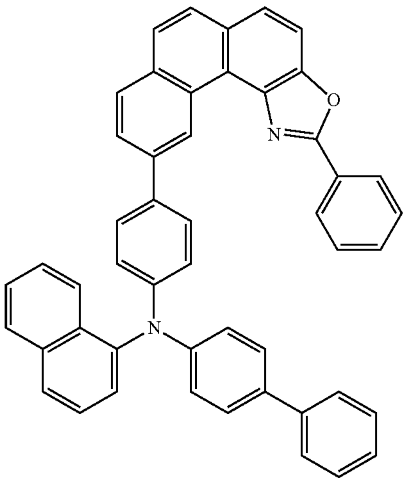
H-58
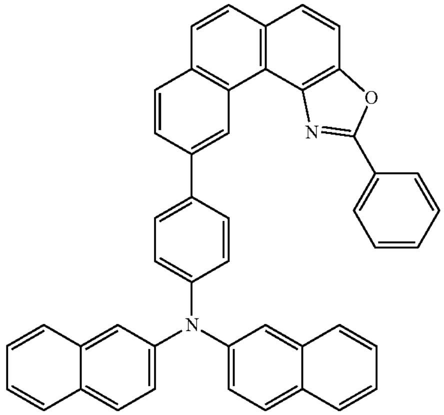

-continued
H-59
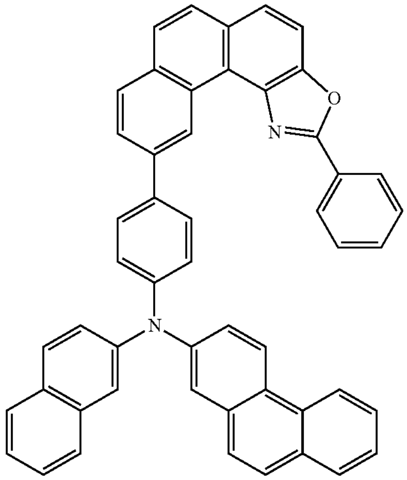
H-60
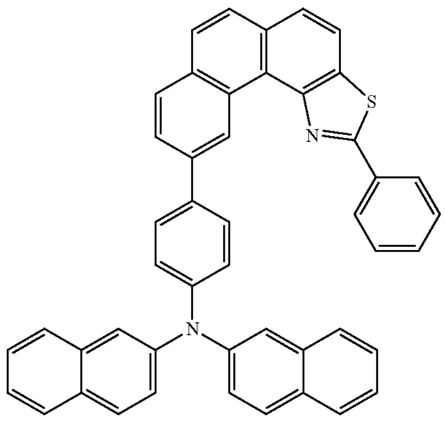
H-61
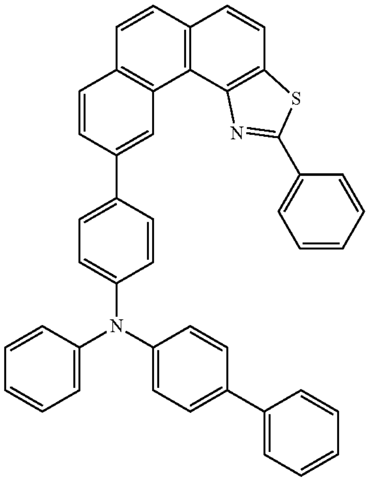
-continued
H-62
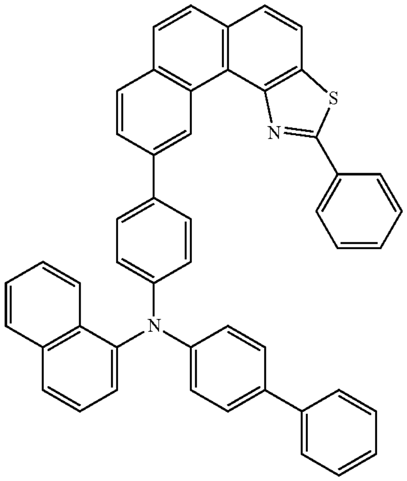
H-63
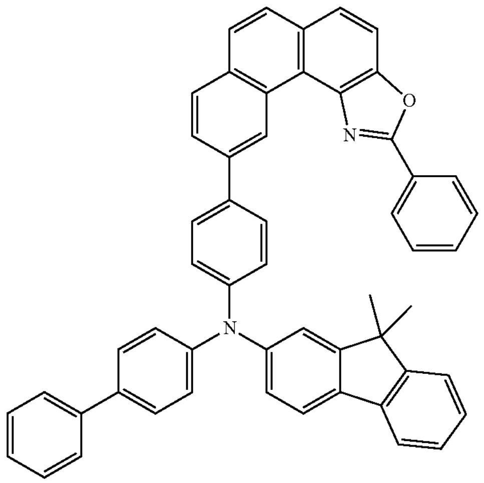
H-64
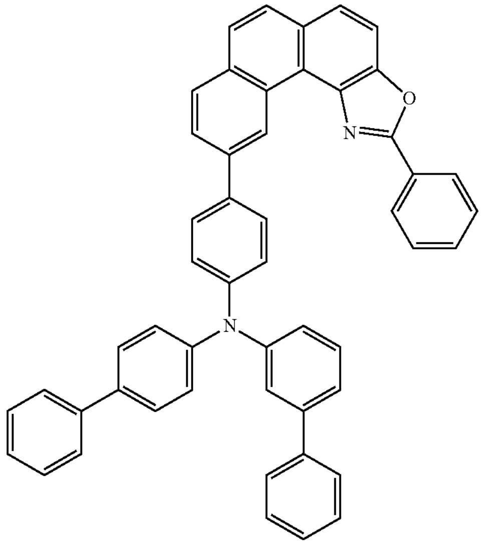

H-65
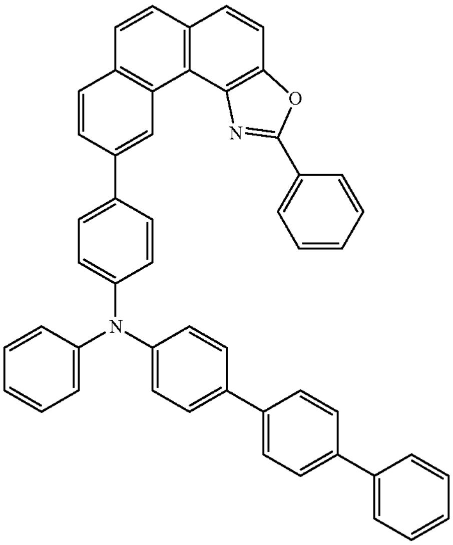
H-66
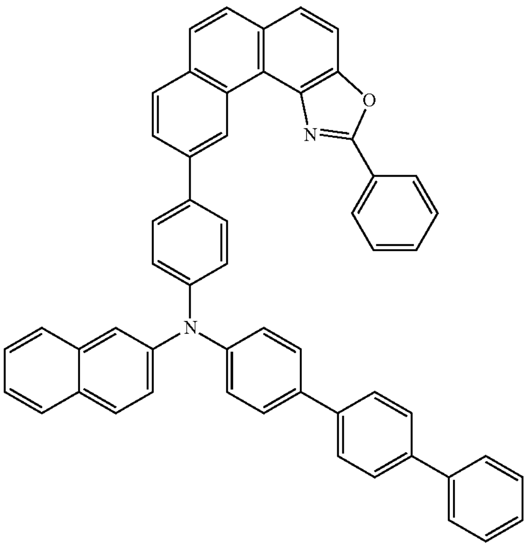
H-67
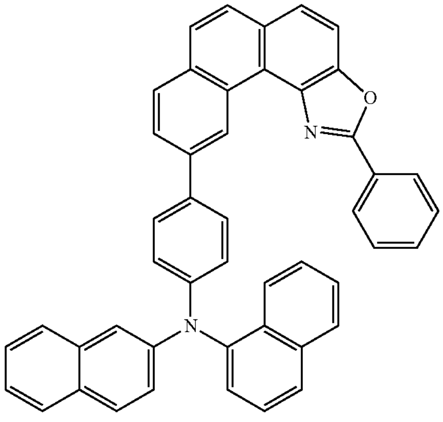
H-68
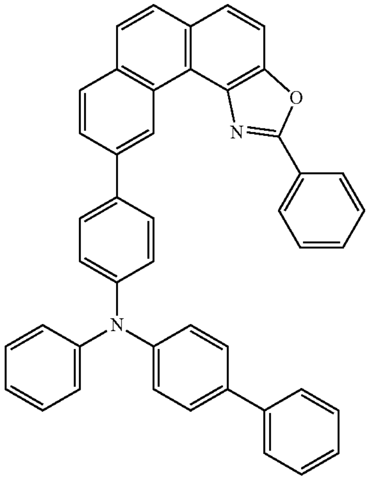
H-69
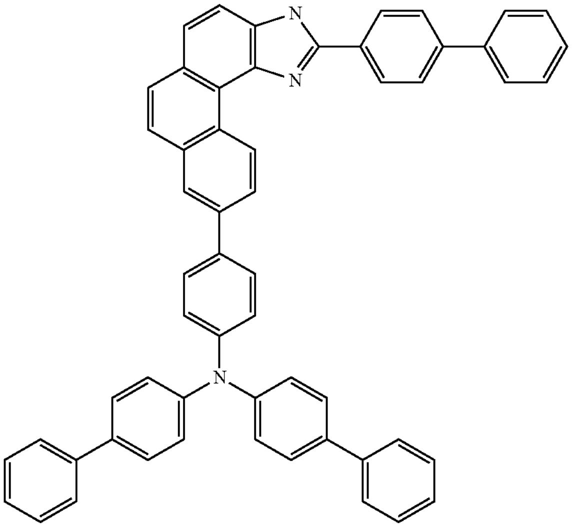
H-70
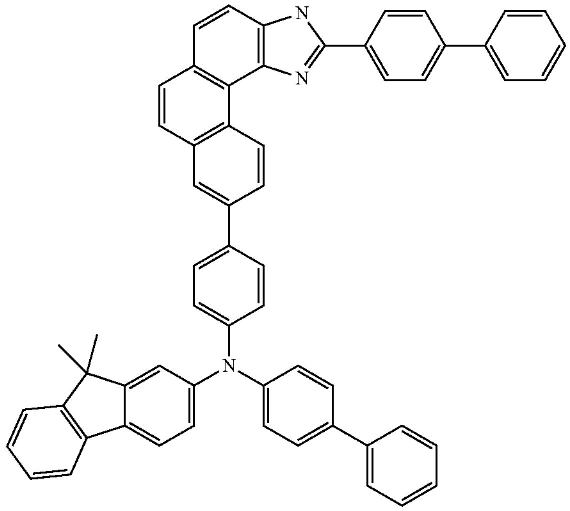

-continued
H-71
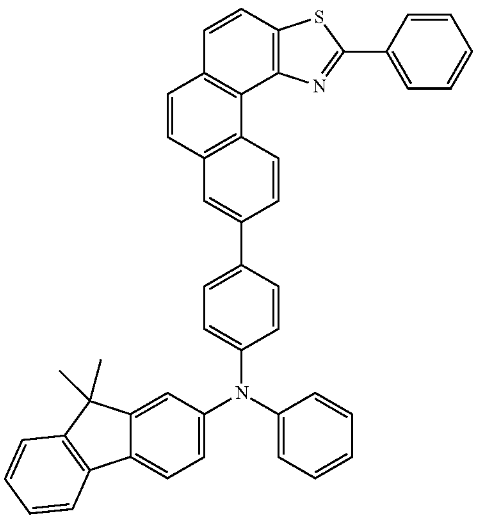
H-72
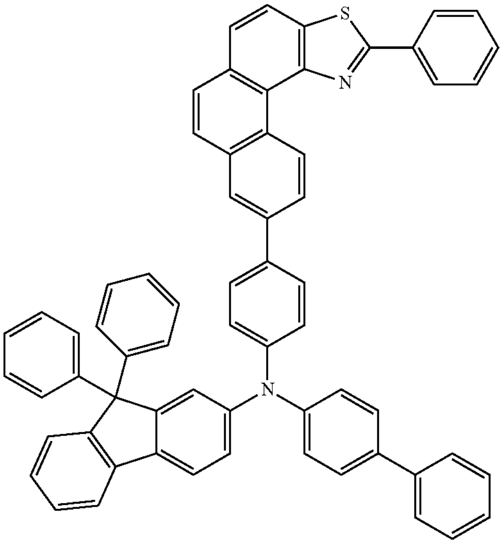
H-73
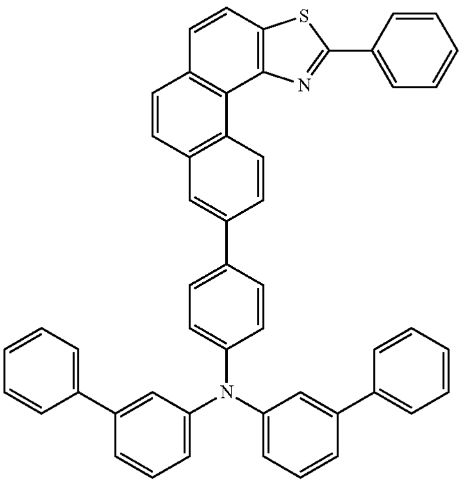
-continued
H-74
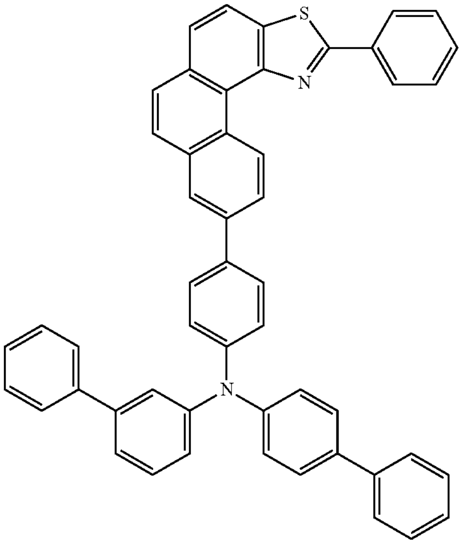
H-75
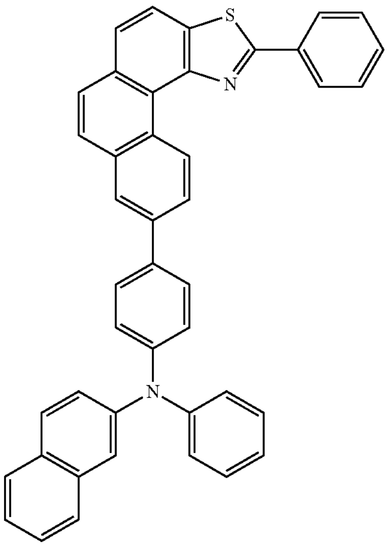
H-76
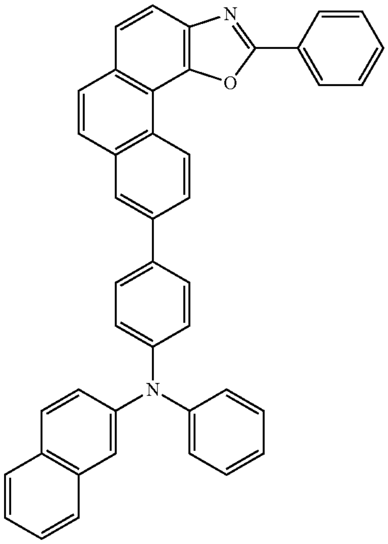

-continued
H-77
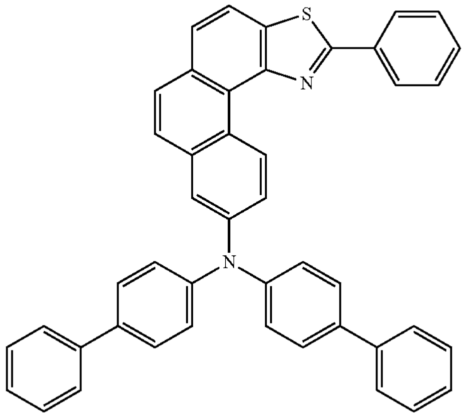
H-78
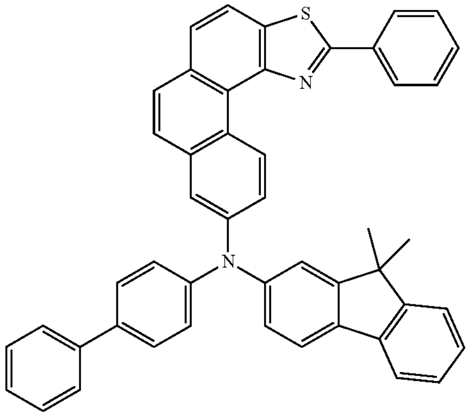
H-79
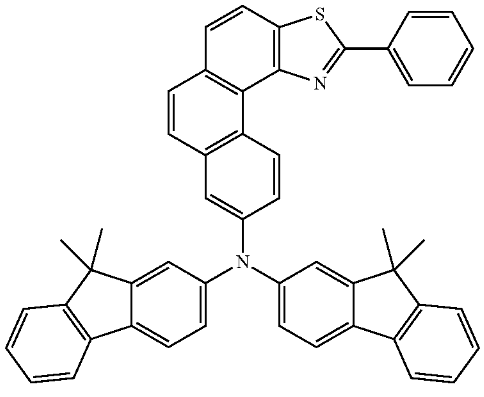
-continued
H-80
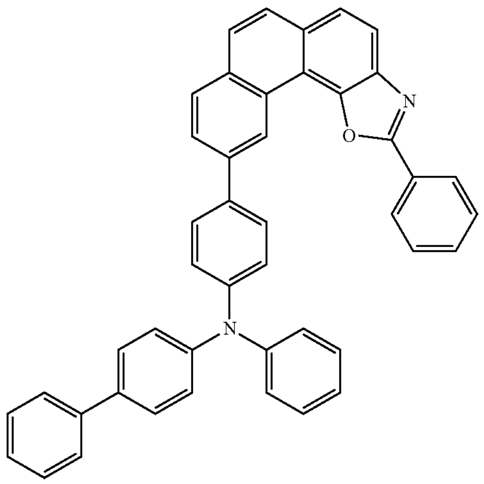
H-81
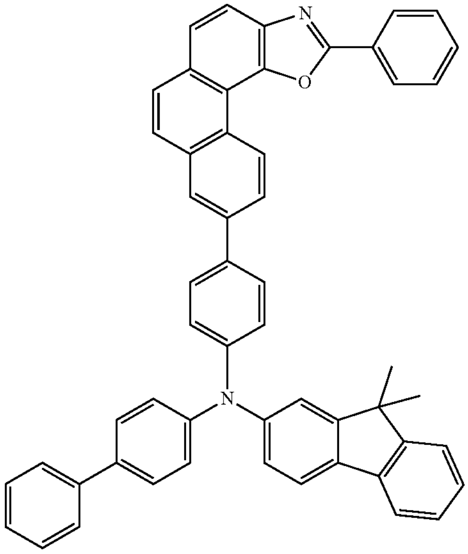
H-82
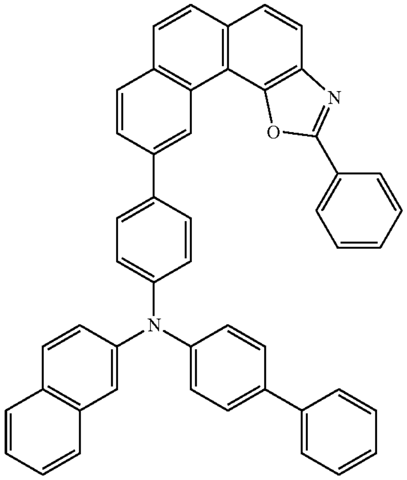

-continued
H-83
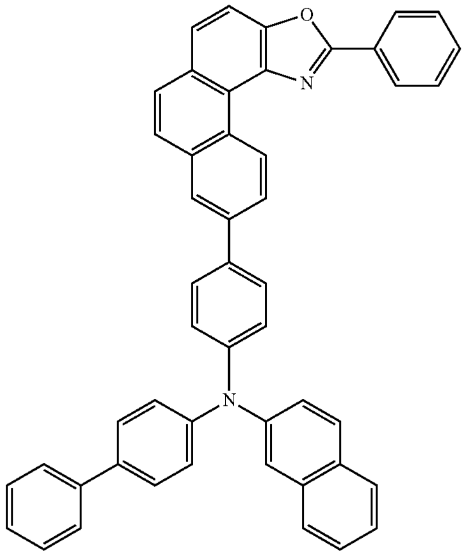
H-84
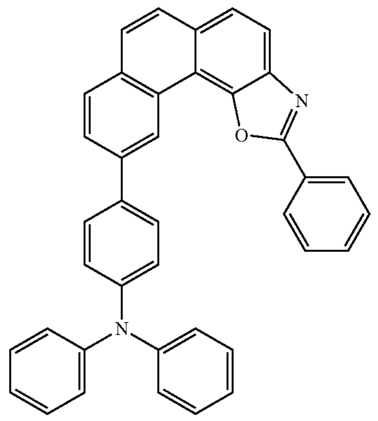
H-85
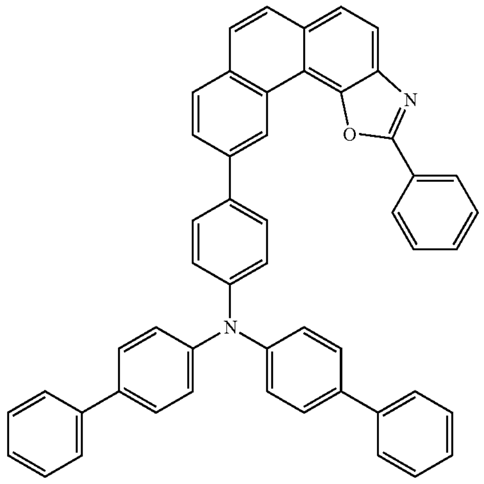
-continued
H-86
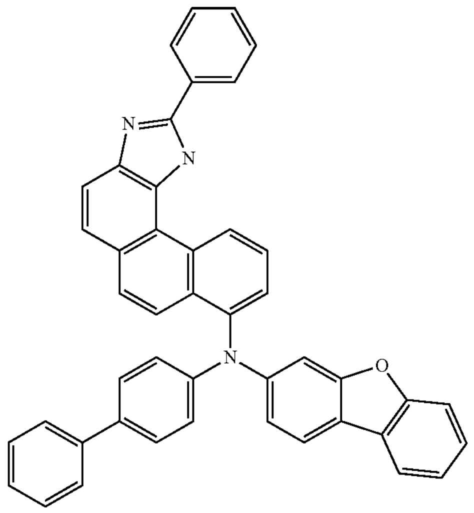
H-87
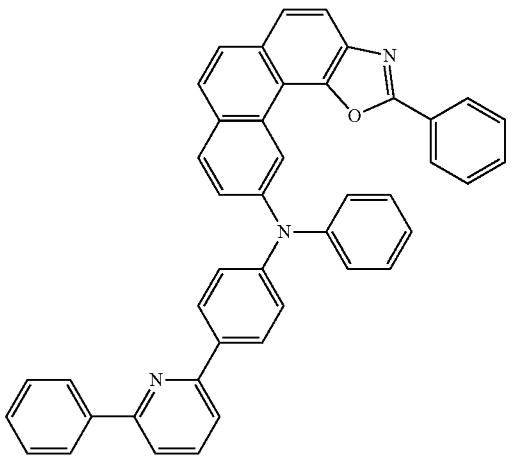
H-88
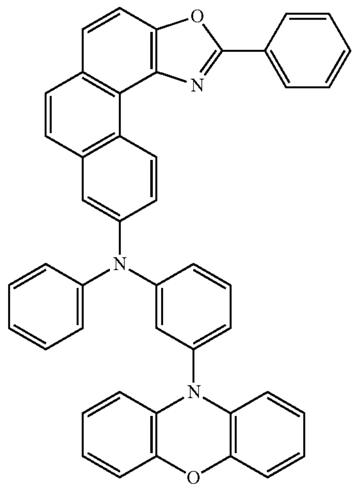

-continued
H-89
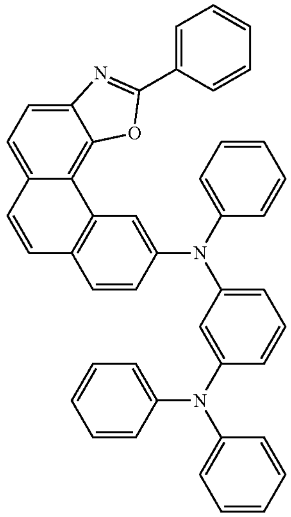
H-90
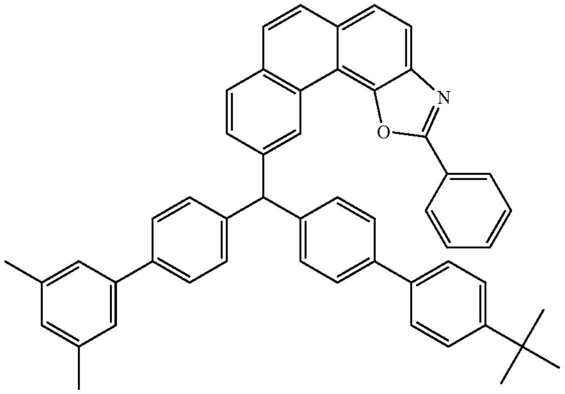
H-91
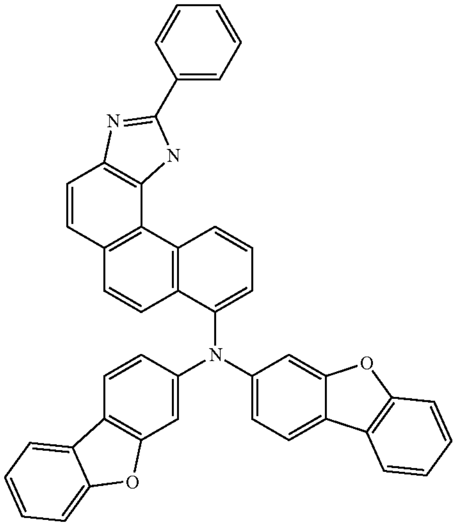
-continued
H-92
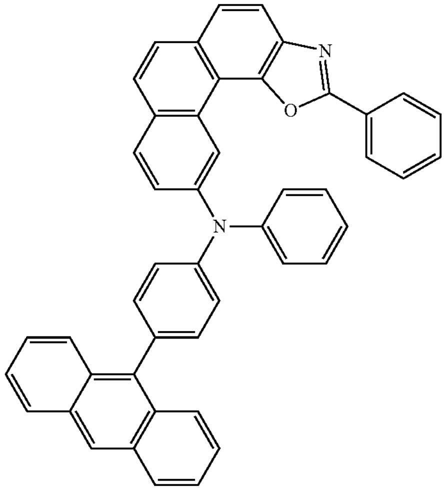
H-93
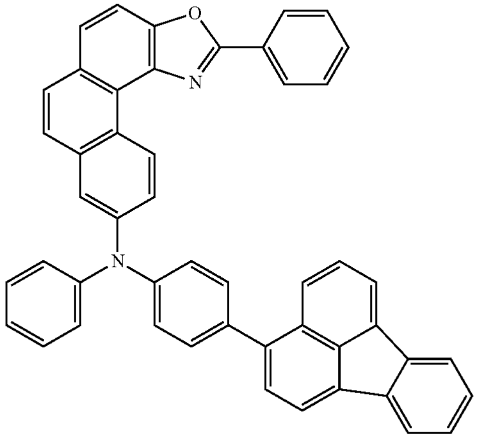
H-94
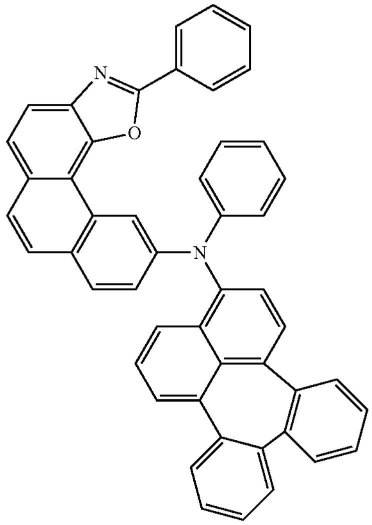

H-95
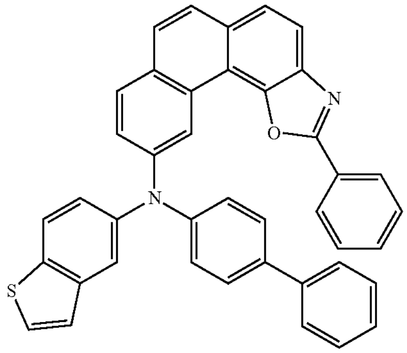
H-96
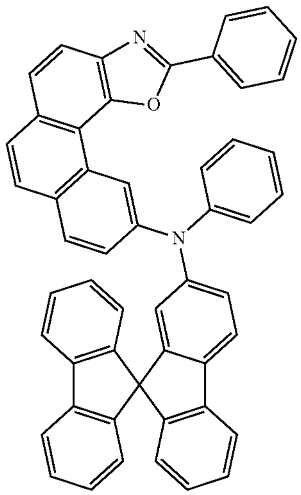
H-97
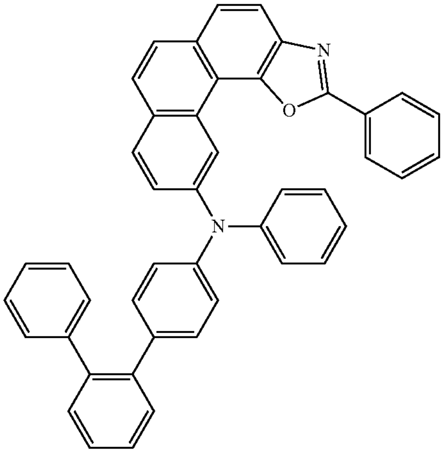
H-98
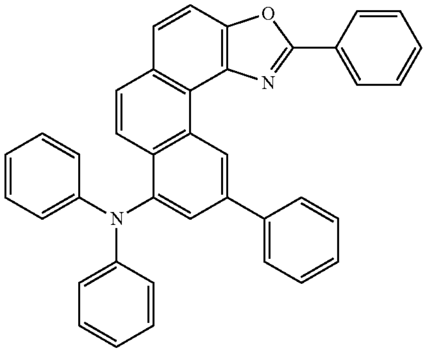
H-99
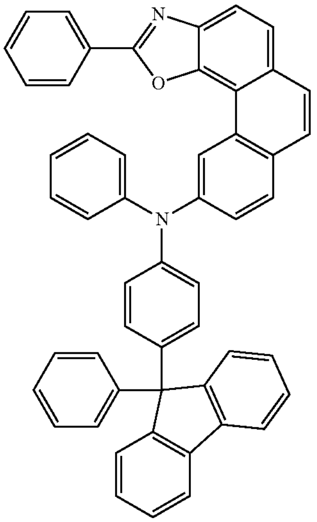
H-100
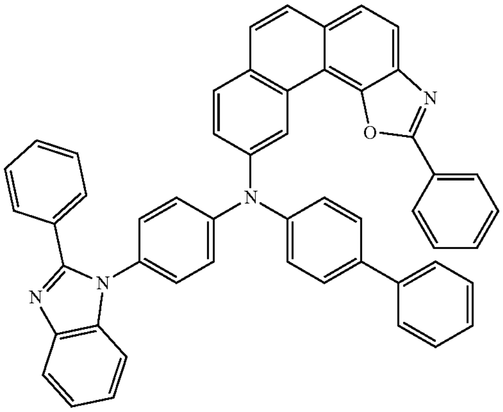

-continued
H-101
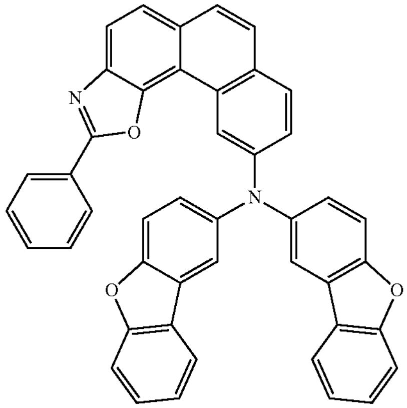
H-102
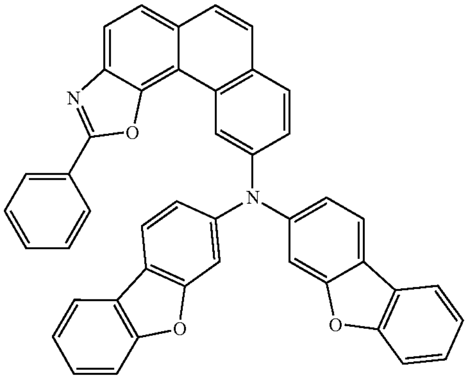
H-103
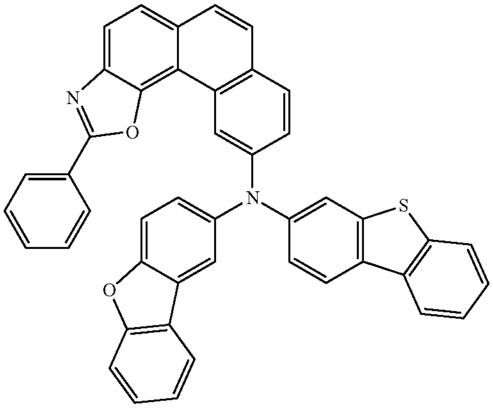
H-104
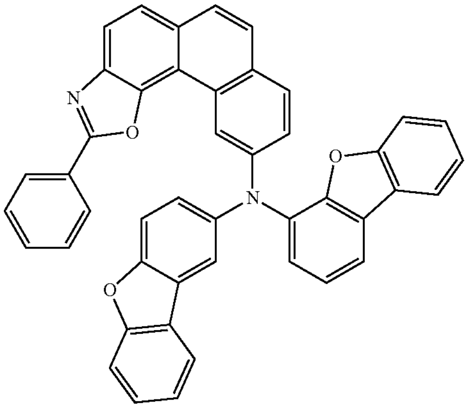
-continued
H-105
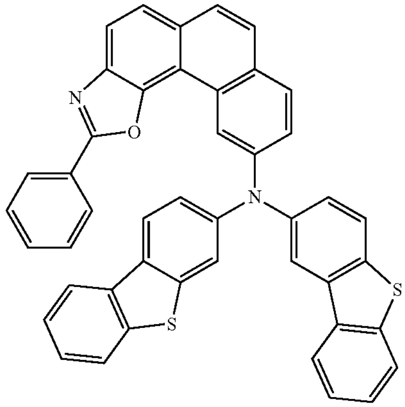
H-106
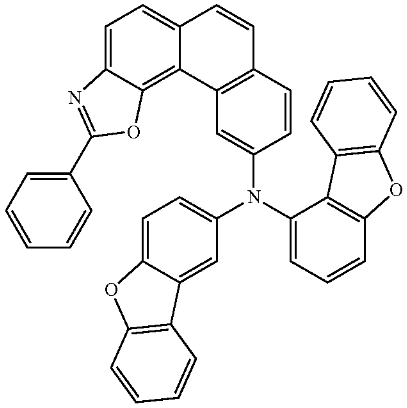
H-107
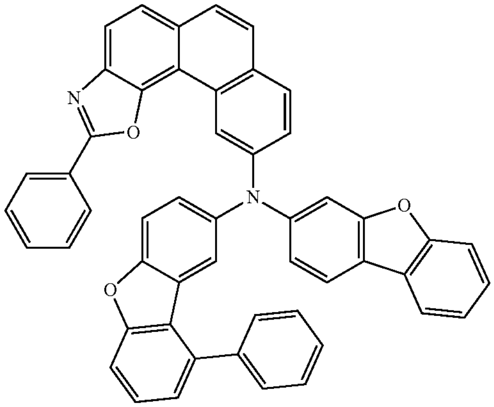

-continued
H-108
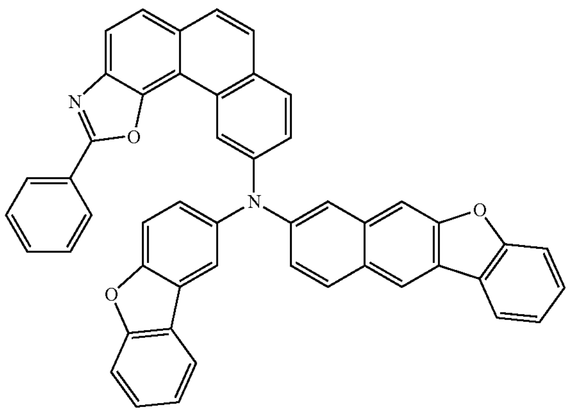
H-109
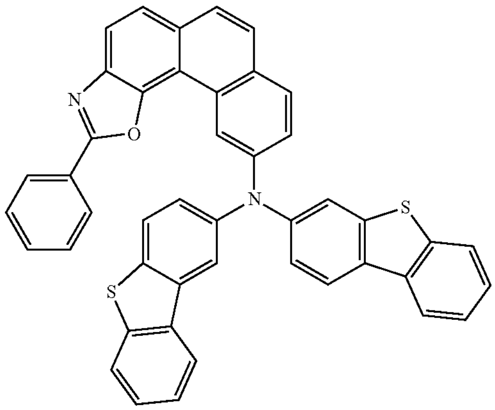
H-110
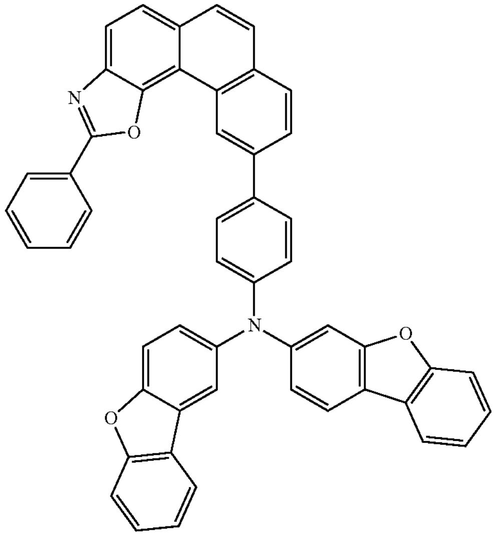
-continued
H-111
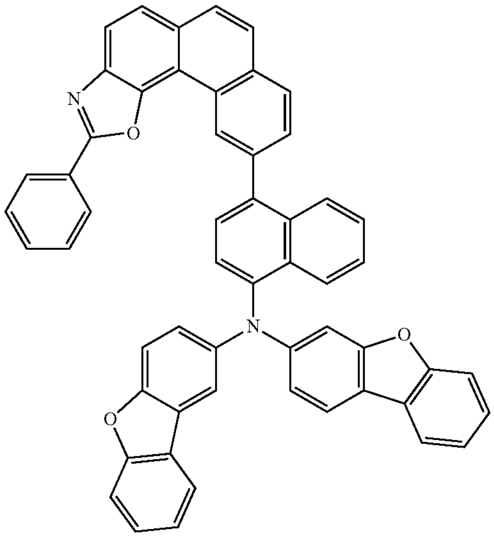
H-112
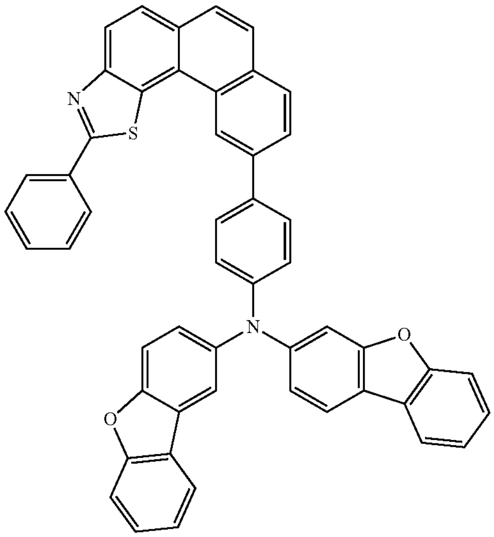
H-113
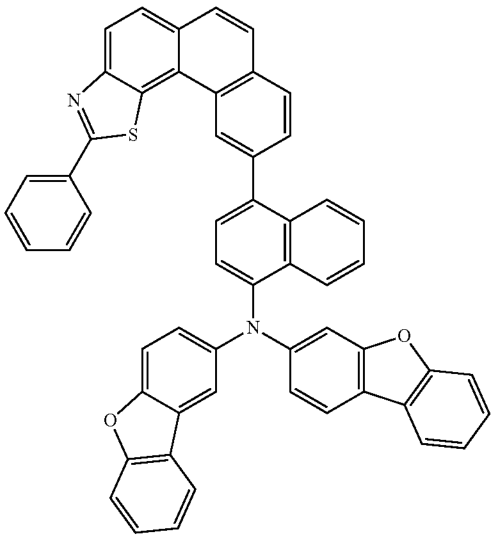

-continued
H-114
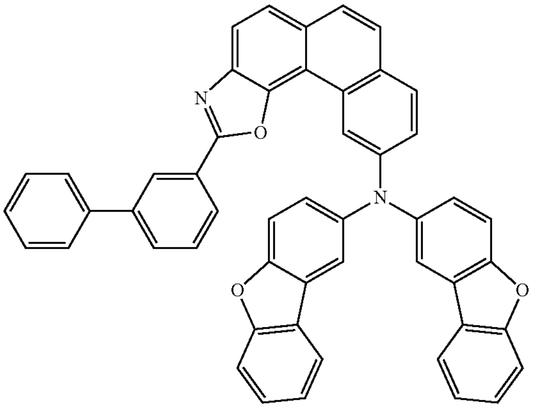
H-115
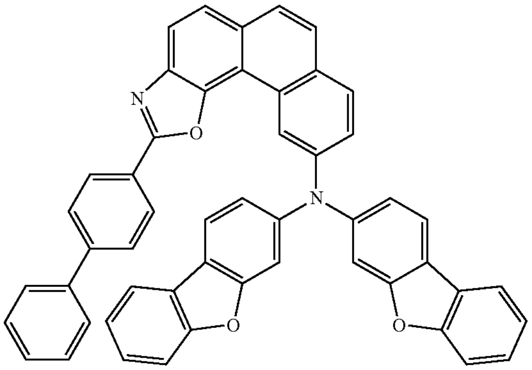
H-116
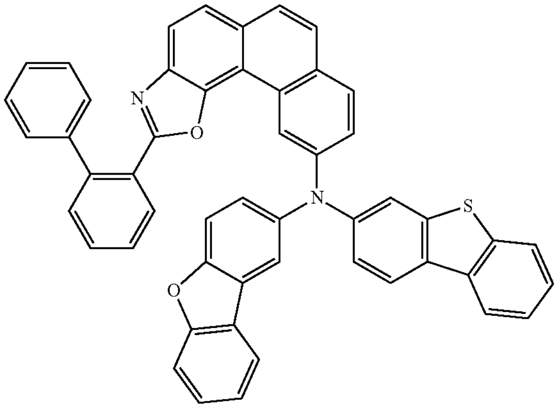
-continued
H-117
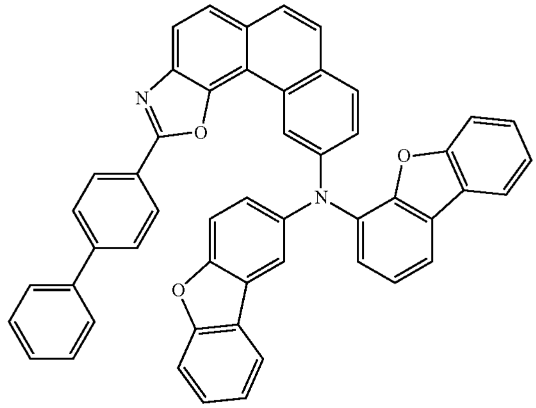
H-118
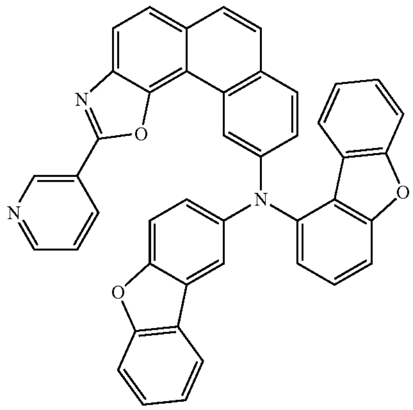
H-119
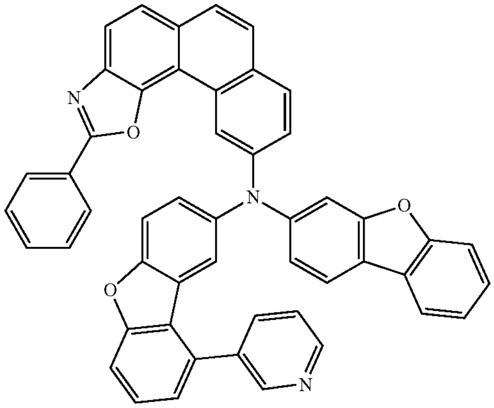

-continued
H-120
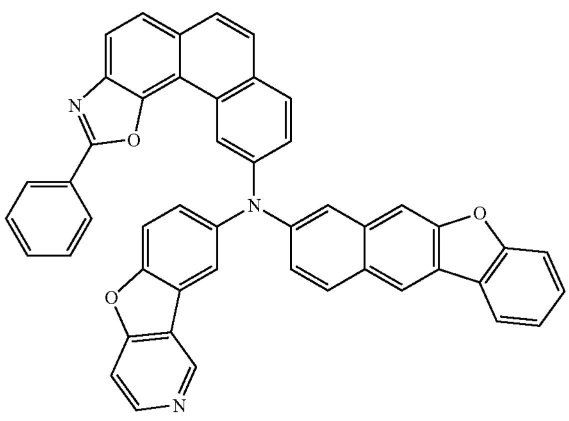
H-121
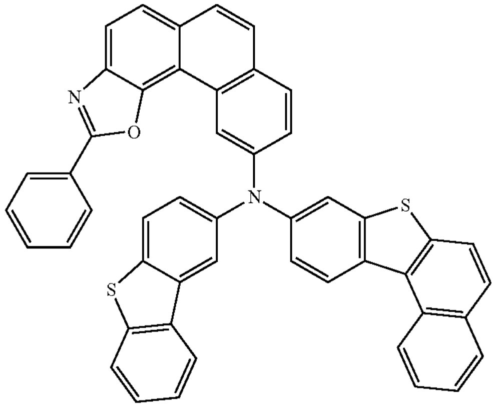
H-122
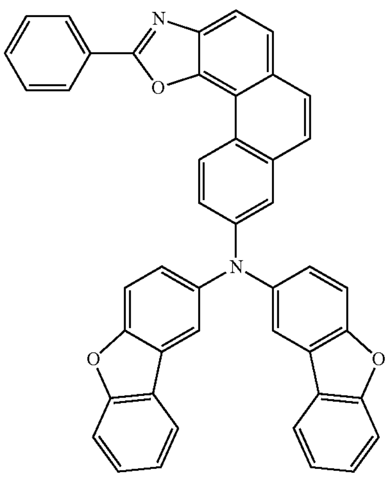
-continued
H-123
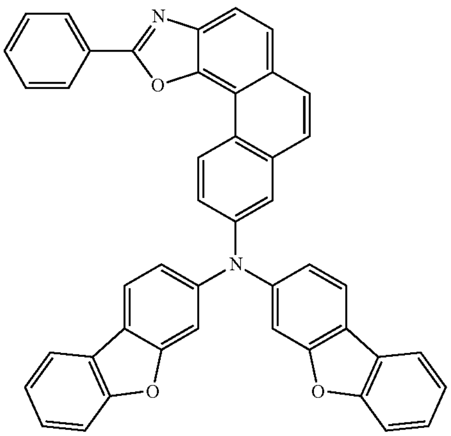
H-124
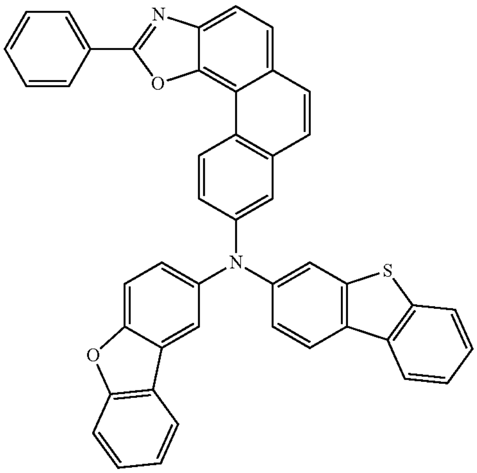
H-125
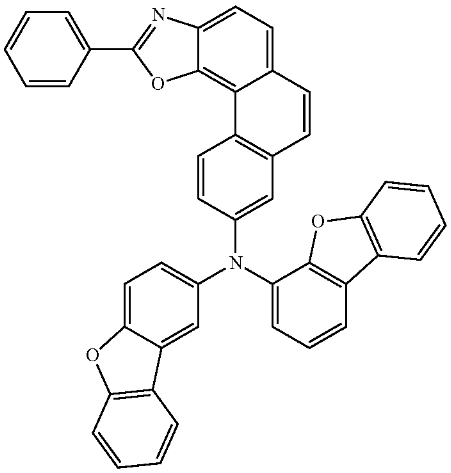

-continued
H-126
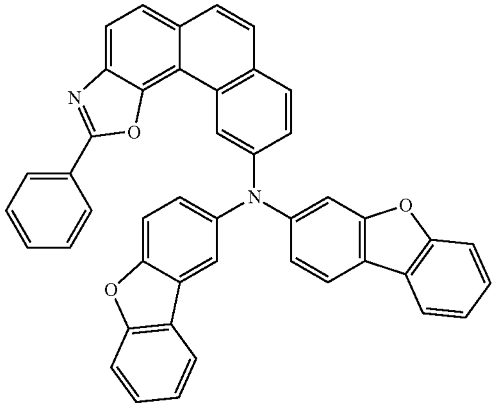
H-127
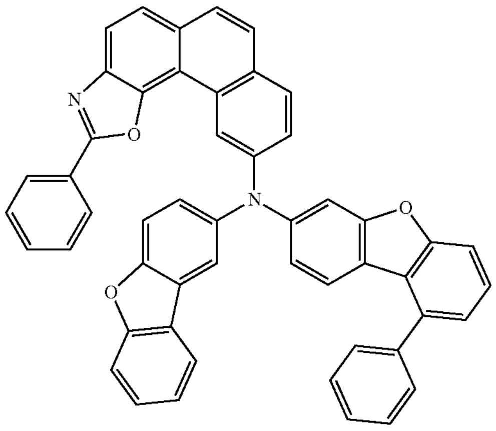
H-128
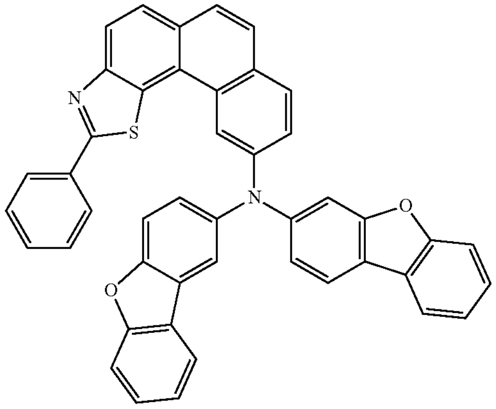
-continued
H-129
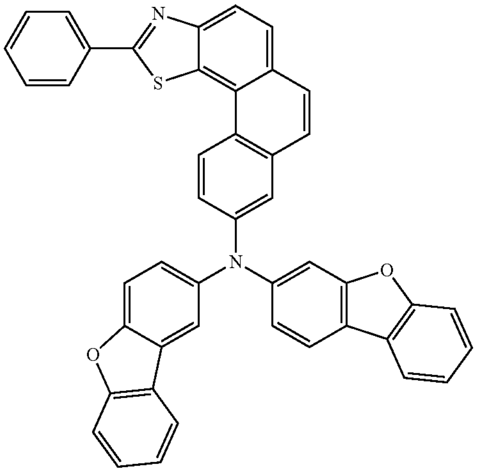
H-130
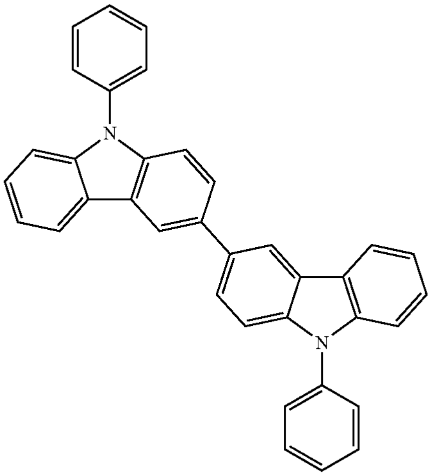

-continued
H-131
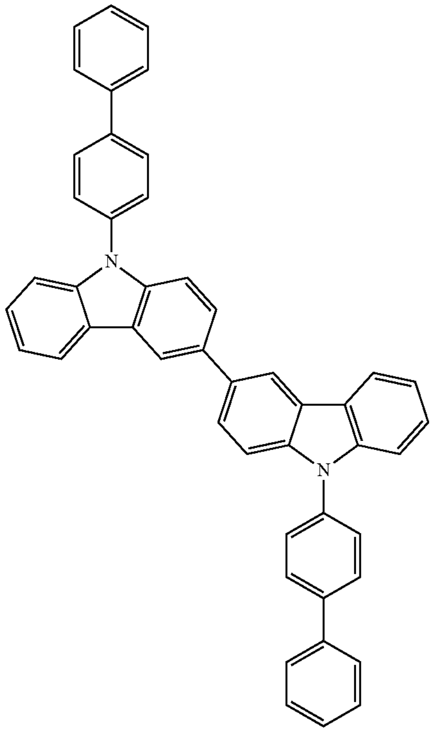
H-132
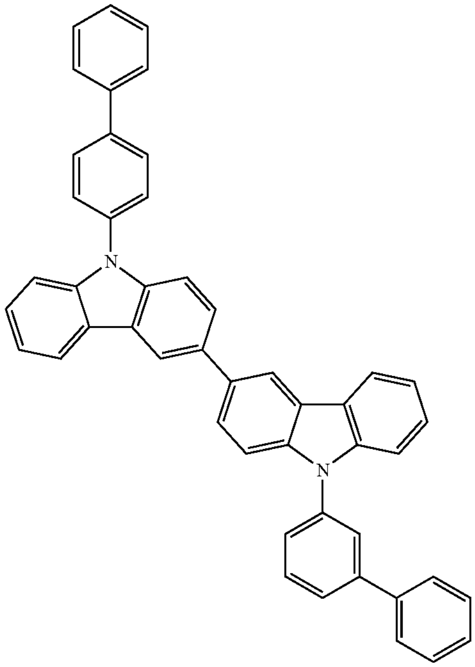
-continued
H-133
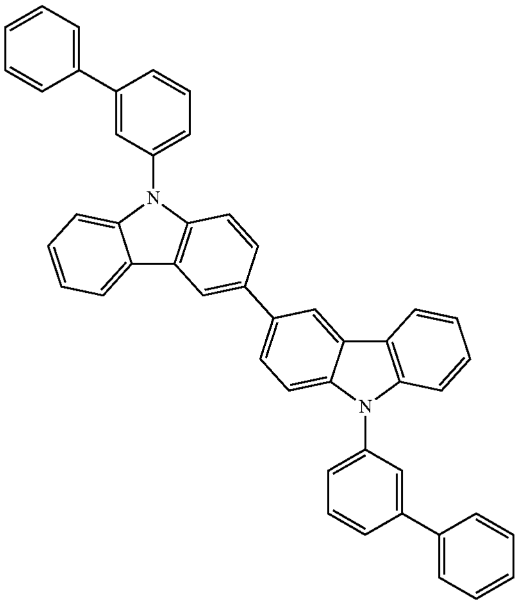
H-134
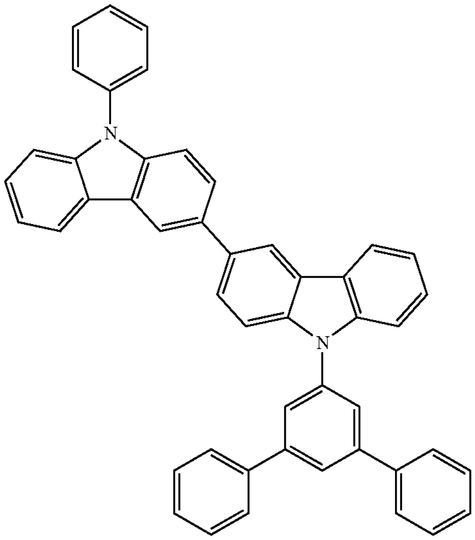

-continued
H-135
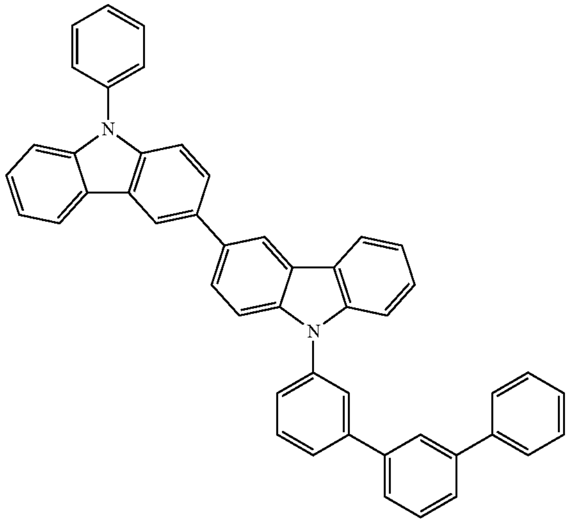
H-136
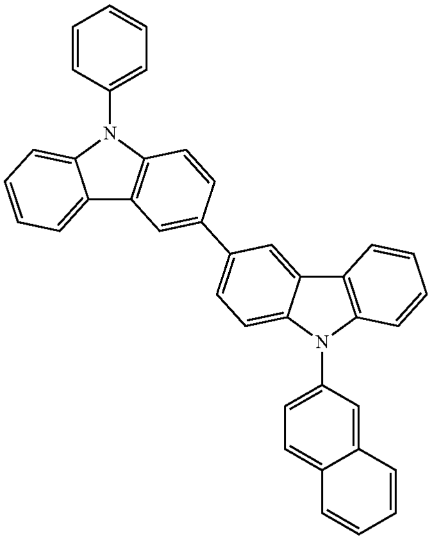
-continued
H-137
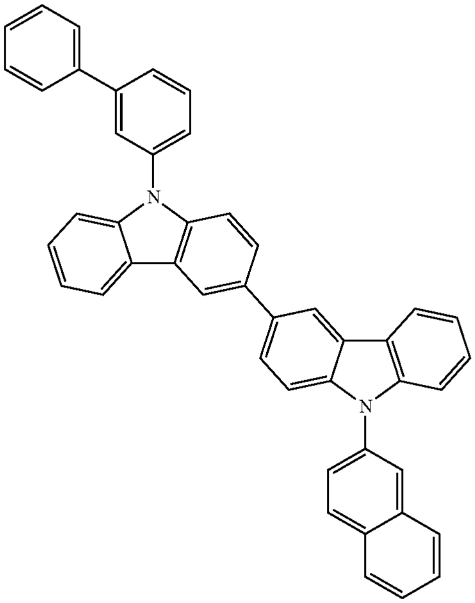
H-138
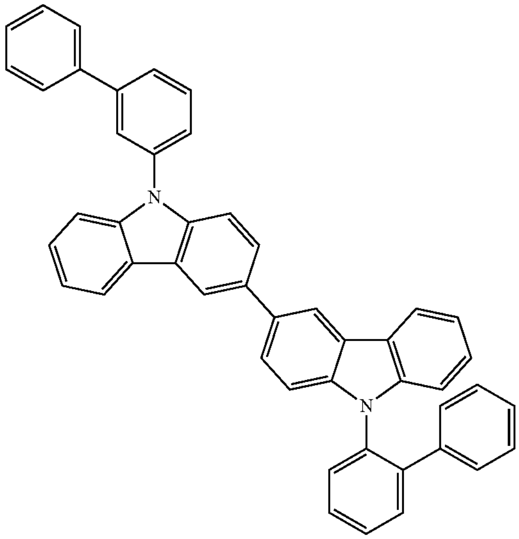
H-139
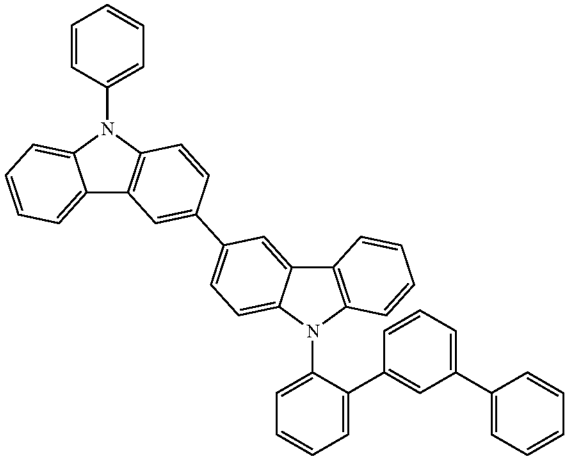

-continued
H-140
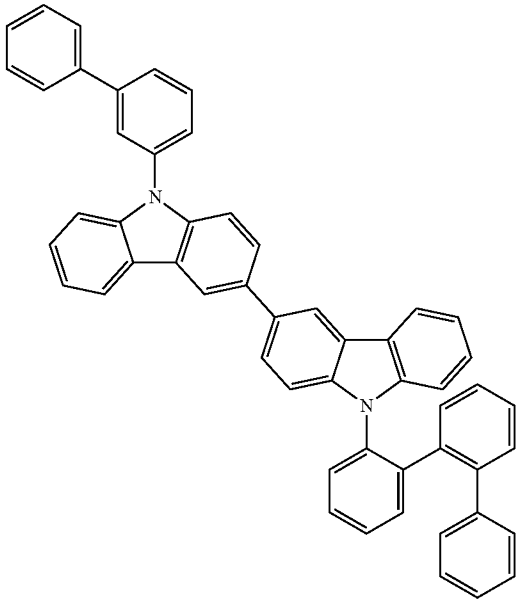
H-141
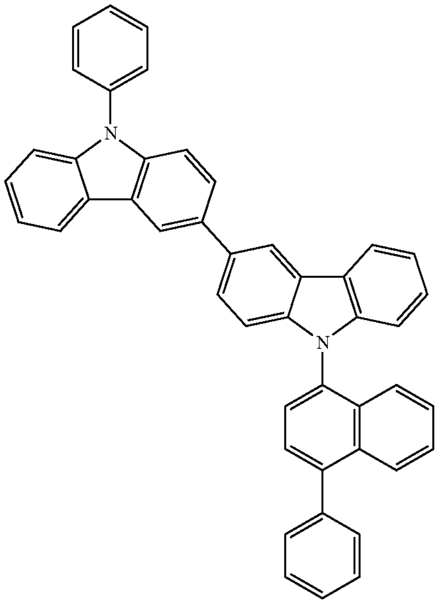
-continued
H-142
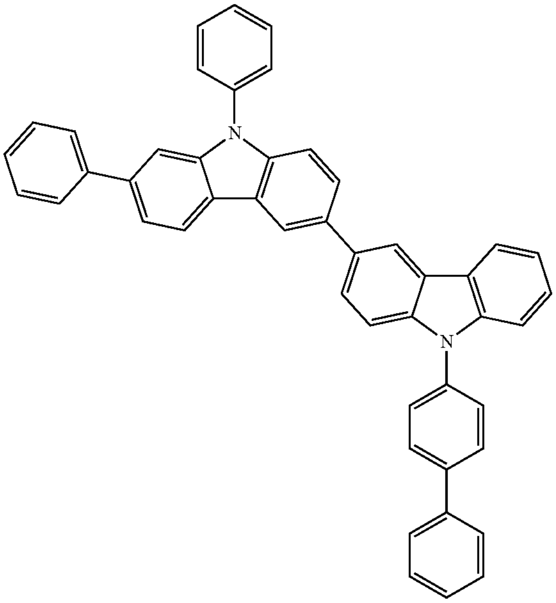
H-143
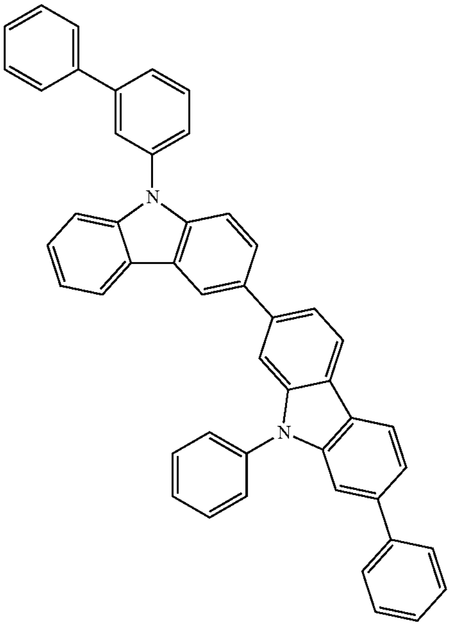

-continued
H-144
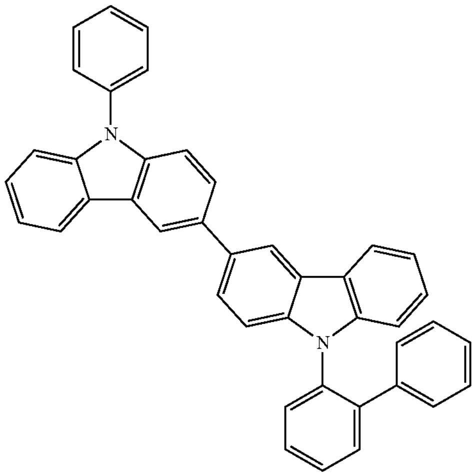
H-145
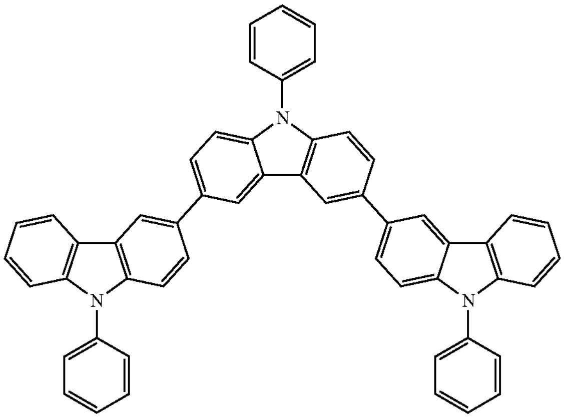
H-146
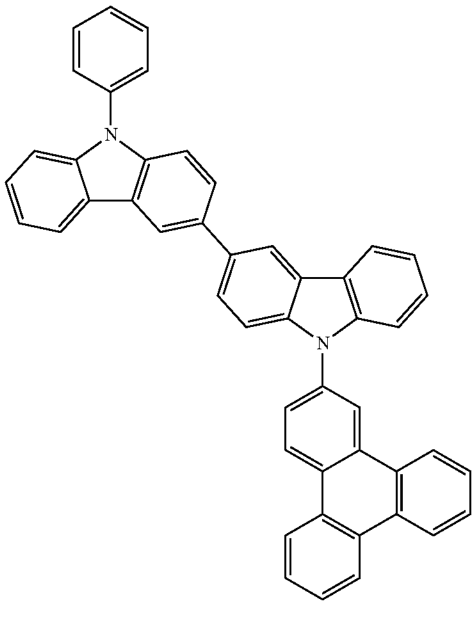
-continued
H-147
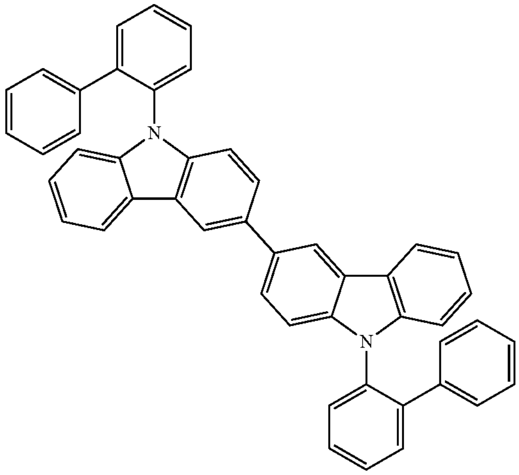
H-148
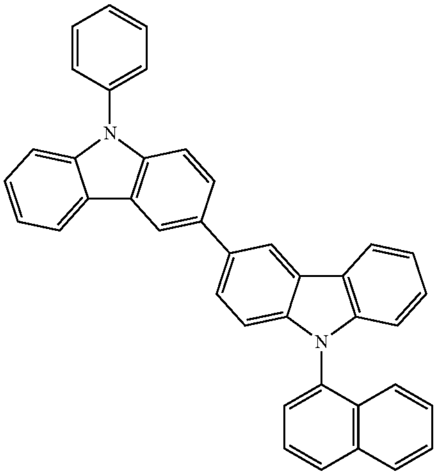
H-149
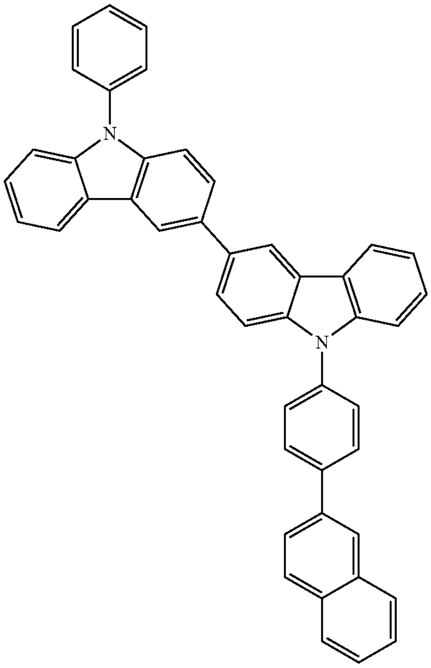

-continued
H-150
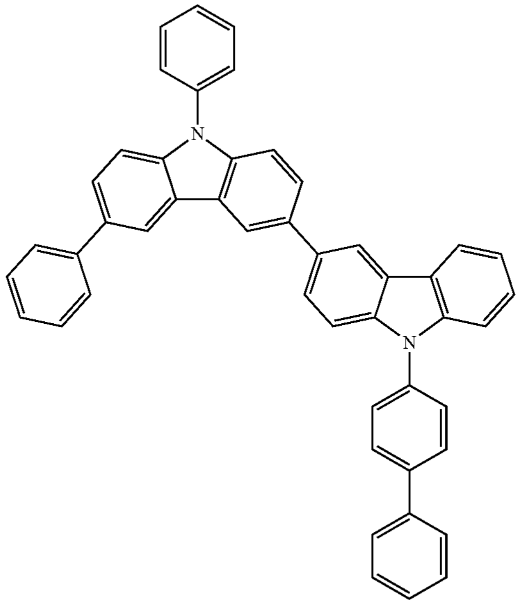
H-151
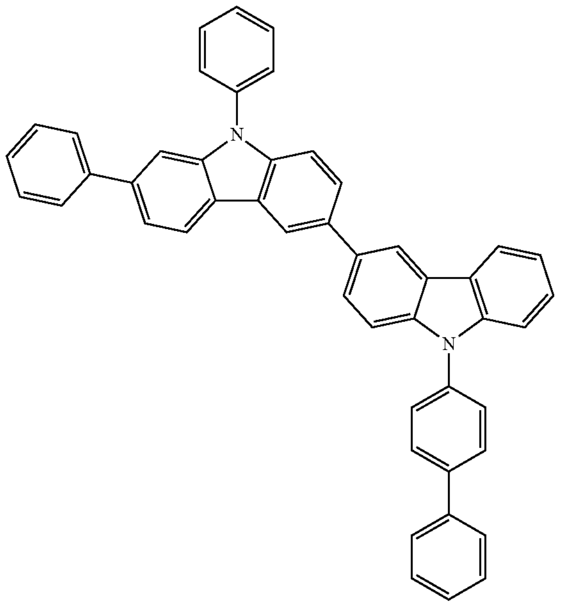
-continued
H-152
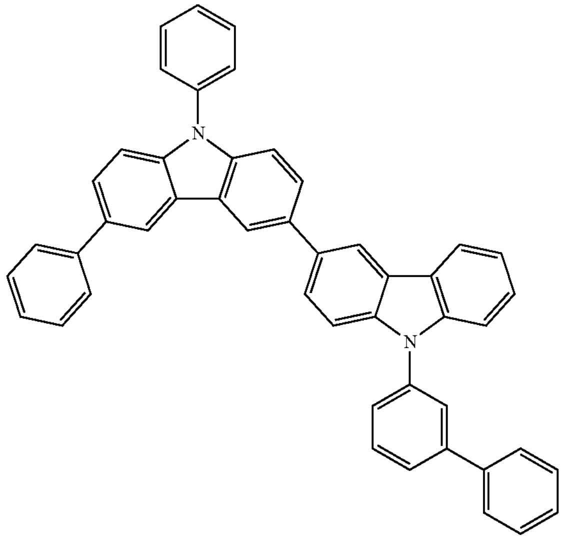
H-153
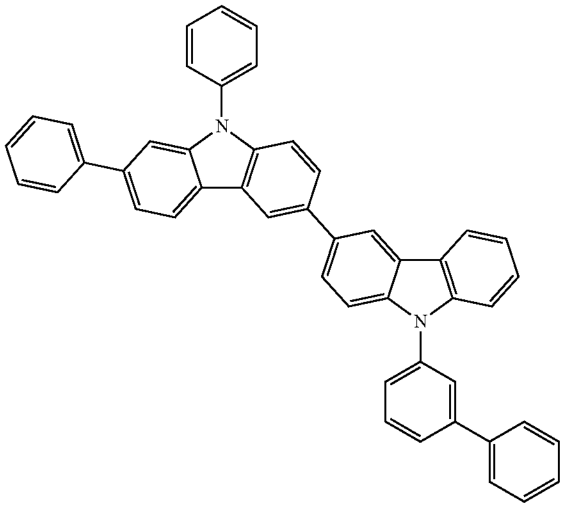

-continued
H-154
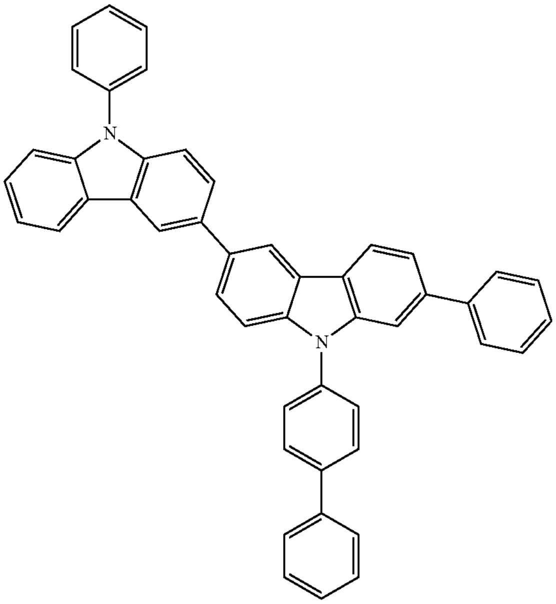
H-155
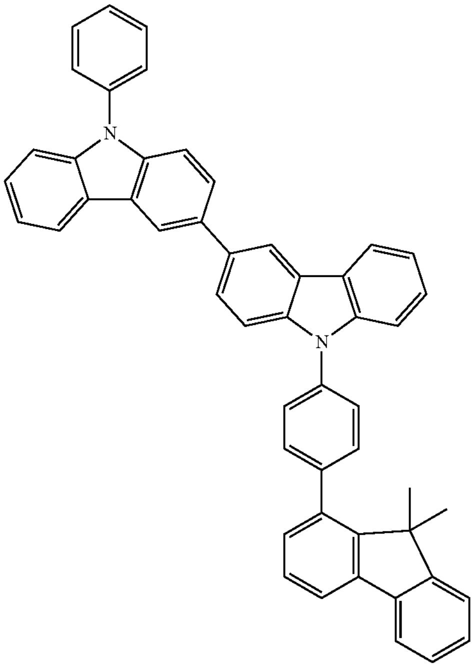
-continued
H-156
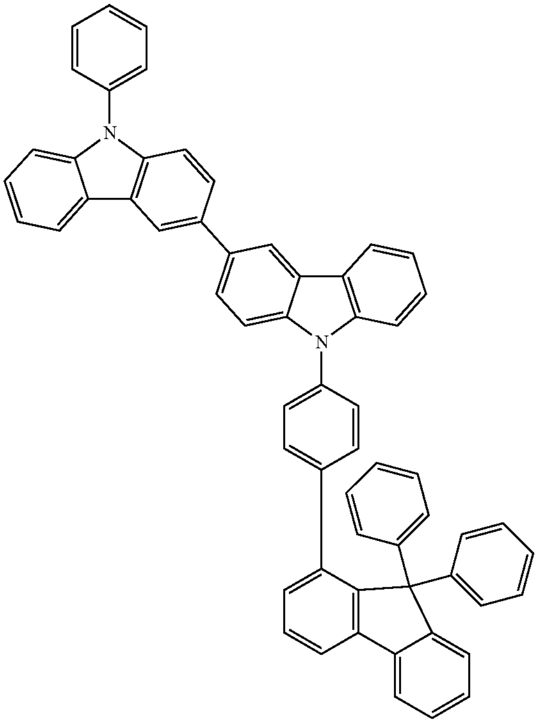
H-157
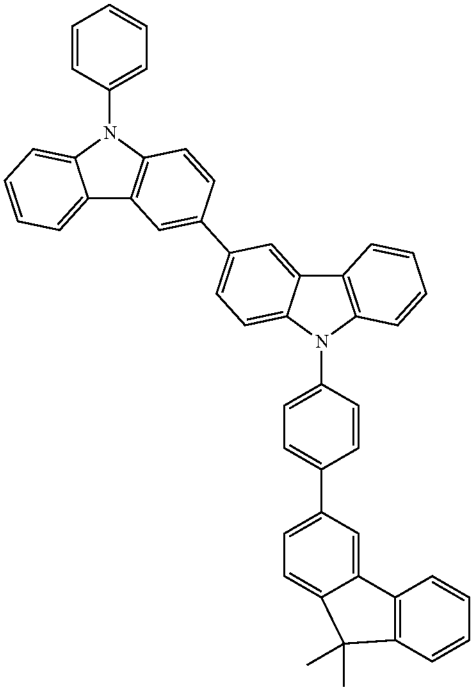

-continued
H-158
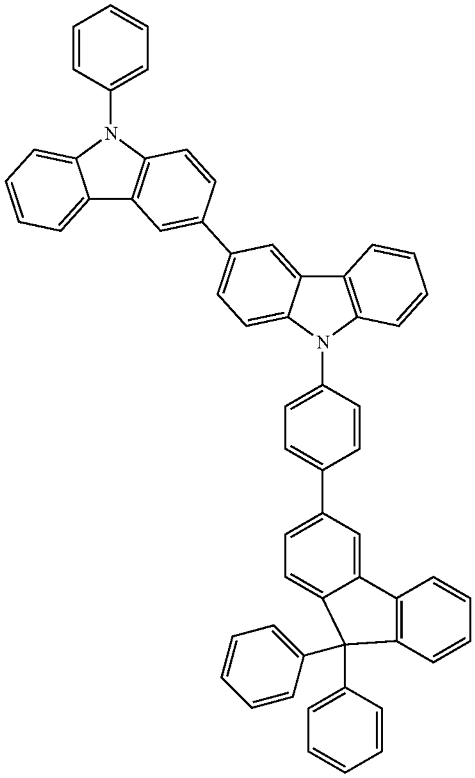
H-159
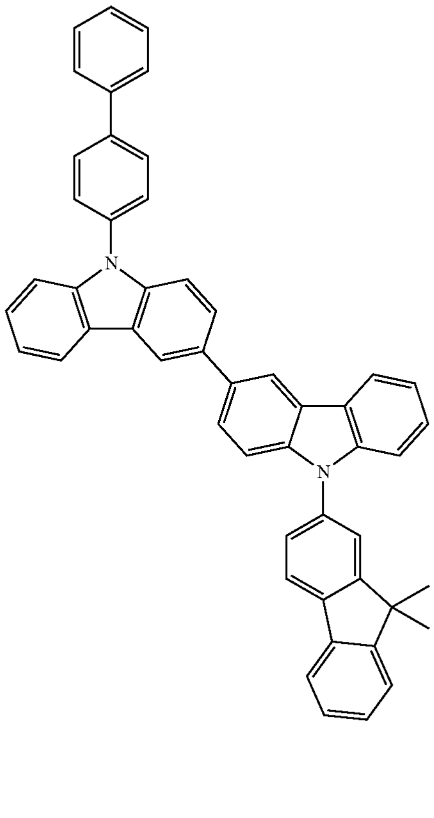
-continued
H-160
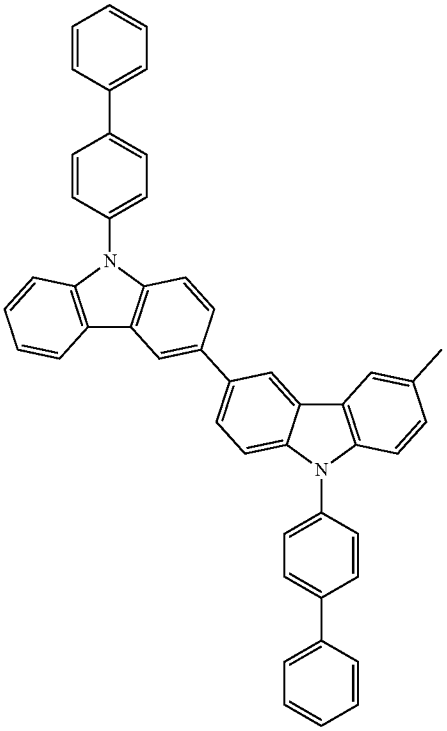
H-161
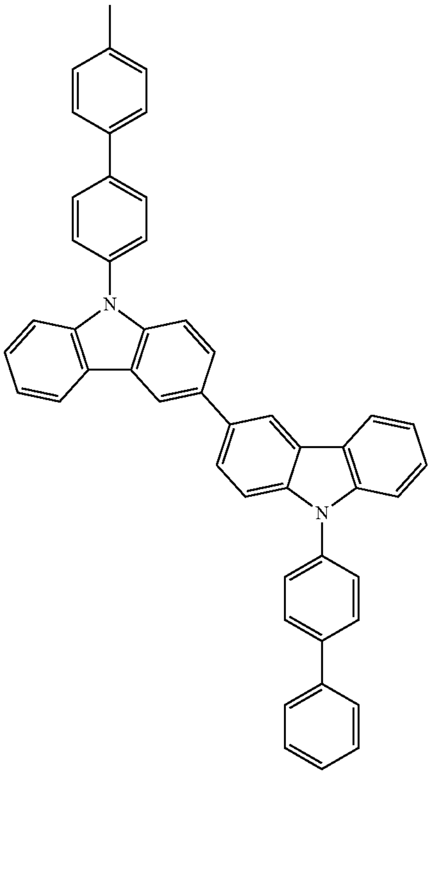

-continued
H-162
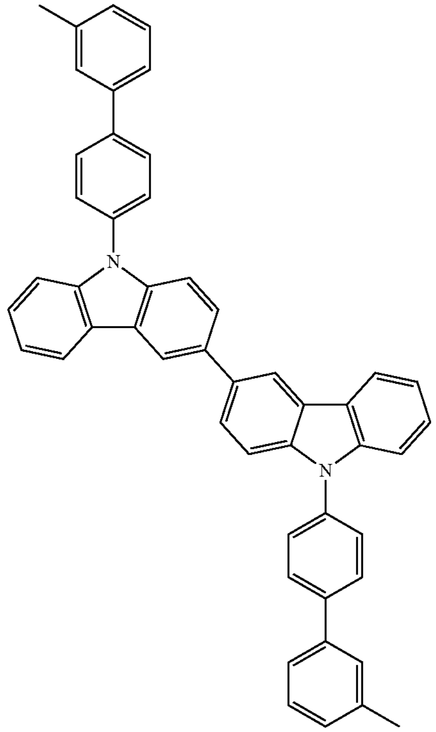
H-163
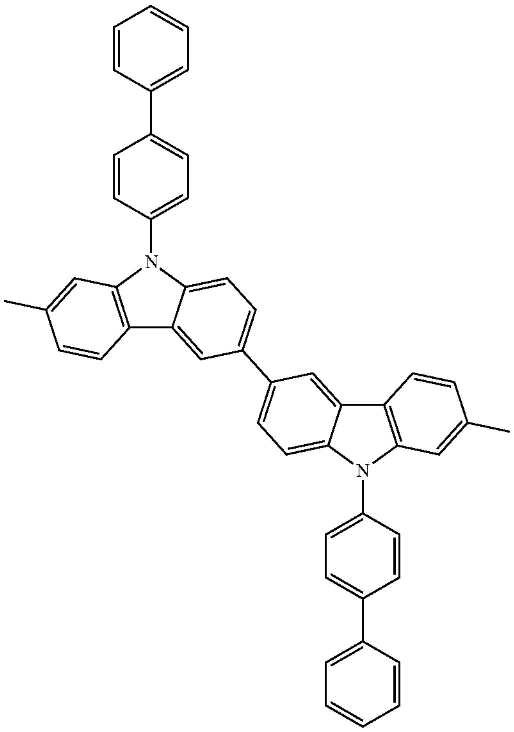
-continued
H-164
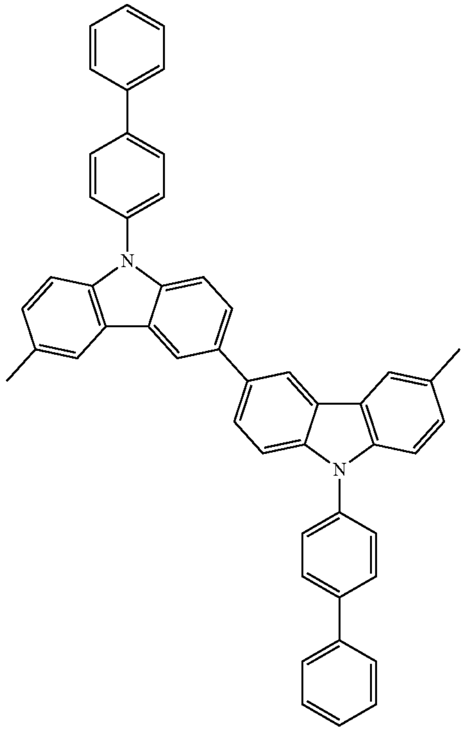
H-165
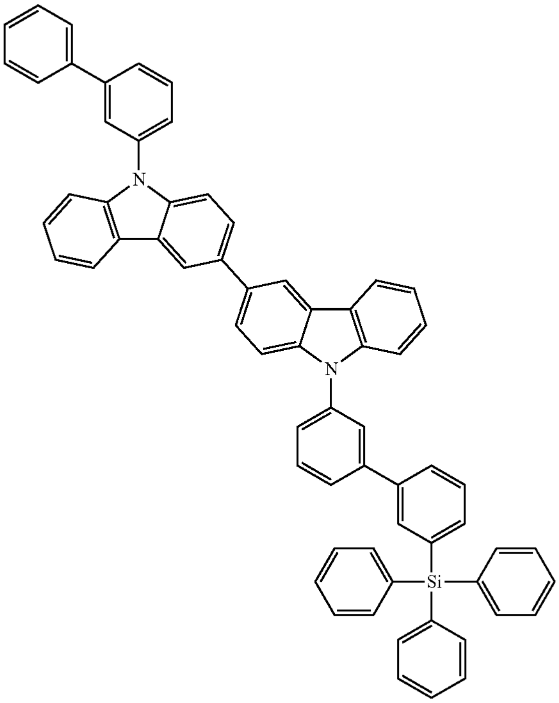

-continued
H-166
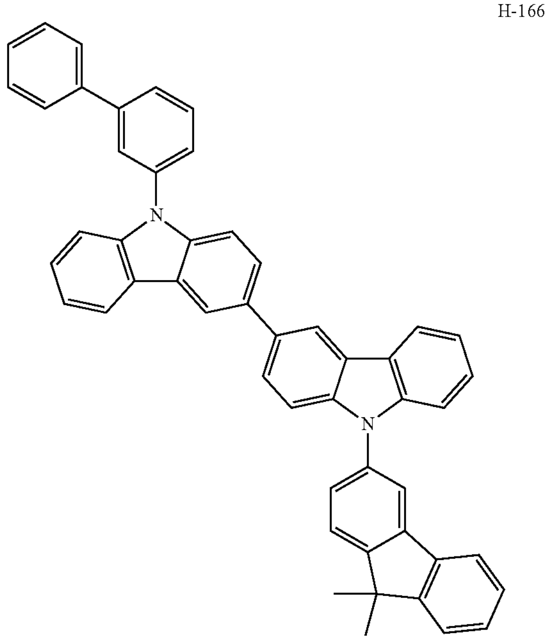
H-167
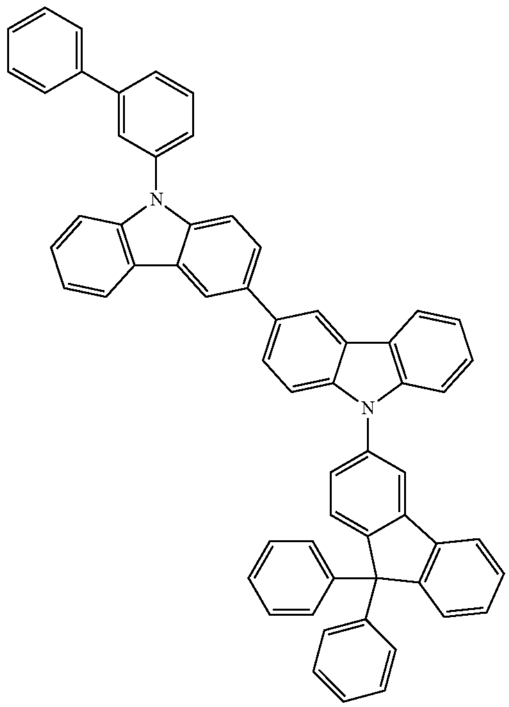
-continued
H-168
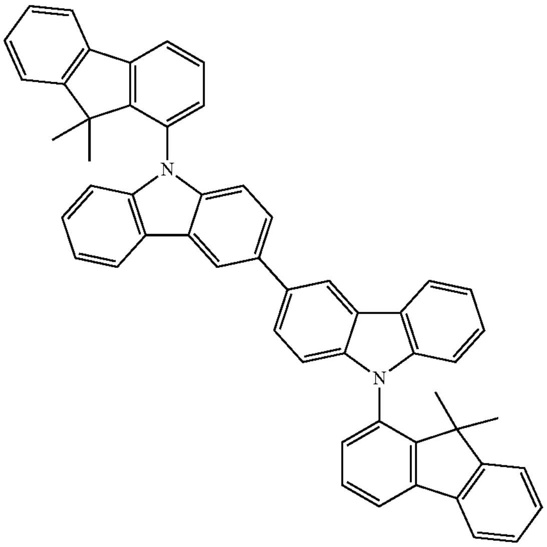
H-169
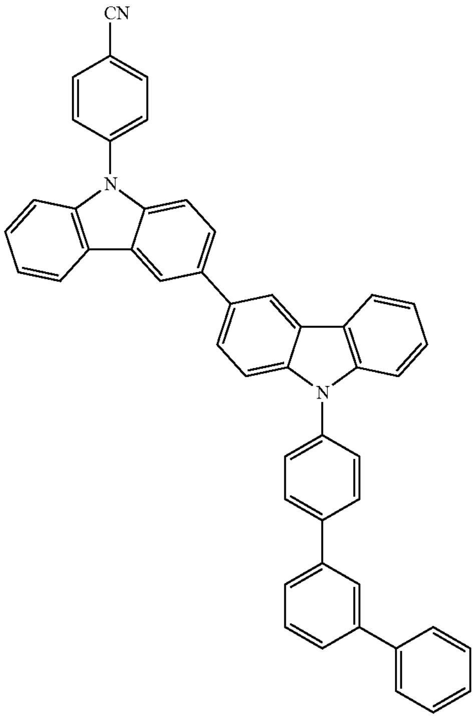

-continued
H-170
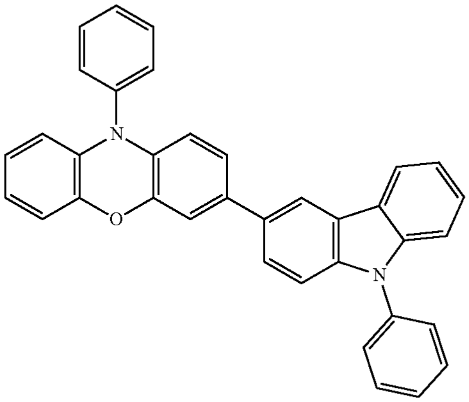
and
-continued
H-171
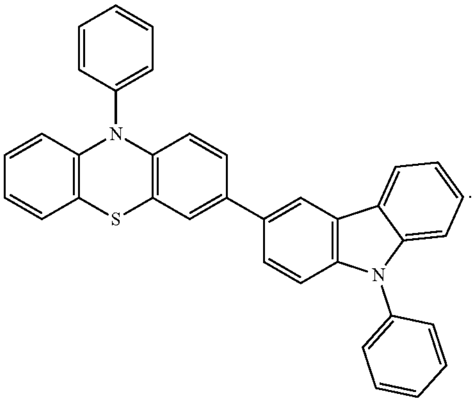
.
6. An organic electroluminescent device comprising the organic electroluminescent compound according to claim 1.
* * * * *